(12) United States Patent
Duvick et al.

(10) Patent No.: US 6,943,279 B1
(45) Date of Patent: Sep. 13, 2005

(54) AMINO POLYOL AMINE OXIDASE POLYNUCLEOTIDES AND RELATED POLYPEPTIDES AND METHODS OF USE

(75) Inventors: Jonathan P. Duvick, Des Moines, IA (US); Jacob T. Gilliam, Norwalk, IA (US); Joyce R. Maddox, Omaha, NE (US); Aragula Gururaj Rao, Urbandale, IA (US); Oswald R. Crasta, Branford, CT (US); Otto Folkerts, Guilford, CT (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 577 days.

(21) Appl. No.: 09/658,835

(22) Filed: Sep. 8, 2000

Related U.S. Application Data

(63) Continuation-in-part of application No. 09/352,159, filed on Jul. 12, 1999, now Pat. No. 6,211,434.

(51) Int. Cl.$^7$ ........................ C12N 15/09; C12N 15/31; C12N 15/82; A10H 1/00; A10H 5/10
(52) U.S. Cl. ...................... 800/279; 800/278; 800/298; 800/288; 800/312; 800/314; 800/322; 800/320.1; 800/320; 800/320.2; 800/320.3; 800/317.2; 435/419; 435/468; 435/320.1; 536/23.2; 536/23.7; 536/24.1
(58) Field of Search ................................ 800/278, 279, 800/288, 298, 320.1, 320.2, 320.3, 312, 322, 314, 320, 317.2; 435/419, 468, 320.1; 536/23.2, 23.7, 24.1

(56) References Cited

U.S. PATENT DOCUMENTS

| | | | |
|---|---|---|---|
| 4,988,586 A | 1/1991 | Toyoda et al. | 424/93.2 |
| 5,178,863 A | 1/1993 | Toyoda et al. | 424/93.28 |
| 5,262,306 A | 11/1993 | Robeson et al. | 435/27 |
| 5,716,820 A | 2/1998 | Duvick et al. | 435/196 |

FOREIGN PATENT DOCUMENTS

| | | |
|---|---|---|
| WO | 93 02673 | 2/1993 |
| WO | 95 06128 | 3/1995 |
| WO | 96 06175 | 2/1996 |
| WO | 96 12414 | 5/1996 |
| WO | 96 20595 | 7/1996 |
| WO | 96 32007 | 10/1996 |
| WO | 99 02703 | 1/1999 |

OTHER PUBLICATIONS

Abbas, et al., 1992, *Weed Technology*, 6: 548–552, "Phytotoxicity of Fumonisin B$_1$ on Weed and Crop Species[1]".
Blackwell, et al., 1994, *J. of AOAC International*, 77(2): 506–511, "Production of Carbon 14–Labeled Fumonisin in Liquid Culture".
Gelderblom, et al., 1993, *Food Chem. Toxic.*, 31(6): 407–414, "Structure–Activity Relationships of Fumonisins in Short–Term Carcinogenesis and Cytotoxicity Assays".
Van Asch, et al., 1992, *Phytopathology*, 82(11): 1330–1332, "Phytotoxicity of Fumonisin B$_1$, Moniliformin, and T–2 Toxin to Corn Callus Cultures".
Vesonder, et al., 1993, *Arch. Environ. Contam. Toxicol.*, 24: 473–477, "Comparison of the Cytotoxicities of Fusarium Metabolites and Alternaria Metabolite AAL–Toxin to Cultured Mammalian Cell Lines".
Tanaka, et al., 1993, *Phytochemistry*, 33(4): 779–785, "Structure–Dependent Phytotoxicity of Fumonisins and Related Compounds in a Duckweek Bioassay".
He P., et al., 1992, *Applied and Environmental Microbiology*, 58(12): 3857–3863, "Microbial Transformation of Deoxynivalenol (Vomitoxin)".
Kneusel, et al., 1994, *The J. of Biological Chemistry*, 269(5): 3449–3456, "Molecular Characterization and Cloning of an Esterase Which Inactivates the Macrolide Toxin Brefeldin A*".
Miller, J.D., et al., 1986, *Canadian J. of Plant Pathology*, 8: 147–150, "Degradation of deoxynivalenol by suspension cultures of the fusarium head blight resistant wheat cultivar Frontana".
Ueno, et al., 1983, *Applied and Environmental Microbiology*, 46: 120–127, "Metabolism of T–2 Toxin in Curtobacterium sp. Strain 114–2".
Utsumi, et al., 1991, *Agric. Biol. Chem.*, 55: 1913–1918, "Molecular Cloning and Characterization of the Fusaric Acid–resistance Gene from *Pseudomonas cepacia*".
Vesonder, et al., 1992, *Arch. Environ. Contam. Toxicol.*, 23: 464–467, Comparative Phytotoxicity of the Fumonisins, AAL–Toxin and Yeast Sphingolipids in *Lemna minor* L. (Duckweed).
Marth, et al., 1978, *J. Food Technol.*, 33: 81–87, "Update on molds: degradation of aflatoxin".
Kneusel, et al., 1990, *FEBS Letters*, 275(1–2): 107–110, "Detoxification of the macrolide toxin brefeldin A by *Bacillus subtilis*".
Toyoda, et al., 1988, *Phytopathology*, 78(10): 1307–1311, "Detoxification of Furasic Acid by a Fusaric Acid–Resistant Mutant of *Pseudomonas solanacearum* and its Application to Biological Control of Fusarium Wilt of Tomato".

(Continued)

Primary Examiner—Elizabeth F. McElwain
Assistant Examiner—Medina A. Ibrahim
(74) Attorney, Agent, or Firm—McKee, Voorhees & Sease, P.L.C.

(57) ABSTRACT

The present invention provides polynucleotides and related polypeptides of the enzyme APAO isolated from *Exophiala spinifera* and *Rhinocladiella airovirens*. The polynucleotides may be mutated to remove glycosylation sites and cysteine residues. Additionally, the present invention provides recombinant expression cassettes, host cells, transgenic plants, and transgenic seed. The present invention also provides for polynucleotides containing both APAO and a fumonisin esterase. In addition, the present invention provides methods for producing the APAO enzyme in both prokaryotic and eukaryotic systems, methods for detecting fumonisins, and methods for identifying transformed plant cells. Methods for degrading fungal toxins in plants, grain, grain processing, silage, food crops and in animal feed are also disclosed.

14 Claims, 2 Drawing Sheets

OTHER PUBLICATIONS

Figures 1A, 1B:
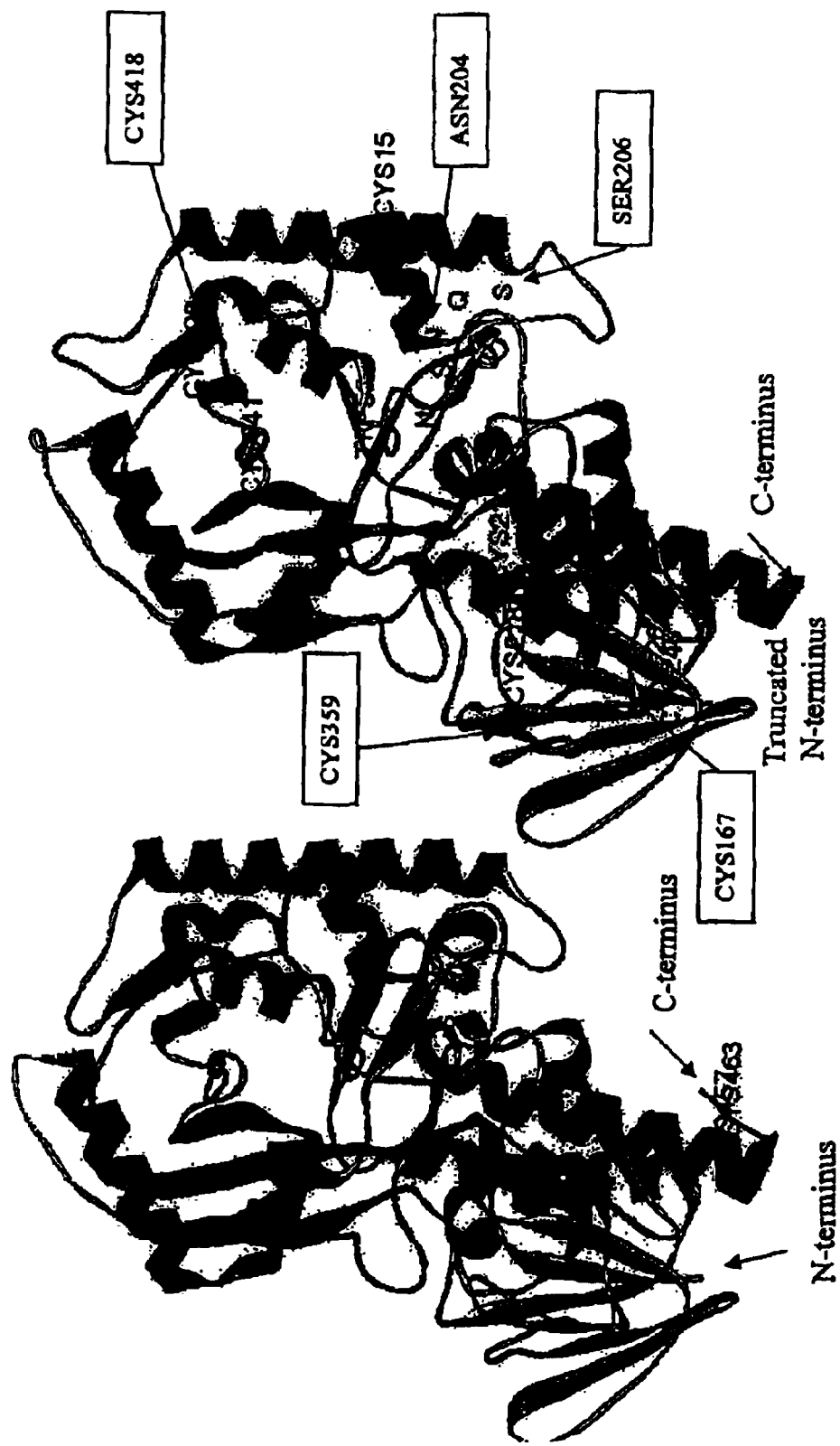

Bunz, et al., 1993, *Biodegradation*, 4: 171–178, "Purification of two isosfunctional hydrolases (EC 3.7.1.8) in the degradative pathway for dibenzofuran in Sphingomonas sp. strain RW1".

Duvick, et al., 1992, *J. of Biol. Chem.*, 267(26): 18814–18820, "Purification and Characterization of a Novel Antimicrobial Peptide from Maize (*Zea mays* L.) Kernels*".

Kraus, et al., 1992, *J. of Agri and Food Chem.*, 40(12): 2331–2332, "Synthesis of Analogs of Fumonisin B1".

Lotti, et al., 1993, *Gene*, 124: 45–55, "Cloning and analysis of *Canidida cylindracea* lipase sequences".

Cygler, et al., 1993, *Protein Science*, 2: 366–382, "Relationship between sequence conservation and three–dimensional structure in a large family of esterases, lipases, and related proteins".

Arpagaus, et al., 1991, *J. of Biol. Chem.*, 266(11): 6966–6974, "Use of the Polymerase Chain Reaction for Homology Probing of Butyrylcholinesterase from Several Vertebrates".

Van Asch, et al., 1992, *Phytopathology*, 82: 1330–1332, "Phytotoxicity of Fumonisin B1, Moniliformin, and T–2 Toxin to Corn Callus Cultures".

Lagu, et al., 1992, *204th American Chemical Society National Meeting*, Washington D.C., USA, "Synthesis of Fumonisin Analogs, Abstracts of Papers (Part 2)".

Zeiss, Hans–Joachim, 1991, *J. Org. Chem.*, 56(5) 1783–1788, "Enantioselective Synthesis of Both Enantiomers of Phosphinothricin via Asymmetric Hydrogenation of α–Acylamido Acrylates".

Ishizuka, H., et al, 1995, *XP002121274 Swissprot Accession No. 40974*, "Putrescine oxidase".

Horinouchi, S., et al., 1993, *XP002121474 EMBL Accession No. D12511*, "M. Rubens gene for putrescine oxidase, complete cds".

Duvick, et al., 1998, *Mol. Geneitcs of Host–Specific Toxins in Plant Disease*, 369–381, "Detoxification of Mycotoxins In Planta as a Strategy for Improving Grain Quality and Disease Resistance: Identification of Fumonisin–Degrading Microbes from Maize".

Blackwell, B.A., et al., 1999, *Natural Toxins*, 7(1): 31–38, "Oxidative Deamination of Hydrolyzed Fumonisin $B_1$ ($AP_1$) by Cultures of *Exophiala spinifera*".

Schilling, B., et al., 1995, *Mol. Gen. Genet.*, 247: 430–438, "Cloning, sequencing and heterologous expression of the monoamine oxidase gene from *Aspergillus niger*".

Anzai, et al., 1989, *Mol. Gen. Genet.*, 219: 492–494, "Transgenic tobacco resistant to a bacterial disease by the detoxification of a pathogenic toxin".

Kunst, F., et al., 1997, *XP 002121402, EMBL Accession No. Z99107*, "*Bacillus subtilis* complete genome".

Papoff, et al., 1996, *J. of Immunology*, 156(12): 4622–4630, "An N–Terminal Domain Shared by Fas/Apo–1 (CD 95) Soluble Variants Prevents Cell Death in Vitro[1,2]".

Alvarez, et al., 1997, *Oxidative Stress and the Molecular Biology of Antioxidant Defenses*, "Oxidative Burst–mediated Defense Responses in Plant Disease Resistance".

Lamb, et al., 1997, *Annu. Rev. Plant Physiol. Plant Mol. Biol.*, 48: 251–275, "The Oxidative Burst in Plant Disease Resistance".

Schrader, et al., 1996, *App. Microbiol Biotechnol*, 45: 458–464, "Studies on the inactivation of the flavoprotein $_D$–amino acid oxidase from *Trigonopsis variabilis*".

Lamprecht, et al., 1994, *Phytopathology*, 84: 383–391, "Phytotoxicity of Fumonisins and TA–Toxin to Corn and Tomato".

Itagaki, et al., 1996, *J. of Biol. Chem.*, 33: 20102–20107, "Expression and Characterization of a Modified Flavin–containing Monooxygenase 4 from Humans*".

Quinet, et al., 1993, *J. of Biol. Chem.*, 23: 16891–16894, "Inhibition of the Cellular Secretion of Cholesteryl Ester Transfer Protein by a Variant Protein Formed by Alternative Splicing of mRNA*".

Bhat, et al., 1996, *Protein Engineering*, 9(8): 713–718, "Expression of recombinant α–$A^{ins}$–crystallin and not αA–crystallin inhibits bacterial growth".

Przemylaw, 1997, *Biochem J.*, 322: 681–692, "Oxidative burst: an early plant response to pathogen infection".

Aguirre, et al., 1989, *J. Bacteriol*, 171: 6243–6250, "Oxidation of *Neurospora crassa* NADP–Specific Glutamate Dehydrogenase by Activated Oxygen Species".

Gould, et al., 1989, *J. Cell Biol.*, 108: 1657–1664, "A Conserved Tripeptide Sorts Proteins to Peroxisomes".

Gilchrist, et al., 1992, *Mycopathologia*, 117: 57–64, "Genetic and physiological response to fumonisin and AAL-toxin by intact tissue of a higher plant".

Schmiedeknecht, et al., 1996, *Eur. J. Biochem.*, 242(2) 339–351, "Isolation and characterization of a 14.5–kDa trichloroacetic–acid–soluble translational inhibitor protein from human monocytes that is upregulated upon cellular differentiation".

Samuel, et al., 1997, *Hepatology*, 25(5) 1213–1222, "Hrp12, a Novel Heat–Responsive, Tissue–Specific Phosphorylated Protein Isolated From Mouse Liver".

SEQUENCE LISTING

<160> NUMBER OF SEQ ID NOS: 53

<210> SEQ ID NO 1
<211> LENGTH: 372
<212> TYPE: DNA
<213> ORGANISM: Exophiala spinifera -continued

```
<220> FEATURE:
<221> NAME/KEY: misc_feature
<222> LOCATION: (346)..(346)
<223> OTHER INFORMATION: n = A, T, C, or G

<400> SEQUENCE: 1
gggccccggc gttctcgtag gctgcgcgga gttggtccca gacagacttt tgtcgtacct    60
gcttggactg ttgggaccac ttccgtcccg ggtctccgac catgaaacag gtaatggacc   120
attgtcgatc gacgtcgatg ctggtatctc tggcaaatga gatgggtca cagctcgatt    180 ggaggacgcc cgagaagcct tgttcgcgcc accacggctt gtcccatacg aagactatct   240
tgctatagta gcccaggata gaattttccg ccaatgcttg cttctcggcg ggaagaggtg   300
gtgaaaatgt caaggtggga tacaaggttg tcggtaacga aaccancacc tttttgcttc   360
ggaacacggc gc                                                       372

<210> SEQ ID NO 2
<211> LENGTH: 182
<212> TYPE: DNA
<213> ORGANISM: Exophiala spinifera

<400> SEQUENCE: 2
gaattttccg ccaatgcttg cttctcggcg ggaagaggtg gtgaaaatgt caaggtggga    60
tacaaggttg tcggtaacga aaccaccacc tttttgcttc ggaacacggc gcccgaggcc   120
gatcgtactg tacagccgga tgccgactgc tcaatttcag cgacggggt gttgaggtgc    180 ac                                                                  182

<210> SEQ ID NO 3
<211> LENGTH: 29
<212> TYPE: DNA
<213> ORGANISM: Artificial Sequence
<220> FEATURE:
<223> OTHER INFORMATION: Designed oligo for 3' RACE N21965 (Exophiala
      spinifera)

<400> SEQUENCE: 3
tggtttcgtt accgacaacc ttgtatccc                                      29

<210> SEQ ID NO 4
<211> LENGTH: 28
<212> TYPE: DNA
<213> ORGANISM: Artificial Sequence
<220> FEATURE:
<223> OTHER INFORMATION: Designed oligo for 5' RACE 21968 (Exophiala
      spinifera)

<400> SEQUENCE: 4
gagttggtcc cagacagact tttgtcgt                                       28

<210> SEQ ID NO 5
<211> LENGTH: 1389
<212> TYPE: DNA
<213> ORGANISM: Exophiala spinifera
<220> FEATURE:
<221> NAME/KEY: CDS
<222> LOCATION: (1)..(1386)
<223> OTHER INFORMATION:

<400> SEQUENCE: 5 gac aac gtt gcg gac gtg gta gtg gtg ggc gct ggc ttg agc ggt ttg    48
Asp Asn Val Ala Asp Val Val Val Val Gly Ala Gly Leu Ser Gly Leu
1               5                   10                  15
```

-continued

| | |
|---|---|
| gag acg gca cgc aaa gtc cag gcc gcc ggt ctg tcc tgc ctc gtt ctt<br>Glu Thr Ala Arg Lys Val Gln Ala Ala Gly Leu Ser Cys Leu Val Leu<br>          20                     25                     30 | 96 |
| gag gcg atg gat cgt gta ggg gga aag act ctg agc gta caa tcg ggt<br>Glu Ala Met Asp Arg Val Gly Gly Lys Thr Leu Ser Val Gln Ser Gly<br>35                    40                     45 | 144 |
| ccc ggc agg acg act atc aac gac ctc ggc gct gcg tgg atc aat gac<br>Pro Gly Arg Thr Thr Ile Asn Asp Leu Gly Ala Ala Trp Ile Asn Asp<br>50                    55                    60 | 192 |
| agc aac caa agc gaa gta tcc aga ttg ttt gaa aga ttt cat ttg gag<br>Ser Asn Gln Ser Glu Val Ser Arg Leu Phe Glu Arg Phe His Leu Glu<br>65                    70                    75                    80 | 240 |
| ggc gag ctc cag agg acg act gga aat tca atc cat caa gca caa gac<br>Gly Glu Leu Gln Arg Thr Thr Gly Asn Ser Ile His Gln Ala Gln Asp<br>                    85                    90                              95 | 288 |
| ggt aca acc act aca gct cct tat ggt gac tcc ttg ctg agc gag gag<br>Gly Thr Thr Thr Thr Ala Pro Tyr Gly Asp Ser Leu Leu Ser Glu Glu<br>                    100                   105                   110 | 336 |
| gtt gca agt gca ctt gcg gaa ctc ctc ccc gta tgg tct cag ctg atc<br>Val Ala Ser Ala Leu Ala Glu Leu Leu Pro Val Trp Ser Gln Leu Ile<br>               115                   120                   125 | 384 |
| gaa gag cat agc ctt caa gac ctc aag gcg agc cct cag gcg aag cgg<br>Glu Glu His Ser Leu Gln Asp Leu Lys Ala Ser Pro Gln Ala Lys Arg<br>130                   135                   140 | 432 |
| ctc gac agt gtg agc ttc gcg cac tac tgt gag aag gaa cta aac ttg<br>Leu Asp Ser Val Ser Phe Ala His Tyr Cys Glu Lys Glu Leu Asn Leu<br>145                   150                   155                   160 | 480 |
| cct gct gtt ctc ggc gta gca aac cag atc aca cgc gct ctg ctc ggt<br>Pro Ala Val Leu Gly Val Ala Asn Gln Ile Thr Arg Ala Leu Leu Gly<br>               165                   170                   175 | 528 |
| gtg gaa gcc cac gag atc agc atg ctt ttt ctc acc gac tac atc aag<br>Val Glu Ala His Glu Ile Ser Met Leu Phe Leu Thr Asp Tyr Ile Lys<br>                   180                   185                   190 | 576 |
| agt gcc acc ggt ctc agt aat att ttc tcg gac aag aaa gac ggc ggg<br>Ser Ala Thr Gly Leu Ser Asn Ile Phe Ser Asp Lys Lys Asp Gly Gly<br>             195                   200                   205 | 624 |
| cag tat atg cga tgc aaa aca ggt atg cag tcg att tgc cat gcc atg<br>Gln Tyr Met Arg Cys Lys Thr Gly Met Gln Ser Ile Cys His Ala Met<br>210                   215                   220 | 672 |
| tca aag gaa ctt gtt cca ggc tca gtg cac ctc aac acc ccc gtc gct<br>Ser Lys Glu Leu Val Pro Gly Ser Val His Leu Asn Thr Pro Val Ala<br>225                   230                   235                   240 | 720 |
| gaa att gag cag tcg gca tcc ggc tgt aca gta cga tcg gcc tcg ggc<br>Glu Ile Glu Gln Ser Ala Ser Gly Cys Thr Val Arg Ser Ala Ser Gly<br>                   245                   250                   255 | 768 |
| gcc gtg ttc cga agc aaa aag gtg gtg gtt tcg tta ccg aca acc ttg<br>Ala Val Phe Arg Ser Lys Lys Val Val Val Ser Leu Pro Thr Thr Leu<br>             260                   265                   270 | 816 |
| tat ccc acc ttg aca ttt tca cca cct ctt ccc gcc gag aag caa gca<br>Tyr Pro Thr Leu Thr Phe Ser Pro Pro Leu Pro Ala Glu Lys Gln Ala<br>275                   280                   285 | 864 |
| ttg gcg gaa aat tct atc ctg ggc tac tat agc aag ata gtc ttc gta<br>Leu Ala Glu Asn Ser Ile Leu Gly Tyr Tyr Ser Lys Ile Val Phe Val<br>             290                   295                   300 | 912 |
| tgg gac aag ccg tgg tgg cgc gaa caa ggc ttc tcg ggc gtc ctc caa<br>Trp Asp Lys Pro Trp Trp Arg Glu Gln Gly Phe Ser Gly Val Leu Gln<br>305                   310                   315                   320 | 960 |
| tcg agc tgt gac ccc atc tca ttt gcc aga gat acc agc atc gac gtc<br>Ser Ser Cys Asp Pro Ile Ser Phe Ala Arg Asp Thr Ser Ile Asp Val<br>             325                   330                   335 | 1008 |

-continued

```
gat cga caa tgg tcc att acc tgt ttc atg gtc gga gac ccg gga cgg     1056
Asp Arg Gln Trp Ser Ile Thr Cys Phe Met Val Gly Asp Pro Gly Arg
        340                 345                 350 aag tgg tcc caa cag tcc aag cag gta cga caa aag tct gtc tgg gac     1104
Lys Trp Ser Gln Gln Ser Lys Gln Val Arg Gln Lys Ser Val Trp Asp
            355                 360                 365 caa ctc cgc gca gcc tac gag aac gcc ggg gcc caa gtc cca gag ccg     1152
Gln Leu Arg Ala Ala Tyr Glu Asn Ala Gly Ala Gln Val Pro Glu Pro
    370                 375                 380 gcc aac gtg ctc gaa atc gag tgg tcg aag cag cag tat ttc caa gga     1200
Ala Asn Val Leu Glu Ile Glu Trp Ser Lys Gln Gln Tyr Phe Gln Gly
385                 390                 395                 400 gct ccg agc gcc gtc tat ggg ctg aac gat ctc atc aca ctg ggt tcg     1248
Ala Pro Ser Ala Val Tyr Gly Leu Asn Asp Leu Ile Thr Leu Gly Ser
                405                 410                 415 gcg ctc aga acg ccg ttc aag agt gtt cat ttc gtt gga acg gag acg     1296
Ala Leu Arg Thr Pro Phe Lys Ser Val His Phe Val Gly Thr Glu Thr
            420                 425                 430 tct tta gtt tgg aaa ggg tat atg gaa ggg gcc ata cga tcg ggt caa     1344
Ser Leu Val Trp Lys Gly Tyr Met Glu Gly Ala Ile Arg Ser Gly Gln
        435                 440                 445 cga ggt gct gca gaa gtt gtg gct agc ctg gtg cca gca gca tag         1389
Arg Gly Ala Ala Glu Val Val Ala Ser Leu Val Pro Ala Ala
    450                 455                 460

<210> SEQ ID NO 6
<211> LENGTH: 462
<212> TYPE: PRT
<213> ORGANISM: Exophiala spinifera

<400> SEQUENCE: 6

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
            20                  25                  30

Glu Ala Met Asp Arg Val Gly Gly Lys Thr Leu Ser Val Gln Ser Gly
        35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205
```

-continued

```
Gln Tyr Met Arg Cys Lys Thr Gly Met Gln Ser Ile Cys His Ala Met
    210                 215                 220

Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
                245                 250                 255

Ala Val Phe Arg Ser Lys Val Val Ser Leu Pro Thr Thr Leu
            260                 265                 270

Tyr Pro Thr Leu Thr Phe Ser Pro Pro Leu Pro Ala Glu Lys Gln Ala
                275                 280                 285

Leu Ala Glu Asn Ser Ile Leu Gly Tyr Tyr Ser Lys Ile Val Phe Val
    290                 295                 300

Trp Asp Lys Pro Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
                325                 330                 335

Asp Arg Gln Trp Ser Ile Thr Cys Phe Met Val Gly Asp Pro Gly Arg
            340                 345                 350

Lys Trp Ser Gln Gln Ser Lys Gln Val Arg Gln Lys Ser Val Trp Asp
        355                 360                 365

Gln Leu Arg Ala Ala Tyr Glu Asn Ala Gly Ala Gln Val Pro Glu Pro
    370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
            420                 425                 430

Ser Leu Val Trp Lys Gly Tyr Met Glu Gly Ala Ile Arg Ser Gly Gln
        435                 440                 445

Arg Gly Ala Ala Glu Val Val Ala Ser Leu Val Pro Ala Ala
    450                 455                 460

<210> SEQ ID NO 7
<211> LENGTH: 1442
<212> TYPE: DNA
<213> ORGANISM: Exophiala spinifera
<220> FEATURE:
<221> NAME/KEY: CDS
<222> LOCATION: (1)..(645)
<223> OTHER INFORMATION:
<220> FEATURE:
<221> NAME/KEY: Intron
<222> LOCATION: (646)..(698)
<223> OTHER INFORMATION:
<220> FEATURE:
<221> NAME/KEY: CDS
<222> LOCATION: (699)..(1439)
<223> OTHER INFORMATION:

<400> SEQUENCE: 7 gac aac gtt gcg gac gtg gta gtg gtg ggc gct ggc ttg agc ggt ttg      48
Asp Asn Val Ala Asp Val Val Val Val Gly Ala Gly Leu Ser Gly Leu
1               5                   10                  15 gag acg gca cgc aaa gtc cag gcc gcc ggt ctg tcc tgc ctc gtt ctt      96
Glu Thr Ala Arg Lys Val Gln Ala Ala Gly Leu Ser Cys Leu Val Leu
            20                  25                  30 gag gcg atg gat cgt gta ggg gga aag act ctg agc gta caa tcg ggt     144
Glu Ala Met Asp Arg Val Gly Gly Lys Thr Leu Ser Val Gln Ser Gly
```

```
                35                  40                  45
ccc ggc agg acg act atc aac gac ctc ggc gct gcg tgg atc aat gac    192
Pro Gly Arg Thr Thr Ile Asn Asp Leu Gly Ala Ala Trp Ile Asn Asp
    50                  55                  60 agc aac caa agc gaa gta tcc aga ttg ttt gaa aga ttt cat ttg gag    240
Ser Asn Gln Ser Glu Val Ser Arg Leu Phe Glu Arg Phe His Leu Glu
65                  70                  75                  80 ggc gag ctc cag agg acg act gga aat tca atc cat caa gca caa gac    288
Gly Glu Leu Gln Arg Thr Thr Gly Asn Ser Ile His Gln Ala Gln Asp
                85                  90                  95 ggt aca acc act aca gct cct tat ggt gac tcc ttg ctg agc gag gag    336
Gly Thr Thr Thr Thr Ala Pro Tyr Gly Asp Ser Leu Leu Ser Glu Glu
            100                 105                 110 gtt gca agt gca ctt gcg gaa ctc ctc ccc gta tgg tct cag ctg atc    384
Val Ala Ser Ala Leu Ala Glu Leu Leu Pro Val Trp Ser Gln Leu Ile
        115                 120                 125 gaa gag cat agc ctt caa gac ctc aag gcg agc cct cag gcg aag cgg    432
Glu Glu His Ser Leu Gln Asp Leu Lys Ala Ser Pro Gln Ala Lys Arg
    130                 135                 140 ctc gac agt gtg agc ttc gcg cac tac tgt gag aag gaa cta aac ttg    480
Leu Asp Ser Val Ser Phe Ala His Tyr Cys Glu Lys Glu Leu Asn Leu
145                 150                 155                 160 cct gct gtt ctc ggc gta gca aac cag atc aca cgc gct ctg ctc ggt    528
Pro Ala Val Leu Gly Val Ala Asn Gln Ile Thr Arg Ala Leu Leu Gly
                165                 170                 175 gtg gaa gcc cac gag atc agc atg ctt ttt ctc acc gac tac atc aag    576
Val Glu Ala His Glu Ile Ser Met Leu Phe Leu Thr Asp Tyr Ile Lys
            180                 185                 190 agt gcc acc ggt ctc agt aat att ttc tcg gac aag aaa gac ggc ggg    624
Ser Ala Thr Gly Leu Ser Asn Ile Phe Ser Asp Lys Lys Asp Gly Gly
        195                 200                 205 cag tat gtg cga tgc aaa aca ggtgcgtgtg gtgtcgtctc aggtggggga      675
Gln Tyr Val Arg Cys Lys Thr
    210             215 ctcgtttctc agtggtcatt cca ggt atg cag tcg att tgc cat gcc atg tca 728
                        Gly Met Gln Ser Ile Cys His Ala Met Ser
                                        220                 225 aag gaa ctt gtt cca ggc tca gtg cac ctc aac acc ccc gtc gct gaa    776
Lys Glu Leu Val Pro Gly Ser Val His Leu Asn Thr Pro Val Ala Glu
            230                 235                 240 att gag cag tcg gca tcc ggc tgt aca gta cga tcg gcc tcg ggc gcc    824
Ile Glu Gln Ser Ala Ser Gly Cys Thr Val Arg Ser Ala Ser Gly Ala
        245                 250                 255 gtg ttc cga agc aaa aag gtg gtg gtt tcg tta ccg aca acc ttg tat    872
Val Phe Arg Ser Lys Lys Val Val Val Ser Leu Pro Thr Thr Leu Tyr
    260                 265                 270 ccc acc ttg aca ttt tca cca cct ctt ccc gcc gag aag caa gca ttg    920
Pro Thr Leu Thr Phe Ser Pro Pro Leu Pro Ala Glu Lys Gln Ala Leu
275                 280                 285 gcg gaa aat tct atc ctg ggc tac tat agc aag ata gtc ttc gta tgg    968
Ala Glu Asn Ser Ile Leu Gly Tyr Tyr Ser Lys Ile Val Phe Val Trp
290                 295                 300                 305 gac aag ccg tgg tgg cgc gaa caa ggc ttc tcg ggc gtc ctc caa tcg    1016
Asp Lys Pro Trp Trp Arg Glu Gln Gly Phe Ser Gly Val Leu Gln Ser
                310                 315                 320 agc tgt gac ccc atc tca ttt gcc aga gat acc agc atc gac gtc gat    1064
Ser Cys Asp Pro Ile Ser Phe Ala Arg Asp Thr Ser Ile Asp Val Asp
            325                 330                 335 cga caa tgg tcc att acc tgt ttc atg gtc gga gac ccg gga cgg aag    1112
Arg Gln Trp Ser Ile Thr Cys Phe Met Val Gly Asp Pro Gly Arg Lys
```

-continued

```
                    Arg Gln Trp Ser Ile Thr Cys Phe Met Val Gly Asp Pro Gly Arg Lys
                            340                 345                 350 tgg tcc caa cag tcc aag cag gta cga caa aag tct gtc tgg gac caa          1160
Trp Ser Gln Gln Ser Lys Gln Val Arg Gln Lys Ser Val Trp Asp Gln
    355                 360                 365 ctc cgc gca gcc tac gag aac gcc ggg gcc caa gtc cca gag ccg gcc          1208
Leu Arg Ala Ala Tyr Glu Asn Ala Gly Ala Gln Val Pro Glu Pro Ala
370                 375                 380                 385 aac gtg ctc gaa atc gag tgg tcg aag cag cag tat ttc caa gga gct          1256
Asn Val Leu Glu Ile Glu Trp Ser Lys Gln Gln Tyr Phe Gln Gly Ala
                390                 395                 400 ccg agc gcc gtc tat ggg ctg aac gat ctc atc aca ctg ggt tcg gcg          1304
Pro Ser Ala Val Tyr Gly Leu Asn Asp Leu Ile Thr Leu Gly Ser Ala
            405                 410                 415 ctc aga acg ccg ttc aag agt gtt cat ttc gtt gga acg gag acg tct          1352
Leu Arg Thr Pro Phe Lys Ser Val His Phe Val Gly Thr Glu Thr Ser
        420                 425                 430 tta gtt tgg aaa ggg tat atg gaa ggg gcc ata cga tcg ggt caa cga          1400
Leu Val Trp Lys Gly Tyr Met Glu Gly Ala Ile Arg Ser Gly Gln Arg
    435                 440                 445 ggt gct gca gaa gtt gtg gct agc ctg gtg cca gca gca tag              1442
Gly Ala Ala Glu Val Val Ala Ser Leu Val Pro Ala Ala
450                 455                 460
```

<210> SEQ ID NO 8
<211> LENGTH: 462
<212> TYPE: PRT
<213> ORGANISM: Exophiala spinifera

<400> SEQUENCE: 8

```
Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
            20                  25                  30

Glu Ala Met Asp Arg Val Gly Gly Lys Thr Leu Ser Val Gln Ser Gly
        35                  40                  45

Pro Gly Arg Thr Thr Ile Asn Asp Leu Gly Ala Ala Trp Ile Asn Asp
    50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125

Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Val Arg Cys Lys Thr Gly Met Gln Ser Ile Cys His Ala Met
```

-continued

```
            210                 215                 220
Ser Lys Glu Leu Val Pro Gly Ser Val His Leu Asn Thr Pro Val Ala
225                 230                 235                 240

Glu Ile Glu Gln Ser Ala Ser Gly Cys Thr Val Arg Ser Ala Ser Gly
                245                 250                 255

Ala Val Phe Arg Ser Lys Lys Val Val Ser Leu Pro Thr Thr Leu
            260                 265                 270

Tyr Pro Thr Leu Thr Phe Ser Pro Leu Pro Ala Glu Lys Gln Ala
            275                 280                 285

Leu Ala Glu Asn Ser Ile Leu Gly Tyr Tyr Ser Lys Ile Val Phe Val
290                 295                 300

Trp Asp Lys Pro Trp Trp Arg Glu Gln Gly Phe Ser Gly Val Leu Gln
305                 310                 315                 320

Ser Ser Cys Asp Pro Ile Ser Phe Ala Arg Asp Thr Ser Ile Asp Val
                325                 330                 335

Asp Arg Gln Trp Ser Ile Thr Cys Phe Met Val Gly Asp Pro Gly Arg
            340                 345                 350

Lys Trp Ser Gln Gln Ser Lys Gln Val Arg Gln Lys Ser Val Trp Asp
            355                 360                 365

Gln Leu Arg Ala Ala Tyr Glu Asn Ala Gly Ala Gln Val Pro Glu Pro
370                 375                 380

Ala Asn Val Leu Glu Ile Glu Trp Ser Lys Gln Gln Tyr Phe Gln Gly
385                 390                 395                 400

Ala Pro Ser Ala Val Tyr Gly Leu Asn Asp Leu Ile Thr Leu Gly Ser
                405                 410                 415

Ala Leu Arg Thr Pro Phe Lys Ser Val His Phe Val Gly Thr Glu Thr
            420                 425                 430

Ser Leu Val Trp Lys Gly Tyr Met Glu Gly Ala Ile Arg Ser Gly Gln
            435                 440                 445

Arg Gly Ala Ala Glu Val Val Ala Ser Leu Val Pro Ala Ala
            450                 455                 460

<210> SEQ ID NO 9
<211> LENGTH: 458
<212> TYPE: PRT
<213> ORGANISM: Exophiala spinifera

<400> SEQUENCE: 9

Asp Asn Val Ala Asp Val Val Val Gly Ala Gly Leu Ser Gly Leu
1               5                   10                  15

Glu Thr Ala Arg Lys Val Gln Ala Ala Gly Leu Ser Cys Leu Val Leu
                20                  25                  30

Glu Ala Met Asp Arg Val Gly Gly Lys Thr Leu Ser Val Gln Ser Gly
            35                  40                  45

Pro Gly Arg Thr Thr Ile Asn Asp Leu Gly Ala Ala Trp Ile Asn Asp
        50                  55                  60

Ser Asn Gln Ser Glu Val Ser Arg Leu Phe Glu Arg Phe His Leu Glu
65                  70                  75                  80

Gly Glu Leu Gln Arg Thr Thr Gly Asn Ser Ile His Gln Ala Gln Asp
                85                  90                  95

Gly Thr Thr Thr Thr Ala Pro Tyr Gly Asp Ser Leu Leu Ser Glu Glu
            100                 105                 110

Val Ala Ser Ala Leu Ala Glu Leu Leu Pro Val Trp Ser Gln Leu Ile
        115                 120                 125
```

```
Glu Glu His Ser Leu Gln Asp Leu Lys Ala Ser Pro Gln Ala Lys Arg
    130                 135                 140

Leu Asp Ser Val Ser Phe Ala His Tyr Cys Glu Lys Glu Leu Asn Leu
145                 150                 155                 160

Pro Ala Val Leu Gly Val Ala Asn Gln Ile Thr Arg Ala Leu Leu Gly
                165                 170                 175

Val Glu Ala His Glu Ile Ser Met Leu Phe Leu Thr Asp Tyr Ile Lys
            180                 185                 190

Ser Ala Thr Gly Leu Ser Asn Ile Phe Ser Asp Lys Lys Asp Gly Gly
        195                 200                 205

Gln Tyr Val Arg Cys Lys Thr Gly Ala Cys Gly Val Val Ser Gly Gly
    210                 215                 220

Gly Leu Val Ser Gln Trp Ser Phe Gln Val Cys Ser Arg Phe Ala Met
225                 230                 235                 240

Pro Cys Gln Arg Asn Leu Phe Gln Ala Gln Cys Thr Ser Thr Pro Pro
                245                 250                 255

Ser Leu Lys Leu Ser Ser Arg His Pro Ala Val Gln Tyr Asp Arg Pro
            260                 265                 270

Arg Ala Pro Cys Ser Glu Ala Lys Arg Trp Trp Phe Tyr Arg Gln
        275                 280                 285

Pro Cys Ile Pro Pro His Phe His His Leu Phe Pro Pro Arg Ser Lys
    290                 295                 300

His Trp Arg Lys Ile Leu Ser Trp Ala Thr Ile Ala Arg Ser Ser Tyr
305                 310                 315                 320

Gly Thr Ser Arg Gly Gly Ala Asn Lys Ala Ser Arg Ala Ser Ser Asn
                325                 330                 335

Arg Ala Val Thr Pro Ser His Leu Pro Glu Ile Pro Ala Ser Thr Ser
            340                 345                 350

Ile Asp Asn Gly Pro Leu Pro Val Ser Trp Ser Glu Thr Arg Asp Gly
        355                 360                 365

Ser Gly Pro Asn Ser Pro Ser Arg Tyr Asp Lys Ser Leu Ser Gly Thr
    370                 375                 380

Asn Ser Ala Gln Pro Thr Arg Thr Pro Gly Pro Lys Ser Gln Ser Arg
385                 390                 395                 400

Pro Thr Cys Ser Lys Ser Ser Gly Arg Ser Ser Ile Ser Lys Glu
                405                 410                 415

Leu Arg Ala Pro Ser Met Gly Thr Ile Ser Ser His Trp Val Arg Arg
            420                 425                 430

Ser Glu Arg Arg Ser Arg Val Phe Ile Ser Leu Glu Arg Arg Arg Leu
        435                 440                 445

Phe Gly Lys Gly Ile Trp Lys Gly Pro Tyr
    450                 455

<210> SEQ ID NO 10
<211> LENGTH: 1392
<212> TYPE: DNA
<213> ORGANISM: Exophiala spinifera
<220> FEATURE:
<221> NAME/KEY: CDS
<222> LOCATION: (1)..(1389)
<223> OTHER INFORMATION:
<220> FEATURE:
<221> NAME/KEY: misc_feature
<222> LOCATION: (1)..(3)
<223> OTHER INFORMATION: Extra lysine in K:trAPAO

<400> SEQUENCE: 10
```

-continued

| | |
|---|---|
| aaa gac aac gtt gcg gac gtg gta gtg gtg ggc gct ggc ttg agc ggt<br>Lys Asp Asn Val Ala Asp Val Val Val Val Gly Ala Gly Leu Ser Gly<br>1                       5                    10                  15 | 48 |
| ttg gag acg gca cgc aaa gtc cag gcc gcc ggt ctg tcc tgc ctc gtt<br>Leu Glu Thr Ala Arg Lys Val Gln Ala Ala Gly Leu Ser Cys Leu Val<br>                 20                   25                    30 | 96 |
| ctt gag gcg atg gat cgt gta ggg gga aag act ctg agc gta caa tcg<br>Leu Glu Ala Met Asp Arg Val Gly Gly Lys Thr Leu Ser Val Gln Ser<br>          35                    40                    45 | 144 |
| ggt ccc ggc agg acg act atc aac gac ctc ggc gct gcg tgg atc aat<br>Gly Pro Gly Arg Thr Thr Ile Asn Asp Leu Gly Ala Ala Trp Ile Asn<br>       50                    55                    60 | 192 |
| gac agc aac caa agc gaa gta tcc aga ttg ttt gaa aga ttt cat ttg<br>Asp Ser Asn Gln Ser Glu Val Ser Arg Leu Phe Glu Arg Phe His Leu<br>65                      70                    75                  80 | 240 |
| gag ggc gag ctc cag agg acg act gga aat tca atc cat caa gca caa<br>Glu Gly Glu Leu Gln Arg Thr Thr Gly Asn Ser Ile His Gln Ala Gln<br>                 85                    90                    95 | 288 |
| gac ggt aca acc act aca gct cct tat ggt gac tcc ttg ctg agc gag<br>Asp Gly Thr Thr Thr Thr Ala Pro Tyr Gly Asp Ser Leu Leu Ser Glu<br>                 100                 105              110 | 336 |
| gag gtt gca agt gca ctt gcg gaa ctc ctc ccc gta tgg tct cag ctg<br>Glu Val Ala Ser Ala Leu Ala Glu Leu Leu Pro Val Trp Ser Gln Leu<br>               115                 120               125 | 384 |
| atc gaa gag cat agc ctt caa gac ctc aag gcg agc cct cag gcg aag<br>Ile Glu Glu His Ser Leu Gln Asp Leu Lys Ala Ser Pro Gln Ala Lys<br>          130                 135                 140 | 432 |
| cgg ctc gac agt gtg agc ttc gcg cac tac tgt gag aag gaa cta aac<br>Arg Leu Asp Ser Val Ser Phe Ala His Tyr Cys Glu Lys Glu Leu Asn<br>145                    150                 155              160 | 480 |
| ttg cct gct gtt ctc ggc gta gca aac cag atc aca cgc gct ctg ctc<br>Leu Pro Ala Val Leu Gly Val Ala Asn Gln Ile Thr Arg Ala Leu Leu<br>                 165                 170              175 | 528 |
| ggt gtg gaa gcc cac gag atc agc atg ctt ttt ctc acc gac tac atc<br>Gly Val Glu Ala His Glu Ile Ser Met Leu Phe Leu Thr Asp Tyr Ile<br>               180                 185               190 | 576 |
| aag agt gcc acc ggt ctc agt aat att ttc tcg gac aag aaa gac ggc<br>Lys Ser Ala Thr Gly Leu Ser Asn Ile Phe Ser Asp Lys Lys Asp Gly<br>          195                 200                 205 | 624 |
| ggg cag tat atg cga tgc aaa aca ggt atg cag tcg att tgc cat gcc<br>Gly Gln Tyr Met Arg Cys Lys Thr Gly Met Gln Ser Ile Cys His Ala<br>210                    215                 220 | 672 |
| atg tca aag gaa ctt gtt cca ggc tca gtg cac ctc aac acc ccc gtc<br>Met Ser Lys Glu Leu Val Pro Gly Ser Val His Leu Asn Thr Pro Val<br>225                    230                 235              240 | 720 |
| gct gaa att gag cag tcg gca tcc ggc tgt aca gta cga tcg gcc tcg<br>Ala Glu Ile Glu Gln Ser Ala Ser Gly Cys Thr Val Arg Ser Ala Ser<br>                 245                 250              255 | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>          260                 265                 270 | 816 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>          275                 280                 285 | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>          290                 295                 300 | 912 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>305                    310                 315              320 | 960 |

-continued

```
caa tcg agc tgt gac ccc atc tca ttt gcc aga gat acc agc atc gac     1008
Gln Ser Ser Cys Asp Pro Ile Ser Phe Ala Arg Asp Thr Ser Ile Asp
            325                 330                 335 gtc gat cga caa tgg tcc att acc tgt ttc atg gtc gga gac ccg gga     1056
Val Asp Arg Gln Trp Ser Ile Thr Cys Phe Met Val Gly Asp Pro Gly
        340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
    355                 360                 365 gac caa ctc cgc gca gcc tac gag aac gcc ggg gcc caa gtc cca gag     1152
Asp Gln Leu Arg Ala Ala Tyr Glu Asn Ala Gly Ala Gln Val Pro Glu
370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
            405                 410                 415 tcg gcg ctc aga acg ccg ttc aag agt gtt cat ttc gtt gga acg gag     1296
Ser Ala Leu Arg Thr Pro Phe Lys Ser Val His Phe Val Gly Thr Glu
        420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala
450                 455                 460
```

<210> SEQ ID NO 11
<211> LENGTH: 463
<212> TYPE: PRT
<213> ORGANISM: Exophiala spinifera
<220> FEATURE:
<221> NAME/KEY: misc_feature
<222> LOCATION: (1)..(3)
<223> OTHER INFORMATION: Extra lysine in K:trAPAO

<400> SEQUENCE: 11

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Met Asp Arg Val Gly Gly Lys Thr Leu Ser Val Gln Ser
            35                  40                  45

Gly Pro Gly Arg Thr Thr Ile Asn Asp Leu Gly Ala Ala Trp Ile Asn
        50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145                 150                 155                 160
```

-continued

```
Leu Pro Ala Val Leu Gly Val Ala Asn Gln Ile Thr Arg Ala Leu Leu
                165                 170                 175
Gly Val Glu Ala His Glu Ile Ser Met Leu Phe Leu Thr Asp Tyr Ile
            180                 185                 190
Lys Ser Ala Thr Gly Leu Ser Asn Ile Phe Ser Asp Lys Lys Asp Gly
        195                 200                 205
Gly Gln Tyr Met Arg Cys Lys Thr Gly Met Gln Ser Ile Cys His Ala
    210                 215                 220
Met Ser Lys Glu Leu Val Pro Gly Ser Val His Leu Asn Thr Pro Val
225                 230                 235                 240
Ala Glu Ile Glu Gln Ser Ala Ser Gly Cys Thr Val Arg Ser Ala Ser
                245                 250                 255
Gly Ala Val Phe Arg Ser Lys Lys Val Val Ser Leu Pro Thr Thr
            260                 265                 270
Leu Tyr Pro Thr Leu Thr Phe Ser Pro Pro Leu Pro Ala Glu Lys Gln
        275                 280                 285
Ala Leu Ala Glu Asn Ser Ile Leu Gly Tyr Tyr Ser Lys Ile Val Phe
    290                 295                 300
Val Trp Asp Lys Pro Trp Trp Arg Glu Gln Gly Phe Ser Gly Val Leu
305                 310                 315                 320
Gln Ser Ser Cys Asp Pro Ile Ser Phe Ala Arg Asp Thr Ser Ile Asp
                325                 330                 335
Val Asp Arg Gln Trp Ser Ile Thr Cys Phe Met Val Gly Asp Pro Gly
            340                 345                 350
Arg Lys Trp Ser Gln Gln Ser Lys Gln Val Arg Gln Lys Ser Val Trp
        355                 360                 365
Asp Gln Leu Arg Ala Ala Tyr Glu Asn Ala Gly Ala Gln Val Pro Glu
    370                 375                 380
Pro Ala Asn Val Leu Glu Ile Glu Trp Ser Lys Gln Gln Tyr Phe Gln
385                 390                 395                 400
Gly Ala Pro Ser Ala Val Tyr Gly Leu Asn Asp Leu Ile Thr Leu Gly
                405                 410                 415
Ser Ala Leu Arg Thr Pro Phe Lys Ser Val His Phe Val Gly Thr Glu
            420                 425                 430
Thr Ser Leu Val Trp Lys Gly Tyr Met Glu Gly Ala Ile Arg Ser Gly
        435                 440                 445
Gln Arg Gly Ala Ala Glu Val Val Ala Ser Leu Val Pro Ala Ala
    450                 455                 460
```

<210> SEQ ID NO 12
<211> LENGTH: 34
<212> TYPE: DNA
<213> ORGANISM: Artificial Sequence
<220> FEATURE:
<223> OTHER INFORMATION: Primer for cloning into vectors N23256
    (Exophiala spinifera)

<400> SEQUENCE: 12
ggggaattca aagacaacgt tgcggacgtg gtag                            34

<210> SEQ ID NO 13
<211> LENGTH: 34
<212> TYPE: DNA
<213> ORGANISM: Artificial Sequence
<220> FEATURE:
<223> OTHER INFORMATION: Primer for cloning into vectors N23256
    (Exophiala spinifera)

-continued

```
<400> SEQUENCE: 13
ggggcggccg cctatgctgc tggcaccagg ctag                                34

<210> SEQ ID NO 14
<211> LENGTH: 29
<212> TYPE: DNA
<213> ORGANISM: Artificial Sequence
<220> FEATURE:
<223> OTHER INFORMATION: Designed oligo for 3' RACE, N21965 (Exophiala
      spinifera)

<400> SEQUENCE: 14
tggtttcgtt accgacaacc ttgtatccc                                      29

<210> SEQ ID NO 15
<211> LENGTH: 28
<212> TYPE: DNA
<213> ORGANISM: Artificial Sequence
<220> FEATURE:
<223> OTHER INFORMATION: Designed oligo for 5' RACE, N21968 (Exophiala
      spinifera)

<400> SEQUENCE: 15
gagttggtcc cagacagact tttgtcgt                                       28

<210> SEQ ID NO 16
<211> LENGTH: 1673
<212> TYPE: DNA
<213> ORGANISM: Exophiala spinifera
<220> FEATURE:
<221> NAME/KEY: sig_peptide
<222> LOCATION: (1)..(267)
<223> OTHER INFORMATION: yeast alpha mating factor secretion signal
<220> FEATURE:
<221> NAME/KEY: CDS
<222> LOCATION: (1)..(1662)
<223> OTHER INFORMATION:

<400> SEQUENCE: 16
```

| | | | | | | | | | | | | | | | | |
|---|---|---|---|---|---|---|---|---|---|---|---|---|---|---|---|---|
| atg | aga | ttt | cct | tca | att | ttt | act | gct | gtt | tta | ttc | gca | gca | tcc | tcc | 48 |
| Met | Arg | Phe | Pro | Ser | Ile | Phe | Thr | Ala | Val | Leu | Phe | Ala | Ala | Ser | Ser | |
| 1 | | | | 5 | | | | | 10 | | | | | 15 | | |
| gca | tta | gct | gct | cca | gtc | aac | act | aca | aca | gaa | gat | gaa | acg | gca | caa | 96 |
| Ala | Leu | Ala | Ala | Pro | Val | Asn | Thr | Thr | Thr | Glu | Asp | Glu | Thr | Ala | Gln | |
| | | 20 | | | | | 25 | | | | | 30 | | | | |
| att | ccg | gct | gaa | gct | gtc | atc | ggt | tac | tca | gat | tta | gaa | ggg | gat | ttc | 144 |
| Ile | Pro | Ala | Glu | Ala | Val | Ile | Gly | Tyr | Ser | Asp | Leu | Glu | Gly | Asp | Phe | |
| | 35 | | | | | 40 | | | | | 45 | | | | | |
| gat | gtt | gct | gtt | ttg | cca | ttt | tcc | aac | agc | aca | aat | aac | ggg | tta | ttg | 192 |
| Asp | Val | Ala | Val | Leu | Pro | Phe | Ser | Asn | Ser | Thr | Asn | Asn | Gly | Leu | Leu | |
| 50 | | | | | 55 | | | | | 60 | | | | | | |
| ttt | ata | aat | act | act | att | gcc | agc | att | gct | gct | aaa | gaa | gaa | ggg | gta | 240 |
| Phe | Ile | Asn | Thr | Thr | Ile | Ala | Ser | Ile | Ala | Ala | Lys | Glu | Glu | Gly | Val | |
| 65 | | | | 70 | | | | | 75 | | | | | 80 | | |
| tct | ctc | gag | aaa | aga | gag | gct | gaa | gct | gaa | ttc | aaa | gac | aac | gtt | gcg | 288 |
| Ser | Leu | Glu | Lys | Arg | Glu | Ala | Glu | Ala | Glu | Phe | Lys | Asp | Asn | Val | Ala | |
| | | | 85 | | | | | 90 | | | | | 95 | | | |
| gac | gtg | gta | gtg | gtg | ggc | gct | ggc | ttg | agc | ggt | ttg | gag | acg | gca | cgc | 336 |
| Asp | Val | Val | Val | Val | Gly | Ala | Gly | Leu | Ser | Gly | Leu | Glu | Thr | Ala | Arg | |
| | | 100 | | | | | 105 | | | | | 110 | | | | |
| aaa | gtc | cag | gcc | gcc | ggt | ctg | tcc | tgc | ctc | gtt | ctt | gag | gcg | atg | gat | 384 |
| Lys | Val | Gln | Ala | Ala | Gly | Leu | Ser | Cys | Leu | Val | Leu | Glu | Ala | Met | Asp | |
| | 115 | | | | | 120 | | | | | 125 | | | | | |
| cgt | gta | ggg | gga | aag | act | ctg | agc | gta | caa | tcg | ggt | ccc | ggc | agg | acg | 432 |

```
                                                         -continued

Arg Val Gly Gly Lys Thr Leu Ser Val Gln Ser Gly Pro Gly Arg Thr
    130                 135                 140 act atc aac gac ctc ggc gct gcg tgg atc aat gac agc aac caa agc        480
Thr Ile Asn Asp Leu Gly Ala Ala Trp Ile Asn Asp Ser Asn Gln Ser
145                 150                 155                 160 gaa gta tcc aga ttg ttt gaa aga ttt cat ttg gag ggc gag ctc cag        528
Glu Val Ser Arg Leu Phe Glu Arg Phe His Leu Glu Gly Glu Leu Gln
                165                 170                 175 agg acg act gga aat tca atc cat caa gca caa gac ggt aca acc act        576
Arg Thr Thr Gly Asn Ser Ile His Gln Ala Gln Asp Gly Thr Thr Thr
            180                 185                 190 aca gct cct tat ggt gac tcc ttg ctg agc gag gag gtt gca agt gca        624
Thr Ala Pro Tyr Gly Asp Ser Leu Leu Ser Glu Glu Val Ala Ser Ala
        195                 200                 205 ctt gcg gaa ctc ctc ccc gta tgg tct cag ctg atc gaa gag cat agc        672
Leu Ala Glu Leu Leu Pro Val Trp Ser Gln Leu Ile Glu Glu His Ser
    210                 215                 220 ctt caa gac ctc aag gcg agc cct cag gcg aag cgg ctc gac agt gtg        720
Leu Gln Asp Leu Lys Ala Ser Pro Gln Ala Lys Arg Leu Asp Ser Val
225                 230                 235                 240 agc ttc gcg cac tac tgt gag aag gaa cta aac ttg cct gct gtt ctc        768
Ser Phe Ala His Tyr Cys Glu Lys Glu Leu Asn Leu Pro Ala Val Leu
                245                 250                 255 ggc gta gca aac cag atc aca cgc gct ctg ctc ggt gtg gaa gcc cac        816
Gly Val Ala Asn Gln Ile Thr Arg Ala Leu Leu Gly Val Glu Ala His
            260                 265                 270 gag atc agc atg ctt ttt ctc acc gac tac atc aag agt gcc acc ggt        864
Glu Ile Ser Met Leu Phe Leu Thr Asp Tyr Ile Lys Ser Ala Thr Gly
        275                 280                 285 ctc agt aat att ttc tcg gac aag aaa gac ggc ggg cag tat atg cga        912
Leu Ser Asn Ile Phe Ser Asp Lys Lys Asp Gly Gly Gln Tyr Met Arg
    290                 295                 300 tgc aaa aca ggt atg cag tcg att tgc cat gcc atg tca aag gaa ctt        960
Cys Lys Thr Gly Met Gln Ser Ile Cys His Ala Met Ser Lys Glu Leu
305                 310                 315                 320 gtt cca ggc tca gtg cac ctc aac acc ccc gtc gct gaa att gag cag       1008
Val Pro Gly Ser Val His Leu Asn Thr Pro Val Ala Glu Ile Glu Gln
                325                 330                 335 tcg gca tcc ggc tgt aca gta cga tcg gcc tcg ggc gcc gtg ttc cga       1056
Ser Ala Ser Gly Cys Thr Val Arg Ser Ala Ser Gly Ala Val Phe Arg
            340                 345                 350 agc aaa aag gtg gtg gtt tcg tta ccg aca acc ttg tat ccc acc ttg       1104
Ser Lys Lys Val Val Val Ser Leu Pro Thr Thr Leu Tyr Pro Thr Leu
        355                 360                 365 aca ttt tca cca cct ctt ccc gcc gag aag caa gca ttg gcg gaa aat       1152
Thr Phe Ser Pro Pro Leu Pro Ala Glu Lys Gln Ala Leu Ala Glu Asn
    370                 375                 380 tct atc ctg ggc tac tat agc aag ata gtc ttc gta tgg gac aag ccg       1200
Ser Ile Leu Gly Tyr Tyr Ser Lys Ile Val Phe Val Trp Asp Lys Pro
385                 390                 395                 400 tgg tgg cgc gaa caa ggc ttc tcg ggc gtc ctc caa tcg agc tgt gac       1248
Trp Trp Arg Glu Gln Gly Phe Ser Gly Val Leu Gln Ser Ser Cys Asp
                405                 410                 415 ccc atc tca ttt gcc aga gat acc agc atc gac gtc gat cga caa tgg       1296
Pro Ile Ser Phe Ala Arg Asp Thr Ser Ile Asp Val Asp Arg Gln Trp
            420                 425                 430 tcc att acc tgt ttc atg gtc gga gac ccg gga cgg aag tgg tcc caa       1344
Ser Ile Thr Cys Phe Met Val Gly Asp Pro Gly Arg Lys Trp Ser Gln
        435                 440                 445
```

-continued

```
cag tcc aag cag gta cga caa aag tct gtc tgg gac caa ctc cgc gca      1392
Gln Ser Lys Gln Val Arg Gln Lys Ser Val Trp Asp Gln Leu Arg Ala
    450                 455                 460 gcc tac gag aac gcc ggg gcc caa gtc cca gag ccg gcc aac gtg ctc      1440
Ala Tyr Glu Asn Ala Gly Ala Gln Val Pro Glu Pro Ala Asn Val Leu
465                 470                 475                 480 gaa atc gag tgg tcg aag cag cag tat ttc caa gga gct ccg agc gcc      1488
Glu Ile Glu Trp Ser Lys Gln Gln Tyr Phe Gln Gly Ala Pro Ser Ala
                485                 490                 495 gtc tat ggg ctg aac gat ctc atc aca ctg ggt tcg gcg ctc aga acg      1536
Val Tyr Gly Leu Asn Asp Leu Ile Thr Leu Gly Ser Ala Leu Arg Thr
            500                 505                 510 ccg ttc aag agt gtt cat ttc gtt gga acg gag acg tct tta gtt tgg      1584
Pro Phe Lys Ser Val His Phe Val Gly Thr Glu Thr Ser Leu Val Trp
        515                 520                 525 aaa ggg tat atg gaa ggg gcc ata cga tcg ggt caa cga ggt gct gca      1632
Lys Gly Tyr Met Glu Gly Ala Ile Arg Ser Gly Gln Arg Gly Ala Ala
    530                 535                 540 gaa gtt gtg gct agc ctg gtg cca gca gca taggcggccg c                 1673
Glu Val Val Ala Ser Leu Val Pro Ala Ala
545                 550
```

<210> SEQ ID NO 17
<211> LENGTH: 554
<212> TYPE: PRT
<213> ORGANISM: Exophiala spinifera

<400> SEQUENCE: 17

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Lys Asp Asn Val Ala
                85                  90                  95

Asp Val Val Val Gly Ala Gly Leu Ser Gly Leu Glu Thr Ala Arg
            100                 105                 110

Lys Val Gln Ala Ala Gly Leu Ser Cys Leu Val Leu Glu Ala Met Asp
        115                 120                 125

Arg Val Gly Gly Lys Thr Leu Ser Val Gln Ser Gly Pro Gly Arg Thr
    130                 135                 140

Thr Ile Asn Asp Leu Gly Ala Ala Trp Ile Asn Asp Ser Asn Gln Ser
145                 150                 155                 160

Glu Val Ser Arg Leu Phe Glu Arg Phe His Leu Glu Gly Glu Leu Gln
                165                 170                 175

Arg Thr Thr Gly Asn Ser Ile His Gln Ala Gln Asp Gly Thr Thr Thr
            180                 185                 190

Thr Ala Pro Tyr Gly Asp Ser Leu Leu Ser Glu Val Ala Ser Ala
        195                 200                 205

Leu Ala Glu Leu Leu Pro Val Trp Ser Gln Leu Ile Glu Glu His Ser
    210                 215                 220

Leu Gln Asp Leu Lys Ala Ser Pro Gln Ala Lys Arg Leu Asp Ser Val
```

```
                   225                 230                 235                 240

Ser Phe Ala His Tyr Cys Glu Lys Glu Leu Asn Leu Pro Ala Val Leu
                        245                 250                 255

Gly Val Ala Asn Gln Ile Thr Arg Ala Leu Leu Gly Val Glu Ala His
                        260                 265                 270

Glu Ile Ser Met Leu Phe Leu Thr Asp Tyr Ile Lys Ser Ala Thr Gly
                        275                 280                 285

Leu Ser Asn Ile Phe Ser Asp Lys Lys Asp Gly Gln Tyr Met Arg
            290                 295                 300

Cys Lys Thr Gly Met Gln Ser Ile Cys His Ala Met Ser Lys Glu Leu
        305                 310                 315                 320

Val Pro Gly Ser Val His Leu Asn Thr Pro Val Ala Glu Ile Glu Gln
                        325                 330                 335

Ser Ala Ser Gly Cys Thr Val Arg Ser Ala Ser Gly Ala Val Phe Arg
                        340                 345                 350

Ser Lys Lys Val Val Ser Leu Pro Thr Thr Leu Tyr Pro Thr Leu
                        355                 360                 365

Thr Phe Ser Pro Pro Leu Pro Ala Glu Lys Gln Ala Leu Ala Glu Asn
            370                 375                 380

Ser Ile Leu Gly Tyr Tyr Ser Lys Ile Val Phe Val Trp Asp Lys Pro
        385                 390                 395                 400

Trp Trp Arg Glu Gln Gly Phe Ser Gly Val Leu Gln Ser Ser Cys Asp
                        405                 410                 415

Pro Ile Ser Phe Ala Arg Asp Thr Ser Ile Asp Val Asp Arg Gln Trp
                        420                 425                 430

Ser Ile Thr Cys Phe Met Val Gly Asp Pro Gly Arg Lys Trp Ser Gln
                        435                 440                 445

Gln Ser Lys Gln Val Arg Gln Lys Ser Val Trp Asp Gln Leu Arg Ala
            450                 455                 460

Ala Tyr Glu Asn Ala Gly Ala Gln Val Pro Glu Pro Ala Asn Val Leu
        465                 470                 475                 480

Glu Ile Glu Trp Ser Lys Gln Gln Tyr Phe Gln Gly Ala Pro Ser Ala
                        485                 490                 495

Val Tyr Gly Leu Asn Asp Leu Ile Thr Leu Gly Ser Ala Leu Arg Thr
                        500                 505                 510

Pro Phe Lys Ser Val His Phe Val Gly Thr Glu Thr Ser Leu Val Trp
            515                 520                 525

Lys Gly Tyr Met Glu Gly Ala Ile Arg Ser Gly Gln Arg Gly Ala Ala
            530                 535                 540

Glu Val Val Ala Ser Leu Val Pro Ala Ala
        545                 550

<210> SEQ ID NO 18
<211> LENGTH: 2079
<212> TYPE: DNA
<213> ORGANISM: Unknown
<220> FEATURE:
<223> OTHER INFORMATION: GST:K:trAPAO 2079 for bacterial expression
      (Exophiala spinifera)
<220> FEATURE:
<221> NAME/KEY: CDS
<222> LOCATION: (1)..(2076)
<223> OTHER INFORMATION:
<220> FEATURE:
<221> NAME/KEY: misc_feature
<222> LOCATION: (1)..(687)
<223> OTHER INFORMATION: gst fusion + polylinker
<220> FEATURE:
```

<221> NAME/KEY: misc_feature
<222> LOCATION: (688)..(2076)
<223> OTHER INFORMATION: K:trAPAO
<220> FEATURE:
<221> NAME/KEY: misc_feature
<222> LOCATION: (688)..(690)
<223> OTHER INFORMATION: Extra lysine

<400> SEQUENCE: 18

| | | | | | | | | | | | | | | | | |
|---|---|---|---|---|---|---|---|---|---|---|---|---|---|---|---|---|
| atg | tcc | cct | ata | cta | ggt | tat | tgg | aaa | att | aag | ggc | ctt | gtg | caa | ccc | 48 |
| Met | Ser | Pro | Ile | Leu | Gly | Tyr | Trp | Lys | Ile | Lys | Gly | Leu | Val | Gln | Pro | |
| 1 | | | | 5 | | | | | 10 | | | | | 15 | | |
| act | cga | ctt | ctt | ttg | gaa | tat | ctt | gaa | gaa | aaa | tat | gaa | gag | cat | ttg | 96 |
| Thr | Arg | Leu | Leu | Leu | Glu | Tyr | Leu | Glu | Glu | Lys | Tyr | Glu | Glu | His | Leu | |
| | | | 20 | | | | | 25 | | | | | 30 | | | |
| tat | gag | cgc | gat | gaa | ggt | gat | aaa | tgg | cga | aac | aaa | aag | ttt | gaa | ttg | 144 |
| Tyr | Glu | Arg | Asp | Glu | Gly | Asp | Lys | Trp | Arg | Asn | Lys | Lys | Phe | Glu | Leu | |
| | 35 | | | | | 40 | | | | | 45 | | | | | |
| ggt | ttg | gag | ttt | ccc | aat | ctt | cct | tat | tat | att | gat | ggt | gat | gtt | aaa | 192 |
| Gly | Leu | Glu | Phe | Pro | Asn | Leu | Pro | Tyr | Tyr | Ile | Asp | Gly | Asp | Val | Lys | |
| 50 | | | | | 55 | | | | | 60 | | | | | | |
| tta | aca | cag | tct | atg | gcc | atc | ata | cgt | tat | ata | gct | gac | aag | cac | aac | 240 |
| Leu | Thr | Gln | Ser | Met | Ala | Ile | Ile | Arg | Tyr | Ile | Ala | Asp | Lys | His | Asn | |
| 65 | | | | 70 | | | | | 75 | | | | | 80 | | |
| atg | ttg | ggt | ggt | tgt | cca | aaa | gag | cgt | gca | gag | att | tca | atg | ctt | gaa | 288 |
| Met | Leu | Gly | Gly | Cys | Pro | Lys | Glu | Arg | Ala | Glu | Ile | Ser | Met | Leu | Glu | |
| | | | | 85 | | | | | 90 | | | | | 95 | | |
| gga | gcg | gtt | ttg | gat | att | aga | tac | ggt | gtt | tcg | aga | att | gca | tat | agt | 336 |
| Gly | Ala | Val | Leu | Asp | Ile | Arg | Tyr | Gly | Val | Ser | Arg | Ile | Ala | Tyr | Ser | |
| | | | 100 | | | | | 105 | | | | | 110 | | | |
| aaa | gac | ttt | gaa | act | ctc | aaa | gtt | gat | ttt | ctt | agc | aag | cta | cct | gaa | 384 |
| Lys | Asp | Phe | Glu | Thr | Leu | Lys | Val | Asp | Phe | Leu | Ser | Lys | Leu | Pro | Glu | |
| | | 115 | | | | | 120 | | | | | 125 | | | | |
| atg | ctg | aaa | atg | ttc | gaa | gat | cgt | tta | tgt | cat | aaa | aca | tat | tta | aat | 432 |
| Met | Leu | Lys | Met | Phe | Glu | Asp | Arg | Leu | Cys | His | Lys | Thr | Tyr | Leu | Asn | |
| | 130 | | | | | 135 | | | | | 140 | | | | | |
| ggt | gat | cat | gta | acc | cat | cct | gac | ttc | atg | ttg | tat | gac | gct | ctt | gat | 480 |
| Gly | Asp | His | Val | Thr | His | Pro | Asp | Phe | Met | Leu | Tyr | Asp | Ala | Leu | Asp | |
| 145 | | | | | 150 | | | | | 155 | | | | | 160 | |
| gtt | gtt | tta | tac | atg | gac | cca | atg | tgc | ctg | gat | gcg | ttc | cca | aaa | tta | 528 |
| Val | Val | Leu | Tyr | Met | Asp | Pro | Met | Cys | Leu | Asp | Ala | Phe | Pro | Lys | Leu | |
| | | | | 165 | | | | | 170 | | | | | 175 | | |
| gtt | tgt | ttt | aaa | aaa | cgt | att | gaa | gct | atc | cca | caa | att | gat | aag | tac | 576 |
| Val | Cys | Phe | Lys | Lys | Arg | Ile | Glu | Ala | Ile | Pro | Gln | Ile | Asp | Lys | Tyr | |
| | | | 180 | | | | | 185 | | | | | 190 | | | |
| ttg | aaa | tcc | agc | aag | tat | ata | gca | tgg | cct | ttg | cag | ggc | tgg | caa | gcc | 624 |
| Leu | Lys | Ser | Ser | Lys | Tyr | Ile | Ala | Trp | Pro | Leu | Gln | Gly | Trp | Gln | Ala | |
| | | | 195 | | | | | 200 | | | | | 205 | | | |
| acg | ttt | ggt | ggt | ggc | gac | cat | cct | cca | aaa | tcg | gat | ctg | gtt | ccg | cgt | 672 |
| Thr | Phe | Gly | Gly | Gly | Asp | His | Pro | Pro | Lys | Ser | Asp | Leu | Val | Pro | Arg | |
| | 210 | | | | | 215 | | | | | 220 | | | | | |
| gga | tcc | ccg | gaa | ttc | aaa | gac | aac | gtt | gcg | gac | gtg | gta | gtg | gtg | ggc | 720 |
| Gly | Ser | Pro | Glu | Phe | Lys | Asp | Asn | Val | Ala | Asp | Val | Val | Val | Val | Gly | |
| 225 | | | | | 230 | | | | | 235 | | | | | 240 | |
| gct | ggc | ttg | agc | ggt | ttg | gag | acg | gca | cgc | aaa | gtc | cag | gcc | gcc | ggt | 768 |
| Ala | Gly | Leu | Ser | Gly | Leu | Glu | Thr | Ala | Arg | Lys | Val | Gln | Ala | Ala | Gly | |
| | | | | 245 | | | | | 250 | | | | | 255 | | |
| ctg | tcc | tgc | ctc | gtt | ctt | gag | gcg | atg | gat | cgt | gta | ggg | gga | aag | act | 816 |
| Leu | Ser | Cys | Leu | Val | Leu | Glu | Ala | Met | Asp | Arg | Val | Gly | Gly | Lys | Thr | |
| | | | 260 | | | | | 265 | | | | | 270 | | | |
| ctg | agc | gta | caa | tcg | ggt | ccc | ggc | agg | acg | act | atc | aac | gac | ctc | ggc | 864 |

```
                                              -continued

Leu Ser Val Gln Ser Gly Pro Gly Arg Thr Thr Ile Asn Asp Leu Gly
        275                 280                 285 gct gcg tgg atc aat gac agc aac caa agc gaa gta tcc aga ttg ttt    912
Ala Ala Trp Ile Asn Asp Ser Asn Gln Ser Glu Val Ser Arg Leu Phe
    290                 295                 300 gaa aga ttt cat ttg gag ggc gag ctc cag agg acg act gga aat tca    960
Glu Arg Phe His Leu Glu Gly Glu Leu Gln Arg Thr Thr Gly Asn Ser
305                 310                 315                 320 atc cat caa gca caa gac ggt aca acc act aca gct cct tat ggt gac   1008
Ile His Gln Ala Gln Asp Gly Thr Thr Thr Thr Ala Pro Tyr Gly Asp
                325                 330                 335 tcc ttg ctg agc gag gag gtt gca agt gca ctt gcg gaa ctc ctc ccc   1056
Ser Leu Leu Ser Glu Glu Val Ala Ser Ala Leu Ala Glu Leu Leu Pro
        340                 345                 350 gta tgg tct cag ctg atc gaa gag cat agc ctt caa gac ctc aag gcg   1104
Val Trp Ser Gln Leu Ile Glu Glu His Ser Leu Gln Asp Leu Lys Ala
            355                 360                 365 agc cct cag gcg aag cgg ctc gac agt gtg agc ttc gcg cac tac tgt   1152
Ser Pro Gln Ala Lys Arg Leu Asp Ser Val Ser Phe Ala His Tyr Cys
    370                 375                 380 gag aag gaa cta aac ttg cct gct gtt ctc ggc gta gca aac cag atc   1200
Glu Lys Glu Leu Asn Leu Pro Ala Val Leu Gly Val Ala Asn Gln Ile
385                 390                 395                 400 aca cgc gct ctg ctc ggt gtg gaa gcc cac gag atc agc atg ctt ttt   1248
Thr Arg Ala Leu Leu Gly Val Glu Ala His Glu Ile Ser Met Leu Phe
                405                 410                 415 ctc acc gac tac atc aag agt gcc acc ggt ctc agt aat att ttc tcg   1296
Leu Thr Asp Tyr Ile Lys Ser Ala Thr Gly Leu Ser Asn Ile Phe Ser
        420                 425                 430 gac aag aaa gac ggc ggg cag tat atg cga tgc aaa aca ggt atg cag   1344
Asp Lys Lys Asp Gly Gly Gln Tyr Met Arg Cys Lys Thr Gly Met Gln
            435                 440                 445 tcg att tgc cat gcc atg tca aag gaa ctt gtt cca ggc tca gtg cac   1392
Ser Ile Cys His Ala Met Ser Lys Glu Leu Val Pro Gly Ser Val His
    450                 455                 460 ctc aac acc ccc gtc gct gaa att gag cag tcg gca tcc ggc tgt aca   1440
Leu Asn Thr Pro Val Ala Glu Ile Glu Gln Ser Ala Ser Gly Cys Thr
465                 470                 475                 480 gta cga tcg gcc tcg ggc gcc gtg ttc cga agc aaa aag gtg gtg gtt   1488
Val Arg Ser Ala Ser Gly Ala Val Phe Arg Ser Lys Lys Val Val Val
                485                 490                 495 tcg tta ccg aca acc ttg tat ccc acc ttg aca ttt tca cca cct ctt   1536
Ser Leu Pro Thr Thr Leu Tyr Pro Thr Leu Thr Phe Ser Pro Pro Leu
        500                 505                 510 ccc gcc gag aag caa gca ttg gcg gaa aat tct atc ctg ggc tac tat   1584
Pro Ala Glu Lys Gln Ala Leu Ala Glu Asn Ser Ile Leu Gly Tyr Tyr
            515                 520                 525 agc aag ata gtc ttc gta tgg gac aag ccg tgg tgg cgc gaa caa ggc   1632
Ser Lys Ile Val Phe Val Trp Asp Lys Pro Trp Trp Arg Glu Gln Gly
    530                 535                 540 ttc tcg ggc gtc ctc caa tcg agc tgt gac ccc atc tca ttt gcc aga   1680
Phe Ser Gly Val Leu Gln Ser Ser Cys Asp Pro Ile Ser Phe Ala Arg
545                 550                 555                 560 gat acc agc atc gac gtc gat cga caa tgg tcc att acc tgt ttc atg   1728
Asp Thr Ser Ile Asp Val Asp Arg Gln Trp Ser Ile Thr Cys Phe Met
                565                 570                 575 gtc gga gac ccg gga cgg aag tgg tcc caa cag tcc aag cag gta cga   1776
Val Gly Asp Pro Gly Arg Lys Trp Ser Gln Gln Ser Lys Gln Val Arg
        580                 585                 590
```

-continued

```
caa aag tct gtc tgg gac caa ctc cgc gca gcc tac gag aac gcc ggg      1824
Gln Lys Ser Val Trp Asp Gln Leu Arg Ala Ala Tyr Glu Asn Ala Gly
    595                 600                 605 gcc caa gtc cca gag ccg gcc aac gtg ctc gaa atc gag tgg tcg aag      1872
Ala Gln Val Pro Glu Pro Ala Asn Val Leu Glu Ile Glu Trp Ser Lys
610                 615                 620 cag cag tat ttc caa gga gct ccg agc gcc gtc tat ggg ctg aac gat      1920
Gln Gln Tyr Phe Gln Gly Ala Pro Ser Ala Val Tyr Gly Leu Asn Asp
625                 630                 635                 640 ctc atc aca ctg ggt tcg gcg ctc aga acg ccg ttc aag agt gtt cat      1968
Leu Ile Thr Leu Gly Ser Ala Leu Arg Thr Pro Phe Lys Ser Val His
                645                 650                 655 ttc gtt gga acg gag acg tct tta gtt tgg aaa ggg tat atg gaa ggg      2016
Phe Val Gly Thr Glu Thr Ser Leu Val Trp Lys Gly Tyr Met Glu Gly
            660                 665                 670 gcc ata cga tcg ggt caa cga ggt gct gca gaa gtt gtg gct agc ctg      2064
Ala Ile Arg Ser Gly Gln Arg Gly Ala Ala Glu Val Val Ala Ser Leu
    675                 680                 685 gtg cca gca gca tag                                                  2079
Val Pro Ala Ala
    690
```

<210> SEQ ID NO 19
<211> LENGTH: 692
<212> TYPE: PRT
<213> ORGANISM: Unknown
<220> FEATURE:
<223> OTHER INFORMATION: GST:K:trAPAO 2079 for bacterial expression
      (Exophiala spinifera)
<220> FEATURE:
<221> NAME/KEY: misc_feature
<222> LOCATION: (1)..(687)
<223> OTHER INFORMATION: gst fusion + polylinker
<220> FEATURE:
<221> NAME/KEY: misc_feature
<222> LOCATION: (688)..(2076)
<223> OTHER INFORMATION: K:trAPAO
<220> FEATURE:
<221> NAME/KEY: misc_feature
<222> LOCATION: (688)..(690)
<223> OTHER INFORMATION: Extra lysine

<400> SEQUENCE: 19

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
```

-continued

```
            145                 150                 155                 160
Val Val Leu Tyr Met Asp Pro Met Cys Leu Asp Ala Phe Pro Lys Leu
                165                 170                 175
Val Cys Phe Lys Lys Arg Ile Glu Ala Ile Pro Gln Ile Asp Lys Tyr
                180                 185                 190
Leu Lys Ser Ser Lys Tyr Ile Ala Trp Pro Leu Gln Gly Trp Gln Ala
                195                 200                 205
Thr Phe Gly Gly Gly Asp His Pro Pro Lys Ser Asp Leu Val Pro Arg
                210                 215                 220
Gly Ser Pro Glu Phe Lys Asp Asn Val Ala Asp Val Val Val Gly
225                 230                 235                 240
Ala Gly Leu Ser Gly Leu Glu Thr Ala Arg Lys Val Gln Ala Ala Gly
                245                 250                 255
Leu Ser Cys Leu Val Leu Glu Ala Met Asp Arg Val Gly Gly Lys Thr
                260                 265                 270
Leu Ser Val Gln Ser Gly Pro Gly Arg Thr Thr Ile Asn Asp Leu Gly
                275                 280                 285
Ala Ala Trp Ile Asn Asp Ser Asn Gln Ser Glu Val Ser Arg Leu Phe
                290                 295                 300
Glu Arg Phe His Leu Glu Gly Glu Leu Gln Arg Thr Thr Gly Asn Ser
305                 310                 315                 320
Ile His Gln Ala Gln Asp Gly Thr Thr Thr Ala Pro Tyr Gly Asp
                325                 330                 335
Ser Leu Leu Ser Glu Glu Val Ala Ser Ala Leu Ala Glu Leu Leu Pro
                340                 345                 350
Val Trp Ser Gln Leu Ile Glu Glu His Ser Leu Gln Asp Leu Lys Ala
                355                 360                 365
Ser Pro Gln Ala Lys Arg Leu Asp Ser Val Ser Phe Ala His Tyr Cys
                370                 375                 380
Glu Lys Glu Leu Asn Leu Pro Ala Val Leu Gly Val Ala Asn Gln Ile
385                 390                 395                 400
Thr Arg Ala Leu Leu Gly Val Glu Ala His Glu Ile Ser Met Leu Phe
                405                 410                 415
Leu Thr Asp Tyr Ile Lys Ser Ala Thr Gly Leu Ser Asn Ile Phe Ser
                420                 425                 430
Asp Lys Lys Asp Gly Gly Gln Tyr Met Arg Cys Lys Thr Gly Met Gln
                435                 440                 445
Ser Ile Cys His Ala Met Ser Lys Glu Leu Val Pro Gly Ser Val His
                450                 455                 460
Leu Asn Thr Pro Val Ala Glu Ile Glu Gln Ser Ala Ser Gly Cys Thr
465                 470                 475                 480
Val Arg Ser Ala Ser Gly Ala Val Phe Arg Ser Lys Val Val Val
                485                 490                 495
Ser Leu Pro Thr Thr Leu Tyr Pro Thr Leu Thr Phe Ser Pro Pro Leu
                500                 505                 510
Pro Ala Glu Lys Gln Ala Leu Ala Glu Asn Ser Ile Leu Gly Tyr Tyr
                515                 520                 525
Ser Lys Ile Val Phe Val Trp Asp Lys Pro Trp Trp Arg Glu Gln Gly
                530                 535                 540
Phe Ser Gly Val Leu Gln Ser Ser Cys Asp Pro Ile Ser Phe Ala Arg
545                 550                 555                 560
Asp Thr Ser Ile Asp Val Asp Arg Gln Trp Ser Ile Thr Cys Phe Met
                565                 570                 575
```

```
Val Gly Asp Pro Gly Arg Lys Trp Ser Gln Gln Ser Lys Gln Val Arg
        580                 585                 590

Gln Lys Ser Val Trp Asp Gln Leu Arg Ala Ala Tyr Glu Asn Ala Gly
            595                 600                 605

Ala Gln Val Pro Glu Pro Ala Asn Val Leu Glu Ile Glu Trp Ser Lys
        610                 615                 620

Gln Gln Tyr Phe Gln Gly Ala Pro Ser Ala Val Tyr Gly Leu Asn Asp
625                 630                 635                 640

Leu Ile Thr Leu Gly Ser Ala Leu Arg Thr Pro Phe Lys Ser Val His
                645                 650                 655

Phe Val Gly Thr Glu Thr Ser Leu Val Trp Lys Gly Tyr Met Glu Gly
            660                 665                 670

Ala Ile Arg Ser Gly Gln Arg Gly Ala Ala Glu Val Val Ala Ser Leu
        675                 680                 685

Val Pro Ala Ala
        690

<210> SEQ ID NO 20
<211> LENGTH: 1464
<212> TYPE: DNA
<213> ORGANISM: Unknown
<220> FEATURE:
<223> OTHER INFORMATION: K:trAPAO fusion with barley alpha amylase
      (Exophiala spinifera)
<220> FEATURE:
<221> NAME/KEY: sig_peptide
<222> LOCATION: (1)..(72)
<223> OTHER INFORMATION: Barley alpha amylase signal sequence
<220> FEATURE:
<221> NAME/KEY: misc_feature
<222> LOCATION: (73)..(1464)
<223> OTHER INFORMATION: K:trAPAO cDNA
<220> FEATURE:
<221> NAME/KEY: CDS
<222> LOCATION: (1)..(1461)
<223> OTHER INFORMATION:
<220> FEATURE:
<221> NAME/KEY: misc_feature
<222> LOCATION: (73)..(75)
<223> OTHER INFORMATION: Added lysine residue

<400> SEQUENCE: 20 atg gcc aac aag cac ctg agc ctc tcc ctc ttc ctc gtg ctc ctc ggc      48
Met Ala Asn Lys His Leu Ser Leu Ser Leu Phe Leu Val Leu Leu Gly
1               5                   10                  15 ctc tcc gcc tcc ctc gcc agc ggc aaa gac aac gtt gcg gac gtg gta      96
Leu Ser Ala Ser Leu Ala Ser Gly Lys Asp Asn Val Ala Asp Val Val
            20                  25                  30 gtg gtg ggc gct ggc ttg agc ggt ttg gag acg gca cgc aaa gtc cag     144
Val Val Gly Ala Gly Leu Ser Gly Leu Glu Thr Ala Arg Lys Val Gln
        35                  40                  45 gcc gcc ggt ctg tcc tgc ctc gtt ctt gag gcg atg gat cgt gta ggg     192
Ala Ala Gly Leu Ser Cys Leu Val Leu Glu Ala Met Asp Arg Val Gly
    50                  55                  60 gga aag act ctg agc gta caa tcg ggt ccc ggc agg acg act atc aac     240
Gly Lys Thr Leu Ser Val Gln Ser Gly Pro Gly Arg Thr Thr Ile Asn
65                  70                  75                  80 gac ctc ggc gct gcg tgg atc aat gac agc aac caa agc gaa gta tcc     288
Asp Leu Gly Ala Ala Trp Ile Asn Asp Ser Asn Gln Ser Glu Val Ser
                85                  90                  95 aga ttg ttt gaa aga ttt cat ttg gag ggc gag ctc cag agg acg act     336
Arg Leu Phe Glu Arg Phe His Leu Glu Gly Glu Leu Gln Arg Thr Thr
            100                 105                 110
```

```
gga aat tca atc cat caa gca caa gac ggt aca acc act aca gct cct      384
Gly Asn Ser Ile His Gln Ala Gln Asp Gly Thr Thr Thr Thr Ala Pro
        115                 120                 125 tat ggt gac tcc ttg ctg agc gag gag gtt gca agt gca ctt gcg gaa      432
Tyr Gly Asp Ser Leu Leu Ser Glu Glu Val Ala Ser Ala Leu Ala Glu
130                 135                 140 ctc ctc ccc gta tgg tct cag ctg atc gaa gag cat agc ctt caa gac      480
Leu Leu Pro Val Trp Ser Gln Leu Ile Glu Glu His Ser Leu Gln Asp
145                 150                 155                 160 ctc aag gcg agc cct cag gcg aag cgg ctc gac agt gtg agc ttc gcg      528
Leu Lys Ala Ser Pro Gln Ala Lys Arg Leu Asp Ser Val Ser Phe Ala
                165                 170                 175 cac tac tgt gag aag gaa cta aac ttg cct gct gtt ctc ggc gta gca      576
His Tyr Cys Glu Lys Glu Leu Asn Leu Pro Ala Val Leu Gly Val Ala
            180                 185                 190 aac cag atc aca cgc gct ctg ctc ggt gtg gaa gcc cac gag atc agc      624
Asn Gln Ile Thr Arg Ala Leu Leu Gly Val Glu Ala His Glu Ile Ser
        195                 200                 205 atg ctt ttt ctc acc gac tac atc aag agt gcc acc ggt ctc agt aat      672
Met Leu Phe Leu Thr Asp Tyr Ile Lys Ser Ala Thr Gly Leu Ser Asn
210                 215                 220 att ttc tcg gac aag aaa gac ggc ggg cag tat atg cga tgc aaa aca      720
Ile Phe Ser Asp Lys Lys Asp Gly Gly Gln Tyr Met Arg Cys Lys Thr
225                 230                 235                 240 ggt atg cag tcg att tgc cat gcc atg tca aag gaa ctt gtt cca ggc      768
Gly Met Gln Ser Ile Cys His Ala Met Ser Lys Glu Leu Val Pro Gly
                245                 250                 255 tca gtg cac ctc aac acc ccc gtc gct gaa att gag cag tcg gca tcc      816
Ser Val His Leu Asn Thr Pro Val Ala Glu Ile Glu Gln Ser Ala Ser
            260                 265                 270 ggc tgt aca gta cga tcg gcc tcg ggc gcc gtg ttc cga agc aaa aag      864
Gly Cys Thr Val Arg Ser Ala Ser Gly Ala Val Phe Arg Ser Lys Lys
        275                 280                 285 gtg gtg gtt tcg tta ccg aca acc ttg tat ccc acc ttg aca ttt tca      912
Val Val Val Ser Leu Pro Thr Thr Leu Tyr Pro Thr Leu Thr Phe Ser
290                 295                 300 cca cct ctt ccc gcc gag aag caa gca ttg gcg gaa aat tct atc ctg      960
Pro Pro Leu Pro Ala Glu Lys Gln Ala Leu Ala Glu Asn Ser Ile Leu
305                 310                 315                 320 ggc tac tat agc aag ata gtc ttc gta tgg gac aag ccg tgg tgg cgc     1008
Gly Tyr Tyr Ser Lys Ile Val Phe Val Trp Asp Lys Pro Trp Trp Arg
                325                 330                 335 gaa caa ggc ttc tcg ggc gtc ctc caa tcg agc tgt gac ccc atc tca     1056
Glu Gln Gly Phe Ser Gly Val Leu Gln Ser Ser Cys Asp Pro Ile Ser
            340                 345                 350 ttt gcc aga gat acc agc atc gac gtc gat cga caa tgg tcc att acc     1104
Phe Ala Arg Asp Thr Ser Ile Asp Val Asp Arg Gln Trp Ser Ile Thr
        355                 360                 365 tgt ttc atg gtc gga gac ccg gga cgg aag tgg tcc caa cag tcc aag     1152
Cys Phe Met Val Gly Asp Pro Gly Arg Lys Trp Ser Gln Gln Ser Lys
370                 375                 380 cag gta cga caa aag tct gtc tgg gac caa ctc cgc gca gcc tac gag     1200
Gln Val Arg Gln Lys Ser Val Trp Asp Gln Leu Arg Ala Ala Tyr Glu
385                 390                 395                 400 aac gcc ggg gcc caa gtc cca gag ccg gcc aac gtg ctc gaa atc gag     1248
Asn Ala Gly Ala Gln Val Pro Glu Pro Ala Asn Val Leu Glu Ile Glu
                405                 410                 415 tgg tcg aag cag cag tat ttc caa gga gct ccg agc gcc gtc tat ggg     1296
Trp Ser Lys Gln Gln Tyr Phe Gln Gly Ala Pro Ser Ala Val Tyr Gly
```

-continued

```
                       420                 425                 430
ctg aac gat ctc atc aca ctg ggt tcg gcg ctc aga acg ccg ttc aag      1344
Leu Asn Asp Leu Ile Thr Leu Gly Ser Ala Leu Arg Thr Pro Phe Lys
            435                 440                 445 agt gtt cat ttc gtt gga acg gag acg tct tta gtt tgg aaa ggg tat      1392
Ser Val His Phe Val Gly Thr Glu Thr Ser Leu Val Trp Lys Gly Tyr
        450                 455                 460 atg gaa ggg gcc ata cga tcg ggt caa cga ggt gct gca gaa gtt gtg      1440
Met Glu Gly Ala Ile Arg Ser Gly Gln Arg Gly Ala Ala Glu Val Val
465                 470                 475                 480 gct agc ctg gtg cca gca gca tag                                      1464
Ala Ser Leu Val Pro Ala Ala
                485
```

<210> SEQ ID NO 21
<211> LENGTH: 487
<212> TYPE: PRT
<213> ORGANISM: Unknown
<220> FEATURE:
<223> OTHER INFORMATION: K:trAPAO fusion with barley alpha amylase
      (Exophiala spinifera)
<220> FEATURE:
<221> NAME/KEY: misc_feature
<222> LOCATION: (73)..(1464)
<223> OTHER INFORMATION: K:trAPAO cDNA
<220> FEATURE:
<221> NAME/KEY: misc_feature
<222> LOCATION: (73)..(75)
<223> OTHER INFORMATION: Added lysine residue

<400> SEQUENCE: 21

```
Met Ala Asn Lys His Leu Ser Leu Ser Leu Phe Leu Val Leu Leu Gly
1               5                   10                  15

Leu Ser Ala Ser Leu Ala Ser Gly Lys Asp Asn Val Ala Asp Val Val
            20                  25                  30

Val Val Gly Ala Gly Leu Ser Gly Leu Glu Thr Ala Arg Lys Val Gln
        35                  40                  45

Ala Ala Gly Leu Ser Cys Leu Val Leu Glu Ala Met Asp Arg Val Gly
    50                  55                  60

Gly Lys Thr Leu Ser Val Gln Ser Gly Pro Gly Arg Thr Thr Ile Asn
65              70                  75                  80

Asp Leu Gly Ala Ala Trp Ile Asn Asp Ser Asn Gln Ser Glu Val Ser
            85                  90                  95

Arg Leu Phe Glu Arg Phe His Leu Glu Gly Glu Leu Gln Arg Thr Thr
            100                 105                 110

Gly Asn Ser Ile His Gln Ala Gln Asp Gly Thr Thr Thr Ala Pro
            115                 120                 125

Tyr Gly Asp Ser Leu Leu Ser Glu Glu Val Ala Ser Ala Leu Ala Glu
    130                 135                 140

Leu Leu Pro Val Trp Ser Gln Leu Ile Glu Glu His Ser Leu Gln Asp
145                 150                 155                 160

Leu Lys Ala Ser Pro Gln Ala Lys Arg Leu Asp Ser Val Ser Phe Ala
                165                 170                 175

His Tyr Cys Glu Lys Glu Leu Asn Leu Pro Ala Val Leu Gly Val Ala
            180                 185                 190

Asn Gln Ile Thr Arg Ala Leu Leu Gly Val Glu Ala His Glu Ile Ser
        195                 200                 205

Met Leu Phe Leu Thr Asp Tyr Ile Lys Ser Ala Thr Gly Leu Ser Asn
    210                 215                 220
```

```
Ile Phe Ser Asp Lys Lys Asp Gly Gly Gln Tyr Met Arg Cys Lys Thr
225                 230                 235                 240

Gly Met Gln Ser Ile Cys His Ala Met Ser Lys Glu Leu Val Pro Gly
            245                 250                 255

Ser Val His Leu Asn Thr Pro Val Ala Glu Ile Glu Gln Ser Ala Ser
            260                 265                 270

Gly Cys Thr Val Arg Ser Ala Ser Gly Ala Val Phe Arg Ser Lys Lys
            275                 280                 285

Val Val Val Ser Leu Pro Thr Thr Leu Tyr Pro Thr Leu Thr Phe Ser
290                 295                 300

Pro Pro Leu Pro Ala Glu Lys Gln Ala Leu Ala Glu Asn Ser Ile Leu
305                 310                 315                 320

Gly Tyr Tyr Ser Lys Ile Val Phe Val Trp Asp Lys Pro Trp Trp Arg
            325                 330                 335

Glu Gln Gly Phe Ser Gly Val Leu Gln Ser Ser Cys Asp Pro Ile Ser
            340                 345                 350

Phe Ala Arg Asp Thr Ser Ile Asp Val Asp Arg Gln Trp Ser Ile Thr
            355                 360                 365

Cys Phe Met Val Gly Asp Pro Gly Arg Lys Trp Ser Gln Gln Ser Lys
370                 375                 380

Gln Val Arg Gln Lys Ser Val Trp Asp Gln Leu Arg Ala Ala Tyr Glu
385                 390                 395                 400

Asn Ala Gly Ala Gln Val Pro Glu Pro Ala Asn Val Leu Glu Ile Glu
                405                 410                 415

Trp Ser Lys Gln Gln Tyr Phe Gln Gly Ala Pro Ser Ala Val Tyr Gly
                420                 425                 430

Leu Asn Asp Leu Ile Thr Leu Gly Ser Ala Leu Arg Thr Pro Phe Lys
                435                 440                 445

Ser Val His Phe Val Gly Thr Glu Thr Ser Leu Val Trp Lys Gly Tyr
            450                 455                 460

Met Glu Gly Ala Ile Arg Ser Gly Gln Arg Gly Ala Ala Glu Val Val
465                 470                 475                 480

Ala Ser Leu Val Pro Ala Ala
                485
```

```
<210> SEQ ID NO 22
<211> LENGTH: 1803
<212> TYPE: DNA
<213> ORGANISM: Exophiala spinifera
<220> FEATURE:
<221> NAME/KEY: CDS
<222> LOCATION: (1)..(1800)
<223> OTHER INFORMATION:

<400> SEQUENCE: 22
```

```
atg gca ctt gca ccg agc tac atc aat ccc cca aac gtc gcc tcc cca      48
Met Ala Leu Ala Pro Ser Tyr Ile Asn Pro Pro Asn Val Ala Ser Pro
1               5                   10                  15 gca ggg tat tct cac gtc ggc gta ggc cca gac gga ggg agg tat gtg      96
Ala Gly Tyr Ser His Val Gly Val Gly Pro Asp Gly Gly Arg Tyr Val
            20                  25                  30 aca ata gct gga cag att gga caa gac gct tcg ggc gtg aca gac cct     144
Thr Ile Ala Gly Gln Ile Gly Gln Asp Ala Ser Gly Val Thr Asp Pro
        35                  40                  45 gcc tac gag aaa cag gtt gcc caa gca ttc gcc aat ctg cga gct tgc     192
Ala Tyr Glu Lys Gln Val Ala Gln Ala Phe Ala Asn Leu Arg Ala Cys
    50                  55                  60
```

-continued

| | | |
|---|---|---|
| ctt gct gca gtt gga gcc act tca aac gac gtc acc aag ctc aat tac<br>Leu Ala Ala Val Gly Ala Thr Ser Asn Asp Val Thr Lys Leu Asn Tyr<br>65                       70                         75                     80 | 240 |
| tac atc gtc gac tac gcc ccg agc aaa ctc acc gca att gga gat ggg<br>Tyr Ile Val Asp Tyr Ala Pro Ser Lys Leu Thr Ala Ile Gly Asp Gly<br>                   85                       90                       95 | 288 |
| ctg aag gct acc ttt gcc ctt gac agg ctc cct cct tgc acg ctg gtg<br>Leu Lys Ala Thr Phe Ala Leu Asp Arg Leu Pro Pro Cys Thr Leu Val<br>           100                       105                     110 | 336 |
| cca gtg tcg gcc ttg tct tca cct gaa tac ctc ttt gag gtt gat gcc<br>Pro Val Ser Ala Leu Ser Ser Pro Glu Tyr Leu Phe Glu Val Asp Ala<br>115                             120                     125 | 384 |
| acg gcg ctg gtg ccg gga cac acg acc cca gac aac gtt gcg gac gtg<br>Thr Ala Leu Val Pro Gly His Thr Thr Pro Asp Asn Val Ala Asp Val<br>130                             135                     140 | 432 |
| gta gtg gtg ggc gct ggc ttg agc ggt ttg gag acg gca cgc aaa gtc<br>Val Val Val Gly Ala Gly Leu Ser Gly Leu Glu Thr Ala Arg Lys Val<br>145                           150                     155                     160 | 480 |
| cag gcc gcc ggt ctg tcc tgc ctc gtt ctt gag gcg atg gat cgt gta<br>Gln Ala Ala Gly Leu Ser Cys Leu Val Leu Glu Ala Met Asp Arg Val<br>                   165                     170                     175 | 528 |
| ggg gga aag act ctg agc gta caa tcg ggt ccc ggc agg acg act atc<br>Gly Gly Lys Thr Leu Ser Val Gln Ser Gly Pro Gly Arg Thr Thr Ile<br>           180                       185                     190 | 576 |
| aac gac ctc ggc gct gcg tgg atc aat gac agc aac caa agc gaa gta<br>Asn Asp Leu Gly Ala Ala Trp Ile Asn Asp Ser Asn Gln Ser Glu Val<br>                   195                     200                     205 | 624 |
| tcc aga ttg ttt gaa aga ttt cat ttg gag ggc gag ctc cag agg acg<br>Ser Arg Leu Phe Glu Arg Phe His Leu Glu Gly Glu Leu Gln Arg Thr<br>210                           215                     220 | 672 |
| act gga aat tca atc cat caa gca caa gac ggt aca acc act aca gct<br>Thr Gly Asn Ser Ile His Gln Ala Gln Asp Gly Thr Thr Thr Thr Ala<br>225                         230                     235                     240 | 720 |
| cct tat ggt gac tcc ttg ctg agc gag gag gtt gca agt gca ctt gcg<br>Pro Tyr Gly Asp Ser Leu Leu Ser Glu Glu Val Ala Ser Ala Leu Ala<br>                   245                     250                     255 | 768 |
| gaa ctc ctc ccc gta tgg tct cag ctg atc gaa gag cat agc ctt caa<br>Glu Leu Leu Pro Val Trp Ser Gln Leu Ile Glu Glu His Ser Leu Gln<br>                   260                     265                     270 | 816 |
| gac ctc aag gcg agc cct cag gcg aag cgg ctc gac agt gtg agc ttc<br>Asp Leu Lys Ala Ser Pro Gln Ala Lys Arg Leu Asp Ser Val Ser Phe<br>275                           280                     285 | 864 |
| gcg cac tac tgt gag aag gaa cta aac ttg cct gct gtt ctc ggc gta<br>Ala His Tyr Cys Glu Lys Glu Leu Asn Leu Pro Ala Val Leu Gly Val<br>290                           295                     300 | 912 |
| gca aac cag atc aca cgc gct ctg ctc ggt gtg gaa gcc cac gag atc<br>Ala Asn Gln Ile Thr Arg Ala Leu Leu Gly Val Glu Ala His Glu Ile<br>305                         310                     315                     320 | 960 |
| agc atg ctt ttt ctc acc gac tac atc aag agt gcc acc ggt ctc agt<br>Ser Met Leu Phe Leu Thr Asp Tyr Ile Lys Ser Ala Thr Gly Leu Ser<br>                   325                     330                     335 | 1008 |
| aat att ttc tcg gac aag aaa gac ggc ggg cag tat atg cga tgc aaa<br>Asn Ile Phe Ser Asp Lys Lys Asp Gly Gly Gln Tyr Met Arg Cys Lys<br>           340                       345                     350 | 1056 |
| aca ggt atg cag tcg att tgc cat gcc atg tca aag gaa ctt gtt cca<br>Thr Gly Met Gln Ser Ile Cys His Ala Met Ser Lys Glu Leu Val Pro<br>                   355                     360                     365 | 1104 |
| ggc tca gtg cac ctc aac acc ccc gtc gct gaa att gag cag tcg gca<br>Gly Ser Val His Leu Asn Thr Pro Val Ala Glu Ile Glu Gln Ser Ala<br>370                           375                     380 | 1152 |

```
tcc ggc tgt aca gta cga tcg gcc tcg ggc gcc gtg ttc cga agc aaa      1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt      1248
Lys Val Val Val Ser Leu Pro Thr Thr Leu Tyr Pro Thr Leu Thr Phe
                405                 410                 415 tca cca cct ctt ccc gcc gag aag caa gca ttg gcg gaa aat tct atc      1296
Ser Pro Pro Leu Pro Ala Glu Lys Gln Ala Leu Ala Glu Asn Ser Ile
            420                 425                 430 ctg ggc tac tat agc aag ata gtc ttc gta tgg gac aag ccg tgg tgg      1344
Leu Gly Tyr Tyr Ser Lys Ile Val Phe Val Trp Asp Lys Pro Trp Trp
        435                 440                 445 cgc gaa caa ggc ttc tcg ggc gtc ctc caa tcg agc tgt gac ccc atc      1392
Arg Glu Gln Gly Phe Ser Gly Val Leu Gln Ser Ser Cys Asp Pro Ile
    450                 455                 460 tca ttt gcc aga gat acc agc atc gac gtc gat cga caa tgg tcc att      1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc      1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac      1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc      1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat      1632
Glu Trp Ser Lys Gln Gln Tyr Phe Gln Gly Ala Pro Ser Ala Val Tyr
    530                 535                 540 ggg ctg aac gat ctc atc aca ctg ggt tcg gcg ctc aga acg ccg ttc      1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg      1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt      1776
Tyr Met Glu Gly Ala Ile Arg Ser Gly Gln Arg Gly Ala Ala Glu Val
            580                 585                 590 gtg gct agc ctg gtg cca gca gca tag                                  1803
Val Ala Ser Leu Val Pro Ala Ala
        595                 600

<210> SEQ ID NO 23
<211> LENGTH: 600
<212> TYPE: PRT
<213> ORGANISM: Exophiala spinifera

<400> SEQUENCE: 23

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
65                  70                  75                  80
```

-continued

```
Tyr Ile Val Asp Tyr Ala Pro Ser Lys Leu Thr Ala Ile Gly Asp Gly
                 85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu Glu His Ser Leu Gln
            260                 265                 270

Asp Leu Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Gln Ser
                485                 490                 495
```

-continued

```
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
            515                 520                 525
Glu Trp Ser Lys Gln Gln Tyr Phe Gln Gly Ala Pro Ser Ala Val Tyr
        530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
            595                 600
```

<210> SEQ ID NO 24
<211> LENGTH: 3003
<212> TYPE: DNA
<213> ORGANISM: unknown
<220> FEATURE:
<223> OTHER INFORMATION: K:trAPAO (Exophiala spinifera)
<220> FEATURE:
<221> NAME/KEY: misc_feature
<222> LOCATION: (73)..(1575)
<223> OTHER INFORMATION: esp1 mat
<220> FEATURE:
<221> NAME/KEY: misc_feature
<222> LOCATION: (1576)..(1611)
<223> OTHER INFORMATION: spacer sequence
<220> FEATURE:
<221> NAME/KEY: misc_feature
<222> LOCATION: (1612)..(3000)
<223> OTHER INFORMATION: K:trAPAO
<220> FEATURE:
<221> NAME/KEY: CDS
<222> LOCATION: (1)..(3000)
<223> OTHER INFORMATION:
<220> FEATURE:
<221> NAME/KEY: misc_feature
<222> LOCATION: (1612)..(1614)
<223> OTHER INFORMATION: extra lysine

<400> SEQUENCE: 24

```
atg gcc aac aag cac ctg agc ctc tcc ctc ttc ctc gtg ctc ctc ggc      48
Met Ala Asn Lys His Leu Ser Leu Ser Leu Phe Leu Val Leu Leu Gly
1               5                   10                  15 ctc tcc gcc tcc ctc gcc agc ggc gct cct act gtc aag att gat gct      96
Leu Ser Ala Ser Leu Ala Ser Gly Ala Pro Thr Val Lys Ile Asp Ala
            20                  25                  30 ggg atg gtg gtc ggc acg act act act gtc ccc ggc acc act gcg acc     144
Gly Met Val Val Gly Thr Thr Thr Thr Val Pro Gly Thr Thr Ala Thr
        35                  40                  45 gtc agc gag ttc ttg ggc gtt cct ttt gcc gcc tct ccg aca cga ttt     192
Val Ser Glu Phe Leu Gly Val Pro Phe Ala Ala Ser Pro Thr Arg Phe
    50                  55                  60 gcg cct cct act cgt ccc gtg cct tgg tca acg cct ttg caa gcc act     240
Ala Pro Pro Thr Arg Pro Val Pro Trp Ser Thr Pro Leu Gln Ala Thr
65                  70                  75                  80 gca tat ggt cca gca tgc cct caa caa ttc aat tac ccc gaa gaa ctc     288
Ala Tyr Gly Pro Ala Cys Pro Gln Gln Phe Asn Tyr Pro Glu Glu Leu
                85                  90                  95 cgt gag att acg atg gcc tgg ttc aat aca ccg ccc ccg tca gct ggt     336
Arg Glu Ile Thr Met Ala Trp Phe Asn Thr Pro Pro Pro Ser Ala Gly
            100                 105                 110
```

```
                                                         -continued gaa agt gag gac tgc ctg aac ctc aac atc tac gtc cca gga act gag      384
Glu Ser Glu Asp Cys Leu Asn Leu Asn Ile Tyr Val Pro Gly Thr Glu
        115                 120                 125 aac aca aac aaa gcc gtc atg gtt tgg ata tac ggt gga gcg ctg gaa      432
Asn Thr Asn Lys Ala Val Met Val Trp Ile Tyr Gly Gly Ala Leu Glu
    130                 135                 140 tat ggt tgg aat tca ttc cac ctt tac gac ggg gct agt ttc gca gcc      480
Tyr Gly Trp Asn Ser Phe His Leu Tyr Asp Gly Ala Ser Phe Ala Ala
145                 150                 155                 160 aat cag gat gtc atc gcc gtg acc atc aac tac aga acg aac att ctg      528
Asn Gln Asp Val Ile Ala Val Thr Ile Asn Tyr Arg Thr Asn Ile Leu
                165                 170                 175 ggg ttc cct gct gcc cct cag ctt cca ata aca cag cga aat ctg ggg      576
Gly Phe Pro Ala Ala Pro Gln Leu Pro Ile Thr Gln Arg Asn Leu Gly
            180                 185                 190 ttc cta gac caa agg ttt gct ttg gat tgg gta cag cgg aac atc gca      624
Phe Leu Asp Gln Arg Phe Ala Leu Asp Trp Val Gln Arg Asn Ile Ala
        195                 200                 205 gcc ttt ggc ggt gat cct cga aag gtc aca ata ttt ggg cag agt gcg      672
Ala Phe Gly Gly Asp Pro Arg Lys Val Thr Ile Phe Gly Gln Ser Ala
    210                 215                 220 ggg ggc aga agt gtc gac gtc ctc ttg acg tct atg cca cac aac cca      720
Gly Gly Arg Ser Val Asp Val Leu Leu Thr Ser Met Pro His Asn Pro
225                 230                 235                 240 ccc ttc cga gca gca atc atg gag tcc ggt gtg gct aac tac aac ttc      768
Pro Phe Arg Ala Ala Ile Met Glu Ser Gly Val Ala Asn Tyr Asn Phe
                245                 250                 255 ccc aag gga gat ttg tcc gaa cct tgg aac acc act gtt caa gct ctc      816
Pro Lys Gly Asp Leu Ser Glu Pro Trp Asn Thr Thr Val Gln Ala Leu
            260                 265                 270 aac tgt acc acc agt atc gac atc ttg agt tgt atg aga aga gtc gat      864
Asn Cys Thr Thr Ser Ile Asp Ile Leu Ser Cys Met Arg Arg Val Asp
        275                 280                 285 ctc gcc act ctg atg aac acg atc gag caa ctc gga ctt ggg ttt gag      912
Leu Ala Thr Leu Met Asn Thr Ile Glu Gln Leu Gly Leu Gly Phe Glu
    290                 295                 300 tac acg ttg gac aac gta acg gct gtg tac cgt tct gaa acg gct cgc      960
Tyr Thr Leu Asp Asn Val Thr Ala Val Tyr Arg Ser Glu Thr Ala Arg
305                 310                 315                 320 acg act ggt gac att gct cgt gta cct gtt ctc gtc ggg acg gtg gcc     1008
Thr Thr Gly Asp Ile Ala Arg Val Pro Val Leu Val Gly Thr Val Ala
                325                 330                 335 aac gac gga ctt ctc ttt gtc ctc ggg gag aat gac acc caa gca tat     1056
Asn Asp Gly Leu Leu Phe Val Leu Gly Glu Asn Asp Thr Gln Ala Tyr
            340                 345                 350 ctc gag gag gca atc ccg aat cag ccc gac ctt tac cag act ctc ctt     1104
Leu Glu Glu Ala Ile Pro Asn Gln Pro Asp Leu Tyr Gln Thr Leu Leu
        355                 360                 365 gga gca tat ccc att gga tcc cca ggg atc gga tcg cct caa gat cag     1152
Gly Ala Tyr Pro Ile Gly Ser Pro Gly Ile Gly Ser Pro Gln Asp Gln
    370                 375                 380 att gcc gcc att gag acc gag gta aga ttc cag tgt cct tct gcc atc     1200
Ile Ala Ala Ile Glu Thr Glu Val Arg Phe Gln Cys Pro Ser Ala Ile
385                 390                 395                 400 gtg gct cag gac tcc cgg aat cgg ggt atc cct tct tgg cgc tac tac     1248
Val Ala Gln Asp Ser Arg Asn Arg Gly Ile Pro Ser Trp Arg Tyr Tyr
                405                 410                 415 tac aat gcg acc ttt gag aat ctg gag ctt ttc cct ggg tcc gaa gtg     1296
Tyr Asn Ala Thr Phe Glu Asn Leu Glu Leu Phe Pro Gly Ser Glu Val
            420                 425                 430
```

-continued

| | | |
|---|---|---|
| tac cac agc tct gaa gtc ggg atg gtg ttt ggc acg tat cct gtc gca<br>Tyr His Ser Ser Glu Val Gly Met Val Phe Gly Thr Tyr Pro Val Ala<br>435 440 445 | 1344 | |
| agt gcg acc gcc ttg gag gcc cag acg agc aaa tac atg cag ggt gcc<br>Ser Ala Thr Ala Leu Glu Ala Gln Thr Ser Lys Tyr Met Gln Gly Ala<br>450 455 460 | 1392 | |
| tgg gcg gcc ttt gcc aaa aac ccc atg aat ggg cct ggg tgg aaa caa<br>Trp Ala Ala Phe Ala Lys Asn Pro Met Asn Gly Pro Gly Trp Lys Gln<br>465 470 475 480 | 1440 | |
| gtg ccg aat gtc gcg gcg ctt ggc tca cca ggc aaa gcc atc cag gtt<br>Val Pro Asn Val Ala Ala Leu Gly Ser Pro Gly Lys Ala Ile Gln Val<br>485 490 495 | 1488 | |
| gac gtc tct cca gcg aca ata gac caa cga tgt gcc ttg tac acg cgt<br>Asp Val Ser Pro Ala Thr Ile Asp Gln Arg Cys Ala Leu Tyr Thr Arg<br>500 505 510 | 1536 | |
| tat tat act gag ttg ggc aca atc gcg ccg agg aca ttt ggc gga ggc<br>Tyr Tyr Thr Glu Leu Gly Thr Ile Ala Pro Arg Thr Phe Gly Gly Gly<br>515 520 525 | 1584 | |
| agc ggc gga ggc agc ggc gga ggc agc aaa gac aac gtt gcg gac gtg<br>Ser Gly Gly Gly Ser Gly Gly Gly Ser Lys Asp Asn Val Ala Asp Val<br>530 535 540 | 1632 | |
| gta gtg gtg ggc gct ggc ttg agc ggt ttg gag acg gca cgc aaa gtc<br>Val Val Val Gly Ala Gly Leu Ser Gly Leu Glu Thr Ala Arg Lys Val<br>545 550 555 560 | 1680 | |
| cag gcc gcc ggt ctg tcc tgc ctc gtt ctt gag gcg atg gat cgt gta<br>Gln Ala Ala Gly Leu Ser Cys Leu Val Leu Glu Ala Met Asp Arg Val<br>565 570 575 | 1728 | |
| ggg gga aag act ctg agc gta caa tcg ggt ccc ggc agg acg act atc<br>Gly Gly Lys Thr Leu Ser Val Gln Ser Gly Pro Gly Arg Thr Thr Ile<br>580 585 590 | 1776 | |
| aac gac ctc ggc gct gcg tgg atc aat gac agc aac caa agc gaa gta<br>Asn Asp Leu Gly Ala Ala Trp Ile Asn Asp Ser Asn Gln Ser Glu Val<br>595 600 605 | 1824 | |
| tcc aga ttg ttt gaa aga ttt cat ttg gag ggc gag ctc cag agg acg<br>Ser Arg Leu Phe Glu Arg Phe His Leu Glu Gly Glu Leu Gln Arg Thr<br>610 615 620 | 1872 | |
| act gga aat tca atc cat caa gca caa gac ggt aca acc act aca gct<br>Thr Gly Asn Ser Ile His Gln Ala Gln Asp Gly Thr Thr Thr Thr Ala<br>625 630 635 640 | 1920 | |
| cct tat ggt gac tcc ttg ctg agc gag gag gtt gca agt gca ctt gcg<br>Pro Tyr Gly Asp Ser Leu Leu Ser Glu Glu Val Ala Ser Ala Leu Ala<br>645 650 655 | 1968 | |
| gaa ctc ctc ccc gta tgg tct cag ctg atc gaa gag cat agc ctt caa<br>Glu Leu Leu Pro Val Trp Ser Gln Leu Ile Glu Glu His Ser Leu Gln<br>660 665 670 | 2016 | |
| gac ctc aag gcg agc cct cag gcg aag cgg ctc gac agt gtg agc ttc<br>Asp Leu Lys Ala Ser Pro Gln Ala Lys Arg Leu Asp Ser Val Ser Phe<br>675 680 685 | 2064 | |
| gcg cac tac tgt gag aag gaa cta aac ttg cct gct gtt ctc ggc gta<br>Ala His Tyr Cys Glu Lys Glu Leu Asn Leu Pro Ala Val Leu Gly Val<br>690 695 700 | 2112 | |
| gca aac cag atc aca cgc gct ctg ctc ggt gtg gaa gcc cac gag atc<br>Ala Asn Gln Ile Thr Arg Ala Leu Leu Gly Val Glu Ala His Glu Ile<br>705 710 715 720 | 2160 | |
| agc atg ctt ttt ctc acc gac tac atc aag agt gcc acc ggt ctc agt<br>Ser Met Leu Phe Leu Thr Asp Tyr Ile Lys Ser Ala Thr Gly Leu Ser<br>725 730 735 | 2208 | |
| aat att ttc tcg gac aag aaa gac ggc ggg cag tat atg cga tgc aaa<br>Asn Ile Phe Ser Asp Lys Lys Asp Gly Gly Gln Tyr Met Arg Cys Lys | 2256 | |

```
                    740                 745                 750
aca ggt atg cag tcg att tgc cat gcc atg tca aag gaa ctt gtt cca      2304
Thr Gly Met Gln Ser Ile Cys His Ala Met Ser Lys Glu Leu Val Pro
        755                 760                 765 ggc tca gtg cac ctc aac acc ccc gtc gct gaa att gag cag tcg gca      2352
Gly Ser Val His Leu Asn Thr Pro Val Ala Glu Ile Glu Gln Ser Ala
        770                 775                 780 tcc ggc tgt aca gta cga tcg gcc tcg ggc gcc gtg ttc cga agc aaa      2400
Ser Gly Cys Thr Val Arg Ser Ala Ser Gly Ala Val Phe Arg Ser Lys
785                 790                 795                 800 aag gtg gtg gtt tcg tta ccg aca acc ttg tat ccc acc ttg aca ttt      2448
Lys Val Val Val Ser Leu Pro Thr Thr Leu Tyr Pro Thr Leu Thr Phe
                805                 810                 815 tca cca cct ctt ccc gcc gag aag caa gca ttg gcg gaa aat tct atc      2496
Ser Pro Pro Leu Pro Ala Glu Lys Gln Ala Leu Ala Glu Asn Ser Ile
        820                 825                 830 ctg ggc tac tat agc aag ata gtc ttc gta tgg gac aag ccg tgg tgg      2544
Leu Gly Tyr Tyr Ser Lys Ile Val Phe Val Trp Asp Lys Pro Trp Trp
        835                 840                 845 cgc gaa caa ggc ttc tcg ggc gtc ctc caa tcg agc tgt gac ccc atc      2592
Arg Glu Gln Gly Phe Ser Gly Val Leu Gln Ser Ser Cys Asp Pro Ile
        850                 855                 860 tca ttt gcc aga gat acc agc atc gac gtc gat cga caa tgg tcc att      2640
Ser Phe Ala Arg Asp Thr Ser Ile Asp Val Asp Arg Gln Trp Ser Ile
865                 870                 875                 880 acc tgt ttc atg gtc gga gac ccg gga cgg aag tgg tcc caa cag tcc      2688
Thr Cys Phe Met Val Gly Asp Pro Gly Arg Lys Trp Ser Gln Gln Ser
                885                 890                 895 aag cag gta cga caa aag tct gtc tgg gac caa ctc cgc gca gcc tac      2736
Lys Gln Val Arg Gln Lys Ser Val Trp Asp Gln Leu Arg Ala Ala Tyr
        900                 905                 910 gag aac gcc ggg gcc caa gtc cca gag ccg gcc aac gtg ctc gaa atc      2784
Glu Asn Ala Gly Ala Gln Val Pro Glu Pro Ala Asn Val Leu Glu Ile
        915                 920                 925 gag tgg tcg aag cag cag tat ttc caa gga gct ccg agc gcc gtc tat      2832
Glu Trp Ser Lys Gln Gln Tyr Phe Gln Gly Ala Pro Ser Ala Val Tyr
930                 935                 940 ggg ctg aac gat ctc atc aca ctg ggt tcg gcg ctc aga acg ccg ttc      2880
Gly Leu Asn Asp Leu Ile Thr Leu Gly Ser Ala Leu Arg Thr Pro Phe
945                 950                 955                 960 aag agt gtt cat ttc gtt gga acg gag acg tct tta gtt tgg aaa ggg      2928
Lys Ser Val His Phe Val Gly Thr Glu Thr Ser Leu Val Trp Lys Gly
                965                 970                 975 tat atg gaa ggg gcc ata cga tcg ggt caa cga ggt gct gca gaa gtt      2976
Tyr Met Glu Gly Ala Ile Arg Ser Gly Gln Arg Gly Ala Ala Glu Val
                980                 985                 990 gtg gct agc ctg gtg cca gca gca tag                                  3003
Val Ala Ser Leu Val Pro Ala Ala
        995                 1000

<210> SEQ ID NO 25
<211> LENGTH: 1000
<212> TYPE: PRT
<213> ORGANISM: unknown
<220> FEATURE:
<223> OTHER INFORMATION: K:trAPAO (Exophiala spinifera)
<220> FEATURE:
<221> NAME/KEY: misc_feature
<222> LOCATION: (73)..(1575)
<223> OTHER INFORMATION: espl mat
<220> FEATURE:
<221> NAME/KEY: misc_feature
```

```
<222> LOCATION: (1576)..(1611)
<223> OTHER INFORMATION: spacer sequence
<220> FEATURE:
<221> NAME/KEY: misc_feature
<222> LOCATION: (1612)..(3000)
<223> OTHER INFORMATION: K:trAPAO
<220> FEATURE:
<221> NAME/KEY: misc_feature
<222> LOCATION: (1612)..(1614)
<223> OTHER INFORMATION: extra lysine

<400> SEQUENCE: 25
```

| Met | Ala | Asn | Lys | His | Leu | Ser | Leu | Ser | Leu | Phe | Leu | Val | Leu | Leu | Gly |
|---|---|---|---|---|---|---|---|---|---|---|---|---|---|---|---|
| 1 | | | | 5 | | | | | 10 | | | | | 15 | |

| Leu | Ser | Ala | Ser | Leu | Ala | Ser | Gly | Ala | Pro | Thr | Val | Lys | Ile | Asp | Ala |
|---|---|---|---|---|---|---|---|---|---|---|---|---|---|---|---|
| | | | 20 | | | | | 25 | | | | | 30 | | |

| Gly | Met | Val | Val | Gly | Thr | Thr | Thr | Val | Pro | Gly | Thr | Thr | Ala | Thr |
|---|---|---|---|---|---|---|---|---|---|---|---|---|---|---|
| | | 35 | | | | | 40 | | | | | 45 | | |

| Val | Ser | Glu | Phe | Leu | Gly | Val | Pro | Phe | Ala | Ala | Ser | Pro | Thr | Arg | Phe |
|---|---|---|---|---|---|---|---|---|---|---|---|---|---|---|---|
| | 50 | | | | | 55 | | | | | 60 | | | | |

| Ala | Pro | Pro | Thr | Arg | Pro | Val | Pro | Trp | Ser | Thr | Pro | Leu | Gln | Ala | Thr |
|---|---|---|---|---|---|---|---|---|---|---|---|---|---|---|---|
| 65 | | | | | 70 | | | | | 75 | | | | | 80 |

| Ala | Tyr | Gly | Pro | Ala | Cys | Pro | Gln | Gln | Phe | Asn | Tyr | Pro | Glu | Glu | Leu |
|---|---|---|---|---|---|---|---|---|---|---|---|---|---|---|---|
| | | | | 85 | | | | | 90 | | | | | 95 | |

| Arg | Glu | Ile | Thr | Met | Ala | Trp | Phe | Asn | Thr | Pro | Pro | Ser | Ala | Gly |
|---|---|---|---|---|---|---|---|---|---|---|---|---|---|---|
| | | | 100 | | | | | 105 | | | | | 110 | |

| Glu | Ser | Glu | Asp | Cys | Leu | Asn | Leu | Asn | Ile | Tyr | Val | Pro | Gly | Thr | Glu |
|---|---|---|---|---|---|---|---|---|---|---|---|---|---|---|---|
| | | 115 | | | | | 120 | | | | | 125 | | | |

| Asn | Thr | Asn | Lys | Ala | Val | Met | Val | Trp | Ile | Tyr | Gly | Gly | Ala | Leu | Glu |
|---|---|---|---|---|---|---|---|---|---|---|---|---|---|---|---|
| | 130 | | | | | 135 | | | | | 140 | | | | |

| Tyr | Gly | Trp | Asn | Ser | Phe | His | Leu | Tyr | Asp | Gly | Ala | Ser | Phe | Ala | Ala |
|---|---|---|---|---|---|---|---|---|---|---|---|---|---|---|---|
| 145 | | | | | 150 | | | | | 155 | | | | | 160 |

| Asn | Gln | Asp | Val | Ile | Ala | Val | Thr | Ile | Asn | Tyr | Arg | Thr | Asn | Ile | Leu |
|---|---|---|---|---|---|---|---|---|---|---|---|---|---|---|---|
| | | | | 165 | | | | | 170 | | | | | 175 | |

| Gly | Phe | Pro | Ala | Ala | Pro | Gln | Leu | Pro | Ile | Thr | Gln | Arg | Asn | Leu | Gly |
|---|---|---|---|---|---|---|---|---|---|---|---|---|---|---|---|
| | | | 180 | | | | | 185 | | | | | 190 | | |

| Phe | Leu | Asp | Gln | Arg | Phe | Ala | Leu | Asp | Trp | Val | Gln | Arg | Asn | Ile | Ala |
|---|---|---|---|---|---|---|---|---|---|---|---|---|---|---|---|
| | | 195 | | | | | 200 | | | | | 205 | | | |

| Ala | Phe | Gly | Gly | Asp | Pro | Arg | Lys | Val | Thr | Ile | Phe | Gly | Gln | Ser | Ala |
|---|---|---|---|---|---|---|---|---|---|---|---|---|---|---|---|
| | 210 | | | | | 215 | | | | | 220 | | | | |

| Gly | Gly | Arg | Ser | Val | Asp | Val | Leu | Leu | Thr | Ser | Met | Pro | His | Asn | Pro |
|---|---|---|---|---|---|---|---|---|---|---|---|---|---|---|---|
| 225 | | | | | 230 | | | | | 235 | | | | | 240 |

| Pro | Phe | Arg | Ala | Ala | Ile | Met | Glu | Ser | Gly | Val | Ala | Asn | Tyr | Asn | Phe |
|---|---|---|---|---|---|---|---|---|---|---|---|---|---|---|---|
| | | | | 245 | | | | | 250 | | | | | 255 | |

| Pro | Lys | Gly | Asp | Leu | Ser | Glu | Pro | Trp | Asn | Thr | Thr | Val | Gln | Ala | Leu |
|---|---|---|---|---|---|---|---|---|---|---|---|---|---|---|---|
| | | | 260 | | | | | 265 | | | | | 270 | | |

| Asn | Cys | Thr | Thr | Ser | Ile | Asp | Ile | Leu | Ser | Cys | Met | Arg | Arg | Val | Asp |
|---|---|---|---|---|---|---|---|---|---|---|---|---|---|---|---|
| | | 275 | | | | | 280 | | | | | 285 | | | |

| Leu | Ala | Thr | Leu | Met | Asn | Thr | Ile | Glu | Gln | Leu | Gly | Leu | Gly | Phe | Glu |
|---|---|---|---|---|---|---|---|---|---|---|---|---|---|---|---|
| | 290 | | | | | 295 | | | | | 300 | | | | |

| Tyr | Thr | Leu | Asp | Asn | Val | Thr | Ala | Val | Tyr | Arg | Ser | Glu | Thr | Ala | Arg |
|---|---|---|---|---|---|---|---|---|---|---|---|---|---|---|---|
| 305 | | | | | 310 | | | | | 315 | | | | | 320 |

| Thr | Thr | Gly | Asp | Ile | Ala | Arg | Val | Pro | Val | Leu | Val | Gly | Thr | Val | Ala |
|---|---|---|---|---|---|---|---|---|---|---|---|---|---|---|---|
| | | | | 325 | | | | | 330 | | | | | 335 | |

| Asn | Asp | Gly | Leu | Leu | Phe | Val | Leu | Gly | Glu | Asn | Asp | Thr | Gln | Ala | Tyr |
|---|---|---|---|---|---|---|---|---|---|---|---|---|---|---|---|
| | | | 340 | | | | | 345 | | | | | 350 | | |

-continued

```
Leu Glu Glu Ala Ile Pro Asn Gln Pro Asp Leu Tyr Gln Thr Leu Leu
            355                 360                 365
Gly Ala Tyr Pro Ile Gly Ser Pro Gly Ile Gly Ser Pro Gln Asp Gln
        370                 375                 380
Ile Ala Ala Ile Glu Thr Glu Val Arg Phe Gln Cys Pro Ser Ala Ile
385                 390                 395                 400
Val Ala Gln Asp Ser Arg Asn Arg Gly Ile Pro Ser Trp Arg Tyr Tyr
                405                 410                 415
Tyr Asn Ala Thr Phe Glu Asn Leu Glu Leu Phe Pro Gly Ser Glu Val
            420                 425                 430
Tyr His Ser Ser Glu Val Gly Met Val Phe Gly Thr Tyr Pro Val Ala
        435                 440                 445
Ser Ala Thr Ala Leu Glu Ala Gln Thr Ser Lys Tyr Met Gln Gly Ala
    450                 455                 460
Trp Ala Ala Phe Ala Lys Asn Pro Met Asn Gly Pro Gly Trp Lys Gln
465                 470                 475                 480
Val Pro Asn Val Ala Ala Leu Gly Ser Pro Gly Lys Ala Ile Gln Val
                485                 490                 495
Asp Val Ser Pro Ala Thr Ile Asp Gln Arg Cys Ala Leu Tyr Thr Arg
            500                 505                 510
Tyr Tyr Thr Glu Leu Gly Thr Ile Ala Pro Arg Thr Phe Gly Gly Gly
        515                 520                 525
Ser Gly Gly Gly Ser Gly Gly Gly Ser Lys Asp Asn Val Ala Asp Val
    530                 535                 540
Val Val Val Gly Ala Gly Leu Ser Gly Leu Glu Thr Ala Arg Lys Val
545                 550                 555                 560
Gln Ala Ala Gly Leu Ser Cys Leu Val Leu Glu Ala Met Asp Arg Val
                565                 570                 575
Gly Gly Lys Thr Leu Ser Val Gln Ser Gly Pro Gly Arg Thr Thr Ile
            580                 585                 590
Asn Asp Leu Gly Ala Ala Trp Ile Asn Asp Ser Asn Gln Ser Glu Val
        595                 600                 605
Ser Arg Leu Phe Glu Arg Phe His Leu Glu Gly Glu Leu Gln Arg Thr
    610                 615                 620
Thr Gly Asn Ser Ile His Gln Ala Gln Asp Gly Thr Thr Thr Thr Ala
625                 630                 635                 640
Pro Tyr Gly Asp Ser Leu Leu Ser Glu Glu Val Ala Ser Ala Leu Ala
                645                 650                 655
Glu Leu Leu Pro Val Trp Ser Gln Leu Ile Glu Glu His Ser Leu Gln
            660                 665                 670
Asp Leu Lys Ala Ser Pro Gln Ala Lys Arg Leu Asp Ser Val Ser Phe
        675                 680                 685
Ala His Tyr Cys Glu Lys Glu Leu Asn Leu Pro Ala Val Leu Gly Val
    690                 695                 700
Ala Asn Gln Ile Thr Arg Ala Leu Leu Gly Val Glu Ala His Glu Ile
705                 710                 715                 720
Ser Met Leu Phe Leu Thr Asp Tyr Ile Lys Ser Ala Thr Gly Leu Ser
                725                 730                 735
Asn Ile Phe Ser Asp Lys Lys Asp Gly Gly Gln Tyr Met Arg Cys Lys
            740                 745                 750
Thr Gly Met Gln Ser Ile Cys His Ala Met Ser Lys Glu Leu Val Pro
        755                 760                 765
Gly Ser Val His Leu Asn Thr Pro Val Ala Glu Ile Glu Gln Ser Ala
```

```
                    770             775             780
Ser Gly Cys Thr Val Arg Ser Ala Ser Gly Ala Val Phe Arg Ser Lys
785                 790             795                 800

Lys Val Val Ser Leu Pro Thr Thr Leu Tyr Pro Thr Leu Thr Phe
                805             810              815

Ser Pro Pro Leu Pro Ala Glu Lys Gln Ala Leu Ala Glu Asn Ser Ile
            820             825             830

Leu Gly Tyr Tyr Ser Lys Ile Val Phe Val Trp Asp Lys Pro Trp Trp
            835             840             845

Arg Glu Gln Gly Phe Ser Gly Val Leu Gln Ser Ser Cys Asp Pro Ile
850             855             860

Ser Phe Ala Arg Asp Thr Ser Ile Asp Val Asp Arg Gln Trp Ser Ile
865             870             875             880

Thr Cys Phe Met Val Gly Asp Pro Gly Arg Lys Trp Ser Gln Gln Ser
                885             890             895

Lys Gln Val Arg Gln Lys Ser Val Trp Asp Gln Leu Arg Ala Ala Tyr
            900             905             910

Glu Asn Ala Gly Ala Gln Val Pro Glu Pro Ala Asn Val Leu Glu Ile
            915             920             925

Glu Trp Ser Lys Gln Gln Tyr Phe Gln Gly Ala Pro Ser Ala Val Tyr
            930             935             940

Gly Leu Asn Asp Leu Ile Thr Leu Gly Ser Ala Leu Arg Thr Pro Phe
945             950             955             960

Lys Ser Val His Phe Val Gly Thr Glu Thr Ser Leu Val Trp Lys Gly
                965             970             975

Tyr Met Glu Gly Ala Ile Arg Ser Gly Gln Arg Gly Ala Ala Glu Val
            980             985             990

Val Ala Ser Leu Val Pro Ala Ala
            995             1000

<210> SEQ ID NO 26
<211> LENGTH: 2976
<212> TYPE: DNA
<213> ORGANISM: Unknown
<220> FEATURE:
<223> OTHER INFORMATION: signal:BEST1 mature:spacer:K:trAPAO (Exophiala
      spinifera)
<220> FEATURE:
<221> NAME/KEY: sig_peptide
<222> LOCATION: (1)..(72)
<223> OTHER INFORMATION: Barley alpha amylase signal sequence
<220> FEATURE:
<221> NAME/KEY: mat_peptide
<222> LOCATION: (73)..(1545)
<223> OTHER INFORMATION: BEST1 mature
<220> FEATURE:
<221> NAME/KEY: misc_feature
<222> LOCATION: (1546)..(1584)
<223> OTHER INFORMATION: spacer sequence
<220> FEATURE:
<221> NAME/KEY: misc_feature
<222> LOCATION: (1585)..(2973)
<223> OTHER INFORMATION: K:trAPAO
<220> FEATURE:
<221> NAME/KEY: CDS
<222> LOCATION: (1)..(2973)
<223> OTHER INFORMATION:
<220> FEATURE:
<221> NAME/KEY: misc_feature
<222> LOCATION: (1585)..(1587)
<223> OTHER INFORMATION: Extra lysine

<400> SEQUENCE: 26
```

```
atg gcc aac aag cac ctg agc ctc tcc ctc ttc ctc gtg ctc ctc ggc         48
Met Ala Asn Lys His Leu Ser Leu Ser Leu Phe Leu Val Leu Leu Gly
            -20             -15             -10 ctc tcc gcc tcc ctc gcc agc ggc acg gat ttt ccg gtc cgc agg acc         96
Leu Ser Ala Ser Leu Ala Ser Gly Thr Asp Phe Pro Val Arg Arg Thr
         -5              -1  1                   5 gat ctg ggc cag gtt cag gga ctg gcc ggg gac gtg atg agc ttt cgc        144
Asp Leu Gly Gln Val Gln Gly Leu Ala Gly Asp Val Met Ser Phe Arg
     10              15                  20 gga ata ccc tat gca gcg ccg ccg gtg ggc ggg ctg cgt tgg aag ccg        192
Gly Ile Pro Tyr Ala Ala Pro Pro Val Gly Gly Leu Arg Trp Lys Pro
 25              30              35                      40 ccc caa cac gcc cgg ccc tgg gcg ggc gtt cgc ccc gcc acc caa ttt        240
Pro Gln His Ala Arg Pro Trp Ala Gly Val Arg Pro Ala Thr Gln Phe
             45              50                  55 ggc tcc gac tgc ttc ggc gcg gcc tat ctt cgc aaa ggc agc ctc gcc        288
Gly Ser Asp Cys Phe Gly Ala Ala Tyr Leu Arg Lys Gly Ser Leu Ala
             60              65              70 ccc ggc gtg agc gag gac tgt ctt tac ctc aac gta tgg gcg ccg tca        336
Pro Gly Val Ser Glu Asp Cys Leu Tyr Leu Asn Val Trp Ala Pro Ser
             75              80              85 ggc gct aaa ccc ggc cag tac ccc gtc atg gtc tgg gtc tac ggc ggc        384
Gly Ala Lys Pro Gly Gln Tyr Pro Val Met Val Trp Val Tyr Gly Gly
         90              95              100 ggc ttc gcc ggc ggc acg gcc gcc atg ccc tac tac gac ggc gag gcg        432
Gly Phe Ala Gly Gly Thr Ala Ala Met Pro Tyr Tyr Asp Gly Glu Ala
105             110             115                 120 ctt gcg cga cag ggc gtc gtc gtg gtg acg ttt aac tat cgg acg aac        480
Leu Ala Arg Gln Gly Val Val Val Val Thr Phe Asn Tyr Arg Thr Asn
                125             130                 135 atc ctg ggc ttt ttc gcc cat cct ggt ctc tcg cgc gag agc ccc acc        528
Ile Leu Gly Phe Phe Ala His Pro Gly Leu Ser Arg Glu Ser Pro Thr
             140             145             150 gga act tcg ggc aac tac ggc cta ctc gac att ctc gcc gct ctt cgg        576
Gly Thr Ser Gly Asn Tyr Gly Leu Leu Asp Ile Leu Ala Ala Leu Arg
         155             160             165 tgg gtg cag agc aac gcc cgc gcc ttc gga ggg gac ccc ggc cga gtg        624
Trp Val Gln Ser Asn Ala Arg Ala Phe Gly Gly Asp Pro Gly Arg Val
     170             175             180 acg gtc ttt ggt gaa tcg gcc gga gcg agc gcg atc gga ctt ctg ctc        672
Thr Val Phe Gly Glu Ser Ala Gly Ala Ser Ala Ile Gly Leu Leu Leu
185             190             195                 200 acc tcg ccg ctg agc aag ggt ctc ttc cgt ggc gct atc ctc gaa agt        720
Thr Ser Pro Leu Ser Lys Gly Leu Phe Arg Gly Ala Ile Leu Glu Ser
             205             210             215 cca ggg ctg acg cga ccg ctc gcg acg ctc gcc gac agc gcc gcc tcg        768
Pro Gly Leu Thr Arg Pro Leu Ala Thr Leu Ala Asp Ser Ala Ala Ser
         220             225             230 ggc gag cgc ctc gac gcc gat ctt tcg cga ctg cgc tcg acc gac cca        816
Gly Glu Arg Leu Asp Ala Asp Leu Ser Arg Leu Arg Ser Thr Asp Pro
     235             240             245 gcc acc ctg atg gcg cgc gcc gac gcg gcc cgc ccg gca tcg cgg gac        864
Ala Thr Leu Met Ala Arg Ala Asp Ala Ala Arg Pro Ala Ser Arg Asp
 250             255             260 ctg cgc agg ccg cgt ccg acc gga ccg atc gtc gat ggc cat gtg ctg        912
Leu Arg Arg Pro Arg Pro Thr Gly Pro Ile Val Asp Gly His Val Leu
265             270             275                 280 ccg cag acc gac agc gcg gcg atc gcg gcg ggg cag ctg gcg ccg gtt        960
Pro Gln Thr Asp Ser Ala Ala Ile Ala Ala Gly Gln Leu Ala Pro Val
             285             290             295
```

```
                                                         -continued cgg gtc ctg atc gga acc aat gcc gac gaa ggc cgc gcc ttc ctc ggg    1008
Arg Val Leu Ile Gly Thr Asn Ala Asp Glu Gly Arg Ala Phe Leu Gly
        300                 305                 310 cgc gcg ccg atg gag acg cca gcg gac tac caa gcc tat ctg gag gcg    1056
Arg Ala Pro Met Glu Thr Pro Ala Asp Tyr Gln Ala Tyr Leu Glu Ala
    315                 320                 325 cag ttt ggc gac caa gcc gcc gcc gtg gcg gcg tgc tat ccc ctc gac    1104
Gln Phe Gly Asp Gln Ala Ala Ala Val Ala Ala Cys Tyr Pro Leu Asp
330                 335                 340 ggc cgg gcc acg ccc aag gaa atg gtc gcg cgc atc ttc ggc gac aat    1152
Gly Arg Ala Thr Pro Lys Glu Met Val Ala Arg Ile Phe Gly Asp Asn
345                 350                 355                 360 cag ttc aat cgg ggg gtc tcg gcc ttc tcg gaa gcg ctt gtg cgc cag    1200
Gln Phe Asn Arg Gly Val Ser Ala Phe Ser Glu Ala Leu Val Arg Gln
            365                 370                 375 ggc gcg ccc gtg tgg cgt tat cag ttc aac ggt aat acc gag ggt gga    1248
Gly Ala Pro Val Trp Arg Tyr Gln Phe Asn Gly Asn Thr Glu Gly Gly
        380                 385                 390 aga gcg ccg gct acc cac gga gcc gaa att ccc tac gtt ttc ggg gtg    1296
Arg Ala Pro Ala Thr His Gly Ala Glu Ile Pro Tyr Val Phe Gly Val
    395                 400                 405 ttc aag ctc gac gag ttg ggt ctg ttc gat tgg ccg ccc gag ggg ccc    1344
Phe Lys Leu Asp Glu Leu Gly Leu Phe Asp Trp Pro Pro Glu Gly Pro
410                 415                 420 acg ccc gcc gac cgt gcg ctg ggc caa ctg atg tcc tcc gcc tgg gtc    1392
Thr Pro Ala Asp Arg Ala Leu Gly Gln Leu Met Ser Ser Ala Trp Val
425                 430                 435                 440 cgg ttc gcc aag aat ggc gac ccc gcc ggg gac gcc ctt acc tgg cct    1440
Arg Phe Ala Lys Asn Gly Asp Pro Ala Gly Asp Ala Leu Thr Trp Pro
            445                 450                 455 gcc tat tct acg ggc aag tcg acc atg aca ttc ggt ccc gag ggc cgc    1488
Ala Tyr Ser Thr Gly Lys Ser Thr Met Thr Phe Gly Pro Glu Gly Arg
        460                 465                 470 gcg gcg gtg gtg tcg ccc gga cct tcc atc ccc cct tgc gcg gat ggc    1536
Ala Ala Val Val Ser Pro Gly Pro Ser Ile Pro Pro Cys Ala Asp Gly
    475                 480                 485 gcc aag gcg ggg ggc gga ggc agc ggc gga ggc agc ggc gga ggc agc    1584
Ala Lys Ala Gly Gly Gly Ser Gly Gly Gly Ser Gly Gly Gly Ser
490                 495                 500 aaa gac aac gtt gcg gac gtg gta gtg gtg ggc gct ggc ttg agc ggt    1632
Lys Asp Asn Val Ala Asp Val Val Val Val Gly Ala Gly Leu Ser Gly
505                 510                 515                 520 ttg gag acg gca cgc aaa gtc cag gcc gcc ggt ctg tcc tgc ctc gtt    1680
Leu Glu Thr Ala Arg Lys Val Gln Ala Ala Gly Leu Ser Cys Leu Val
            525                 530                 535 ctt gag gcg atg gat cgt gta ggg gga aag act ctg agc gta caa tcg    1728
Leu Glu Ala Met Asp Arg Val Gly Gly Lys Thr Leu Ser Val Gln Ser
        540                 545                 550 ggt ccc ggc agg acg act atc aac gac ctc ggc gct gcg tgg atc aat    1776
Gly Pro Gly Arg Thr Thr Ile Asn Asp Leu Gly Ala Ala Trp Ile Asn
    555                 560                 565 gac agc aac caa agc gaa gta tcc aga ttg ttt gaa aga ttt cat ttg    1824
Asp Ser Asn Gln Ser Glu Val Ser Arg Leu Phe Glu Arg Phe His Leu
570                 575                 580 gag ggc gag ctc cag agg acg act gga aat tca atc cat caa gca caa    1872
Glu Gly Glu Leu Gln Arg Thr Thr Gly Asn Ser Ile His Gln Ala Gln
585                 590                 595                 600 gac ggt aca acc act aca gct cct tat ggt gac tcc ttg ctg agc gag    1920
Asp Gly Thr Thr Thr Thr Ala Pro Tyr Gly Asp Ser Leu Leu Ser Glu
```

|   |   |
|---|---|
| 605 610 615 | |
| gag gtt gca agt gca ctt gcg gaa ctc ctc ccc gta tgg tct cag ctg<br>Glu Val Ala Ser Ala Leu Ala Glu Leu Leu Pro Val Trp Ser Gln Leu<br>620 625 630 | 1968 |
| atc gaa gag cat agc ctt caa gac ctc aag gcg agc cct cag gcg aag<br>Ile Glu Glu His Ser Leu Gln Asp Leu Lys Ala Ser Pro Gln Ala Lys<br>635 640 645 | 2016 |
| cgg ctc gac agt gtg agc ttc gcg cac tac tgt gag aag gaa cta aac<br>Arg Leu Asp Ser Val Ser Phe Ala His Tyr Cys Glu Lys Glu Leu Asn<br>650 655 660 | 2064 |
| ttg cct gct gtt ctc ggc gta gca aac cag atc aca cgc gct ctg ctc<br>Leu Pro Ala Val Leu Gly Val Ala Asn Gln Ile Thr Arg Ala Leu Leu<br>665 670 675 680 | 2112 |
| ggt gtg gaa gcc cac gag atc agc atg ctt ttt ctc acc gac tac atc<br>Gly Val Glu Ala His Glu Ile Ser Met Leu Phe Leu Thr Asp Tyr Ile<br>685 690 695 | 2160 |
| aag agt gcc acc ggt ctc agt aat att ttc tcg gac aag aaa gac ggc<br>Lys Ser Ala Thr Gly Leu Ser Asn Ile Phe Ser Asp Lys Lys Asp Gly<br>700 705 710 | 2208 |
| ggg cag tat atg cga tgc aaa aca ggt atg cag tcg att tgc cat gcc<br>Gly Gln Tyr Met Arg Cys Lys Thr Gly Met Gln Ser Ile Cys His Ala<br>715 720 725 | 2256 |
| atg tca aag gaa ctt gtt cca ggc tca gtg cac ctc aac acc ccc gtc<br>Met Ser Lys Glu Leu Val Pro Gly Ser Val His Leu Asn Thr Pro Val<br>730 735 740 | 2304 |
| gct gaa att gag cag tcg gca tcc ggc tgt aca gta cga tcg gcc tcg<br>Ala Glu Ile Glu Gln Ser Ala Ser Gly Cys Thr Val Arg Ser Ala Ser<br>745 750 755 760 | 2352 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>765 770 775 | 2400 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>780 785 790 | 2448 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>795 800 805 | 2496 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>810 815 820 | 2544 |
| caa tcg agc tgt gac ccc atc tca ttt gcc aga gat acc agc atc gac<br>Gln Ser Ser Cys Asp Pro Ile Ser Phe Ala Arg Asp Thr Ser Ile Asp<br>825 830 835 840 | 2592 |
| gtc gat cga caa tgg tcc att acc tgt ttc atg gtc gga gac ccg gga<br>Val Asp Arg Gln Trp Ser Ile Thr Cys Phe Met Val Gly Asp Pro Gly<br>845 850 855 | 2640 |
| cgg aag tgg tcc caa cag tcc aag cag gta cga caa aag tct gtc tgg<br>Arg Lys Trp Ser Gln Gln Ser Lys Gln Val Arg Gln Lys Ser Val Trp<br>860 865 870 | 2688 |
| gac caa ctc cgc gca gcc tac gag aac gcc ggg gcc caa gtc cca gag<br>Asp Gln Leu Arg Ala Ala Tyr Glu Asn Ala Gly Ala Gln Val Pro Glu<br>875 880 885 | 2736 |
| ccg gcc aac gtg ctc gaa atc gag tgg tcg aag cag cag tat ttc caa<br>Pro Ala Asn Val Leu Glu Ile Glu Trp Ser Lys Gln Gln Tyr Phe Gln<br>890 895 900 | 2784 |
| gga gct ccg agc gcc gtc tat ggg ctg aac gat ctc atc aca ctg ggt<br>Gly Ala Pro Ser Ala Val Tyr Gly Leu Asn Asp Leu Ile Thr Leu Gly<br>905 910 915 920 | 2832 |
| tcg gcg ctc aga acg ccg ttc aag agt gtt cat ttc gtt gga acg gag | 2880 |

```
Ser Ala Leu Arg Thr Pro Phe Lys Ser Val His Phe Val Gly Thr Glu
                925                 930                 935 acg tct tta gtt tgg aaa ggg tat atg gaa ggg gcc ata cga tcg ggt       2928
Thr Ser Leu Val Trp Lys Gly Tyr Met Glu Gly Ala Ile Arg Ser Gly
                940                 945                 950 caa cga ggt gct gca gaa gtt gtg gct agc ctg gtg cca gca gca tag       2976
Gln Arg Gly Ala Ala Glu Val Val Ala Ser Leu Val Pro Ala Ala
                955                 960                 965

<210> SEQ ID NO 27
<211> LENGTH: 991
<212> TYPE: PRT
<213> ORGANISM: Unknown
<220> FEATURE:
<223> OTHER INFORMATION: signal:BEST1 mature:spacer:K:trAPAO (Exophiala
      spinifera)
<220> FEATURE:
<221> NAME/KEY: misc_feature
<222> LOCATION: (1546)..(1584)
<223> OTHER INFORMATION: spacer sequence
<220> FEATURE:
<221> NAME/KEY: misc_feature
<222> LOCATION: (1585)..(2973)
<223> OTHER INFORMATION: K:trAPAO
<220> FEATURE:
<221> NAME/KEY: misc_feature
<222> LOCATION: (1585)..(1587)
<223> OTHER INFORMATION: Extra lysine

<400> SEQUENCE: 27

Met Ala Asn Lys His Leu Ser Leu Ser Leu Phe Leu Val Leu Leu Gly
                -20                 -15                 -10

Leu Ser Ala Ser Leu Ala Ser Gly Thr Asp Phe Pro Val Arg Arg Thr
            -5              -1  1                   5

Asp Leu Gly Gln Val Gln Gly Leu Ala Gly Asp Val Met Ser Phe Arg
        10                  15                  20

Gly Ile Pro Tyr Ala Ala Pro Pro Val Gly Gly Leu Arg Trp Lys Pro
25                  30                  35                  40

Pro Gln His Ala Arg Pro Trp Ala Gly Val Arg Pro Ala Thr Gln Phe
                45                  50                  55

Gly Ser Asp Cys Phe Gly Ala Ala Tyr Leu Arg Lys Gly Ser Leu Ala
                60                  65                  70

Pro Gly Val Ser Glu Asp Cys Leu Tyr Leu Asn Val Trp Ala Pro Ser
            75                  80                  85

Gly Ala Lys Pro Gly Gln Tyr Pro Val Met Val Trp Val Tyr Gly Gly
        90                  95                  100

Gly Phe Ala Gly Gly Thr Ala Ala Met Pro Tyr Tyr Asp Gly Glu Ala
105                 110                 115                 120

Leu Ala Arg Gln Gly Val Val Val Thr Phe Asn Tyr Arg Thr Asn
                125                 130                 135

Ile Leu Gly Phe Phe Ala His Pro Gly Leu Ser Arg Glu Ser Pro Thr
                140                 145                 150

Gly Thr Ser Gly Asn Tyr Gly Leu Leu Asp Ile Leu Ala Ala Leu Arg
            155                 160                 165

Trp Val Gln Ser Asn Ala Arg Ala Phe Gly Gly Asp Pro Gly Arg Val
        170                 175                 180

Thr Val Phe Gly Glu Ser Ala Gly Ala Ser Ala Ile Gly Leu Leu Leu
185                 190                 195                 200

Thr Ser Pro Leu Ser Lys Gly Leu Phe Arg Gly Ala Ile Leu Glu Ser
                205                 210                 215
```

-continued

```
Pro Gly Leu Thr Arg Pro Leu Ala Thr Leu Ala Asp Ser Ala Ala Ser
            220                 225                 230
Gly Glu Arg Leu Asp Ala Asp Leu Ser Arg Leu Arg Ser Thr Asp Pro
        235                 240                 245
Ala Thr Leu Met Ala Arg Ala Asp Ala Ala Arg Pro Ala Ser Arg Asp
    250                 255                 260
Leu Arg Arg Pro Arg Pro Thr Gly Pro Ile Val Asp Gly His Val Leu
265                 270                 275                 280
Pro Gln Thr Asp Ser Ala Ala Ile Ala Ala Gly Gln Leu Ala Pro Val
            285                 290                 295
Arg Val Leu Ile Gly Thr Asn Ala Asp Glu Gly Arg Ala Phe Leu Gly
            300                 305                 310
Arg Ala Pro Met Glu Thr Pro Ala Asp Tyr Gln Ala Tyr Leu Glu Ala
        315                 320                 325
Gln Phe Gly Asp Gln Ala Ala Ala Val Ala Ala Cys Tyr Pro Leu Asp
    330                 335                 340
Gly Arg Ala Thr Pro Lys Glu Met Val Ala Arg Ile Phe Gly Asp Asn
345                 350                 355                 360
Gln Phe Asn Arg Gly Val Ser Ala Phe Ser Glu Ala Leu Val Arg Gln
            365                 370                 375
Gly Ala Pro Val Trp Arg Tyr Gln Phe Asn Gly Asn Thr Glu Gly Gly
        380                 385                 390
Arg Ala Pro Ala Thr His Gly Ala Glu Ile Pro Tyr Val Phe Gly Val
    395                 400                 405
Phe Lys Leu Asp Glu Leu Gly Leu Phe Asp Trp Pro Pro Glu Gly Pro
410                 415                 420
Thr Pro Ala Asp Arg Ala Leu Gly Gln Leu Met Ser Ser Ala Trp Val
425                 430                 435                 440
Arg Phe Ala Lys Asn Gly Asp Pro Ala Gly Asp Ala Leu Thr Trp Pro
            445                 450                 455
Ala Tyr Ser Thr Gly Lys Ser Thr Met Thr Phe Gly Pro Glu Gly Arg
        460                 465                 470
Ala Ala Val Val Ser Pro Gly Pro Ser Ile Pro Pro Cys Ala Asp Gly
    475                 480                 485
Ala Lys Ala Gly Gly Gly Gly Ser Gly Gly Ser Gly Gly Gly Ser
490                 495                 500
Lys Asp Asn Val Ala Asp Val Val Val Gly Ala Gly Leu Ser Gly
505                 510                 515                 520
Leu Glu Thr Ala Arg Lys Val Gln Ala Ala Gly Leu Ser Cys Leu Val
            525                 530                 535
Leu Glu Ala Met Asp Arg Val Gly Gly Lys Thr Leu Ser Val Gln Ser
        540                 545                 550
Gly Pro Gly Arg Thr Thr Ile Asn Asp Leu Gly Ala Ala Trp Ile Asn
    555                 560                 565
Asp Ser Asn Gln Ser Glu Val Ser Arg Leu Phe Glu Arg Phe His Leu
570                 575                 580
Glu Gly Glu Leu Gln Arg Thr Thr Gly Asn Ser Ile His Gln Ala Gln
585                 590                 595                 600
Asp Gly Thr Thr Thr Thr Ala Pro Tyr Gly Asp Ser Leu Leu Ser Glu
            605                 610                 615
Glu Val Ala Ser Ala Leu Ala Glu Leu Leu Pro Val Trp Ser Gln Leu
        620                 625                 630
Ile Glu Glu His Ser Leu Gln Asp Leu Lys Ala Ser Pro Gln Ala Lys
```

```
                    635                 640                 645
Arg Leu Asp Ser Val Ser Phe Ala His Tyr Cys Glu Lys Glu Leu Asn
    650                 655                 660

Leu Pro Ala Val Leu Gly Val Ala Asn Gln Ile Thr Arg Ala Leu Leu
665                 670                 675                 680

Gly Val Glu Ala His Glu Ile Ser Met Leu Phe Leu Thr Asp Tyr Ile
                685                 690                 695

Lys Ser Ala Thr Gly Leu Ser Asn Ile Phe Ser Asp Lys Lys Asp Gly
                700                 705                 710

Gly Gln Tyr Met Arg Cys Lys Thr Gly Met Gln Ser Ile Cys His Ala
            715                 720                 725

Met Ser Lys Glu Leu Val Pro Gly Ser Val His Leu Asn Thr Pro Val
    730                 735                 740

Ala Glu Ile Glu Gln Ser Ala Ser Gly Cys Thr Val Arg Ser Ala Ser
745                 750                 755                 760

Gly Ala Val Phe Arg Ser Lys Lys Val Val Ser Leu Pro Thr Thr
                765                 770                 775

Leu Tyr Pro Thr Leu Thr Phe Ser Pro Pro Leu Pro Ala Glu Lys Gln
                780                 785                 790

Ala Leu Ala Glu Asn Ser Ile Leu Gly Tyr Tyr Ser Lys Ile Val Phe
            795                 800                 805

Val Trp Asp Lys Pro Trp Trp Arg Glu Gln Gly Phe Ser Gly Val Leu
    810                 815                 820

Gln Ser Ser Cys Asp Pro Ile Ser Phe Ala Arg Asp Thr Ser Ile Asp
825                 830                 835                 840

Val Asp Arg Gln Trp Ser Ile Thr Cys Phe Met Val Gly Asp Pro Gly
                845                 850                 855

Arg Lys Trp Ser Gln Gln Ser Lys Gln Val Arg Gln Lys Ser Val Trp
                860                 865                 870

Asp Gln Leu Arg Ala Ala Tyr Glu Asn Ala Gly Ala Gln Val Pro Glu
            875                 880                 885

Pro Ala Asn Val Leu Glu Ile Glu Trp Ser Lys Gln Gln Tyr Phe Gln
    890                 895                 900

Gly Ala Pro Ser Ala Val Tyr Gly Leu Asn Asp Leu Ile Thr Leu Gly
905                 910                 915                 920

Ser Ala Leu Arg Thr Pro Phe Lys Ser Val His Phe Val Gly Thr Glu
                925                 930                 935

Thr Ser Leu Val Trp Lys Gly Tyr Met Glu Gly Ala Ile Arg Ser Gly
            940                 945                 950

Gln Arg Gly Ala Ala Glu Val Val Ala Ser Leu Val Pro Ala Ala
    955                 960                 965

<210> SEQ ID NO 28
<211> LENGTH: 3618
<212> TYPE: DNA
<213> ORGANISM: Unknown
<220> FEATURE:
<223> OTHER INFORMATION: gst:esp1:sp:K:trAPAO (Exophiala spinifera)
<220> FEATURE:
<221> NAME/KEY: CDS
<222> LOCATION: (1)..(3615)
<223> OTHER INFORMATION:
<220> FEATURE:
<221> NAME/KEY: misc_feature
<222> LOCATION: (1)..(687)
<223> OTHER INFORMATION: gst + polylinker
<220> FEATURE:
<221> NAME/KEY: mat_peptide
```

```
<222> LOCATION: (688)..(2190)
<223> OTHER INFORMATION: esp1 mat
<220> FEATURE:
<221> NAME/KEY: misc_feature
<222> LOCATION: (2191)..(2226)
<223> OTHER INFORMATION: spacer sequence
<220> FEATURE:
<221> NAME/KEY: misc_feature
<222> LOCATION: (2227)..(3615)
<223> OTHER INFORMATION: K:trAPAO
<220> FEATURE:
<221> NAME/KEY: misc_feature
<222> LOCATION: (2227)..(2229)
<223> OTHER INFORMATION: extra lysine

<400> SEQUENCE: 28 atg tcc cct ata cta ggt tat tgg aaa att aag ggc ctt gtg caa         45
Met Ser Pro Ile Leu Gly Tyr Trp Lys Ile Lys Gly Leu Val Gln
        -225                -220                -215 ccc act cga ctt ctt ttg gaa tat ctt gaa gaa aaa tat gaa gag         90
Pro Thr Arg Leu Leu Leu Glu Tyr Leu Glu Glu Lys Tyr Glu Glu
        -210                -205                -200 cat ttg tat gag cgc gat gaa ggt gat aaa tgg cga aac aaa aag        135
His Leu Tyr Glu Arg Asp Glu Gly Asp Lys Trp Arg Asn Lys Lys
        -195                -190                -185 ttt gaa ttg ggt ttg gag ttt ccc aat ctt cct tat tat att gat        180
Phe Glu Leu Gly Leu Glu Phe Pro Asn Leu Pro Tyr Tyr Ile Asp
        -180                -175                -170 ggt gat gtt aaa tta aca cag tct atg gcc atc ata cgt tat ata        225
Gly Asp Val Lys Leu Thr Gln Ser Met Ala Ile Ile Arg Tyr Ile
        -165                -160                -155 gct gac aag cac aac atg ttg ggt ggt tgt cca aaa gag cgt gca        270
Ala Asp Lys His Asn Met Leu Gly Gly Cys Pro Lys Glu Arg Ala
        -150                -145                -140 gag att tca atg ctt gaa gga gcg gtt ttg gat att aga tac ggt        315
Glu Ile Ser Met Leu Glu Gly Ala Val Leu Asp Ile Arg Tyr Gly
        -135                -130                -125 gtt tcg aga att gca tat agt aaa gac ttt gaa act ctc aaa gtt        360
Val Ser Arg Ile Ala Tyr Ser Lys Asp Phe Glu Thr Leu Lys Val
        -120                -115                -110 gat ttt ctt agc aag cta cct gaa atg ctg aaa atg ttc gaa gat cgt   408
Asp Phe Leu Ser Lys Leu Pro Glu Met Leu Lys Met Phe Glu Asp Arg
        -105                -100                 -95 tta tgt cat aaa aca tat tta aat ggt gat cat gta acc cat cct gac   456
Leu Cys His Lys Thr Tyr Leu Asn Gly Asp His Val Thr His Pro Asp
         -90                 -85                 -80 ttc atg ttg tat gac gct ctt gat gtt gtt tta tac atg gac cca atg   504
Phe Met Leu Tyr Asp Ala Leu Asp Val Val Leu Tyr Met Asp Pro Met
     -75                 -70                 -65 tgc ctg gat gcg ttc cca aaa tta gtt tgt ttt aaa aaa cgt att gaa   552
Cys Leu Asp Ala Phe Pro Lys Leu Val Cys Phe Lys Lys Arg Ile Glu
     -60                 -55                 -50 gct atc cca caa att gat aag tac ttg aaa tcc agc aag tat ata gca   600
Ala Ile Pro Gln Ile Asp Lys Tyr Leu Lys Ser Ser Lys Tyr Ile Ala
-45                 -40                 -35                 -30 tgg cct ttg cag ggc tgg caa gcc acg ttt ggt ggt ggc gac cat cct   648
Trp Pro Leu Gln Gly Trp Gln Ala Thr Phe Gly Gly Gly Asp His Pro
         -25                 -20                 -15 cca aaa tcg gat ctg gtt ccg cgt gga tcc ccg gaa ttc gct cct act   696
Pro Lys Ser Asp Leu Val Pro Arg Gly Ser Pro Glu Phe Ala Pro Thr
             -10                 -5                 -1   1 gtc aag att gat gct ggg atg gtg gtc ggc acg act act act gtc ccc   744
Val Lys Ile Asp Ala Gly Met Val Val Gly Thr Thr Thr Thr Val Pro
```

-continued

```
          5                      10                      15
ggc acc act gcg acc gtc agc gag ttc ttg ggc gtt cct ttt gcc gcc    792
Gly Thr Thr Ala Thr Val Ser Glu Phe Leu Gly Val Pro Phe Ala Ala
 20              25                      30                  35 tct ccg aca cga ttt gcg cct cct act cgt ccc gtg cct tgg tca acg    840
Ser Pro Thr Arg Phe Ala Pro Pro Thr Arg Pro Val Pro Trp Ser Thr
                 40                      45                  50 cct ttg caa gcc act gca tat ggt cca gca tgc cct caa caa ttc aat    888
Pro Leu Gln Ala Thr Ala Tyr Gly Pro Ala Cys Pro Gln Gln Phe Asn
                     55                      60              65 tac ccc gaa gaa ctc cgt gag att acg atg gcc tgg ttc aat aca ccg    936
Tyr Pro Glu Glu Leu Arg Glu Ile Thr Met Ala Trp Phe Asn Thr Pro
             70                      75                  80 ccc ccg tca gct ggt gaa agt gag gac tgc ctg aac ctc aac atc tac    984
Pro Pro Ser Ala Gly Glu Ser Glu Asp Cys Leu Asn Leu Asn Ile Tyr
         85                      90                  95 gtc cca gga act gag aac aca aac aaa gcc gtc atg gtt tgg ata tac   1032
Val Pro Gly Thr Glu Asn Thr Asn Lys Ala Val Met Val Trp Ile Tyr
100                     105                     110             115 ggt gga gcg ctg gaa tat ggt tgg aat tca ttc cac ctt tac gac ggg   1080
Gly Gly Ala Leu Glu Tyr Gly Trp Asn Ser Phe His Leu Tyr Asp Gly
                    120                     125             130 gct agt ttc gca gcc aat cag gat gtc atc gcc gtg acc atc aac tac   1128
Ala Ser Phe Ala Ala Asn Gln Asp Val Ile Ala Val Thr Ile Asn Tyr
                135                     140             145 aga acg aac att ctg ggg ttc cct gct gcc cct cag ctt cca ata aca   1176
Arg Thr Asn Ile Leu Gly Phe Pro Ala Ala Pro Gln Leu Pro Ile Thr
            150                     155                 160 cag cga aat ctg ggg ttc cta gac caa agg ttt gct ttg gat tgg gta   1224
Gln Arg Asn Leu Gly Phe Leu Asp Gln Arg Phe Ala Leu Asp Trp Val
        165                     170                 175 cag cgg aac atc gca gcc ttt ggc ggt gat cct cga aag gtc aca ata   1272
Gln Arg Asn Ile Ala Ala Phe Gly Gly Asp Pro Arg Lys Val Thr Ile
180                     185                 190                 195 ttt ggg cag agt gcg ggg ggc aga agt gtc gac gtc ctc ttg acg tct   1320
Phe Gly Gln Ser Ala Gly Gly Arg Ser Val Asp Val Leu Leu Thr Ser
                    200                     205             210 atg cca cac aac cca ccc ttc cga gca gca atc atg gag tcc ggt gtg   1368
Met Pro His Asn Pro Pro Phe Arg Ala Ala Ile Met Glu Ser Gly Val
                215                     220             225 gct aac tac aac ttc ccc aag gga gat ttg tcc gaa cct tgg aac acc   1416
Ala Asn Tyr Asn Phe Pro Lys Gly Asp Leu Ser Glu Pro Trp Asn Thr
            230                     235                 240 act gtt caa gct ctc aac tgt acc acc agt atc gac atc ttg agt tgt   1464
Thr Val Gln Ala Leu Asn Cys Thr Thr Ser Ile Asp Ile Leu Ser Cys
        245                     250                 255 atg aga aga gtc gat ctc gcc act ctg atg aac acg atc gag caa ctc   1512
Met Arg Arg Val Asp Leu Ala Thr Leu Met Asn Thr Ile Glu Gln Leu
260                     265                     270             275 gga ctt ggg ttt gag tac acg ttg gac aac gta acg gct gtg tac cgt   1560
Gly Leu Gly Phe Glu Tyr Thr Leu Asp Asn Val Thr Ala Val Tyr Arg
                    280                     285             290 tct gaa acg gct cgc acg act ggt gac att gct cgt gta cct gtt ctc   1608
Ser Glu Thr Ala Arg Thr Thr Gly Asp Ile Ala Arg Val Pro Val Leu
                295                     300             305 gtc ggg acg gtg gcc aac gac gga ctt ctc ttt gtc ctc ggg gag aat   1656
Val Gly Thr Val Ala Asn Asp Gly Leu Leu Phe Val Leu Gly Glu Asn
            310                     315                 320 gac acc caa gca tat ctc gag gag gca atc ccg aat cag ccc gac ctt   1704
```

```
                                                        -continued

Asp Thr Gln Ala Tyr Leu Glu Glu Ala Ile Pro Asn Gln Pro Asp Leu
    325                 330                 335 tac cag act ctc ctt gga gca tat ccc att gga tcc cca ggg atc gga    1752
Tyr Gln Thr Leu Leu Gly Ala Tyr Pro Ile Gly Ser Pro Gly Ile Gly
340                 345                 350                 355 tcg cct caa gat cag att gcc gcc att gag acc gag gta aga ttc cag    1800
Ser Pro Gln Asp Gln Ile Ala Ala Ile Glu Thr Glu Val Arg Phe Gln
                360                 365                 370 tgt cct tct gcc atc gtg gct cag gac tcc cgg aat cgg ggt atc cct    1848
Cys Pro Ser Ala Ile Val Ala Gln Asp Ser Arg Asn Arg Gly Ile Pro
            375                 380                 385 tct tgg cgc tac tac tac aat gcg acc ttt gag aat ctg gag ctt ttc    1896
Ser Trp Arg Tyr Tyr Tyr Asn Ala Thr Phe Glu Asn Leu Glu Leu Phe
        390                 395                 400 cct ggg tcc gaa gtg tac cac agc tct gaa gtc ggg atg gtg ttt ggc    1944
Pro Gly Ser Glu Val Tyr His Ser Ser Glu Val Gly Met Val Phe Gly
    405                 410                 415 acg tat cct gtc gca agt gcg acc gcc ttg gag gcc cag acg agc aaa    1992
Thr Tyr Pro Val Ala Ser Ala Thr Ala Leu Glu Ala Gln Thr Ser Lys
420                 425                 430                 435 tac atg cag ggt gcc tgg gcg gcc ttt gcc aaa aac ccc atg aat ggg    2040
Tyr Met Gln Gly Ala Trp Ala Ala Phe Ala Lys Asn Pro Met Asn Gly
                440                 445                 450 cct ggg tgg aaa caa gtg ccg aat gtc gcg gcg ctt ggc tca cca ggc    2088
Pro Gly Trp Lys Gln Val Pro Asn Val Ala Ala Leu Gly Ser Pro Gly
            455                 460                 465 aaa gcc atc cag gtt gac gtc tct cca gcg aca ata gac caa cga tgt    2136
Lys Ala Ile Gln Val Asp Val Ser Pro Ala Thr Ile Asp Gln Arg Cys
        470                 475                 480 gcc ttg tac acg cgt tat tat act gag ttg ggc aca atc gcg ccg agg    2184
Ala Leu Tyr Thr Arg Tyr Tyr Thr Glu Leu Gly Thr Ile Ala Pro Arg
    485                 490                 495 aca ttt ggc gga ggc agc ggc gga ggc agc ggc gga ggc agc aaa gac    2232
Thr Phe Gly Gly Gly Ser Gly Gly Gly Ser Gly Gly Gly Ser Lys Asp
500                 505                 510                 515 aac gtt gcg gac gtg gta gtg gtg ggc gct ggc ttg agc ggt ttg gag    2280
Asn Val Ala Asp Val Val Val Val Gly Ala Gly Leu Ser Gly Leu Glu
                520                 525                 530 acg gca cgc aaa gtc cag gcc gcc ggt ctg tcc tgc ctc gtt ctt gag    2328
Thr Ala Arg Lys Val Gln Ala Ala Gly Leu Ser Cys Leu Val Leu Glu
            535                 540                 545 gcg atg gat cgt gta ggg gga aag act ctg agc gta caa tcg ggt ccc    2376
Ala Met Asp Arg Val Gly Gly Lys Thr Leu Ser Val Gln Ser Gly Pro
    550                 555                 560 ggc agg acg act atc aac gac ctc ggc gct gcg tgg atc aat gac agc    2424
Gly Arg Thr Thr Ile Asn Asp Leu Gly Ala Ala Trp Ile Asn Asp Ser
565                 570                 575 aac caa agc gaa gta tcc aga ttg ttt gaa aga ttt cat ttg gag ggc    2472
Asn Gln Ser Glu Val Ser Arg Leu Phe Glu Arg Phe His Leu Glu Gly
580                 585                 590                 595 gag ctc cag agg acg act gga aat tca atc cat caa gca caa gac ggt    2520
Glu Leu Gln Arg Thr Thr Gly Asn Ser Ile His Gln Ala Gln Asp Gly
                600                 605                 610 aca acc act aca gct cct tat ggt gac tcc ttg ctg agc gag gag gtt    2568
Thr Thr Thr Thr Ala Pro Tyr Gly Asp Ser Leu Leu Ser Glu Glu Val
            615                 620                 625 gca agt gca ctt gcg gaa ctc ctc ccc gta tgg tct cag ctg atc gaa    2616
Ala Ser Ala Leu Ala Glu Leu Leu Pro Val Trp Ser Gln Leu Ile Glu
        630                 635                 640
```

-continued

| | |
|---|---|
| gag cat agc ctt caa gac ctc aag gcg agc cct cag gcg aag cgg ctc<br>Glu His Ser Leu Gln Asp Leu Lys Ala Ser Pro Gln Ala Lys Arg Leu<br>645                        650                        655 | 2664 |
| gac agt gtg agc ttc gcg cac tac tgt gag aag gaa cta aac ttg cct<br>Asp Ser Val Ser Phe Ala His Tyr Cys Glu Lys Glu Leu Asn Leu Pro<br>660                        665                        670                        675 | 2712 |
| gct gtt ctc ggc gta gca aac cag atc aca cgc gct ctg ctc ggt gtg<br>Ala Val Leu Gly Val Ala Asn Gln Ile Thr Arg Ala Leu Leu Gly Val<br>                        680                        685                        690 | 2760 |
| gaa gcc cac gag atc agc atg ctt ttt ctc acc gac tac atc aag agt<br>Glu Ala His Glu Ile Ser Met Leu Phe Leu Thr Asp Tyr Ile Lys Ser<br>                        695                        700                        705 | 2808 |
| gcc acc ggt ctc agt aat att ttc tcg gac aag aaa gac ggc ggg cag<br>Ala Thr Gly Leu Ser Asn Ile Phe Ser Asp Lys Lys Asp Gly Gly Gln<br>710                        715                        720 | 2856 |
| tat atg cga tgc aaa aca ggt atg cag tcg att tgc cat gcc atg tca<br>Tyr Met Arg Cys Lys Thr Gly Met Gln Ser Ile Cys His Ala Met Ser<br>725                        730                        735 | 2904 |
| aag gaa ctt gtt cca ggc tca gtg cac ctc aac acc ccc gtc gct gaa<br>Lys Glu Leu Val Pro Gly Ser Val His Leu Asn Thr Pro Val Ala Glu<br>740                        745                        750                        755 | 2952 |
| att gag cag tcg gca tcc ggc tgt aca gta cga tcg gcc tcg ggc gcc<br>Ile Glu Gln Ser Ala Ser Gly Cys Thr Val Arg Ser Ala Ser Gly Ala<br>                        760                        765                        770 | 3000 |
| gtg ttc cga agc aaa aag gtg gtg gtt tcg tta ccg aca acc ttg tat<br>Val Phe Arg Ser Lys Lys Val Val Val Ser Leu Pro Thr Thr Leu Tyr<br>                        775                        780                        785 | 3048 |
| ccc acc ttg aca ttt tca cca cct ctt ccc gcc gag aag caa gca ttg<br>Pro Thr Leu Thr Phe Ser Pro Pro Leu Pro Ala Glu Lys Gln Ala Leu<br>                        790                        795                        800 | 3096 |
| gcg gaa aat tct atc ctg ggc tac tat agc aag ata gtc ttc gta tgg<br>Ala Glu Asn Ser Ile Leu Gly Tyr Tyr Ser Lys Ile Val Phe Val Trp<br>805                        810                        815 | 3144 |
| gac aag ccg tgg tgg cgc gaa caa ggc ttc tcg ggc gtc ctc caa tcg<br>Asp Lys Pro Trp Trp Arg Glu Gln Gly Phe Ser Gly Val Leu Gln Ser<br>820                        825                        830                        835 | 3192 |
| agc tgt gac ccc atc tca ttt gcc aga gat acc agc atc gac gtc gat<br>Ser Cys Asp Pro Ile Ser Phe Ala Arg Asp Thr Ser Ile Asp Val Asp<br>                        840                        845                        850 | 3240 |
| cga caa tgg tcc att acc tgt ttc atg gtc gga gac ccg gga cgg aag<br>Arg Gln Trp Ser Ile Thr Cys Phe Met Val Gly Asp Pro Gly Arg Lys<br>                        855                        860                        865 | 3288 |
| tgg tcc caa cag tcc aag cag gta cga caa aag tct gtc tgg gac caa<br>Trp Ser Gln Gln Ser Lys Gln Val Arg Gln Lys Ser Val Trp Asp Gln<br>870                        875                        880 | 3336 |
| ctc cgc gca gcc tac gag aac gcc ggg gcc caa gtc cca gag ccg gcc<br>Leu Arg Ala Ala Tyr Glu Asn Ala Gly Ala Gln Val Pro Glu Pro Ala<br>885                        890                        895 | 3384 |
| aac gtg ctc gaa atc gag tgg tcg aag cag cag tat ttc caa gga gct<br>Asn Val Leu Glu Ile Glu Trp Ser Lys Gln Gln Tyr Phe Gln Gly Ala<br>900                        905                        910                        915 | 3432 |
| ccg agc gcc gtc tat ggg ctg aac gat ctc atc aca ctg ggt tcg gcg<br>Pro Ser Ala Val Tyr Gly Leu Asn Asp Leu Ile Thr Leu Gly Ser Ala<br>                        920                        925                        930 | 3480 |
| ctc aga acg ccg ttc aag agt gtt cat ttc gtt gga acg gag acg tct<br>Leu Arg Thr Pro Phe Lys Ser Val His Phe Val Gly Thr Glu Thr Ser<br>                        935                        940                        945 | 3528 |
| tta gtt tgg aaa ggg tat atg gaa ggg gcc ata cga tcg ggt caa cga<br>Leu Val Trp Lys Gly Tyr Met Glu Gly Ala Ile Arg Ser Gly Gln Arg<br>950                        955                        960 | 3576 |

```
ggt gct gca gaa gtt gtg gct agc ctg gtg cca gca gca tag         3618
Gly Ala Ala Glu Val Val Ala Ser Leu Val Pro Ala Ala
965                 970                 975
```

<210> SEQ ID NO 29
<211> LENGTH: 1205
<212> TYPE: PRT
<213> ORGANISM: Unknown
<220> FEATURE:
<223> OTHER INFORMATION: gst:esp1:sp:K:trAPAO (Exophiala spinifera)
<220> FEATURE:
<221> NAME/KEY: misc_feature
<222> LOCATION: (1)..(687)
<223> OTHER INFORMATION: gst + polylinker
<220> FEATURE:
<221> NAME/KEY: misc_feature
<222> LOCATION: (2191)..(2226)
<223> OTHER INFORMATION: spacer sequence
<220> FEATURE:
<221> NAME/KEY: misc_feature
<222> LOCATION: (2227)..(3615)
<223> OTHER INFORMATION: K:trAPAO
<220> FEATURE:
<221> NAME/KEY: misc_feature
<222> LOCATION: (2227)..(2229)
<223> OTHER INFORMATION: extra lysine

<400> SEQUENCE: 29

```
Met Ser Pro Ile Leu  Gly Tyr Trp Lys Ile  Lys Gly Leu Val Gln
                -225                 -220                 -215

Pro Thr Arg Leu Leu  Leu Glu Tyr Leu Glu  Glu Lys Tyr Glu Glu
                -210                 -205                 -200

His Leu Tyr Glu Arg  Asp Glu Gly Asp Lys  Trp Arg Asn Lys Lys
                -195                 -190                 -185

Phe Glu Leu Gly Leu  Glu Phe Pro Asn Leu  Pro Tyr Tyr Ile Asp
                -180                 -175                 -170

Gly Asp Val Lys Leu  Thr Gln Ser Met Ala  Ile Ile Arg Tyr Ile
                -165                 -160                 -155

Ala Asp Lys His Asn  Met Leu Gly Gly Cys  Pro Lys Glu Arg Ala
                -150                 -145                 -140

Glu Ile Ser Met Leu  Glu Gly Ala Val Leu  Asp Ile Arg Tyr Gly
                -135                 -130                 -125

Val Ser Arg Ile Ala  Tyr Ser Lys Asp Phe  Glu Thr Leu Lys Val
                -120                 -115                 -110

Asp Phe Leu Ser Lys  Leu Pro Glu Met Leu  Lys Met Phe Glu Asp Arg
                -105                 -100                  -95

Leu Cys His Lys Thr  Tyr Leu Asn Gly Asp  His Val Thr His Pro Asp
                 -90                  -85                  -80

Phe Met Leu Tyr Asp  Ala Leu Asp Val Val  Leu Tyr Met Asp Pro Met
             -75                  -70                  -65

Cys Leu Asp Ala Phe  Pro Lys Leu Val Cys  Phe Lys Lys Arg Ile Glu
             -60                  -55                  -50

Ala Ile Pro Gln Ile  Asp Lys Tyr Leu Lys  Ser Ser Lys Tyr Ile Ala
-45                  -40                  -35                  -30

Trp Pro Leu Gln Gly  Trp Gln Ala Thr Phe  Gly Gly Asp His Pro
                 -25                  -20                  -15

Pro Lys Ser Asp Leu  Val Pro Arg Gly Ser  Pro Glu Phe Ala Pro Thr
                 -10                   -5                   -1  1

Val Lys Ile Asp Ala  Gly Met Val Val Gly  Thr Thr Thr Val Pro
  5                   10                   15
```

-continued

```
Gly Thr Thr Ala Thr Val Ser Glu Phe Leu Gly Val Pro Phe Ala Ala
 20              25                  30                  35

Ser Pro Thr Arg Phe Ala Pro Pro Thr Arg Pro Val Pro Trp Ser Thr
             40                  45                  50

Pro Leu Gln Ala Thr Ala Tyr Gly Pro Ala Cys Pro Gln Gln Phe Asn
             55                  60                  65

Tyr Pro Glu Glu Leu Arg Glu Ile Thr Met Ala Trp Phe Asn Thr Pro
         70                  75                  80

Pro Pro Ser Ala Gly Ser Glu Asp Cys Leu Asn Leu Asn Ile Tyr
         85                  90                  95

Val Pro Gly Thr Glu Asn Thr Asn Lys Ala Val Met Val Trp Ile Tyr
100             105                 110                 115

Gly Gly Ala Leu Glu Tyr Gly Trp Asn Ser Phe His Leu Tyr Asp Gly
            120                 125                 130

Ala Ser Phe Ala Ala Asn Gln Asp Val Ile Ala Val Thr Ile Asn Tyr
            135                 140                 145

Arg Thr Asn Ile Leu Gly Phe Pro Ala Ala Pro Gln Leu Pro Ile Thr
            150                 155                 160

Gln Arg Asn Leu Gly Phe Leu Asp Gln Arg Phe Ala Leu Asp Trp Val
        165                 170                 175

Gln Arg Asn Ile Ala Ala Phe Gly Gly Asp Pro Arg Lys Val Thr Ile
180                 185                 190                 195

Phe Gly Gln Ser Ala Gly Gly Arg Ser Val Asp Val Leu Leu Thr Ser
                200                 205                 210

Met Pro His Asn Pro Pro Phe Arg Ala Ala Ile Met Glu Ser Gly Val
                215                 220                 225

Ala Asn Tyr Asn Phe Pro Lys Gly Asp Leu Ser Glu Pro Trp Asn Thr
            230                 235                 240

Thr Val Gln Ala Leu Asn Cys Thr Thr Ser Ile Asp Ile Leu Ser Cys
        245                 250                 255

Met Arg Arg Val Asp Leu Ala Thr Leu Met Asn Thr Ile Glu Gln Leu
260                 265                 270                 275

Gly Leu Gly Phe Glu Tyr Thr Leu Asp Asn Val Thr Ala Val Tyr Arg
                280                 285                 290

Ser Glu Thr Ala Arg Thr Thr Gly Asp Ile Ala Arg Val Pro Val Leu
                295                 300                 305

Val Gly Thr Val Ala Asn Asp Gly Leu Leu Phe Val Leu Gly Glu Asn
            310                 315                 320

Asp Thr Gln Ala Tyr Leu Glu Glu Ala Ile Pro Asn Gln Pro Asp Leu
        325                 330                 335

Tyr Gln Thr Leu Leu Gly Ala Tyr Pro Ile Gly Ser Pro Gly Ile Gly
340                 345                 350                 355

Ser Pro Gln Asp Gln Ile Ala Ala Ile Glu Thr Glu Val Arg Phe Gln
                360                 365                 370

Cys Pro Ser Ala Ile Val Ala Gln Asp Ser Arg Asn Arg Gly Ile Pro
            375                 380                 385

Ser Trp Arg Tyr Tyr Tyr Asn Ala Thr Phe Glu Asn Leu Glu Leu Phe
        390                 395                 400

Pro Gly Ser Glu Val Tyr His Ser Ser Glu Val Gly Met Val Phe Gly
    405                 410                 415

Thr Tyr Pro Val Ala Ser Ala Thr Ala Leu Glu Ala Gln Thr Ser Lys
420                 425                 430                 435

Tyr Met Gln Gly Ala Trp Ala Ala Phe Ala Lys Asn Pro Met Asn Gly
```

-continued

```
                440             445             450
Pro Gly Trp Lys Gln Val Pro Asn Val Ala Ala Leu Gly Ser Pro Gly
            455                 460             465
Lys Ala Ile Gln Val Asp Val Ser Pro Ala Thr Ile Asp Gln Arg Cys
            470                 475             480
Ala Leu Tyr Thr Arg Tyr Tyr Thr Glu Leu Gly Thr Ile Ala Pro Arg
            485                 490             495
Thr Phe Gly Gly Gly Ser Gly Gly Ser Gly Gly Gly Ser Lys Asp
500             505                 510                 515
Asn Val Ala Asp Val Val Val Gly Ala Gly Leu Ser Gly Leu Glu
                520                 525             530
Thr Ala Arg Lys Val Gln Ala Ala Gly Leu Ser Cys Leu Val Leu Glu
            535                 540             545
Ala Met Asp Arg Val Gly Gly Lys Thr Leu Ser Val Gln Ser Gly Pro
            550                 555             560
Gly Arg Thr Thr Ile Asn Asp Leu Gly Ala Ala Trp Ile Asn Asp Ser
            565                 570             575
Asn Gln Ser Glu Val Ser Arg Leu Phe Glu Arg Phe His Leu Glu Gly
580             585                 590             595
Glu Leu Gln Arg Thr Thr Gly Asn Ser Ile His Gln Ala Gln Asp Gly
            600                 605             610
Thr Thr Thr Thr Ala Pro Tyr Gly Asp Ser Leu Leu Ser Glu Glu Val
            615                 620             625
Ala Ser Ala Leu Ala Glu Leu Leu Pro Val Trp Ser Gln Leu Ile Glu
            630                 635             640
Glu His Ser Leu Gln Asp Leu Lys Ala Ser Pro Gln Ala Lys Arg Leu
            645                 650             655
Asp Ser Val Ser Phe Ala His Tyr Cys Glu Lys Glu Leu Asn Leu Pro
660             665                 670             675
Ala Val Leu Gly Val Ala Asn Gln Ile Thr Arg Ala Leu Leu Gly Val
                680                 685             690
Glu Ala His Glu Ile Ser Met Leu Phe Leu Thr Asp Tyr Ile Lys Ser
            695                 700             705
Ala Thr Gly Leu Ser Asn Ile Phe Ser Asp Lys Lys Asp Gly Gly Gln
            710                 715             720
Tyr Met Arg Cys Lys Thr Gly Met Gln Ser Ile Cys His Ala Met Ser
            725                 730             735
Lys Glu Leu Val Pro Gly Ser Val His Leu Asn Thr Pro Val Ala Glu
740             745                 750             755
Ile Glu Gln Ser Ala Ser Gly Cys Thr Val Arg Ser Ala Ser Gly Ala
                760                 765             770
Val Phe Arg Ser Lys Lys Val Val Ser Leu Pro Thr Thr Leu Tyr
            775                 780             785
Pro Thr Leu Thr Phe Ser Pro Leu Pro Ala Glu Lys Gln Ala Leu
            790                 795             800
Ala Glu Asn Ser Ile Leu Gly Tyr Tyr Ser Lys Ile Val Phe Val Trp
            805                 810             815
Asp Lys Pro Trp Trp Arg Glu Gln Gly Phe Ser Gly Val Leu Gln Ser
820             825                 830             835
Ser Cys Asp Pro Ile Ser Phe Ala Arg Asp Thr Ser Ile Asp Val Asp
                840                 845             850
Arg Gln Trp Ser Ile Thr Cys Phe Met Val Gly Asp Pro Gly Arg Lys
            855                 860             865
```

-continued

```
Trp Ser Gln Gln Ser Lys Gln Val Arg Gln Lys Ser Val Trp Asp Gln
            870                 875                 880

Leu Arg Ala Ala Tyr Glu Asn Ala Gly Ala Gln Val Pro Glu Pro Ala
        885                 890                 895

Asn Val Leu Glu Ile Glu Trp Ser Lys Gln Gln Tyr Phe Gln Gly Ala
900                 905                 910                 915

Pro Ser Ala Val Tyr Gly Leu Asn Asp Leu Ile Thr Leu Gly Ser Ala
            920                 925                 930

Leu Arg Thr Pro Phe Lys Ser Val His Phe Val Gly Thr Glu Thr Ser
        935                 940                 945

Leu Val Trp Lys Gly Tyr Met Glu Gly Ala Ile Arg Ser Gly Gln Arg
            950                 955                 960

Gly Ala Ala Glu Val Val Ala Ser Leu Val Pro Ala Ala
        965                 970                 975
```

<210> SEQ ID NO 30
<211> LENGTH: 3591
<212> TYPE: DNA
<213> ORGANISM: Unknown
<220> FEATURE:
<223> OTHER INFORMATION: Orf of BEST1:K:trAPAO fusion pGEX-4T-1
      (Exophiala spinifera)
<220> FEATURE:
<221> NAME/KEY: misc_feature
<222> LOCATION: (1)..(687)
<223> OTHER INFORMATION: gst + polylinker
<220> FEATURE:
<221> NAME/KEY: mat_peptide
<222> LOCATION: (688)..(2163)
<223> OTHER INFORMATION: BEST1 mature
<220> FEATURE:
<221> NAME/KEY: misc_feature
<222> LOCATION: (2164)..(2199)
<223> OTHER INFORMATION: spacer sequence
<220> FEATURE:
<221> NAME/KEY: misc_feature
<222> LOCATION: (2200)..(3588)
<223> OTHER INFORMATION: K:trAPAO
<220> FEATURE:
<221> NAME/KEY: CDS
<222> LOCATION: (1)..(3588)
<223> OTHER INFORMATION:
<220> FEATURE:
<221> NAME/KEY: misc_feature
<222> LOCATION: (2200)..(2202)
<223> OTHER INFORMATION: extra lysine

<400> SEQUENCE: 30

```
atg tcc cct ata cta ggt tat tgg aaa att aag ggc ctt gtg caa        45
Met Ser Pro Ile Leu Gly Tyr Trp Lys Ile Lys Gly Leu Val Gln
            -225                -220                -215 ccc act cga ctt ctt ttg gaa tat ctt gaa gaa aaa tat gaa gag        90
Pro Thr Arg Leu Leu Leu Glu Tyr Leu Glu Glu Lys Tyr Glu Glu
        -210                -205                -200 cat ttg tat gag cgc gat gaa ggt gat aaa tgg cga aac aaa aag       135
His Leu Tyr Glu Arg Asp Glu Gly Asp Lys Trp Arg Asn Lys Lys
            -195                -190                -185 ttt gaa ttg ggt ttg gag ttt ccc aat ctt cct tat tat att gat       180
Phe Glu Leu Gly Leu Glu Phe Pro Asn Leu Pro Tyr Tyr Ile Asp
        -180                -175                -170 ggt gat gtt aaa tta aca cag tct atg gcc atc ata cgt tat ata       225
Gly Asp Val Lys Leu Thr Gln Ser Met Ala Ile Ile Arg Tyr Ile
            -165                -160                -155 gct gac aag cac aac atg ttg ggt ggt tgt cca aaa gag cgt gca       270
Ala Asp Lys His Asn Met Leu Gly Gly Cys Pro Lys Glu Arg Ala
```

-continued

```
                   -150                -145                -140
gag att tca atg ctt gaa gga gcg gtt ttg gat att aga tac ggt          315
Glu Ile Ser Met Leu Glu Gly Ala Val Leu Asp Ile Arg Tyr Gly
                -135                -130                -125 gtt tcg aga att gca tat agt aaa gac ttt gaa act ctc aaa gtt          360
Val Ser Arg Ile Ala Tyr Ser Lys Asp Phe Glu Thr Leu Lys Val
            -120                -115                -110 gat ttt ctt agc aag cta cct gaa atg ctg aaa atg ttc gaa gat cgt      408
Asp Phe Leu Ser Lys Leu Pro Glu Met Leu Lys Met Phe Glu Asp Arg
                -105                -100                 -95 tta tgt cat aaa aca tat tta aat ggt gat cat gta acc cat cct gac      456
Leu Cys His Lys Thr Tyr Leu Asn Gly Asp His Val Thr His Pro Asp
             -90                 -85                 -80 ttc atg ttg tat gac gct ctt gat gtt gtt tta tac atg gac cca atg      504
Phe Met Leu Tyr Asp Ala Leu Asp Val Val Leu Tyr Met Asp Pro Met
             -75                 -70                 -65 tgc ctg gat gcg ttc cca aaa tta gtt tgt ttt aaa aaa cgt att gaa      552
Cys Leu Asp Ala Phe Pro Lys Leu Val Cys Phe Lys Lys Arg Ile Glu
         -60                 -55                 -50 gct atc cca caa att gat aag tac ttg aaa tcc agc aag tat ata gca      600
Ala Ile Pro Gln Ile Asp Lys Tyr Leu Lys Ser Ser Lys Tyr Ile Ala
-45                 -40                 -35                 -30 tgg cct ttg cag ggc tgg caa gcc acg ttt ggt ggt ggc gac cat cct      648
Trp Pro Leu Gln Gly Trp Gln Ala Thr Phe Gly Gly Gly Asp His Pro
                 -25                 -20                 -15 cca aaa tcg gat ctg gtt ccg cgt gga tcc ccg gaa ttc acg gat ttt      696
Pro Lys Ser Asp Leu Val Pro Arg Gly Ser Pro Glu Phe Thr Asp Phe
             -10                  -5                  -1   1 ccg gtc cgc agg acc gat ctg ggc cag gtt cag gga ctg gcc ggg gac      744
Pro Val Arg Arg Thr Asp Leu Gly Gln Val Gln Gly Leu Ala Gly Asp
      5                  10                  15 gtg atg agc ttt cgc gga ata ccc tat gca gcg ccg ccg gtg ggc ggg      792
Val Met Ser Phe Arg Gly Ile Pro Tyr Ala Ala Pro Pro Val Gly Gly
 20                  25                  30                  35 ctg cgt tgg aag ccg ccc caa cac gcc cgg ccc tgg gcg ggc gtt cgc      840
Leu Arg Trp Lys Pro Pro Gln His Ala Arg Pro Trp Ala Gly Val Arg
                  40                  45                  50 ccc gcc acc caa ttt ggc tcc gac tgc ttc ggc gcg gcc tat ctt cgc      888
Pro Ala Thr Gln Phe Gly Ser Asp Cys Phe Gly Ala Ala Tyr Leu Arg
                   55                  60                  65 aaa ggc agc ctc gcc ccc ggc gtg agc gag gac tgt ctt tac ctc aac      936
Lys Gly Ser Leu Ala Pro Gly Val Ser Glu Asp Cys Leu Tyr Leu Asn
              70                  75                  80 gta tgg gcg ccg tca ggc gct aaa ccc ggc cag tac ccc gtc atg gtc      984
Val Trp Ala Pro Ser Gly Ala Lys Pro Gly Gln Tyr Pro Val Met Val
 85                  90                  95 tgg gtc tac ggc ggc ggc ttc gcc ggc ggc acg gcc gcc atg ccc tac     1032
Trp Val Tyr Gly Gly Gly Phe Ala Gly Gly Thr Ala Ala Met Pro Tyr
100                 105                 110                 115 tac gac ggc gag gcg ctt gcg cga cag ggc gtc gtg gtg acg ttt         1080
Tyr Asp Gly Glu Ala Leu Ala Arg Gln Gly Val Val Val Thr Phe
                 120                 125                 130 aac tat cgg acg aac atc ctg ggc ttt ttc gcc cat cct ggt ctc tcg     1128
Asn Tyr Arg Thr Asn Ile Leu Gly Phe Phe Ala His Pro Gly Leu Ser
                 135                 140                 145 cgc gag agc ccc acc gga act tcg ggc aac tac ggc cta ctc gac att     1176
Arg Glu Ser Pro Thr Gly Thr Ser Gly Asn Tyr Gly Leu Leu Asp Ile
             150                 155                 160 ctc gcc gct ctt cgg tgg gtg cag agc aac gcc cgc gcc ttc gga ggg     1224
```

-continued

| | | |
|---|---|---|
| Leu Ala Ala Leu Arg Trp Val Gln Ser Asn Ala Arg Ala Phe Gly Gly<br>165                    170                  175 | | |
| gac ccc ggc cga gtg acg gtc ttt ggt gaa tcg gcc gga gcg agc gcg<br>Asp Pro Gly Arg Val Thr Val Phe Gly Glu Ser Ala Gly Ala Ser Ala<br>180                    185                  190                  195 | 1272 |
| atc gga ctt ctg ctc acc tcg ccg ctg agc aag ggt ctc ttc cgt ggc<br>Ile Gly Leu Leu Leu Thr Ser Pro Leu Ser Lys Gly Leu Phe Arg Gly<br>200                  205                  210 | 1320 |
| gct atc ctc gaa agt cca ggg ctg acg cga ccg ctc gcg acg ctc gcc<br>Ala Ile Leu Glu Ser Pro Gly Leu Thr Arg Pro Leu Ala Thr Leu Ala<br>215                    220                  225 | 1368 |
| gac agc gcc gcc tcg ggc gag cgc ctc gac gcc gat ctt tcg cga ctg<br>Asp Ser Ala Ala Ser Gly Glu Arg Leu Asp Ala Asp Leu Ser Arg Leu<br>230                    235                  240 | 1416 |
| cgc tcg acc gac cca gcc acc ctg atg gcg cgc gcc gac gcg gcc cgc<br>Arg Ser Thr Asp Pro Ala Thr Leu Met Ala Arg Ala Asp Ala Ala Arg<br>245                    250                  255 | 1464 |
| ccg gca tcg cgg gac ctg cgc agg ccg cgt ccg acc gga ccg atc gtc<br>Pro Ala Ser Arg Asp Leu Arg Arg Pro Arg Pro Thr Gly Pro Ile Val<br>260                    265                  270                  275 | 1512 |
| gat ggc cat gtg ctg ccg cag acc gac agc gcg gcg atc gcg gcg ggg<br>Asp Gly His Val Leu Pro Gln Thr Asp Ser Ala Ala Ile Ala Ala Gly<br>280                    285                  290 | 1560 |
| cag ctg gcg ccg gtt cgg gtc ctg atc gga acc aat gcc gac gaa ggc<br>Gln Leu Ala Pro Val Arg Val Leu Ile Gly Thr Asn Ala Asp Glu Gly<br>295                    300                  305 | 1608 |
| cgc gcc ttc ctc ggg cgc gcg ccg atg gag acg cca gcg gac tac caa<br>Arg Ala Phe Leu Gly Arg Ala Pro Met Glu Thr Pro Ala Asp Tyr Gln<br>310                    315                  320 | 1656 |
| gcc tat ctg gag gcg cag ttt ggc gac caa gcc gcc gcc gtg gcg gcg<br>Ala Tyr Leu Glu Ala Gln Phe Gly Asp Gln Ala Ala Ala Val Ala Ala<br>325                    330                  335 | 1704 |
| tgc tat ccc ctc gac ggc cgg gcc acg ccc aag gaa atg gtc gcg cgc<br>Cys Tyr Pro Leu Asp Gly Arg Ala Thr Pro Lys Glu Met Val Ala Arg<br>340                    345                  350                  355 | 1752 |
| atc ttc ggc gac aat cag ttc aat cgg ggg gtc tcg gcc ttc tcg gaa<br>Ile Phe Gly Asp Asn Gln Phe Asn Arg Gly Val Ser Ala Phe Ser Glu<br>360                    365                  370 | 1800 |
| gcg ctt gtg cgc cag ggc gcg ccc gtg tgg cgt tat cag ttc aac ggt<br>Ala Leu Val Arg Gln Gly Ala Pro Val Trp Arg Tyr Gln Phe Asn Gly<br>375                    380                  385 | 1848 |
| aat acc gag ggt gga aga gcg ccg gct acc cac gga gcc gaa att ccc<br>Asn Thr Glu Gly Gly Arg Ala Pro Ala Thr His Gly Ala Glu Ile Pro<br>390                    395                  400 | 1896 |
| tac gtt ttc ggg gtg ttc aag ctc gac gag ttg ggt ctg ttc gat tgg<br>Tyr Val Phe Gly Val Phe Lys Leu Asp Glu Leu Gly Leu Phe Asp Trp<br>405                    410                  415 | 1944 |
| ccg ccc gag ggg ccc acg ccc gcc gac cgt gcg ctg ggc caa ctg atg<br>Pro Pro Glu Gly Pro Thr Pro Ala Asp Arg Ala Leu Gly Gln Leu Met<br>420                    425                  430                  435 | 1992 |
| tcc tcc gcc tgg gtc cgg ttc gcc aag aat ggc gac ccc gcc ggg gac<br>Ser Ser Ala Trp Val Arg Phe Ala Lys Asn Gly Asp Pro Ala Gly Asp<br>440                    445                  450 | 2040 |
| gcc ctt acc tgg cct gcc tat tct acg ggc aag tcg acc atg aca ttc<br>Ala Leu Thr Trp Pro Ala Tyr Ser Thr Gly Lys Ser Thr Met Thr Phe<br>455                    460                  465 | 2088 |
| ggt ccc gag ggc cgc gcg gcg gtg gtg tcg ccc gga cct tcc atc ccc<br>Gly Pro Glu Gly Arg Ala Ala Val Val Ser Pro Gly Pro Ser Ile Pro<br>470                    475                  480 | 2136 |

```
cct tgc gcg gat ggc gcc aag gcg ggg ggc gga ggc agc ggc gga ggc      2184
Pro Cys Ala Asp Gly Ala Lys Ala Gly Gly Gly Ser Gly Gly Gly
    485                 490                 495 agc ggc gga ggc agc aaa gac aac gtt gcg gac gtg gta gtg gtg ggc      2232
Ser Gly Gly Gly Ser Lys Asp Asn Val Ala Asp Val Val Val Val Gly
500                 505                 510                 515 gct ggc ttg agc ggt ttg gag acg gca cgc aaa gtc cag gcc gcc ggt      2280
Ala Gly Leu Ser Gly Leu Glu Thr Ala Arg Lys Val Gln Ala Ala Gly
            520                 525                 530 ctg tcc tgc ctc gtt ctt gag gcg atg gat cgt gta ggg gga aag act      2328
Leu Ser Cys Leu Val Leu Glu Ala Met Asp Arg Val Gly Gly Lys Thr
        535                 540                 545 ctg agc gta caa tcg ggt ccc ggc agg acg act atc aac gac ctc ggc      2376
Leu Ser Val Gln Ser Gly Pro Gly Arg Thr Thr Ile Asn Asp Leu Gly
    550                 555                 560 gct gcg tgg atc aat gac agc aac caa agc gaa gta tcc aga ttg ttt      2424
Ala Ala Trp Ile Asn Asp Ser Asn Gln Ser Glu Val Ser Arg Leu Phe
565                 570                 575 gaa aga ttt cat ttg gag ggc gag ctc cag agg acg act gga aat tca      2472
Glu Arg Phe His Leu Glu Gly Glu Leu Gln Arg Thr Thr Gly Asn Ser
580                 585                 590                 595 atc cat caa gca caa gac ggt aca acc act aca gct cct tat ggt gac      2520
Ile His Gln Ala Gln Asp Gly Thr Thr Thr Thr Ala Pro Tyr Gly Asp
            600                 605                 610 tcc ttg ctg agc gag gag gtt gca agt gca ctt gcg gaa ctc ctc ccc      2568
Ser Leu Leu Ser Glu Glu Val Ala Ser Ala Leu Ala Glu Leu Leu Pro
        615                 620                 625 gta tgg tct cag ctg atc gaa gag cat agc ctt caa gac ctc aag gcg      2616
Val Trp Ser Gln Leu Ile Glu Glu His Ser Leu Gln Asp Leu Lys Ala
    630                 635                 640 agc cct cag gcg aag cgg ctc gac agt gtg agc ttc gcg cac tac tgt      2664
Ser Pro Gln Ala Lys Arg Leu Asp Ser Val Ser Phe Ala His Tyr Cys
645                 650                 655 gag aag gaa cta aac ttg cct gct gtt ctc ggc gta gca aac cag atc      2712
Glu Lys Glu Leu Asn Leu Pro Ala Val Leu Gly Val Ala Asn Gln Ile
660                 665                 670                 675 aca cgc gct ctg ctc ggt gtg gaa gcc cac gag atc agc atg ctt ttt      2760
Thr Arg Ala Leu Leu Gly Val Glu Ala His Glu Ile Ser Met Leu Phe
            680                 685                 690 ctc acc gac tac atc aag agt gcc acc ggt ctc agt aat att ttc tcg      2808
Leu Thr Asp Tyr Ile Lys Ser Ala Thr Gly Leu Ser Asn Ile Phe Ser
        695                 700                 705 gac aag aaa gac ggc ggg cag tat atg cga tgc aaa aca ggt atg cag      2856
Asp Lys Lys Asp Gly Gly Gln Tyr Met Arg Cys Lys Thr Gly Met Gln
    710                 715                 720 tcg att tgc cat gcc atg tca aag gaa ctt gtt cca ggc tca gtg cac      2904
Ser Ile Cys His Ala Met Ser Lys Glu Leu Val Pro Gly Ser Val His
725                 730                 735 ctc aac acc ccc gtc gct gaa att gag cag tcg gca tcc ggc tgt aca      2952
Leu Asn Thr Pro Val Ala Glu Ile Glu Gln Ser Ala Ser Gly Cys Thr
740                 745                 750                 755 gta cga tcg gcc tcg ggc gcc gtg ttc cga agc aaa aag gtg gtg gtt      3000
Val Arg Ser Ala Ser Gly Ala Val Phe Arg Ser Lys Lys Val Val Val
            760                 765                 770 tcg tta ccg aca acc ttg tat ccc acc ttg aca ttt tca cca cct ctt      3048
Ser Leu Pro Thr Thr Leu Tyr Pro Thr Leu Thr Phe Ser Pro Pro Leu
        775                 780                 785 ccc gcc gag aag caa gca ttg gcg gaa aat tct atc ctg ggc tac tat      3096
Pro Ala Glu Lys Gln Ala Leu Ala Glu Asn Ser Ile Leu Gly Tyr Tyr
    790                 795                 800
```

```
                                                        -continued agc aag ata gtc ttc gta tgg gac aag ccg tgg tgg cgc gaa caa ggc    3144
Ser Lys Ile Val Phe Val Trp Asp Lys Pro Trp Trp Arg Glu Gln Gly
805                 810                 815 ttc tcg ggc gtc ctc caa tcg agc tgt gac ccc atc tca ttt gcc aga    3192
Phe Ser Gly Val Leu Gln Ser Ser Cys Asp Pro Ile Ser Phe Ala Arg
820                 825                 830                 835 gat acc agc atc gac gtc gat cga caa tgg tcc att acc tgt ttc atg    3240
Asp Thr Ser Ile Asp Val Asp Arg Gln Trp Ser Ile Thr Cys Phe Met
                840                 845                 850 gtc gga gac ccg gga cgg aag tgg tcc caa cag tcc aag cag gta cga    3288
Val Gly Asp Pro Gly Arg Lys Trp Ser Gln Gln Ser Lys Gln Val Arg
            855                 860                 865 caa aag tct gtc tgg gac caa ctc cgc gca gcc tac gag aac gcc ggg    3336
Gln Lys Ser Val Trp Asp Gln Leu Arg Ala Ala Tyr Glu Asn Ala Gly
        870                 875                 880 gcc caa gtc cca gag ccg gcc aac gtg ctc gaa atc gag tgg tcg aag    3384
Ala Gln Val Pro Glu Pro Ala Asn Val Leu Glu Ile Glu Trp Ser Lys
885                 890                 895 cag cag tat ttc caa gga gct ccg agc gcc gtc tat ggg ctg aac gat    3432
Gln Gln Tyr Phe Gln Gly Ala Pro Ser Ala Val Tyr Gly Leu Asn Asp
900                 905                 910                 915 ctc atc aca ctg ggt tcg gcg ctc aga acg ccg ttc aag agt gtt cat    3480
Leu Ile Thr Leu Gly Ser Ala Leu Arg Thr Pro Phe Lys Ser Val His
                920                 925                 930 ttc gtt gga acg gag acg tct tta gtt tgg aaa ggg tat atg gaa ggg    3528
Phe Val Gly Thr Glu Thr Ser Leu Val Trp Lys Gly Tyr Met Glu Gly
            935                 940                 945 gcc ata cga tcg ggt caa cga ggt gct gca gaa gtt gtg gct agc ctg    3576
Ala Ile Arg Ser Gly Gln Arg Gly Ala Ala Glu Val Val Ala Ser Leu
        950                 955                 960 gtg cca gca gca tag                                                3591
Val Pro Ala Ala
    965

<210> SEQ ID NO 31
<211> LENGTH: 1196
<212> TYPE: PRT
<213> ORGANISM: Unknown
<220> FEATURE:
<223> OTHER INFORMATION: Orf of BEST1:K:trAPAO fusion pGEX-4T-1
      (Exophiala spinifera)
<220> FEATURE:
<221> NAME/KEY: misc_feature
<222> LOCATION: (1)..(687)
<223> OTHER INFORMATION: gst + polylinker
<220> FEATURE:
<221> NAME/KEY: misc_feature
<222> LOCATION: (2164)..(2199)
<223> OTHER INFORMATION: spacer sequence
<220> FEATURE:
<221> NAME/KEY: misc_feature
<222> LOCATION: (2200)..(3588)
<223> OTHER INFORMATION: K:trAPAO
<220> FEATURE:
<221> NAME/KEY: misc_feature
<222> LOCATION: (2200)..(2202)
<223> OTHER INFORMATION: extra lysine

<400> SEQUENCE: 31

Met Ser Pro Ile Leu  Gly Tyr Trp Lys Ile  Lys Gly Leu Val Gln
                -225                -220                -215

Pro Thr Arg Leu Leu  Leu Glu Tyr Leu Glu  Lys Tyr Glu Glu
                -210                -205                -200

His Leu Tyr Glu Arg  Asp Glu Gly Asp Lys  Trp Arg Asn Lys Lys
```

-continued

```
                    -195              -190              -185
Phe Glu Leu Gly Leu Glu Phe Pro Asn Leu Pro Tyr Tyr Ile Asp
                -180              -175              -170
Gly Asp Val Lys Leu Thr Gln Ser Met Ala Ile Ile Arg Tyr Ile
                -165              -160              -155
Ala Asp Lys His Asn Met Leu Gly Gly Cys Pro Lys Glu Arg Ala
                -150              -145              -140
Glu Ile Ser Met Leu Glu Gly Ala Val Leu Asp Ile Arg Tyr Gly
                -135              -130              -125
Val Ser Arg Ile Ala Tyr Ser Lys Asp Phe Glu Thr Leu Lys Val
                -120              -115              -110
Asp Phe Leu Ser Lys Leu Pro Glu Met Leu Lys Met Phe Glu Asp Arg
                -105              -100              -95
Leu Cys His Lys Thr Tyr Leu Asn Gly Asp His Val Thr His Pro Asp
                -90               -85                -80
Phe Met Leu Tyr Asp Ala Leu Asp Val Val Leu Tyr Met Asp Pro Met
                -75                -70                -65
Cys Leu Asp Ala Phe Pro Lys Leu Val Cys Phe Lys Lys Arg Ile Glu
    -60                -55                -50
Ala Ile Pro Gln Ile Asp Lys Tyr Leu Lys Ser Ser Lys Tyr Ile Ala
-45                -40                -35                -30
Trp Pro Leu Gln Gly Trp Gln Ala Thr Phe Gly Gly Asp His Pro
                -25                -20                -15
Pro Lys Ser Asp Leu Val Pro Arg Gly Ser Pro Glu Phe Thr Asp Phe
                -10                -5                 -1   1
Pro Val Arg Arg Thr Asp Leu Gly Gln Val Gln Gly Leu Ala Gly Asp
    5                  10                 15
Val Met Ser Phe Arg Gly Ile Pro Tyr Ala Ala Pro Val Gly Gly
20                  25                 30                 35
Leu Arg Trp Lys Pro Pro Gln His Ala Arg Pro Trp Ala Gly Val Arg
                40                 45                 50
Pro Ala Thr Gln Phe Gly Ser Asp Cys Phe Gly Ala Ala Tyr Leu Arg
                55                 60                 65
Lys Gly Ser Leu Ala Pro Gly Val Ser Glu Asp Cys Leu Tyr Leu Asn
                70                 75                 80
Val Trp Ala Pro Ser Gly Ala Lys Pro Gly Gln Tyr Pro Val Met Val
85                  90                 95
Trp Val Tyr Gly Gly Phe Ala Gly Thr Ala Ala Met Pro Tyr
100                 105                110                115
Tyr Asp Gly Glu Ala Leu Ala Arg Gln Gly Val Val Val Thr Phe
                120                125                130
Asn Tyr Arg Thr Asn Ile Leu Gly Phe Phe Ala His Pro Gly Leu Ser
                135                140                145
Arg Glu Ser Pro Thr Gly Thr Ser Gly Asn Tyr Gly Leu Leu Asp Ile
            150                155                160
Leu Ala Ala Leu Arg Trp Val Gln Ser Asn Ala Arg Ala Phe Gly Gly
    165                170                175
Asp Pro Gly Arg Val Thr Val Phe Gly Glu Ser Ala Gly Ala Ser Ala
180                 185                190                195
Ile Gly Leu Leu Leu Thr Ser Pro Leu Ser Lys Gly Leu Phe Arg Gly
                200                205                210
Ala Ile Leu Glu Ser Pro Gly Leu Thr Arg Pro Leu Ala Thr Leu Ala
                215                220                225
```

-continued

```
Asp Ser Ala Ala Ser Gly Glu Arg Leu Asp Ala Asp Leu Ser Arg Leu
            230                 235                 240

Arg Ser Thr Asp Pro Ala Thr Leu Met Ala Arg Ala Asp Ala Ala Arg
        245                 250                 255

Pro Ala Ser Arg Asp Leu Arg Arg Pro Arg Thr Gly Pro Ile Val
260                 265                 270                 275

Asp Gly His Val Leu Pro Gln Thr Asp Ser Ala Ile Ala Ala Gly
                280                 285                 290

Gln Leu Ala Pro Val Arg Val Leu Ile Gly Thr Asn Ala Asp Glu Gly
            295                 300                 305

Arg Ala Phe Leu Gly Arg Ala Pro Met Glu Thr Pro Ala Asp Tyr Gln
        310                 315                 320

Ala Tyr Leu Glu Ala Gln Phe Gly Asp Gln Ala Ala Val Ala Ala
    325                 330                 335

Cys Tyr Pro Leu Asp Gly Arg Ala Thr Pro Lys Glu Met Val Ala Arg
340                 345                 350                 355

Ile Phe Gly Asp Asn Gln Phe Asn Arg Gly Val Ser Ala Phe Ser Glu
                360                 365                 370

Ala Leu Val Arg Gln Gly Ala Pro Val Trp Arg Tyr Gln Phe Asn Gly
            375                 380                 385

Asn Thr Glu Gly Gly Arg Ala Pro Ala Thr His Gly Ala Glu Ile Pro
        390                 395                 400

Tyr Val Phe Gly Val Phe Lys Leu Asp Glu Leu Gly Leu Phe Asp Trp
    405                 410                 415

Pro Pro Glu Gly Pro Thr Pro Ala Asp Arg Ala Leu Gly Gln Leu Met
420                 425                 430                 435

Ser Ser Ala Trp Val Arg Phe Ala Lys Asn Gly Asp Pro Ala Gly Asp
                440                 445                 450

Ala Leu Thr Trp Pro Ala Tyr Ser Thr Gly Lys Ser Thr Met Thr Phe
            455                 460                 465

Gly Pro Glu Gly Arg Ala Ala Val Val Ser Pro Gly Pro Ser Ile Pro
        470                 475                 480

Pro Cys Ala Asp Gly Ala Lys Ala Gly Gly Gly Ser Gly Gly Gly
485                 490                 495

Ser Gly Gly Gly Ser Lys Asp Asn Val Ala Asp Val Val Val Gly
500                 505                 510                 515

Ala Gly Leu Ser Gly Leu Glu Thr Ala Arg Lys Val Gln Ala Ala Gly
            520                 525                 530

Leu Ser Cys Leu Val Leu Glu Ala Met Asp Arg Val Gly Gly Lys Thr
        535                 540                 545

Leu Ser Val Gln Ser Gly Pro Gly Arg Thr Thr Ile Asn Asp Leu Gly
    550                 555                 560

Ala Ala Trp Ile Asn Asp Ser Asn Gln Ser Glu Val Ser Arg Leu Phe
    565                 570                 575

Glu Arg Phe His Leu Glu Gly Glu Leu Gln Arg Thr Gly Asn Ser
580                 585                 590                 595

Ile His Gln Ala Gln Asp Gly Thr Thr Thr Thr Ala Pro Tyr Gly Asp
                600                 605                 610

Ser Leu Leu Ser Glu Glu Val Ala Ser Ala Leu Ala Glu Leu Leu Pro
            615                 620                 625

Val Trp Ser Gln Leu Ile Glu Glu His Ser Leu Gln Asp Leu Lys Ala
        630                 635                 640
```

```
Ser Pro Gln Ala Lys Arg Leu Asp Ser Val Ser Phe Ala His Tyr Cys
    645                 650                 655

Glu Lys Glu Leu Asn Leu Pro Ala Val Leu Gly Val Ala Asn Gln Ile
660                 665                 670                 675

Thr Arg Ala Leu Leu Gly Val Glu Ala His Glu Ile Ser Met Leu Phe
                680                 685                 690

Leu Thr Asp Tyr Ile Lys Ser Ala Thr Gly Leu Ser Asn Ile Phe Ser
            695                 700                 705

Asp Lys Lys Asp Gly Gly Gln Tyr Met Arg Cys Lys Thr Gly Met Gln
        710                 715                 720

Ser Ile Cys His Ala Met Ser Lys Glu Leu Val Pro Gly Ser Val His
    725                 730                 735

Leu Asn Thr Pro Val Ala Glu Ile Glu Gln Ser Ala Ser Gly Cys Thr
740                 745                 750                 755

Val Arg Ser Ala Ser Gly Ala Val Phe Arg Ser Lys Lys Val Val Val
                760                 765                 770

Ser Leu Pro Thr Thr Leu Tyr Pro Thr Leu Thr Phe Ser Pro Pro Leu
            775                 780                 785

Pro Ala Glu Lys Gln Ala Leu Ala Glu Asn Ser Ile Leu Gly Tyr Tyr
        790                 795                 800

Ser Lys Ile Val Phe Val Trp Asp Lys Pro Trp Trp Arg Glu Gln Gly
    805                 810                 815

Phe Ser Gly Val Leu Gln Ser Ser Cys Asp Pro Ile Ser Phe Ala Arg
820                 825                 830                 835

Asp Thr Ser Ile Asp Val Asp Arg Gln Trp Ser Ile Thr Cys Phe Met
                840                 845                 850

Val Gly Asp Pro Gly Arg Lys Trp Ser Gln Gln Ser Lys Gln Val Arg
            855                 860                 865

Gln Lys Ser Val Trp Asp Gln Leu Arg Ala Ala Tyr Glu Asn Ala Gly
        870                 875                 880

Ala Gln Val Pro Glu Pro Ala Asn Val Leu Glu Ile Glu Trp Ser Lys
    885                 890                 895

Gln Gln Tyr Phe Gln Gly Ala Pro Ser Ala Val Tyr Gly Leu Asn Asp
900                 905                 910                 915

Leu Ile Thr Leu Gly Ser Ala Leu Arg Thr Pro Phe Lys Ser Val His
            920                 925                 930

Phe Val Gly Thr Glu Thr Ser Leu Val Trp Lys Gly Tyr Met Glu Gly
        935                 940                 945

Ala Ile Arg Ser Gly Gln Arg Gly Ala Ala Glu Val Val Ala Ser Leu
    950                 955                 960

Val Pro Ala Ala
    965

<210> SEQ ID NO 32
<211> LENGTH: 1803
<212> TYPE: DNA
<213> ORGANISM: Unknown
<220> FEATURE:
<223> OTHER INFORMATION: Glyc(-) mutation in glycosylation sites
      (Exophiala spinifera)
<220> FEATURE:
<221> NAME/KEY: CDS
<222> LOCATION: (1)..(1803)
<223> OTHER INFORMATION:

<400> SEQUENCE: 32 atg gca ctt gca ccg agc tac atc aat ccc cca aac gtc gcc tcc cca      48
```

```
        Met Ala Leu Ala Pro Ser Tyr Ile Asn Pro Pro Asn Val Ala Ser Pro
        1               5                   10                  15 gca ggg tat tct cac gtc ggc gta ggc cca gac gga ggg agg tat gtg         96
Ala Gly Tyr Ser His Val Gly Val Gly Pro Asp Gly Gly Arg Tyr Val
                20                  25                  30 aca ata gct gga cag att gga caa gac gct tcg ggc gtg aca gac cct        144
Thr Ile Ala Gly Gln Ile Gly Gln Asp Ala Ser Gly Val Thr Asp Pro
            35                  40                  45 gcc tac gag aaa cag gtt gcc caa gca ttc gcc aat ctg cga gct tgc        192
Ala Tyr Glu Lys Gln Val Ala Gln Ala Phe Ala Asn Leu Arg Ala Cys
        50                  55                  60 ctt gct gca gtt gga gcc act tca aac gac gtc acc aag ctc aat tac        240
Leu Ala Ala Val Gly Ala Thr Ser Asn Asp Val Thr Lys Leu Asn Tyr
65                  70                  75                  80 tac atc gtc gac tac gcc ccg agc aaa ctc acc gca att gga gat ggg        288
Tyr Ile Val Asp Tyr Ala Pro Ser Lys Leu Thr Ala Ile Gly Asp Gly
                85                  90                  95 ctg aag gct acc ttt gcc ctt gac agg ctc cct cct tgc acg ctg gtg        336
Leu Lys Ala Thr Phe Ala Leu Asp Arg Leu Pro Pro Cys Thr Leu Val
            100                 105                 110 cca gtg tcg gcc ttg tct tca cct gaa tac ctc ttt gag gtt gat gcc        384
Pro Val Ser Ala Leu Ser Ser Pro Glu Tyr Leu Phe Glu Val Asp Ala
        115                 120                 125 acg gcg ctg gtg ccg gga cac acg acc cca gac aac gtt gcg gac gtg        432
Thr Ala Leu Val Pro Gly His Thr Thr Pro Asp Asn Val Ala Asp Val
130                 135                 140 gta gtg gtg ggc gct ggc ttg agc ggt ttg gag acg gca cgc aaa gtc        480
Val Val Val Gly Ala Gly Leu Ser Gly Leu Glu Thr Ala Arg Lys Val
145                 150                 155                 160 cag gcc gcc ggt ctg tcc tgc ctc gtt ctt gag gcg atg gat cgt gta        528
Gln Ala Ala Gly Leu Ser Cys Leu Val Leu Glu Ala Met Asp Arg Val
                165                 170                 175 ggg gga aag act ctg agc gta caa tcg ggt ccc ggc agg acg act atc        576
Gly Gly Lys Thr Leu Ser Val Gln Ser Gly Pro Gly Arg Thr Thr Ile
            180                 185                 190 aac gac ctc ggc gct gcg tgg atc aat gat agc aat cag gcc gaa gta        624
Asn Asp Leu Gly Ala Ala Trp Ile Asn Asp Ser Asn Gln Ala Glu Val
        195                 200                 205 tcc aga ttg ttt gaa aga ttt cat ttg gag ggc gag ctc cag agg acg        672
Ser Arg Leu Phe Glu Arg Phe His Leu Glu Gly Glu Leu Gln Arg Thr
210                 215                 220 act gga aat tca atc cat caa gca caa gac ggt aca acc act aca gct        720
Thr Gly Asn Ser Ile His Gln Ala Gln Asp Gly Thr Thr Thr Thr Ala
225                 230                 235                 240 cct tat ggt gac tcc ttg ctg agc gag gag gtt gca agt gca ctt gcg        768
Pro Tyr Gly Asp Ser Leu Leu Ser Glu Glu Val Ala Ser Ala Leu Ala
                245                 250                 255 gaa ctc ctc ccc gta tgg tct cag ctg atc gaa gag cat agc ctt caa        816
Glu Leu Leu Pro Val Trp Ser Gln Leu Ile Glu Glu His Ser Leu Gln
            260                 265                 270 gac ctc aag gcg agc cct cag gcg aag cgg ctc gac agt gtg agc ttc        864
Asp Leu Lys Ala Ser Pro Gln Ala Lys Arg Leu Asp Ser Val Ser Phe
        275                 280                 285 gcg cac tac tgt gag aag gaa cta aac ttg cct gct gtt ctc ggc gta        912
Ala His Tyr Cys Glu Lys Glu Leu Asn Leu Pro Ala Val Leu Gly Val
290                 295                 300 gca aac cag atc aca cgc gct ctg ctc ggt gtg gaa gcc cac gag atc        960
Ala Asn Gln Ile Thr Arg Ala Leu Leu Gly Val Glu Ala His Glu Ile
305                 310                 315                 320
```

```
agc atg ctt ttt ctc acc gac tac atc aag agt gcc acc ggt ctc agt      1008
Ser Met Leu Phe Leu Thr Asp Tyr Ile Lys Ser Ala Thr Gly Leu Ser
        325                 330                 335 aat att ttc tcg gac aag aaa gac ggc ggg cag tat atg cga tgc aaa      1056
Asn Ile Phe Ser Asp Lys Lys Asp Gly Gly Gln Tyr Met Arg Cys Lys
    340                 345                 350 aca ggt atg cag tcg att tgc cat gcc atg tca aag gaa ctt gtt cca      1104
Thr Gly Met Gln Ser Ile Cys His Ala Met Ser Lys Glu Leu Val Pro
355                 360                 365 ggc tca gtg cac ctc aac acc ccc gtc gct gaa att gag cag tcg gca      1152
Gly Ser Val His Leu Asn Thr Pro Val Ala Glu Ile Glu Gln Ser Ala
    370                 375                 380 tcc ggc tgt aca gta cga tcg gcc tcg ggc gcc gtg ttc cga agc aaa      1200
Ser Gly Cys Thr Val Arg Ser Ala Ser Gly Ala Val Phe Arg Ser Lys
385                 390                 395                 400 aag gtg gtg gtt tcg tta ccg aca acc ttg tat ccc acc ttg aca ttt      1248
Lys Val Val Val Ser Leu Pro Thr Thr Leu Tyr Pro Thr Leu Thr Phe
                405                 410                 415 tca cca cct ctt ccc gcc gag aag caa gca ttg gcg gaa aat tct atc      1296
Ser Pro Pro Leu Pro Ala Glu Lys Gln Ala Leu Ala Glu Asn Ser Ile
            420                 425                 430 ctg ggc tac tat agc aag ata gtc ttc gta tgg gac aag ccg tgg tgg      1344
Leu Gly Tyr Tyr Ser Lys Ile Val Phe Val Trp Asp Lys Pro Trp Trp
        435                 440                 445 cgc gaa caa ggc ttc tcg ggc gtc ctc caa tcg agc tgt gac ccc atc      1392
Arg Glu Gln Gly Phe Ser Gly Val Leu Gln Ser Ser Cys Asp Pro Ile
    450                 455                 460 tca ttt gcc aga gat acc agc atc gac gtc gat cga caa tgg tcc att      1440
Ser Phe Ala Arg Asp Thr Ser Ile Asp Val Asp Arg Gln Trp Ser Ile
465                 470                 475                 480 acc tgt ttc atg gtc gga gac ccg gga cgg aag tgg tcc caa cag tcc      1488
Thr Cys Phe Met Val Gly Asp Pro Gly Arg Lys Trp Ser Gln Gln Ser
                485                 490                 495 aag cag gta cga caa aag tct gtc tgg gac caa ctc cgc gca gcc tac      1536
Lys Gln Val Arg Gln Lys Ser Val Trp Asp Gln Leu Arg Ala Ala Tyr
            500                 505                 510 gag aac gcc ggg gcc caa gtc cca gag ccg gcc aac gtg ctc gaa atc      1584
Glu Asn Ala Gly Ala Gln Val Pro Glu Pro Ala Asn Val Leu Glu Ile
        515                 520                 525 gag tgg tcg aag cag cag tat ttc caa gga gct ccg agc gcc gtc tat      1632
Glu Trp Ser Lys Gln Gln Tyr Phe Gln Gly Ala Pro Ser Ala Val Tyr
    530                 535                 540 ggg ctg aac gat ctc atc aca ctg ggt tcg gcg ctc aga acg ccg ttc      1680
Gly Leu Asn Asp Leu Ile Thr Leu Gly Ser Ala Leu Arg Thr Pro Phe
545                 550                 555                 560 aag agt gtt cat ttc gtt gga acg gag acg tct tta gtt tgg aaa ggg      1728
Lys Ser Val His Phe Val Gly Thr Glu Thr Ser Leu Val Trp Lys Gly
                565                 570                 575 tat atg gaa ggg gcc ata cga tcg ggt caa cga ggt gct gca gaa gtt      1776
Tyr Met Glu Gly Ala Ile Arg Ser Gly Gln Arg Gly Ala Ala Glu Val
            580                 585                 590 gtg gct agc ctg gtg cca gca gca tag                                  1803
Val Ala Ser Leu Val Pro Ala Ala
        595                 600

<210> SEQ ID NO 33
<211> LENGTH: 600
<212> TYPE: PRT
<213> ORGANISM: Unknown
<220> FEATURE:
<223> OTHER INFORMATION: Glyc(-) APAO; mutation in glycosylation sites
```

-continued (Exophiala spinifera)

<400> SEQUENCE: 33

```
Met Ala Leu Ala Pro Ser Tyr Ile Asn Pro Asn Val Ala Ser Pro
1               5                  10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
 50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ala Glu Val
            195                 200                 205

Ser Arg Leu Phe Glu Arg Phe His Leu Glu Gly Glu Leu Gln Arg Thr
        210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu His Ser Leu Gln
                260                 265                 270

Asp Leu Lys Ala Ser Pro Gln Ala Lys Arg Leu Asp Ser Val Ser Phe
            275                 280                 285

Ala His Tyr Cys Glu Lys Glu Leu Asn Leu Pro Ala Val Leu Gly Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400
```

-continued

```
Lys Val Val Ser Leu Pro Thr Thr Leu Tyr Pro Thr Leu Thr Phe
            405                 410                 415
Ser Pro Pro Leu Pro Ala Glu Lys Gln Ala Leu Ala Glu Asn Ser Ile
            420                 425                 430
Leu Gly Tyr Tyr Ser Lys Ile Val Phe Val Trp Asp Lys Pro Trp Trp
            435                 440                 445
Arg Glu Gln Gly Phe Ser Gly Val Leu Gln Ser Ser Cys Asp Pro Ile
450                 455                 460
Ser Phe Ala Arg Asp Thr Ser Ile Asp Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
            515                 520                 525
Glu Trp Ser Lys Gln Gln Tyr Phe Gln Gly Ala Pro Ser Ala Val Tyr
            530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
            595                 600
```

<210> SEQ ID NO 34
<211> LENGTH: 37
<212> TYPE: DNA
<213> ORGANISM: Artificial Sequence
<220> FEATURE:
<223> OTHER INFORMATION: 37-mer oligonucleotide (Exophiala spinifera)

<400> SEQUENCE: 34
ggggaattca tggcacttgc accgagctac atcaatc                                37

<210> SEQ ID NO 35
<211> LENGTH: 1929
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:

<400> SEQUENCE: 35
atggcacttg caccgagcta catcaatccc ccaaacgtcg cctccccagc agggtattcc        60
cacatcggcg taggcccaaa cgaagcgagg tatgtgacaa tagctggaca gattggacaa       120
gacgctttgg gcgtgacaga cccagcctac gagaaacagg ttgcccaagc attcgccaat       180
ctgcgagctt gccttgctgc agttggagcc tcttcaaacg acgtcaccaa gctcaattac       240
tacatcgtcg actacgcccc gagcaaactc accgcaattg agatgggct gaagtctacc       300 tttgcccttg acaggctccc tccttgcacg ctggtgccag taccggcctt ggcttcacct       360

```
gaatacctct tgaggttga tgccacggcg ctggtgccag gacactcgac cccagacaac    420
gttgcggacg tggtagtggt gggcgctggc ttgagcggtt tggagacggc acgcaaagtc    480
caggccgccg gtctgtcctg cctcgttctt gaggcgatgg atcgtgtagg gggaaagact    540
ctgagcgtac aatcgggtcc cggcaggacg actatcaacg acctcggcgc tgcgtggatc    600
aatgacagca accaaagcga agtatccaga ttgtttgaaa gatttcattt ggagggcgag    660
ctccagagga cgaccggaaa ttcaatccat caagcacaag acggtacaac cactacagct    720
ccttatggtg actccccggt aagcacaatc ccactttgtg atgagacctc tgtcgagtgt    780
agaatacagt cactgactcc acttcgtcca gctgagcgag gaggttgcaa gtgcacttgc    840
ggaactcctc cccgtatggt ctcagctgat cgaagagtat agccttgaag accccaaggc    900
gagccctcag gcgaagcggc tcgacagtgt gagcttcgcg cactactgtg agaaggacct    960
aaacttgcct gctgttctca gcgtggcaaa ccagatcaca cgcgctctgc tcggtgtgga   1020
agcccacgag atcagcatgc tttttctcac cgactacatc aagagtgcca ccggtctcag   1080
taatattgtc tcggacaaga agacggcgg gcagtatatg cgatgcaaaa caggtgcgtg   1140
cggtgtcctc tcaggtaggg gactcgtttc ttagtggtca ttccaggtat gcagtcgatt   1200
tgccatgcca tgtcaaagga acttgttcca ggctcagtgc acctcaacac ccccgtcgct   1260
ggaattgagc agtcggcgtc cggctgtata gtacgatcgg cctcgggcgc cgtgttccga   1320
agcaaaaagg tggtggtttc gttaccgaca acattgtatc ccaccttgac attttcacca   1380
cctcttcccg ccgagaagca agcattggcg gaaaaatcta tcctcggcta ctatagcaag   1440
atagtcttcg tatgggacaa cccgtggtgg cgcgaacaag gcttctcggg cgtcctccaa   1500
tcgagctgtg accccatctc atttgccaga gataccagca tcgaagtcga tcggcaatgg   1560
tccattacct gtttcatggt cggagacccg ggacggaagt ggtcccaaca gtccaagcag   1620
gtacgacaaa agtctgtctg ggaccaactc cgcgcagcct acgagaacgc cggggcccaa   1680
gtcccagagc cggccaacgt gctcgaaatc gagtggtcga agcagcagta tttccaagga   1740
gctccgagcg ccgtctatgg gctgaacgat ctcatcacac tgggttcggc gctcagaacg   1800
ccgttcaagt gtgttcattt cgttggaacg gagacgtctt tagtttggaa agggtatatg   1860 gaagggggcca tacgatcggg tcaacgaggt gctgcagaag ttgtggctag cctggtgcca   1920
gcagcatag                                                           1929
```

<210> SEQ ID NO 36
<211> LENGTH: 600
<212> TYPE: PRT
<213> ORGANISM: Exophilia spinifera

<400> SEQUENCE: 36

```
Met Ala Leu Ala Pro Ser Tyr Ile Asn Pro Pro Asn Val Ala Ser Pro
1               5                   10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95
```

```
Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
            115                 120                 125

Thr Ala Leu Val Pro Gly His Ser Thr Pro Asp Asn Val Ala Asp Val
            130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
            195                 200                 205

Ser Arg Leu Phe Glu Arg Phe His Leu Glu Gly Glu Leu Gln Arg Thr
            210                 215                 220

Thr Gly Asn Ser Ile His Gln Ala Gln Asp Gly Thr Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Arg Leu Asp Ser Val Ser Phe
            275                 280                 285

Ala His Tyr Cys Glu Lys Asp Leu Asn Leu Pro Ala Val Leu Ser Val
            290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
            355                 360                 365

Gly Ser Val His Leu Asn Thr Pro Val Ala Gly Ile Glu Gln Ser Ala
            370                 375                 380

Ser Gly Cys Ile Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Asn Pro Trp Trp
            435                 440                 445

Arg Glu Gln Gly Phe Ser Gly Val Leu Gln Ser Ser Cys Asp Pro Ile
450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510
```

-continued

| | | | | | | | | | | | |
|---|---|---|---|---|---|---|---|---|---|---|---|
|Glu|Asn|Ala|Gly|Ala|Gln|Val|Pro|Glu|Pro|Ala|Asn|Val|Leu|Glu|Ile|
| |515| | | | |520| | | | |525| | | | |

Glu Trp Ser Lys Gln Gln Tyr Phe Gln Gly Ala Pro Ser Ala Val Tyr
      530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 37
<211> LENGTH: 1929
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:

<400> SEQUENCE: 37

| | | |
|---|---|---|
|atggcacttg caccgagcta catcaatccc ccaaacgtcg cctccccagc agggtattcc|60|
|cacatcggcg taggcccaaa cgaagcgagg tatgtgacaa tagctggaca gattggacaa|120|
|gacgctttgg gcgtgacaga cccagcctac gagaaacagg ttgcccaagc attcgccaat|180|
|ctgcgagctt gccttgctgc agttggagcc tcttcaaacg acgtcaccaa gctcaattac|240|
|tacatcgtcg actacgcccc gagcaaactc accgcaattg agatgggct gaagtctacc|300|
|tttgcccttg acaggctccc tccttgcacg ctggtgccag taccggcctt ggcttcacct|360|
|gaatacctct ttgaggttga cgccacggcg ctggtgccag acactcgac cccagacaac|420|
|gttgcggacg tggtagtggt gggcgctggc ttgagcggct tggagacggc acgcaaagtc|480|
|caggccgccg tctgtcctg cctcgttctt gaggcgatgg atcgtgtagg gggaaagact|540|
|ctgagcgtac aatcgggtcc cggcaggacg actatcaacg acctcggcgc tgcgtggatc|600|
|aatgacagca accaaagcga agtatccaga ttgtttgaaa gatttcattt ggagggcgag|660|
|ctccagagga cgaccggaaa ttcaatccat caagcacaag acgtacaac cactacagct|720|
|ccttatggtg actccccggt aagcacaatc ccactttgtg atgagacctc tgtcgagtgt|780|
|agaatacagt cactgactcc acttcgtcca gctgagcgag gaggttgcaa gtgcacttgc|840|
|ggaactcctc cccgtatggt ctcagctgat cgaagagtat agccttgaag accccaaggc|900|
|gagccctcag gcgaagcggc tcgacagtgt gagcttcgcg cactactgtg aaggacct|960|
|aaacttgcct gctgttctca gcgtggcaaa ccagatcaca cgcgctctgc tcggtgtgga|1020|
|agcccacgag atcagcatgc tttttctcac cgactacatc aagagtgcca ccggtctcag|1080|
|taatattgtc tcggacaaga aagacggcgg gcagtatatg cgatgcaaaa caggtgcgtg|1140|
|cggtgtcctc tcaggtaggg gactcgtttc ttagtggtca ttccaggtat gcagtcgatt|1200|
|tgccatgcca tgtcaaagga acttgttcca ggctcagtgc acctcaacac ccccgtcgct|1260|
|ggaattgagc agtcggcgtc cggctgtata gtacgatcgg cctcgggcgc cgtgttccga|1320|
|agcaaaaagg tggtggtttc gttaccgaca acattgtatc ccaccttgac attttcacca|1380|

-continued

```
cctcttcccg ccgagaagca agcattggcg gaaaaatcta tcctcggcta ctatagcaag    1440
atagtcttcg tatgggacaa cccgtggtgg cgcgaacaag gcttctcggg cgtcctccaa    1500
tcgagctgtg accccatctc atttgccaga gataccagca tcgaagtcga tcggcaatgg    1560
tccattacct gtttcatggt cggagacccg ggacggaagt ggtcccaaca gtccaagcag    1620
gtacgacaaa agtctgtctg ggaccaactc cgcgcagcct acgagaacgc cggggcccaa    1680
gtcccagagc cggccaacgt gctcgaaatc gagtggtcga agcagcagta tttccaagga    1740
gctccgagcg ccgtctatgg gctgaacgat ctcatcacac tgggttcggc gctcagaacg    1800
ccgttcaagt gtgttcattt cgttggaacg gagacgtctt tagtttggaa agggtatatg    1860 gaagggggcca tacgatcggg tcaacgaggt gctgcagaag ttgtggctag cctggtgcca    1920
gcagcatag                                                           1929
```

<210> SEQ ID NO 38
<211> LENGTH: 600
<212> TYPE: PRT
<213> ORGANISM: Exophiala spinifera

<400> SEQUENCE: 38

```
Met Ala Leu Ala Pro Ser Tyr Ile Asn Pro Asn Val Ala Ser Pro
1               5                   10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270
```

```
Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Ser Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
        370                 375                 380

Ser Gly Cys Ile Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
                420                 425                 430

Leu Gly Tyr Tyr Ser Lys Ile Val Phe Val Trp Asp Asn Pro Trp Trp
                435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
        500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
        580                 585                 590

Val Ala Ser Leu Val Pro Ala Ala
        595                 600

<210> SEQ ID NO 39
<211> LENGTH: 1930
<212> TYPE: DNA
<213> ORGANISM: Exophiala spinifera
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1187)
<223> OTHER INFORMATION:
<220> FEATURE:
<221> NAME/KEY: misc_feature
```

<222> LOCATION: (649)..(649)
<223> OTHER INFORMATION: n = A,T,C or G

<400> SEQUENCE: 39

| | | | | | |
|---|---|---|---|---|---|
| atggcacttg | caccgagcta | catcaatccc | ccaaacgtcg | cctccccagc | agggtattct | 60 |
| cacgtcggcg | taggcccaga | cggagggagg | tatgtgacaa | tagctggaca | gattggacaa | 120 |
| gacgcttcgg | gcgtgacaga | ccctgcctac | gagaaacagg | ttgcccaagc | attcgccaat | 180 |
| ctgcgagctt | gccttgctgc | agttggagcc | acttcaaacg | acgtcaccaa | gctcaattac | 240 |
| tacatcgtcg | actacgcccc | gagcaaactc | accgcaattg | gagatgggct | gaaggctacc | 300 |
| tttgcccttg | acaggctccc | tccttgcacg | ctggtgccag | tgtcggcctt | gtcttcacct | 360 |
| gaatacctct | ttgaggttga | tgccacggcg | ctggtgccgg | acacacgac | cccagacaac | 420 |
| gttgcggacg | tggtagtggt | gggcgctggc | ttgagcggtt | tggagacggc | acgcaaagtc | 480 |
| caggccgccg | gtctgtcctg | cctcgttctt | gaggcgatgg | atcgtgtagg | gggaaagact | 540 |
| ctgagcgtac | aatcgggtcc | cggcaggacg | actatcaacg | acctcggcgc | tgcgtggatc | 600 |
| aatgacagca | accaaagcga | agtatccaga | ttgtttgaaa | gatttcatnt | ggagggcgag | 660 |
| ctccagagga | cgactggaaa | ttcaatccat | caagcacaag | acggtacaac | cactacagct | 720 |
| ccttatggtg | actccttggt | aagcacaatc | ccactttgtg | atgagacctc | tgtcgagtgt | 780 |
| agaatacagt | cactgattcc | acttcgtcca | gctgagcgag | gaggttgcaa | gtgcacttgc | 840 |
| ggaactcctc | cccgtatggt | ctcagctgat | cgaagagcat | agccttcaag | acctcaaggc | 900 |
| gagccctcag | gcgaagcggc | tcgacagtgt | gagcttcgcg | cactactgtg | agaaggaact | 960 |
| aaacttgcct | gctgttctcg | gcgtagcaaa | ccagatcaca | cgcgctctgc | tcggtgtgga | 1020 |
| agcccacgag | atcagcatgc | ttttctcac | cgactacatc | aagagtgcca | ccggtctcag | 1080 |
| taatattttc | tcggacaaga | aagacggcgg | gcagtatatg | cgatgcaaaa | caggtgcgtg | 1140 |
| tggtgtcgtc | tcaggtgggg | gactcgtttc | tcaagtggtc | atttcaggta | tgcagtcgat | 1200 |
| ttgccatgcc | atgtcaaagg | aacttgttcc | aggctcagtg | cacctcaaca | ccccgtcgc | 1260 |
| tgaaattgag | cagtcggcat | ccggctgtac | agtacgatcg | gctcgggcg | ccgtgttccg | 1320 |
| aagcaaaaag | gtggtggttt | cgttaccgac | aaccttgtat | cccaccttga | cattttcacc | 1380 |
| acctctcccc | gccgagaagc | aagcattggc | ggaaaattct | atcctgggct | actatagcaa | 1440 |
| gatagtcttc | gtatgggaca | agccgtggtg | gcgcgaacaa | ggcttctcgg | gcgtcctcca | 1500 |
| atcgagctgt | gacccatct | catttgccag | agataccagc | atcgacgtcg | atcgacaatg | 1560 |
| gtccattacc | tgtttcatgg | tcggagaccc | gggacggaag | tggtcccaac | agtccaagca | 1620 |
| ggtacgacaa | aagtctgtct | gggaccaact | ccgcgcagcc | tacgagaacg | ccggggccca | 1680 |
| agtcccagag | ccggccaacg | tgctcgaaat | cgagtggtcg | aagcagcagt | atttccaagg | 1740 |
| agctccgagc | gccgtctatg | ggctgaacga | tctcatcaca | ctgggttcgg | cgctcagaac | 1800 |
| gccgttcaag | agtgttcatt | tcgttggaac | ggagacgtct | ttagtttgga | aagggtatat | 1860 |
| ggaaggggcc | atacgatcgg | gtcaacgagg | tgctgcagaa | gttgtggcta | gcctggtgcc | 1920 |
| agcagcatag | | | | | | 1930 |

<210> SEQ ID NO 40
<211> LENGTH: 598
<212> TYPE: PRT
<213> ORGANISM: Exophiala spinifera
<220> FEATURE:
<221> NAME/KEY: MISC_FEATURE
<222> LOCATION: (216)..(216)

<223> OTHER INFORMATION: Xaa = any amino acid

<400> SEQUENCE: 40

```
Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Gly Val Thr Asp Pro
                35                  40                  45

Ala Tyr Glu Lys Gln Val Ala Gln Ala Phe Ala Asn Leu Arg Ala Cys
    50                  55                  60

Leu Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
130                 135                 140

Val Val Gly Ala Gly Leu Ser Gly Leu Glu Thr Ala Arg Lys Val Gln
145                 150                 155                 160

Ala Ala Gly Leu Ser Cys Leu Val Leu Glu Ala Met Asp Arg Val Gly
                165                 170                 175

Gly Lys Thr Leu Ser Val Gln Ser Gly Pro Gly Arg Thr Thr Ile Asn
            180                 185                 190

Asp Leu Gly Ala Ala Trp Ile Asn Asp Ser Asn Gln Ser Glu Val Ser
        195                 200                 205

Arg Leu Phe Glu Arg Phe His Xaa Glu Gly Glu Leu Gln Arg Thr Thr
210                 215                 220

Gly Asn Ser Ile His Gln Ala Gln Asp Gly Thr Thr Thr Thr Ala Pro
225                 230                 235                 240

Tyr Gly Asp Ser Leu Leu Ser Glu Glu Val Ala Ser Ala Leu Ala Glu
                245                 250                 255

Leu Leu Pro Val Trp Ser Gln Leu Ile Glu His Ser Leu Gln Asp
            260                 265                 270

Leu Lys Ala Ser Pro Gln Ala Lys Arg Leu Asp Ser Val Ser Phe Ala
    275                 280                 285

His Tyr Cys Glu Lys Glu Leu Asn Leu Pro Ala Val Leu Gly Val Asn
290                 295                 300

Gln Ile Thr Arg Ala Leu Leu Gly Val Glu Ala His Glu Ile Ser Met
305                 310                 315                 320

Leu Phe Leu Thr Asp Tyr Ile Lys Ser Ala Thr Gly Leu Ser Asn Ile
                325                 330                 335

Phe Ser Asp Lys Lys Asp Gly Gly Gln Tyr Met Arg Cys Lys Thr Gly
            340                 345                 350

Met Gln Ser Ile Cys His Ala Met Ser Lys Glu Leu Val Pro Gly Ser
        355                 360                 365

Val His Leu Asn Thr Pro Val Ala Glu Ile Glu Gln Ser Ala Ser Gly
370                 375                 380

Cys Thr Val Arg Ser Ala Ser Gly Ala Val Phe Arg Ser Lys Lys Val
385                 390                 395                 400
```

-continued

```
Val Val Ser Leu Pro Thr Thr Leu Tyr Pro Thr Leu Thr Phe Ser Pro
            405                 410                 415
Pro Leu Pro Ala Glu Lys Gln Ala Leu Ala Glu Asn Ser Ile Leu Gly
            420                 425                 430
Tyr Tyr Ser Lys Ile Val Phe Val Trp Asp Lys Pro Trp Trp Arg Glu
            435                 440                 445
Gln Gly Phe Ser Gly Val Leu Gln Ser Ser Cys Asp Pro Ile Ser Phe
        450                 455                 460
Ala Arg Asp Thr Ser Ile Asp Val Asp Arg Gln Trp Ser Ile Thr Cys
465                 470                 475                 480
Phe Met Val Gly Asp Pro Gly Arg Lys Trp Ser Gln Gln Ser Lys Gln
                485                 490                 495
Val Arg Gln Lys Ser Val Trp Asp Gln Leu Arg Ala Ala Tyr Glu Asn
            500                 505                 510
Ala Gly Ala Gln Val Pro Glu Pro Ala Asn Val Leu Glu Ile Glu Trp
            515                 520                 525
Ser Lys Gln Gln Tyr Phe Gln Gly Ala Pro Ser Ala Val Tyr Gly Leu
        530                 535                 540
Asn Asp Leu Ile Thr Leu Gly Ser Ala Leu Arg Thr Pro Phe Lys Ser
545                 550                 555                 560
Val His Phe Val Gly Thr Glu Thr Ser Leu Val Trp Lys Gly Tyr Met
                565                 570                 575
Glu Gly Ala Ile Arg Ser Gly Gln Arg Gly Ala Glu Val Val Ala
            580                 585                 590
Ser Leu Val Pro Ala Ala
        595
```

```
<210> SEQ ID NO 41
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1185)
<223> OTHER INFORMATION:

<400> SEQUENCE: 41
atggcacttg caccgagcta catcaatccc ccaaacctcg cctccccagc agggtattcc      60
cacgtcggcg taggcccaaa cggagggagg tatgcgacaa tagctggaca gattggacaa     120
gacgcttcgg ccgtgacaga ccctgcctac gagaaacagg ttgcccaagc attcgccaac     180
ctgcgagctt gtcttgctgc agttggagcc acttcaaacg acattaccaa gctcaattac     240
tacatcgtcg actacaaccc gagcaaactc accgcaattg agatgggct gaaggctacc     300
tttgcccttg acaggctccc tccttgcacg ctggtgccag tgccggccct ggcttcacct     360
gaataccct tgaggttga tgccacggcg ctggttccag acactcaac cccagacaat      420
gttgcggacg tggtcgtggt gggcgctggc ttgagcggtt tggagacggc acgcaaagtc     480
caggctgccg gctgtcctg cctcgttctt gaggcgatgg atcgtgtggg gggaaagact     540
ctgagcgtac aatcgggtcc cggcaggacg gctatcaatg acctcggcgc tgcgtggatc     600
aatgacagca accaaagcga agtattcaaa ttatttgaaa gatttcattt ggagggcgag     660
ctccagagga cgaccggaaa ttcaatccat caagcacaag acggtacaac cactacagct     720
```

-continued

```
ccttatggtg attccctggt aagcacaatt ccatcttgtg atgagacctc tgtcgtgtgt    780
agaatacagt cgctgactcc acatcgtcca gctgagcgag gaggttgcaa gtgcactcgc    840
ggaactcctt cccgcatggt ctcagctgat cgaagagcat agtcttgaag accccaaggc    900
gagccctcaa gcgaagcagc tcgacagtgt gagcttcgca cactactgtg agaaggatct    960
aagcttgcct gctgttctcg gcgtggcaaa ccagatcaca cgcgctctgc tcggtgtgga   1020
agcccacgag atcagcatgc tttttctcac cgactacatc aagagtgcca ccggtctcag   1080
taatattgtc tcggataaga agacggtgg gcagtatatg cgatgcaaaa caggtgcgtg    1140
tggtgttctc tcagtgggag actcgttcct tagtggtcat tccaggtatg cagtcgcttt   1200
gccatgccat gtcaaaggaa cttgttccag gctcagtgca cctcaacacc cccgtcgccg   1260
aaattgagca gtcggcatcc ggctgtacag tacgatcggc ctcgggcggc gtgttccgaa   1320
gtaaaaaggt ggtggtttcg ttaccgacaa ccttgtatcc caccttgata ttttcaccac   1380
ctcttcccgc cgagaagcaa gcattggctg aaaaatccat cctgggctac tatagcaaga   1440
tagtcttcgt atgggacaag ccgtggtggc gcgaacaagg cttctcgggc gtcctccaat   1500
cgagctgtga ccccatctca tttgccagag ataccagcat cgaagtcgat cggcaatggt   1560
ccattacctg tttcatggtc ggagacccgg gacggaagtg gtcccaacag tccaagcagg   1620
tacgacagaa gtctgtctgg aaccaactcc gcgcagccta cgagaacgcc ggggcccaag   1680
tcccagagcc ggccaacgtg ctcgagatcg agtggtcgaa gcagcagtat ttccaaggag   1740
cgccgagcgt cgtctatggg ctgaactgtc tcaacacact gggttcggcg ctcagaacgc   1800
cgttcaaggg tgttcatttc gttggaacgg agacgtcttt ggtttggaaa gggtatatgg   1860
aaggggccat acgatcgggt cagcgaggcg ctgcagaagt tgtggctagc ctggtgccag   1920
cagcatag                                                           1928
```

<210> SEQ ID NO 42
<211> LENGTH: 598
<212> TYPE: PRT
<213> ORGANISM: Rhinocladiella atrovirens

<400> SEQUENCE: 42

```
Met Ala Leu Ala Pro Ser Tyr Ile Asn Pro Asn Leu Ala Ser Pro
1               5                   10                  15

Ala Gly Tyr Ser His Val Gly Val Gly Pro Asn Gly Gly Arg Tyr Ala
                20                  25                  30

Thr Ile Ala Gly Gln Ile Gly Gln Asp Ala Ser Ala Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Pro Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160
```

```
Gln Ala Ala Gly Leu Ser Cys Leu Val Leu Glu Ala Met Asp Arg Val
                165                 170                 175
Gly Gly Lys Thr Leu Ser Val Gln Ser Gly Pro Gly Arg Thr Ala Ile
                180                 185                 190
Asn Asp Leu Gly Ala Ala Trp Ile Asn Asp Ser Asn Gln Ser Glu Val
                195                 200                 205
Phe Lys Leu Phe Glu Arg Leu Glu Gly Glu Leu Gln Arg Thr Thr Gly
            210                 215                 220
Asn Ser Ile His Gln Ala Gln Asp Gly Thr Thr Thr Ala Pro Tyr
225                 230                 235                 240
Gly Asp Ser Leu Leu Ser Glu Val Ala Ser Ala Leu Ala Glu Leu
                245                 250                 255
Leu Pro Ala Trp Ser Gln Leu Ile Glu His Ser Leu Glu Asp Pro
                260                 265                 270
Lys Ala Ser Pro Gln Ala Lys Gln Leu Asp Ser Val Ser Phe Ala His
                275                 280                 285
Tyr Cys Glu Lys Asp Leu Ser Leu Pro Ala Val Leu Gly Val Ala Asn
290                 295                 300
Gln Ile Thr Arg Ala Leu Leu Gly Val Glu Ala His Glu Ile Ser Met
305                 310                 315                 320
Leu Phe Leu Thr Asp Tyr Ile Lys Ser Ala Thr Gly Leu Ser Asn Ile
                325                 330                 335
Val Ser Asp Lys Lys Asp Gly Gly Gln Tyr Met Arg Cys Lys Thr Gly
                340                 345                 350
Met Gln Ser Leu Cys His Ala Met Ser Lys Glu Leu Val Pro Gly Ser
                355                 360                 365
Val His Leu Asn Thr Pro Val Ala Glu Ile Glu Gln Ser Ala Ser Gly
                370                 375                 380
Cys Thr Val Arg Ser Ala Ser Gly Gly Val Phe Arg Ser Lys Lys Val
385                 390                 395                 400
Val Val Ser Leu Pro Thr Thr Leu Tyr Pro Thr Leu Ile Phe Ser Pro
                405                 410                 415
Pro Leu Pro Ala Glu Lys Gln Ala Leu Ala Glu Lys Ser Ile Leu Gly
                420                 425                 430
Tyr Tyr Ser Lys Ile Val Phe Val Trp Asp Lys Pro Trp Trp Arg Glu
                435                 440                 445
Gln Gly Phe Ser Gly Val Leu Gln Ser Ser Cys Asp Pro Ile Ser Phe
                450                 455                 460
Ala Arg Asp Thr Ser Ile Glu Val Asp Arg Gln Trp Ser Ile Thr Cys
465                 470                 475                 480
Phe Met Val Gly Asp Pro Gly Arg Lys Trp Ser Gln Ser Lys Gln
                485                 490                 495
Val Arg Gln Lys Ser Val Trp Asn Gln Leu Arg Ala Ala Tyr Glu Asn
                500                 505                 510
Ala Gly Ala Gln Val Pro Glu Pro Ala Asn Val Leu Glu Ile Glu Trp
                515                 520                 525
Ser Lys Gln Gln Tyr Phe Gln Gly Ala Pro Ser Val Val Tyr Gly Leu
                530                 535                 540
Asn Cys Leu Asn Thr Leu Gly Ser Ala Leu Arg Thr Pro Phe Lys Gly
545                 550                 555                 560
Val His Phe Val Gly Thr Glu Thr Ser Leu Val Trp Lys Gly Tyr Met
                565                 570                 575
```

-continued

Glu Gly Ala Ile Arg Ser Gly Gln Arg Gly Ala Ala Glu Val Val Ala
        580                 585                 590

Ser Leu Val Pro Ala Ala
        595

<210> SEQ ID NO 43
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1186)
<223> OTHER INFORMATION:

<400> SEQUENCE: 43

| | |
|---|---|
| atggcacttg caccgagcta catcaatccc ccaaacctcg cctccccagc agggtattcc | 60 |
| tacgtcggcg taggcccaaa cggagggagg tatgtgacaa tagctggaca gattggacaa | 120 |
| gacgcttcgg ccgtgacaga ccctgcctac gagaaacagg ttgcccaagc attcgccaac | 180 |
| ctgcgagctt gtcttgctgc agttggagcc acttcaaacg acattaccaa gctcaattac | 240 |
| tacatcgtcg actacaaccc gagcaaactc accgcaattg agatgggct gaaggctacc | 300 |
| tttgcccttg acaggctccc tccttgcacg ctggtgccag tgccggccct ggcttcacct | 360 |
| gaatacctct ttgaggttga tgccacggcg ctggttccag acactcaac cccagacaat | 420 |
| gttgcggacg tggtcgtggt gggcgctggc ttgagcggtt tggagacggc acgcaaagtc | 480 |
| caggctgccg gctgtcctg cctcgttctt gaggcgatgg atcgtgtggg gggaaagact | 540 |
| ctgagcgtac aatcgggtcc cggcaggacg actatcaatg acctcggcgc tgcgtggatc | 600 |
| aatgacagca accaaagcga agtattcaaa ttatttgaaa gatttcattt ggagggcgag | 660 |
| ctccagagga cgaccggaaa ttcaatccat caagcacaag acggtacaac cactacagct | 720 |
| ccttatggtg attccctggt aagcacaatt ccatcttgtg atgagacctc tgtcgtgtgt | 780 |
| agaatacagt cgctgactcc acatcgtcca gctgagcgag gaggttgcaa gtgcactcgc | 840 |
| ggaactcctt cccgcatggt ctcagctgat cgaagagcat agtcttgaag accccaaggc | 900 |
| gagccctcaa gcgaagcagc tcgacagtgt gagcttcgca cactactgtg agaaggatct | 960 |
| aaacttgcct gctgttctcg gcgtggcaaa ccagatcaca cgcgctctgc tcggtgtgga | 1020 |
| agcccacgag atcagcatgt tttttctcac cgactacatc aagagtgcca ccggtctcag | 1080 |
| taatattgtc tcggataaga aagacggtgg gcagtatatg cgatgcaaaa caggtgcgtg | 1140 |
| tggtgttctc tcagtgggag actcgtttct tagtggtcat tccaggtatg cagtcgcttt | 1200 |
| gccatgccat gtcaaaggaa cttgttccag gctcagtgca cctcaacacc cccgtcgccg | 1260 |
| aaattgagca gtcggcatcc ggctgtacag tacgatcggc tcgggcggc gtgttccgaa | 1320 |
| gtaaaaaggt ggtggttcg ttaccgacaa ccttgtatcc caccttgata ttttcaccac | 1380 |
| ctcttcccgc cgagaagcaa gcattggctg aaaaatccat cctgggctac tatagcaaga | 1440 |
| tagtcttcgt atgggacaag ccgtggtggc gcgaacaagg cttctcgggc gtcctccaat | 1500 |
| cgagctgtga ccccatctca tttgccagag ataccagcat cgaagtcgat cggcaatggt | 1560 |
| ccattacctg tttcatggtc ggagacccgg gacggaagtg gtcccaacag tccaagcagg | 1620 |
| tacgacagaa gtctgtctgg aaccaactcc gcgcagccta cgagaacgcc ggggcccaag | 1680 |
| tcccagagcc ggccaacgtg ctcgagatcg agtggtcgaa gcagcagtat ttccaaggag | 1740 |

```
cgccgagcgc cgtctatggg ctgaactgtc tcaacacact gggttcggcg ctcagaacgc    1800
cgttcaaggg tgttcatttc gttggaacgg agacgtcttt ggtttggaaa gggtatatgg    1860 aagggccat acgatcgggt cagcgaggcg ctgcagaagt tgtggctagc ctggtgccag     1920
cagcatag                                                             1928
```

<210> SEQ ID NO 44
<211> LENGTH: 591
<212> TYPE: PRT
<213> ORGANISM: Rhinocladiella atrovirens

<400> SEQUENCE: 44

```
Met Ala Leu Ala Pro Ser Tyr Ile Asn Pro Asn Leu Ala Ser Pro
1               5                   10                  15

Ala Gly Tyr Ser Tyr Val Gly Val Gly Pro Asn Gly Gly Arg Tyr Val
                20                  25                  30

Thr Ile Ala Gly Gln Ile Gly Gln Asp Ala Ser Ala Val Thr Asp Pro
            35                  40                  45

Ala Tyr Glu Lys Gln Val Ala Gln Ala Phe Ala Asn Leu Arg Ala Cys
50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Gly Arg Thr Thr Ile Asn
            180                 185                 190

Asp Leu Gly Ala Ala Trp Ile Asn Asp Ser Asn Gln Ser Glu Val Lys
        195                 200                 205

Leu Phe Glu Arg Phe His Leu Glu Gly Glu Leu Gln Arg Thr Thr Gly
    210                 215                 220

Asn Ser Ile His Gln Ala Gln Asp Gly Thr Thr Thr Ala Pro Tyr
225                 230                 235                 240

Gly Ser Leu Leu Ser Glu Glu Val Ala Ser Leu Ala Glu Leu Leu
                245                 250                 255

Pro Ala Ser Gln Leu Ile Glu Glu His Ser Leu Glu Asp Pro Lys Ala
            260                 265                 270

Ser Pro Gln Ala Lys Gln Leu Asp Ser Val Ser Phe Ala His Tyr Cys
        275                 280                 285

Glu Lys Leu Asn Leu Ala Val Leu Gly Val Ala Asn Gln Ile Thr Arg
    290                 295                 300

Ala Leu Leu Gly Val Glu Ala His Glu Ile Ser Met Phe Phe Leu Thr
305                 310                 315                 320

Asp Tyr Ile Lys Ser Ala Thr Gly Leu Ser Asn Ile Val Ser Asp Lys
                325                 330                 335
```

```
Lys Asp Gly Gly Gln Tyr Met Arg Cys Lys Thr Gly Met Gln Ser Leu
            340                 345                 350

Cys His Ala Met Ser Lys Glu Leu Val Pro Gly Ser Val His Leu Asn
            355                 360                 365

Thr Pro Val Ala Glu Ile Glu Gln Ser Ala Ser Gly Cys Thr Val Arg
            370                 375                 380

Ser Ala Ser Gly Gly Val Phe Arg Ser Lys Val Val Leu Pro Thr
385                 390                 395                 400

Leu Tyr Pro Thr Leu Ile Phe Ser Pro Pro Leu Pro Ala Glu Lys Gln
                405                 410                 415

Ala Leu Ala Glu Lys Ser Ile Leu Gly Tyr Tyr Ser Lys Ile Val Phe
            420                 425                 430

Val Trp Asp Lys Pro Trp Trp Arg Glu Gln Gly Phe Ser Gly Val Leu
            435                 440                 445

Gln Ser Ser Cys Asp Pro Ile Ser Phe Ala Arg Asp Thr Ser Ile Glu
        450                 455                 460

Val Asp Arg Gln Trp Ser Ile Thr Cys Phe Met Val Gly Asp Pro Gly
465                 470                 475                 480

Arg Lys Trp Ser Gln Gln Ser Lys Gln Val Arg Gln Lys Ser Val Trp
                485                 490                 495

Asn Gln Leu Arg Ala Ala Tyr Glu Asn Ala Gly Ala Gln Val Pro Glu
            500                 505                 510

Pro Ala Asn Val Leu Glu Ile Glu Trp Ser Lys Gln Gln Tyr Phe Gln
            515                 520                 525

Gly Ala Pro Ser Ala Val Tyr Gly Leu Asn Cys Leu Asn Thr Leu Gly
            530                 535                 540

Ser Ala Leu Arg Thr Pro Phe Lys Gly Val His Phe Val Gly Thr Glu
545                 550                 555                 560

Thr Ser Leu Val Trp Lys Gly Tyr Met Glu Gly Ala Ile Arg Ser Gly
                565                 570                 575

Gln Arg Gly Ala Ala Glu Val Val Ala Ser Leu Val Pro Ala Ala
            580                 585                 590
```

<210> SEQ ID NO 45
<211> LENGTH: 1928
<212> TYPE: DNA
<213> ORGANISM: Rhinocladiella atrovirens
<220> FEATURE:
<221> NAME/KEY: Intron
<222> LOCATION: (739)..(811)
<223> OTHER INFORMATION:
<220> FEATURE:
<221> NAME/KEY: Intron
<222> LOCATION: (1134)..(1185)
<223> OTHER INFORMATION:

<400> SEQUENCE: 45
atggcacttg caccgagcta catcaatccc ccaaacctcg cctccccagc agggtattcc      60
cacgtcggcg taggcccaaa cggagggagg tatgtgacaa tagctggaca gattggacaa     120
gacgcttcgg ccgtgacaga ccctgcctac gagaaacagg ttgcccaagc attcgccaac     180
ctgcgagctt gtcttgctgc agttggagcc acttcaaacg acattaccaa gctcaattac     240
tacatcgtca actacaaccc gagcaaactc accgcaattg gagatgggct gaaggctacc     300
tttgcccttg acaggctccc tccttgcacg ctggtgccag tgccggccct ggcttcacct     360 gaataccct cttgaggttga tgctacggcg ctggttccag acactcaac cccagacaat     420

-continued

```
gttgcggacg tggtcgtggt gggcgctggc ttgagcggtt tggagacggc acgcaaagtc      480
caggctgccg ggctgtcctg cctcgttctt gaggcgatgg atcgtgtggg gggaaagact      540
ctgagcgtac aatcgggtcc cggcaggacg actatcaatg acctcggcgc tgcgtggatc      600
aatgacagca accaaagcga agtattcaaa ttatttgaaa gatttcattt ggagggcgag      660
ctccagagga cgaccggaaa ttcaatccat caagcacaag acgtacaac cactacagct       720 ccttatggtg attccctggt aggcacaatt ccatcttgtg atgagacctc tgtcgtgtgt      780
agaatacagt cgctgactcc acatcgtcca gctgagcgag gaggttgcaa gtgcactcgc      840
ggaactcctt cccgcatggt ctcagctgat cgaagagcat agtcttgaag accccaaggc      900
gagccctcaa gcgaagcagc tcgacagtgt gagcttcgca cactactgtg agaaggatct      960
aaacttgcct gctgttctcg gcgtggcaaa ccagatcaca cgcgctctgc tcggtgtgga     1020
agcccacgag atcagcatgc tttttctcac cgactacatc aagagtgcca ccggtctcag     1080
taatattgtc tcggataaga aagacggtgg gcagtatatg cgatgcaaaa caggtgcgtg     1140
tggtgttctc tcagtgggag actcgtttct tagtggtcat tccaggtatg cagtcgcttt     1200
gccatgccat gtcaaaggaa cttgttccag gctcagtgca cctcaacacc cccgtcgccg     1260
aaattgagca gtcggcatcc ggctgtacag tacgatcggc ctcgggcggc gtgttccgaa     1320
gtaaaaaggt ggtggtttcg ttaccgacaa ccttgtatcc caccttgata ttttcaccac     1380
ctcttcccgc cgagaagcaa gcattggctg aaaaatccat cctgggctac tatagcaaga     1440
tagtcttcgt atgggacaag ctgtggtggc gcgaacaagg cttctcgggc gtcctccaat     1500
cgagctgtga ccccatctca tttgccagag ataccagcat cgaagtcgat cggcaatggt     1560
ccattacctg tttcatggtc ggagacccgg gacggaagtg gtcccaacag tccaagcagg     1620
tacgacagaa gtctgtctgg aaccaactcc gcgcagccta cgagaacgcc ggggcccaag     1680
tcccagagcc ggccaacgtg ctcgagatcg agtggtcgaa gcagcagtat ttccaaggag     1740
cgccgagcgc cgtctatggg ctgaactgtc tcaacacact gggttcggcg ctcagaacgc     1800
cgttcaaggg tgttcatttc gttggaacgg agacgtcttt ggtttggaaa gggtatatgg     1860 aagggccat acgatcgggt cagcgaggcg ctgcagaagt tgtgcctagc ctggtgccag      1920
cagcatag                                                               1928
```

<210> SEQ ID NO 46
<211> LENGTH: 591
<212> TYPE: PRT
<213> ORGANISM: Rhinocladiella atrovirens

<400> SEQUENCE: 46

Met Ala Leu Ala Pro Ser Tyr Ile Asn Pro Asn Ala Ser Pro Ala
1               5                   10                  15

Gly Tyr Ser His Val Gly Val Gly Pro Asn Gly Gly Arg Tyr Val Thr
            20                  25                  30

Ile Ala Gly Gln Ile Gly Gln Asp Ala Ser Ala Val Thr Asp Pro Ala
        35                  40                  45

Tyr Glu Lys Gln Val Ala Gln Ala Phe Ala Asn Leu Arg Ala Cys Leu
    50                  55                  60

Ala Ala Val Gly Ala Thr Ser Asn Asp Ile Thr Lys Leu Asn Tyr Tyr
65                  70                  75                  80

Ile Val Asp Tyr Asn Pro Ser Lys Leu Thr Ala Ile Gly Asp Gly Leu
                85                  90                  95

Lys Ala Thr Phe Ala Leu Asp Arg Leu Pro Pro Cys Thr Leu Val Pro

-continued

```
              100                 105                 110
Val Pro Ala Leu Ala Ser Pro Glu Tyr Leu Phe Glu Val Asp Ala Thr
            115                 120                 125
Ala Leu Val Pro Gly His Ser Thr Pro Asp Asn Val Ala Asp Val Val
130                 135                 140
Val Val Gly Ala Gly Leu Ser Gly Leu Glu Thr Ala Arg Lys Val Gln
145                 150                 155                 160
Ala Ala Gly Leu Ser Cys Leu Val Leu Glu Ala Met Asp Arg Val Gly
                165                 170                 175
Gly Lys Thr Leu Ser Val Gln Ser Gly Pro Gly Arg Thr Thr Ile Asn
            180                 185                 190
Asp Leu Gly Ala Ala Trp Ile Asn Asp Ser Asn Gln Ser Glu Val Phe
            195                 200                 205
Lys Leu Phe Glu Arg Phe His Leu Glu Gly Glu Leu Gln Arg Thr Thr
            210                 215                 220
Gly Asn Ser Ile His Gln Ala Gln Asp Gly Thr Thr Thr Ala Pro
225                 230                 235                 240
Tyr Gly Asp Ser Leu Leu Ser Glu Glu Val Ala Ser Ala Leu Ala Glu
                245                 250                 255
Leu Leu Pro Ala Trp Ser Gln Leu Ile Glu Glu His Ser Leu Glu Asp
            260                 265                 270
Pro Lys Ala Ser Pro Gln Ala Lys Gln Leu Asp Ser Val Ser Phe Ala
            275                 280                 285
His Tyr Cys Glu Lys Asp Leu Asn Leu Pro Ala Val Leu Gly Val Ala
            290                 295                 300
Asn Gln Ile Thr Arg Ala Leu Leu Gly Val Glu Ala His Glu Ile Ser
305                 310                 315                 320
Met Leu Phe Leu Thr Asp Tyr Ile Lys Ser Ala Thr Gly Leu Ser Asn
                325                 330                 335
Ile Val Ser Asp Lys Lys Asp Gly Gly Gln Tyr Met Arg Cys Lys Thr
            340                 345                 350
Gly Met Gln Ser Leu Cys His Ala Met Ser Lys Glu Leu Val Pro Gly
            355                 360                 365
Ser Val His Leu Asn Thr Pro Val Ala Glu Ile Glu Gln Ser Ala Ser
370                 375                 380
Gly Cys Thr Val Arg Ser Ala Ser Gly Gly Val Phe Arg Ser Lys Lys
385                 390                 395                 400
Val Ser Leu Pro Thr Thr Leu Tyr Pro Thr Leu Ile Phe Ser Pro Leu
                405                 410                 415
Pro Ala Glu Lys Gln Ala Leu Ala Glu Lys Ser Ile Gly Tyr Tyr Ser
            420                 425                 430
Lys Ile Val Phe Val Asp Lys Leu Trp Trp Arg Glu Gln Gly Phe Ser
            435                 440                 445
Gly Val Leu Gln Ser Ser Cys Asp Pro Ile Ser Phe Ala Arg Asp Thr
            450                 455                 460
Ser Ile Glu Val Asp Arg Gln Ser Ile Thr Cys Phe Met Val Gly Asp
465                 470                 475                 480
Pro Arg Lys Trp Ser Gln Gln Ser Lys Gln Val Arg Gln Lys Ser Val
                485                 490                 495
Trp Asn Gln Leu Arg Ala Ala Tyr Glu Asn Ala Gly Ala Gln Val Pro
            500                 505                 510
Glu Pro Ala Asn Val Leu Glu Ile Glu Trp Ser Lys Gln Gln Tyr Phe
            515                 520                 525
```

```
Gln Ala Pro Ser Ala Val Tyr Gly Leu Asn Cys Leu Asn Thr Leu Gly
    530                 535                 540

Ser Ala Leu Arg Thr Pro Phe Lys Gly Val His Phe Val Gly Thr Glu
545                 550                 555                 560

Thr Ser Leu Val Trp Lys Gly Tyr Met Glu Gly Ala Ile Arg Ser Gly
                565                 570                 575

Gln Arg Gly Ala Ala Glu Val Val Pro Ser Leu Val Pro Ala Ala
            580                 585                 590

<210> SEQ ID NO 47
<211> LENGTH: 600
<212> TYPE: PRT
<213> ORGANISM: Exophiala spinifera

<400> SEQUENCE: 47

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu His Ser Leu Gln
            260                 265                 270

Asp Leu Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
```

-continued

```
            305                 310                 315                 320
Ser Met Leu Phe Leu Thr Asp Tyr Ile Lys Ser Ala Thr Gly Leu Ser
                325                 330                 335

Asn Ile Phe Ser Asp Lys Lys Asp Gly Gln Tyr Met Arg Cys Lys
                340                 345                 350

Thr Gly Met Gln Ser Ile Cys His Ala Met Ser Lys Glu Leu Val Pro
                355                 360                 365

Gly Ser Val His Leu Asn Thr Pro Val Ala Glu Ile Glu Gln Ser Ala
            370                 375                 380

Ser Gly Cys Thr Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
                420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
                500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
            530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600
```

<210> SEQ ID NO 48
<211> LENGTH: 1392
<212> TYPE: DNA
<213> ORGANISM: Unknown
<220> FEATURE:
<223> OTHER INFORMATION: Cys (-) APAO; removal of cys 461 (Exophiala
      spinifera)
<220> FEATURE:
<221> NAME/KEY: CDS
<222> LOCATION: (1)..(1392)
<223> OTHER INFORMATION:

<400> SEQUENCE: 48

```
aaa gac aac gtt gcg gac gtg gta gtg gtg ggc gct ggc ttg agc ggt       48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt       96
Leu Glu Thr Ala Arg Lys Val Gln Ala Ala Gly Leu Ser Cys Leu Val
                20                  25                  30
```

-continued

| | |
|---|---|
| ctt gag gcg atg gat cgt gta ggg gga aag act ctg agc gta caa tcg<br>Leu Glu Ala Met Asp Arg Val Gly Gly Lys Thr Leu Ser Val Gln Ser<br>             35                        40                        45 | 144 |
| ggt ccc ggc agg acg act atc aac gac ctc ggc gct gcg tgg atc aat<br>Gly Pro Gly Arg Thr Thr Ile Asn Asp Leu Gly Ala Ala Trp Ile Asn<br>   50                        55                        60 | 192 |
| gac agc aac caa agc gaa gta tcc aga ttg ttt gaa aga ttt cat ttg<br>Asp Ser Asn Gln Ser Glu Val Ser Arg Leu Phe Glu Arg Phe His Leu<br>65                  70                       75                   80 | 240 |
| gag ggc gag ctc cag agg acg act gga aat tca atc cat caa gca caa<br>Glu Gly Glu Leu Gln Arg Thr Thr Gly Asn Ser Ile His Gln Ala Gln<br>             85                        90                       95 | 288 |
| gac ggt aca acc act aca gct cct tat ggt gac tcc ttg ctg agc gag<br>Asp Gly Thr Thr Thr Thr Ala Pro Tyr Gly Asp Ser Leu Leu Ser Glu<br>          100                        105                   110 | 336 |
| gag gtt gca agt gca ctt gcg gaa ctc ctc ccc gta tgg tct cag ctg<br>Glu Val Ala Ser Ala Leu Ala Glu Leu Leu Pro Val Trp Ser Gln Leu<br>             115                      120                   125 | 384 |
| atc gaa gag cat agc ctt caa gac ctc aag gcg agc cct cag gcg aag<br>Ile Glu Glu His Ser Leu Gln Asp Leu Lys Ala Ser Pro Gln Ala Lys<br>130                  135                      140 | 432 |
| cgg ctc gac agt gtg agc ttc gcg cac tac tgt gag aag gaa cta aac<br>Arg Leu Asp Ser Val Ser Phe Ala His Tyr Cys Glu Lys Glu Leu Asn<br>145                  150                   155                   160 | 480 |
| ttg cct gct gtt ctc ggc gta gca aac cag atc aca cgc gct ctg ctc<br>Leu Pro Ala Val Leu Gly Val Ala Asn Gln Ile Thr Arg Ala Leu Leu<br>                  165                      170                   175 | 528 |
| ggt gtg gaa gcc cac gag atc agc atg ctt ttt ctc acc gac tac atc<br>Gly Val Glu Ala His Glu Ile Ser Met Leu Phe Leu Thr Asp Tyr Ile<br>             180                      185                   190 | 576 |
| aag agt gcc acc ggt ctc agt aat att ttc tcg gac aag aaa gac ggc<br>Lys Ser Ala Thr Gly Leu Ser Asn Ile Phe Ser Asp Lys Lys Asp Gly<br>                  195                      200                   205 | 624 |
| ggg cag tat atg cga tgc aaa aca ggt atg cag tcg att tgc cat gcc<br>Gly Gln Tyr Met Arg Cys Lys Thr Gly Met Gln Ser Ile Cys His Ala<br>210                  215                      220 | 672 |
| atg tca aag gaa ctt gtt cca ggc tca gtg cac ctc aac acc ccc gtc<br>Met Ser Lys Glu Leu Val Pro Gly Ser Val His Leu Asn Thr Pro Val<br>225                  230                   235                   240 | 720 |
| gct gaa att gag cag tcg gca tcc ggc tgt aca gta cga tcg gcc tcg<br>Ala Glu Ile Glu Gln Ser Ala Ser Gly Cys Thr Val Arg Ser Ala Ser<br>                  245                      250                   255 | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>             260                      265                   270 | 816 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>             275                      280                   285 | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>         290                      295                   300 | 912 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>305                  310                   315                   320 | 960 |
| caa tcg agc tcc gac ccc atc tca ttt gcc aga gat acc agc atc gac<br>Gln Ser Ser Ser Asp Pro Ile Ser Phe Ala Arg Asp Thr Ser Ile Asp<br>                  325                      330                   335 | 1008 |
| gtc gat cga caa tgg tcc att acc tgt ttc atg gtc gga gac ccg gga<br>Val Asp Arg Gln Trp Ser Ile Thr Cys Phe Met Val Gly Asp Pro Gly<br>             340                      345                   350 | 1056 |

```
cgg aag tgg tcc caa cag tcc aag cag gta cga caa aag tct gtc tgg      1104
Arg Lys Trp Ser Gln Gln Ser Lys Gln Val Arg Gln Lys Ser Val Trp
        355                 360                 365 gac caa ctc cgc gca gcc tac gag aac gcc ggg gcc caa gtc cca gag      1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
            405                 410                 415 tcg gcg ctc aga acg ccg ttc aag agt gtt cat ttc gtt gga acg gag      1296
Ser Ala Leu Arg Thr Pro Phe Lys Ser Val His Phe Val Gly Thr Glu
        420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala
450                 455                 460
```

<210> SEQ ID NO 49
<211> LENGTH: 463
<212> TYPE: PRT
<213> ORGANISM: Unknown
<220> FEATURE:
<223> OTHER INFORMATION: Cys (-) APAO; removal of cysteine 461
      (Exophiala spinifera)

<400> SEQUENCE: 49

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Met Asp Arg Val Gly Gly Lys Thr Leu Ser Val Gln Ser
            35                  40                  45

Gly Pro Gly Arg Thr Thr Ile Asn Asp Leu Gly Ala Ala Trp Ile Asn
        50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205
```

```
Gly Gln Tyr Met Arg Cys Lys Thr Gly Met Gln Ser Ile Cys His Ala
    210                 215                 220

Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Ser Asp Pro Ile Ser Phe Ala Arg Asp Thr Ser Ile Asp
                325                 330                 335

Val Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 50
<211> LENGTH: 1392
<212> TYPE: DNA
<213> ORGANISM: Unknown
<220> FEATURE:
<223> OTHER INFORMATION: Cys (-) APAO; removal of cys 359 and 461
      (Exophiala spinifera)
<220> FEATURE:
<221> NAME/KEY: CDS
<222> LOCATION: (1)..(1392)
<223> OTHER INFORMATION:

<400> SEQUENCE: 50 aaa gac aac gtt gcg gac gtg gta gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
        35                  40                  45 ggt ccc ggc agg acg act atc aac gac ctc ggc gct gcg tgg atc aat     192
Gly Pro Gly Arg Thr Thr Ile Asn Asp Leu Gly Ala Ala Trp Ile Asn
    50                  55                  60
```

```
gac agc aac caa agc gaa gta tcc aga ttg ttt gaa aga ttt cat ttg      240
Asp Ser Asn Gln Ser Glu Val Ser Arg Leu Phe Glu Arg Phe His Leu
 65              70                  75                  80 gag ggc gag ctc cag agg acg act gga aat tca atc cat caa gca caa      288
Glu Gly Glu Leu Gln Arg Thr Thr Gly Asn Ser Ile His Gln Ala Gln
             85                  90                  95 gac ggt aca acc act aca gct cct tat ggt gac tcc ttg ctg agc gag      336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg      384
Glu Val Ala Ser Ala Leu Ala Glu Leu Leu Pro Val Trp Ser Gln Leu
            115                 120                 125 atc gaa gag cat agc ctt caa gac ctc aag gcg agc cct cag gcg aag      432
Ile Glu Glu His Ser Leu Gln Asp Leu Lys Ala Ser Pro Gln Ala Lys
130                 135                 140 cgg ctc gac agt gtg agc ttc gcg cac tac tgt gag aag gaa cta aac      480
Arg Leu Asp Ser Val Ser Phe Ala His Tyr Cys Glu Lys Glu Leu Asn
145                 150                 155                 160 ttg cct gct gtt ctc ggc gta gca aac cag atc aca cgc gct ctg ctc      528
Leu Pro Ala Val Leu Gly Val Ala Asn Gln Ile Thr Arg Ala Leu Leu
                165                 170                 175 ggt gtg gaa gcc cac gag atc agc atg ctt ttt ctc acc gac tac atc      576
Gly Val Glu Ala His Glu Ile Ser Met Leu Phe Leu Thr Asp Tyr Ile
            180                 185                 190 aag agt gcc acc ggt ctc agt aat att ttc tcg gac aag aaa gac ggc      624
Lys Ser Ala Thr Gly Leu Ser Asn Ile Phe Ser Asp Lys Lys Asp Gly
            195                 200                 205 ggg cag tat atg cga tgc aaa aca ggt atg cag tcg att tcg cat gcc      672
Gly Gln Tyr Met Arg Cys Lys Thr Gly Met Gln Ser Ile Ser His Ala
210                 215                 220 atg tca aag gaa ctt gtt cca ggc tca gtg cac ctc aac acc ccc gtc      720
Met Ser Lys Glu Leu Val Pro Gly Ser Val His Leu Asn Thr Pro Val
225                 230                 235                 240 gct gaa att gag cag tcg gca tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa      864
Leu Tyr Pro Thr Leu Thr Phe Ser Pro Pro Leu Pro Ala Glu Lys Gln
            275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc tcc gac ccc atc tca ttt gcc aga gat acc agc atc gac     1008
Gln Ser Ser Ser Asp Pro Ile Ser Phe Ala Arg Asp Thr Ser Ile Asp
                325                 330                 335 gtc gat cga caa tgg tcc att acc tgt ttc atg gtc gga gac ccg gga     1056
Val Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
            355                 360                 365 gac caa ctc cgc gca gcc tac gag aac gcc ggg gcc caa gtc cca gag     1152
Asp Gln Leu Arg Ala Ala Tyr Glu Asn Ala Gly Ala Gln Val Pro Glu
370                 375                 380
```

-continued

```
ccg gcc aac gtg ctc gaa atc gag tgg tcg aag cag cag tat ttc caa    1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
            405                 410                 415 tcg gcg ctc aga acg ccg ttc aag agt gtt cat ttc gtt gga acg gag    1296
Ser Ala Leu Arg Thr Pro Phe Lys Ser Val His Phe Val Gly Thr Glu
        420                 425                 430 acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala
450                 455                 460
```

<210> SEQ ID NO 51
<211> LENGTH: 463
<212> TYPE: PRT
<213> ORGANISM: Unknown
<220> FEATURE:
<223> OTHER INFORMATION: Cys (-) APAO; removal of cys 359 and 461
      (Exophiala spinifera)

<400> SEQUENCE: 51

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asn Asp Leu Gly Ala Ala Trp Ile Asn
    50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
    130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Ile Ser His Ala
    210                 215                 220

Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
                245                 250                 255
```

```
Gly Ala Val Phe Arg Ser Lys Lys Val Val Ser Leu Pro Thr Thr
        260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
        290                 295                 300

Val Trp Asp Lys Pro Trp Trp Arg Glu Gln Gly Phe Ser Gly Val Leu
305                 310                 315                 320

Gln Ser Ser Ser Asp Pro Ile Ser Phe Ala Arg Asp Thr Ser Ile Asp
                325                 330                 335

Val Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
        370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
        450                 455                 460
```

<210> SEQ ID NO 52
<211> LENGTH: 1392
<212> TYPE: DNA
<213> ORGANISM: Unknown
<220> FEATURE:
<223> OTHER INFORMATION: Cys (-) APAO; removal of cys 169, 359, and 461
      (Exophiala spinifera)
<220> FEATURE:
<221> NAME/KEY: CDS
<222> LOCATION: (1)..(1392)
<223> OTHER INFORMATION:

<400> SEQUENCE: 52

```
aaa gac aac gtt gcg gac gtg gta gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg agc tcc ctc gtt      96
Leu Glu Thr Ala Arg Lys Val Gln Ala Ala Gly Leu Ser Ser Leu Val
            20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
        35                  40                  45 ggt ccc ggc agg acg act atc aac gac ctc ggc gct gcg tgg atc aat    192
Gly Pro Gly Arg Thr Thr Ile Asn Asp Leu Gly Ala Ala Trp Ile Asn
    50                  55                  60 gac agc aac caa agc gaa gta tcc aga ttg ttt gaa aga ttt cat ttg    240
Asp Ser Asn Gln Ser Glu Val Ser Arg Leu Phe Glu Arg Phe His Leu
65                  70                  75                  80 gag ggc gag ctc cag agg acg act gga aat tca atc cat caa gca caa    288
Glu Gly Glu Leu Gln Arg Thr Thr Gly Asn Ser Ile His Gln Ala Gln
                85                  90                  95
```

```
                                                     -continued gac ggt aca acc act aca gct cct tat ggt gac tcc ttg ctg agc gag     336
Asp Gly Thr Thr Thr Thr Ala Pro Tyr Gly Asp Ser Leu Leu Ser Glu
            100                 105                 110 gag gtt gca agt gca ctt gcg gaa ctc ctc ccc gta tgg tct cag ctg     384
Glu Val Ala Ser Ala Leu Ala Glu Leu Leu Pro Val Trp Ser Gln Leu
            115                 120                 125 atc gaa gag cat agc ctt caa gac ctc aag gcg agc cct cag gcg aag     432
Ile Glu Glu His Ser Leu Gln Asp Leu Lys Ala Ser Pro Gln Ala Lys
            130                 135                 140 cgg ctc gac agt gtg agc ttc gcg cac tac tgt gag aag gaa cta aac     480
Arg Leu Asp Ser Val Ser Phe Ala His Tyr Cys Glu Lys Glu Leu Asn
145                 150                 155                 160 ttg cct gct gtt ctc ggc gta gca aac cag atc aca cgc gct ctg ctc     528
Leu Pro Ala Val Leu Gly Val Ala Asn Gln Ile Thr Arg Ala Leu Leu
                165                 170                 175 ggt gtg gaa gcc cac gag atc agc atg ctt ttt ctc acc gac tac atc     576
Gly Val Glu Ala His Glu Ile Ser Met Leu Phe Leu Thr Asp Tyr Ile
                180                 185                 190 aag agt gcc acc ggt ctc agt aat att ttc tcg gac aag aaa gac ggc     624
Lys Ser Ala Thr Gly Leu Ser Asn Ile Phe Ser Asp Lys Lys Asp Gly
                195                 200                 205 ggg cag tat atg cga tgc aaa aca ggt atg cag tcg att tcg cat gcc     672
Gly Gln Tyr Met Arg Cys Lys Thr Gly Met Gln Ser Ile Ser His Ala
210                 215                 220 atg tca aag gaa ctt gtt cca ggc tca gtg cac ctc aac acc ccc gtc     720
Met Ser Lys Glu Leu Val Pro Gly Ser Val His Leu Asn Thr Pro Val
225                 230                 235                 240 gct gaa att gag cag tcg gca tcc ggc tgt aca gta cga tcg gcc tcg     768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc     816
Gly Ala Val Phe Arg Ser Lys Lys Val Val Val Ser Leu Pro Thr Thr
                260                 265                 270 ttg tat ccc acc ttg aca ttt tca cca cct ctt ccc gcc gag aag caa     864
Leu Tyr Pro Thr Leu Thr Phe Ser Pro Pro Leu Pro Ala Glu Lys Gln
                275                 280                 285 gca ttg gcg gaa aat tct atc ctg ggc tac tat agc aag ata gtc ttc     912
Ala Leu Ala Glu Asn Ser Ile Leu Gly Tyr Tyr Ser Lys Ile Val Phe
            290                 295                 300 gta tgg gac aag ccg tgg tgg cgc gaa caa ggc ttc tcg ggc gtc ctc     960
Val Trp Asp Lys Pro Trp Trp Arg Glu Gln Gly Phe Ser Gly Val Leu
305                 310                 315                 320 caa tcg agc tcc gac ccc atc tca ttt gcc aga gat acc agc atc gac    1008
Gln Ser Ser Ser Asp Pro Ile Ser Phe Ala Arg Asp Thr Ser Ile Asp
                325                 330                 335 gtc gat cga caa tgg tcc att acc tgt ttc atg gtc gga gac ccg gga    1056
Val Asp Arg Gln Trp Ser Ile Thr Cys Phe Met Val Gly Asp Pro Gly
                340                 345                 350 cgg aag tgg tcc caa cag tcc aag cag gta cga caa aag tct gtc tgg    1104
Arg Lys Trp Ser Gln Gln Ser Lys Gln Val Arg Gln Lys Ser Val Trp
            355                 360                 365 gac caa ctc cgc gca gcc tac gag aac gcc ggg gcc caa gtc cca gag    1152
Asp Gln Leu Arg Ala Ala Tyr Glu Asn Ala Gly Ala Gln Val Pro Glu
370                 375                 380 ccg gcc aac gtg ctc gaa atc gag tgg tcg aag cag cag tat ttc caa    1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
                405                 410                 415
```

```
tcg gcg ctc aga acg ccg ttc aag agt gtt cat ttc gtt gga acg gag     1296
Ser Ala Leu Arg Thr Pro Phe Lys Ser Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
            435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala
            450                 455                 460
```

<210> SEQ ID NO 53
<211> LENGTH: 463
<212> TYPE: PRT
<213> ORGANISM: Unknown
<220> FEATURE:
<223> OTHER INFORMATION: Cys (-) APAO; removal of cys 169, 359, and 461
      (Exophiala spinifera)

<400> SEQUENCE: 53

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Ser Leu Val
            20                  25                  30

Leu Glu Ala Met Asp Arg Val Gly Gly Lys Thr Leu Ser Val Gln Ser
            35                  40                  45

Gly Pro Gly Arg Thr Thr Ile Asn Asp Leu Gly Ala Ala Trp Ile Asn
        50                  55                  60

Asp Ser Asn Gln Ser Glu Val Ser Arg Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Thr Thr Thr Ala Pro Tyr Gly Asp Ser Leu Leu Ser Glu
            100                 105                 110

Glu Val Ala Ser Ala Leu Ala Glu Leu Leu Pro Val Trp Ser Gln Leu
        115                 120                 125

Ile Glu Glu His Ser Leu Gln Asp Leu Lys Ala Ser Pro Gln Ala Lys
130                 135                 140

Arg Leu Asp Ser Val Ser Phe Ala His Tyr Cys Glu Lys Glu Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Ile Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Ile Ser His Ala
    210                 215                 220

Met Ser Lys Glu Leu Val Pro Gly Ser Val His Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
```

```
                290                     295                     300
Val Trp Asp Lys Pro Trp Trp Arg Glu Gln Gly Phe Ser Gly Val Leu
305                 310                 315                 320

Gln Ser Ser Ser Asp Pro Ile Ser Phe Ala Arg Asp Thr Ser Ile Asp
            325                 330                 335

Val Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
            405                 410                 415

Ser Ala Leu Arg Thr Pro Phe Lys Ser Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460
```

AMINO POLYOL AMINE OXIDASE POLYNUCLEOTIDES AND RELATED POLYPEPTIDES AND METHODS OF USE

CROSS REFERENCE TO RELATED APPLICATION

This application is a continuation-in-part of U.S. application Ser. No. 09/352,159, filed Jul. 2, 1999 now U.S. Pat. No. 6,211,434, which is hereby incorporated by reference. This application also claims the benefit of U.S. application Ser. No. 09/352,168, now U.S. Pat. No. 6,211,435, which is hereby incorporated by reference.

TECHNICAL FIELD

The present invention relates generally to the detection and isolation of fumonisin and AP1 degrading enzymes and to compositions and methods for degradation of fumonisin, a structurally related mycotoxin, or its hydrolysis product AP1. This method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. Still another method, in the case of pathogens that produce toxins that are undesirable to mammals or other animals that feed on the crop plants, is interference with toxin production, storage, or activity. This invention falls into the latter two categories.

Since their discovery and structural elucidation in 1988 (Bezuidenhout el al., Journal *Chem Soc, Chem Commun* 1988: 743–745 (1988)), fumonisins have been recognized as a potentially serious problem in maize-fed livestock. They are linked to several animal toxicoses including leukoencephalomalacia (Marasas, et al., *Onderstepoort Journal of Veterinary Research* 55: 197–204 (1988); Wilson, el al., *American Association of Veterinarv Laboratorv Diagnosticians: Abstracts* 33rd *Annual Meeting*, Denver, Col., Oct. 7–9, 1990, Madison, Wis., USA) and porcine pulmonary edema (Colvin, et al., *Mycopathologia* 117: 79–82 (1992)). Fumonisins are also suspected carcinogens (Geary W (1971) *Coord Chem Rev* 7: 81; Gelderblom, el al., Carcinogenesis 12: 1247–1251 (1991); Gelderblom, et al., Carcinogeiiesis 13: 433–437 (1992)). Fusarium isolates in section Liseola produce fumonisins in culture at levels from 2 to >4000 ppm (Leslie, et al., *Phytopathology* 82: 341–345 (1992)). Isolates from maize (predominantly mating population A) are among the highest producers of fumonisin. (Leslie et al., supra). Fumonisin levels detected in field-grown maize have fluctuated widely depending on location and growing season, but both preharvest and postharvest surveys of field maize have indicated that the potential for high levels of funionisins exists (Murphy, el al., *J Agr Food Chem* 41: 263–266 (1993)). Surveys of food and feed products have also detected fumonisin (Holcomb, et al, *J Agr Food Chem* 41: 764–767 (1993); Hopmans, el al., *J Agr Food Chess* 41: 1655–1658 (1993); Sydenhamn, el al., *J Agr Food Chem* 39: 2014–2018 (1991)). The etiology of Fusarium ear mold is poorly understood, although physical damage to the ear and certain environmental conditions can contribute to its occurrence (Nelson, *Mycvopathologia* 117: 29–36 (1992)). Fusarium can be isolated from most field grown maize, even when no visible mold is present. The relationship between seedling infection and stalk and ear diseases caused by Fusarium is not clear. Genetic resistance to visible kernel mold has been identified (Gendloff, et al., *Phytopathology* 76: 684–688 (1986): Holley, el al., *Plant Dis* 73: 578–580 (1989)), but the relationship to visible mold to fumonisin production has yet to be elucidated.

Fumonisins have been shown in in vitro mammalian cell studies to inhibit sphingolipid biosynthesis through inhibition of the enzyme sphingosine N-acetyl transferase, resulting in the accumulation of the precursor sphinganine (Norred, et al., *Mycopathologia* 117: 73–78 (1992); Wang, et al, *Biol Chem* 266: 14486 (1991); Yoo, et ail., *Toxicol Appl Pharmacol* 114: 9–15 (1992); Nelson, et al., *Annu Rev Phyitputhol* 31:233–252 (1993)). It is likely that inhibition of this pathway accounts for at least some of fumonisin's toxicity, and support for this comes from measures of sphinganine: sphingosine ratios in animals fed purified fumonisin (Wang, et al., *J Nutr* 122: 1706–1716 (1992)). Fumonisins also affect plant cell growth (Abbas, et al., *Weed Technol* 6: 548–552 (1992); Vanasch, et al., *Phytopathology* 82: 1330–1332 (1992); Vesonder, et al, *Arch Environ Contam Toxicol* 23: 464467 (1992)). Kuti et al., (Abstract, Annual Meeting American Phytopathological Society, Memphis, TN: APS Press 1993) reported on the ability of exogenously added fumonisins to accelerate disease development and increase sporulation of *Fusarium moniliforme* and *Fusarium oxysporum* on tomato.

Enzymes that degrade the fungal toxin fumonisin to its de-esterified form (e.g. AP1 from FB1) have been identified in U.S. Pat. No. 5,716,820, issued Feb. 10, 1998, U.S. Pat. No. 5,792,931, issued Aug. 11, 1998; U.S. Pat. No. 6,025,188, issued Feb. 15, 2000; and pending U.S. application Ser. No. 08/888,950, filed Jul. 7, 1997, and all hereby incorporated by reference. It is understood that AP1 as used here designates the hydrolyzed form of any fumonisin, FB1, FB2, FB3, FB4, or any other AP1-like compounds, including synthetically produced AP1 like compounds, that contain a C-2 or C-1 amine group and one or more adjacent hydroxyl groups. Plants expressing a fumonisin esterase enzyme, infected by fumonisin producing fungus, and tested for fumonisin and AP1 were found to have low levels of fumonisin but high levels of AP1. AP1 is less toxic than fumonisin to plants and probably also to animals but contamination with AP1 is still a concern (Lamprecht, el al., *Phytopathology*, 84:383–391 (1991)). The preferred result would be complete detoxification of fumonisin to a nontoxic form. Therefore enzymes capable of degrading AP1 are necessary for the further detoxification of fumonisin.

The present invention provides newly discovered polynucleotides and related polypeptides of amino polyol amine oxidase (abbreviated APAO, formerly known as AP1 catabolase, U.S. Pat. No. 5,716,820, supra, U.S. Pat. No. 5,792,931, supra; U.S. Pat. No. 6,025,188, supra, pending U.S. application Ser. No. 08/888,950, supra; trAPAO is the abbreviation for a truncated, but still functional APAO), capable of oxidatively deaminating the AP1 to a compound identified as the 2-oxo derivative of AP1 or its cyclic ketal form (abbreviated as 2-OP, formerly called AP1-N1, U.S. Pat. No. 5,716,820, U.S. Pat. No. 5,792,931, U.S. Pat. No. 6,025,188, supra; pending US application no. 08/888,950, supra), isolated from *Exophiala spinifera*, ATCC 74269. The partially purified APAO enzyme from *Exophiala spinifera* has little or no activity on intact FB1, a form of fumonisin. However, recombinant APAO enzyme from *Exophiala spinifera*, expressed in *E. coli*, has significant but reduced activity on intact FB1 and other B-series fumonisins. APAO or trAPAO thus could potentially be used without fumonisin esterase since the amine group is the major target for detoxification. Alternatively, fumoninsin esterase and APAO (or trAPAO) can be used together for degrading toxins.

APAO is a type of flavin amine oxidase (EC 1.4.3.4, enzyme class nomeclature, see *Enzyme Nomenclature* 1992, Recommendations of the Nomenclature Committee of the IUBMB on the Nomenclature and Classification of Enzymes, Academic Press, Inc. (1992)). One class of flavin amine oxidases in mammals is known as monoamine oxidases, where they participate in the conversion of amines involved in neuronal function. A prokaryotic flavin amine oxidase that deaminates putrescine has been described (Ishizuka et al., *J Gen Microbiol*. 139:425–432 (1993)). A single fungal gene, from *Aspergillus niger* has been cloned (Schilling et al., *Mol Gen Genet*. 247:430–438 (1995)). It deaminates a variety of alkyl and aryl amines, but when tested for its ability to oxidize AP1, was found to not contain AP1 oxidizing activity.

The toxicity of fumonisins and their potential widespread occurrence in food and feed makes it imperative to find detoxification or elimination strategies to remove the compound from the food chain.

SUMMARY OF THE INVENTION

The present invention provides polynucleotides and related polypeptides of newly discovered APAOs. SEQ ID NO: 5 contains the nucleotide sequence of an active, truncated APAO (trAPAO), SEQ ID NO: 10 contains the nucleotide sequence of trAPAO with an additional lysine and SEQ ID NO: 22, 35, 37, 39, 41, 43, and 45 comprise full length nucleotide sequences of APAOs isolated from different organisms. In addition, APAO can be modified to eliminate glycosylation sites and/or cysteine residues, for example, see SEQ ID NOS: 32, 48, 50, and 52. Another aspect of the present invention is the method of predicting possible mutagenesis sites on APAO by developing a 3-dimensional model of APAO and then identifying the possible sites that may contribute to misfolding of the protein. The present invention also includes the 3-dimensional model of APAO generated by a computer modeling program, preferably the Modeler program. For expression in a plant, the polynucleotide of the present invention can be operably linked to a targeting sequence. It is an object of the present invention to provide transgenic plants comprising the nucleic acids of the present invention.

Therefore, in one aspect, the present invention relates to an isolated APAO encoding polynucleotide ligated to a fumonisin esterase encoding polynucleotide wherein the APAO encoding polynucleotide comprises a member selected from (a) a polynucleotide encoding a polypeptide of the present invention; (b) a polynucleotide having at least 70% sequence identity to the polynucleotides of the present invention; and (c) a polynucleotide of the present invention. The isolated nucleic acid can be DNA. The isolated nucleic acid can also be RNA. Examples of fumonisin esterase genes include, but are not limited to ESPI and BESTI.

In another aspect, the present invention relates to vectors comprising the polynucleotides of the present invention, including ligated and non-ligated polynucleotides. Also the present invention relates to recombinant expression cassettes, comprising a polynucleotide of the present invention operably linked to a promoter.

In another aspect, the present invention is directed to a host cell into which has been introduced the polynucleotides of the present invention, including a host cell comprising a fumonisin esterase ligated to an APAO or a fumonisin esterase not ligated to an APAO.

In yet another aspect, the present invention relates to a transgenic plant or plant cell comprising a recombinant expression cassette with a promoter operably linked to any of the isolated polynucleotides of the present invention. Preferred plants containing the recombinant expression cassette of the present invention include but are not limited to maize, soybean, sunflower, sorghum, canola, wheat, alfalfa, cotton, rice, barley, tomato, and millet. The present invention also provides transgenic seed from the transgenic plant.

In another aspect, the present invention relates to an isolated protein selected from the group consisting of (a) a polypeptide comprising at least 70% sequence identity to a polypeptide of the present invention; (b) a polypeptide encoded by a nucleic acid of the present invention; and (c) a polypeptide characterized by a polypeptide of the present invention.

This invention further provides methods of degrading fumonisin, a structurally related mycotoxin, a fumonisin breakdown product, or a structurally related mycotoxin breakdown product, by applying APAO as a spray or wash. Additionally, fumonisins and related mycotoxins can be degraded by the application of both fumonisin esterase enzymes and APAO enzymes. Mycotoxins can be degraded in harvested grain, during the processing of harvested grain, in animal feed, or in plant tissue as, for example, during the use of the plant for silage or as a spray on grain, fruit or vegetables. Further, this invention provides methods of degrading fumonisin, a structurally related mycotoxin, a fumonisin breakdown product, or a structurally related mycotoxin breakdown product, by transforming the APAO polynucleotide, alone or in combination with polynucleotides encoding a fumonisin esterase, into plant cells.

The polynucleotides of the present invention can also be used as a selectable marker for plant transformation. By transforming plant cells with an expression cassette comprising a polynucleotide of the present invention and then placing the plant cells on media containing FB1, AP1 or a phytotoxic analog, only the plant cells expressing the polynucleotide of the present invention would survive.

Another embodiment of the present invention is the use of the enzyme fumonisin esterase and APAO by themselves or in combination as reagents for detecting fumonisin and structurally related toxins.

BRIEF DESCRIPTION OF THE DRAWINGS

FIG. 1 shows a 3-dimensional model of APAO (1B) based on the crystal structure of a related amine oxidase from maize, maize polyamine oxidase (MPAO) (1A). The sites for possible mutation of APAO to alter glycosylation sites or cysteine residues are shown.

FIG. 2 shows a 3-dimensional model of APAO (2B) based on the crystal structure of a related amine oxidase from maize MPAO (2B). The substrate binding holes are shown as circles.

DETAILED DESCRIPTION OF THE INVENTION

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and is not intended to limit the scope of the invention.

The practice of the present invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., J. H. Langenheim and K. V. Thimann, *Botany: Plant Biology and Its Relation to Human Affairs* (1982) John Wiley; *Cell Culture and Somatic Cell Genetics of Plants*, Vol. I (I. K. Vasil, ed. 1984); R. V. Stanier, J. L. Ingraham, M. L. Wheelis, and P. R. Painter, *The Microbial World*, (1986) 5th Ed., Prentice-Hall; O. D. Dhringra and J. B. Sinclair, *Basic Plant Pathology Methods*, (1985) CRC Press; Maniatis, Fritsch & Sambrook, *Molecular Cloning: A Laboratory Manual* (1982); *DNA Cloning*, Vols. I and II (D. N. Glover ed. 1985); *Oligonucleotide Synthesis* (M. J. Gait ed. 1984); Nucleic Acid Hybridization (B. D. Hames & S. J. Higgins eds. 1984); and the series *Methods in Enzymology* (S. Colowick and N. Kaplan. eds., Academic Press, Inc.).

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae and protozoa, as well as other unicellular structures.

A "fumonisin-producing microbe" is any microbe capable of producing the mycotoxin fumonisin or analogs thereof. Such microbes are generally members of the fungal genus Fusarium, as well as recombinantly derived organisms, which have been genetically altered to enable them to produce fumonisin or analogs thereof.

By "degrading fumonisin" is meant any modification to fumonisin, AP1, or any derivative of fumonisin or AP1 which causes a decrease or loss in its toxic activity, such as degradation to less than 1%, 5%, 10%, or 50% of original toxicity, with less than 10% being preferred. Such a change can comprise cleavage of any of the various bonds, oxidation, reduction, the addition or deletion of a chemical moiety, or any other change that affects the activity of the molecule. In a preferred embodiment, the modification includes hydrolysis of the ester linkage in the molecule as a first step and then oxidative deamination. Furthermore, chemically altered fumonisin can be isolated from cultures of microbes that produce an enzyme of this invention, such as growing the organisms on media containing radioactively-labeled fumonisin, tracing the label, and isolating the degraded toxin for further study. The degraded fumonisin can be compared to the active compound for its phytotoxicity or mammalian toxicity in known sensitive species, such as porcines, rabbits, and equines or in cell or tissue culture assays. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures.

By "fumonisin esterase" is meant any enzyme capable of hydrolysis of the ester linkage in fumonisin or a structurally similar molecule such as AAL toxin. Two examples of such enzymes are ESP1 and BEST1 found in U.S. Pat. No. 5,716,820, issued Feb. 10, 1998; 5,792,931, issued Aug. 11, 1998; U.S. Pat. No. 6,025,188, issued Feb. 15, 2000; and U.S. Pat. No. 6,229,091, filed Jul. 7, 1997.

By "structurally related mycotoxin" is meant any mycotoxin having a chemical structure related to a fumonisin or AP1 such as AAL toxin, fumonisin B1, fumonisin B2, fumonisin B3, fumonisin B4, fumonisin C1, fumonisin A1 and A2, and their analogs or hydrolyzed forms, as well as other mycotoxins having similar chemical structures, including synthetically made analogs that contain a C-2 or C-1 amine group and one or more adjacent hydroxyl groups, that would be expected to be degraded by the activity of an enzyme of the present invention. The present invention is the first flavin amine oxidase known to attack a primary amine not located at C-1 (i.e. C-2 of AP1) and resulting in a keto rather than an aldehydic product.

It is understood that "AP1" or "amino polyol" as used here is to designate the hydrolyzed form of any fumonisin, FB1, FB2, FB3, FB4, AAL, or any other AP1-like compound, including a compound made synthetically, that contains a C-2 or C-1 amine group and one or more adjacent hydroxyl groups.

By "amplified" is meant the construction of multiple copies of a nucleic acid sequence or multiple copies complementary to the nucleic acid sequence using at least one of the nucleic acid sequences as a template. Amplification systems include the polymnerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, DC (1993). The product of amplification is termed an amplicon.

The term "conservatively modified variants" applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine, one exception is *Micrococcuus rubens*, for which GTG is the methionine codon (Ishizuka, et al., *J. Gen'l Microbiol*, 139:425–432 (1993)) can be modified to yield a functionally identical molecule. Accordingly, each silent variation of a nucleic acid, which encodes a polypeptide of the present invention, is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90%, preferably 60–90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
See also, Creighton (1984) Proteins W. H. Freeman and Company.

As used herein, consisting essentially of means the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci. (USA)*, 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al. Nucl. Acids Res. 17: 477–498 (1989) and herein incorporated by reference). Thus, the maize preferred codon for a particular amino acid might be derived from known gene sequences from maize. Maize codon usage for 28 genes from maize plants is listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" or "recombinantly engineered cell" is meant a cell, which contains a vector and supports the replication and/or expression of the expression vector. Host cells may be prokaryotic cells such as *E. coli*, or eukaryotic cells such as yeast, Pichia, insect, plant, amphibian, or mammalian cells. Preferably, host cells are monocotyledonous or dicotyledonous plant cells, including but not limited to maize, sorghum, sunflower, soybean, wheat, alfalfa, rice, cotton, canola, barley, millet, and tomato. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is substantially or essentially free from components which normally accompany or interact with it as found in its naturally occurring environment. The isolated material optionally comprises material not found with the material in its natural environment. Nucleic acids, which are "isolated", as defined herein, are also referred to as "heterologous" nucleic acids.

Unless otherwise stated, the term "APAO nucleic acid" means a nucleic acid comprising a polynucleotide ("APAO polynucleotide") encoding an APAO polypeptide. The term APAO, unless otherwise stated can encompass both APAO and the functional, truncated version of APAO designated trAPAO.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules, which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook el al, *Molecular Cloning—A Laboratory Manual*, 2nd ed., Vol. 1–3 (1989); and Current *Protocols in Molecular Biology*. F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

The term "ligated" or "ligation" refers to the process of forming phosphodiester bonds between two or more polynucleotides, which most often are double stranded DNAs. Techniques for ligation are well known in the art and protocols are described in standard laboratory manuals and references, such as, Sambrook, et al. *Molecular Cloning: A Laboratory Manual*, 2ed., Cold Spring Harbor Laboratory Press, Cold Spring Harbor, N.Y. (1989). The two polynucleotides can include, but are not limited to, a polynucleotide, which can function as a promoter, ligated to a polynucleotide capable of encoding a polypeptide or linking two polynucleotides each capable of encoding a polypeptide. In the case of joining two polynucleotides that each encode a polypeptide, a polynucleotide spacer region between the two polynucleotides may or may not be present. The spacer region may encode a polypeptide containing a protease cleavage site. Optionally, the spacer region may contain a polynucleotide cleavage site such as but not limited to a site for RNAse cleavage or a self-cleaving ribozyme (See, e.g, Tanner, *FEAMS Microbiol Rev*, 23(3):257–75 (1999)). Alternatively, the transcription of the two or more ligated polynucleotides may result in a polycistronic message. An example of a spacer sequence that would direct translation of downstream coding sequences is an intervening ribosomal entry site (IRES) (See, e.g., Liu, et al., *Anal Biochem*, 280(1):20–28 (2000)). The length of the spacer region may be of any length that results in a functional polypeptide or polypeptides. For example, the spacer region may be from 1 nucleotide to 1000 nucleotides, preferably 24 nucleotides in length.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants including species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Mfajorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, and Triticum. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the termn includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynuclcotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such Agrobacterium or Rhizobium. Examples are promoters that preferentially initiate transcription in certain tissues, such as leaves, roots, seeds, fibres, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" or "regulatable" promoter is a promoter, which is under environmental control. Examples of environmental conditions that may effect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "APAO polypeptide or trAPAO polypeptide" refers to one or more amino acid sequences. The term is also inclusive of fragments, variants, homologs, alleles or precursors (e.g., preproproteins or proproteins) thereof. An "APAO or trAPAO protein" comprises an APAO or trAPAO polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an. amino acid that is incorporated into a protein, polypeptide, or peptide (collectively "protein"). The amino acid may be a naturally occurring amino acid and, unless otherwise limited, may encompass knowvn analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60–90% sequence identity, and most preferably 100% sequence identity (i.e., complementary) with each other.

The terms "stringent conditions" or "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. Lower than the thermal melting point ($T_m$) for the specific sequence and its complement at a defined ionic strength and pH. However, severely stringent conditions can utilize a hybridization and/or wash at 1, 2, 3, or 4° C. Lower than the thermal melting point ($T_m$); moderately stringent conditions can utilize a hybridization and/or wash at 6, 7, 8, 9, or 10° C. Lower than the thermal melting point ($T_m$); low stringency conditions can utilize a hybridization and/or wash at 11, 12, 1, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology— Hybridization with Nucleic Acid Probes*, Part I, Chapter 2 "Overview of principles of hybridization and the strategy of nucleic acid probe assays", Elsevier, N.Y. (1993); and, Current Protocols in Afoleciilar Biology, Chapter 2, Ausubel, et al., Eds., Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

As used herein, "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein. The following terms are used to describe the sequence relationships between two or more nucleic acids or polynucleotides or polypeptides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (Best Fit) of Smith and Waterman, Adv. Appl. Math may conduct optimal alignment of sequences for comparison 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc. Natl. Acad Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wiscousin Genetics Software Package, Genetics Computer Group (GCG), 575 Science Dr., Madison, Wis., USA; the CLUSTAL, program is well described by Higgins and Sharp, *Gene* 73: 237–244 (1988); Higgins and Sharp, *CABIOS* 5: 151–153 (1989); Corpet, el al., *Nucleic Acids Research* 16: 10881–90 (1988); Huang, el al., *Computer Applicalions in the Biosciences* 8: 155–65 (1992), and Pearson, et at, *Methods in Molecular Biology* 24: 307–331 (1994). The preferred program to use for optimal global alignment of multiple sequences is PileUp (Feng and Doolittle, *Journal of Molecular Evolution*, 25:351–360 (1987) which is similar to the method described by Higgins and Sharp, *CABIOS*, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*. Chapter 19, Ausubel, et al., Eds., Greene Publishing and Wiley-Interscience, New York (1995).

GAP uses the algorithm of Needleman and Wunsch (J. Mol. Biol. 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gapcreation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50, or greater.

GAP presents one member of the family of best alignments. There may be many members of this family, but no other member has a better quality. GAP displays. four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89:10915).

Unless otherwise stated, sequence identity/similarity values provided herein refer to the value obtained using the BLAST 2.0 suite of programs using default parameters. Altschul et al., *Nucleic Acids Res.* 25: 3389–3402(1997).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163

(1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions. dividing the number of matched positions by the total number of positions in the window of comparison and multiplying the result by 100 to yield the percentage of sequence identity.

(e) ii) The term "substantial identity" of polynucleotide sequences means that a polynucleotide comprises a sequence that has between 50–100% sequence identity, preferably at least 50% sequence identity, preferably at least 60% sequence identity, preferably at least 70% more preferably at least 80% more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 40–100%, preferably at least 55%, preferably at least 60%, more preferably at least 70%, 80%, 90%, and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

(e) (ii) The terns "substantial identity" in the context of a peptide indicates that a peptide comprises a sequence with between 55–100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

Fumonisin Degrading Organisms

The present invention is based on the discovery of organisms with the ability to degrade the mycotoxin fumonisin. In a search for a biological means of detoxifying fumonisins, several dematiaceous hyphomycetes were isolated from field-grown maize kernels. The fungi were found to be capable of growing on fumonisin B1 or B2 (FB1 or FB2) as a sole carbon source, degrading it partially or completely in the process. One species, identified as *Exophiala spinifera*, a "black yeast", was recovered from maize seed from diverse locations in the southeastern and south central US. The enzyme-active strain of *Exophiala spinifera* (ATCC 74269) was deposited (see U.S. Pat. No. 5,716,820, issued Feb. 10, 1998, U.S. Pat. No. 5,792,931, issued Aug. 11, 1998; U.S. Pat. No. 6,025,188, issued Feb. 15, 2000; and pending U.S. application Ser. No. 08/888,950, filed Jul. 7, 1997). Other enzyme-active strains of *Exophiala spinifera* were used to isolate APAO polynucleotides. Isolate ESP002 was isolated from palm trees (ATCC 26089) and isolate ESP003 was isolated from maize seed. Another fungus from which APAO polynucleotides were isolated was *Rhinocladiella alrovirens* (RAT 011).

Nucleic Acids

The present invention provides, inter alia, isolated nucleic acids of RNA, DNA, and analogs and/or chimeras thereof, comprising an APAO or trAPAO polynucleotide.

The present invention also includes polynucleotides optimized for expression in different organisms. For example, for expression of the polynucleotide in a maize plant, the sequence can be altered to account for specific codon preferences and to alter GC content as according to Murray el al, supra. Maize codon usage for 28 genes from maize plants is listed in Table 4 of Murray, et al., supra.

The APAO or trAPAO nucleic acids of the present invention comprise isolated APAO or trAPAO polynucleotides which, are inclusive of:

(a) a polynucleotide encoding an APAO or trAPAO polypeptide of the sequences shown in SEQ ID NOS: 36, 38, 40, 42, 44, and 46, and conservatively modified and polymorphic variants thereof;

(b) a polynucleotide which selectively hybridizes to a polynucleotide of (a) or (b);

(c) a polynucleotide having at least 50% sequence identity with polynucleotides of (a) or (b);

(d) complementary sequences of polynucleotides of (a), (b), or (c); and (e) a polynucleotide comprising at least 25 contiguous nucleotides from a polynucleotide of (a), (b), (c), or (d).

In addition, polynucleotides are presented that are a fusion of an APAO or trAPAO polynucleotide and the polynucleotide of a fumonisin esterase. The invention encompasses the sequences from Exophiala or Rhinocladiella as well as sequences having sequence similarity with such sequences. It is recognized that the sequences of the invention can be used to isolate corresponding sequences in other organisms. Methods such as PCR, hybridization, and the like can be used to identify sequences having substantial sequence similarity to the sequences of the invention. See, for example, Sambrook, et al., (1989) *Molecular Cloning: A Laborator Manual* (2d ed., Cold Spring Harbor Laboratory Press, Planview, N.Y.) and Innis el al., (1990) *PCR Protocols: Guide to Methods and Applications* (Academic Press, New York). Coding sequences isolated based on their sequence identity to the entire fumonisin degrading coding sequences set forth herein or to fragments thereof are encompassed by the present invention.

It is recognized that the sequences of the invention can be used to isolate similar sequences from other fumonisin degrading organisms. Likewise sequences from other furnonisin degrading organisms may be used in combination with the sequences of the present invention. See, for example, copending application entitled "Compositions and Methods for Fumonisin Detoxification", U.S. application Ser. No. 60/092,953, filed concurrently herewith and herein incorporated by reference.

Plasmids containing the polynucleotide sequences of the invention were deposited with American Type Culture Collection (ATCC), Manassas, Va., and assigned Accession Nos. 98812, 98813, 98814, 98815, 98816, and PTA-32. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a fungus or bacteria.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt 11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3'SS, pGEM, pSK+/−, pGEX, pSPORTI and II, pOPRSVI CAT, pOPI3 CAT, pXT1, pSG5, pPbac, pMbac, pMClneo, pOG44, pOG45, pFRTβGAL, pNEOβGAL, pRS403, pRS404, pRS405, pRS406, pRS413, pRS414, pRS415, pRS416, lambda MOSSlox, and lambda MOSElox. Optional vectors for the present invention, include but are not limited to, lambda ZAP II, and pGEX. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al, *Meth. Enzymol.* 68: 109–151 (1979); the diethylphosphoramidite method of Beaucage et al., Tetra. Lett. 22: 1859–1862 (1981); the solid phase phosphoramidite triester method described by Beaucage and Caruthers, Tetra. Letts. 22(20): 1859–1862 (1981), e.g., using an automated synthesizer, e.g., as described in Needham-VanDevanter et al., *Nucleic Acids Res.*, 12: 6159–6168 (1984): and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, Nucleic Acids Res. 15:8125 (1987)) and the 5<G>7 methyl GpppG RNA cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a is desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn). Thus, the present invention provides a codon usage frequency characteristic of the coding region of at least one of the polynucleotides of the present invention. The number of polynucleotides (3 nucleotides per amino acid) that can be used to determine a codon usage frequency can be any integer from 3 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. 96/19256. See also, Zhang, J.-H., el al. *Proc. NaH Acad. Sci. USA* 94:4504–4509 (1997) and Zhao, et al., *Nature Biotech* 16:258–261 (1998). Generally, sequence shuffling provides a means for generating libraries of polynucleotides having a desired characteristic, which can be selected or screened for. Libraries of recombinant polynucleotides are generated from a population of related sequence polynucleotides, which comprise sequence regions, which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be analtered $K_m$ and/or Kca, over the wild-type protein as provided herein. In other embodiments, a protein or polynucleotide generated from sequence shuffling will have a substrate binding affinity greater than the non-shuffled wild-type polynucleotide. In yet other embodiments, a protein or polynucleotide generated from sequence shuffling will have an altered pH optimum as compared to the non-shuffled wild-type polynucleotide. The increase in such properties can be at least 110%, 120%, 130%, 140% or greater than 150% of the wild-type value.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a polypeptide long enough to code for an active protein of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP18 promoter, the 35S promoter from cauliflower mosaic virus (CaMV), as described in, Odell et al., (1985), *Nature*, 313:810–812, rice actin (McElroy et al., (1990), *Plant Cell*, 163–171); ubiquitin (Christensen et al., (1992), *Plant Mol. Biol.* 12:619–632; and Christensen, et al., (1992), *Plant Mol. Biol.* 18:675–689); pEMU (Last, et al., (1991), *Theor. Appl. Genet.* 81:581–588); MAS (Velten et al., (1984), *EMBO J* 3:2723–2730); and maize H3 histone (Lepetit et al., (1992), *Mol. Gen. Genet.* 231:276–285; and Atanassvoa et al., (1992), *Plant Journal* 2(3):291–300), the Rsyn7 as described in published PCT Application WO 97/44756, ALS promoter, as described in published PCT Application WO 96/30530, and other transcription initiation regions from various plant genes known to those of skill. For the present invention ubiquitin is the preferred promoter for expression in monocot plants.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

If polypeptide expression is desired, it is generally desirable to include a polyadenylation region at the 3'-end of a polynucleotide coding region. The lo polyadenylation region can be derived from a variety of plant genes, or from T-DNA. The 3' end sequence to be added can be derived from, for example, the nopaline synthase or octopine synthase genes, or alternatively from another plant gene, or less preferably from any other eukaryotic gene. Examples of such regulatory elements include, but are not limited to, 3' termination and/or polyadenylation regions such as those of the *grobacterium tumefaciens* nopaline synthase (nos) gene (Bevan et al., (1983), *Nucl. Acids Res.* 12:369–385); the potato proteinase inhibitor II (PINII) gene (Keil, et al., (1986), *Nucl. Acids Res.* 14:5641–5650; and An et al., (1989), *Plant Cell* 1:115–122); and the CaMV 19S gene (Mogen et al., (1990), *Plant Cell* 2:1261–1272).

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

Plant signal sequences, including, but not limited to, signal-peptide encoding DNA/RNA sequences which target proteins to the extracellular matrix of the plant cell (Dratewka-Kos, et al., (1989), *J. Biol. Chem.* 264:4896–4900), the *Nicotiana plumbaginifolia* extension gene (DeLoose, et al., (1991), *Gene* 99:95–100), signal peptides which target proteins to the vacuole like the sweet potato sporamin gene (Matsuka, et al., (1991), *PNAS* 88:834) and the barley lectin gene (Wilkins, et al., (1990), *Plant Cell*, 2:301–313), signal peptides which cause proteins to be secreted such as that of PRIb (Lind, et al., (1992), *Plant Mol. Biol.* 18:47–53), or the barley alpha amylase (BAA) (Rahmatullah, et al., *Plant Mol. Biol.* 12:119 (1989)) and hereby incorporated byreference), or from the present invention the signal peptide from the ESP1 or BESTL1 gene, or signal peptides which target proteins to the plastids such as that of rapeseed enoyl-Acp reductase (Verwaert, et al., (1994), *Plant Mol. Biol.* 26:189–202) are useful in the invention. The barley alpha amylase signal sequence operably linked to the trAPAO or APAO polynucleotide is the preferred construct for expression in maize for the present invention.

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

Alternatively, the invention, itself, could be used as a method for selection of transformants, in other words as a selectable marker. An APAO or trAPAO polynucleotide operably linked to a promoter and then transformed into a plant cell by any of the methods described in the present application would express the degradative enzyme. When the plant cells are placed in the presence of fumonisin, AP1, or a phytotoxic analog in culture only the transformed cells would be able to grow. In another embodiment, the plant cell could be transformed with both a polynucleotide for APAO and a polynucleotide for fumonisin esterase. The selective agent in this case could be either AP1 or fuimonisin or any structural analog. Thus, growth of plant cells in the presence of a mycotoxin favors the survival of plant cells that have been transformed to express the coding sequence that codes for one of the enzymes of this invention and degrades the toxin. When the APAO or trAPAO cassette with or without the fumonisin esterase polynucleotide, is co-transformed with another gene of interest and then placed in the presence of fumonisin, AP1 or a phytotoxic analog, this invention would allow for selection of only those plant cells that contain the gene of interest. In the past antibiotic resistance genes have been used as selectable markers. Given the current concerns by consumers and environmentalist over use of antibiotic genes and the possibility of resistant microorganisms arising due to this use, a non-antibiotic resistant selectable marker system such as the present invention, fulfills this very important need.

Typical vectors useful for expression of genes in higher plants are well known in the art and include vectors derived from the tumor-inducing (Ti) plasmid of *Agrobacterium tumefaciens* described by Rogers et al., Meth. In Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene*, 61:1–11 (1987) and Berger et al., Proc. Natl useful vector herein is plasmid pBI 101.2 that is available from CLONTECH Laboratories, Inc. (Palo Alto, Calif.).

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about 1/10,000 transcripts to about 1/100,000 transcripts to about 1/500,000 transcripts. Conversely, a "strong promoter" drives expression of a coding sequence at a "high level", or about 1/10 transcripts to about 1/100 transcripts to about 1/1,000 transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokariotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction of the gene of interest into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)). The pGEX-4T-1 plasmid vector from Pharmacia is the preferred *E. coli* expression vector for the present invention.

B. Expression in Eukaryotes

A variety of eukaryotic expression systems such as yeast, insect cell lines, plant and mammalian cells, are known to those of skill in the art. As explained briefly below, the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in *Saccharomyces and Pichia are known in the art and available from commercial suppliers (e.g., Invitrogen). Suitable vectors usually have expression control sequences, such as promoters, including* 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates or the pellets. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al. *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells usefull for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armnyworm, moth, and Drosophila cell lines such as a Schneider cell line (See Schneider, *J. Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et. al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213–238 (1985).

In addition, one of the genes for fumonisin esterase or the APAO or trAPAO placed in the appropriate plant expression vector can be used to transform plant cells. The enzyme can then be isolated from plant callus or the transformed cells can be used to regenerate transgenic plants. Such transgenic plants can be harvested, and the appropriate tissues (seed or leaves, for example) can be subjected to large scale protein extraction and purification techniques, and the fumonisin degradation enzymes or APAO can be isolated for use in fumonisin and fumonisin hydrolysis product detoxification processes.

Plant Transformation Methods

Numerous methods for introducing foreign genes into plants are known and can be used to insert an APAO or trAPAO polynucleotide into a plant host, including biological and physical plant transformation protocols. See, for example, Miki et al., (1993), "Procedure for Introducing Foreign DNA into Plants", In: *Methods in Plant Molecular Biology and Biotechnology*, Glick and Thompson, eds., CRC Press, Inc., Boca Raton, pages 67–88. The methods chosen vary with the host plant, and include chemical transfection methods such as calcium phosphate, microorganism-mediated gene transfer such as Agrobacterium (Horsch, et al., (1985), *Science* 227:1229–31), electroporation, micro-injcction, and biolistic bombardment.

Expression cassettes and vectors and in vitro culture methods for plant cell or tissue transformation and regeneration of plants are known and available. See, for example, Gruber, et al., (1993), "Vectors for Plant Transformation" In: *Methods in Plant Molecular Biology and Biotechnology*, Glick and Thompson, eds. CRC Press, Inc., Boca Raton, pages 89–119.

Agrobacterium-mediated Transformation

The most widely utilized method for introducing an expression vector into plants is based on the natural transformation system of Agrobacterium. *A. tumefalciens* and *A. rhizogenes* are plant pathogenic soil bacteria, which genetically transform plant cells. The Ti and Ri plasmids of *A. tumefiaciens* and *A. rhizogenes*, respectively, carry genes responsible for genetic transformation of plants. See, for example, Kado, (1991), *Crit. Rev. Plant Sci*. 10:1. Descriptions of the Agrobacterium vector systems and methods for Agrobacterirni-mediated gene transfer are provided in Gruber et al., supra; Miki, et al., supra; and Moloney et al., (1989), *Plant Cell Reports* 8:238.

Similarly, the gene can be inserted into the T-DNA region of a Ti or Ri plasmid derived from *A. tumefaciens* or *A. rhizogenes*, respectively. Thus, expression cassettes can be constructed as above, using these plasmids. Many control sequences are known which when coupled to a heterologous coding sequence and transformed into a host organism show fidelity in gene expression with respect to tissue/organ specificity of the original coding sequence. See, e.g., Benfey, P. N., and Chua, N. H. (1989) *Science* 244: 174–181.

Particularly suitable control sequences for use in these plasmids are promoters for constitutive leaf-specific expression of the gene in the various target plants. Other useful control sequences include a promoter and terminator from the nopaline synthase gene (NOS). The NOS promoter and terminator are present in the plasmid pARC2, available from the American Type Culture Collection and designated ATCC 67238. If such a system is used, the virulence (vir) gene from either the Ti or Ri plasmid must also be present, either along with the T-DNA portion, or via a binary system where the vir gene is present on a separate vector. Such systems, vectors for use therein, and methods of transforming plant cells are described in U.S. Pat. No. 4,658,082; U.S. application Ser. No. 913,914, filed Oct. 1, 1986, as referenced in U.S. Pat. No. 5,262,306, issued Nov. 16, 1993 to Robeson, et al.; and Simpson, R. B., et al. (1986) *Plant Mol. Biol.* 6: 403–415 (also referenced in the '306 patent); all incorporated by reference in their entirety.

Once constructed, these plasmids can be placed into *A. rhizogenes* or *A. lumefaciens* and these vectors used to transform cells of plant species, which are ordinarily susceptible to Fusarium or Alternaria infection. Several other transgenic plants are also contemplated by the present invention including but not limited to soybean, corn, sorghum, alfalfa, rice, clover, cabbage, banana, coffee, celery, tobacco, cowpea, cotton, melon and pepper. The selection of either *A. lumefaciens* or *A. rhizogenes* will depend on the plant being transformed thereby. In general *A. tumefaciens* is the preferred organism for transformation. Most dicotyledonous plants, some gymnosperms, and a few monocotyledonous plants (e.g. certain members of the Liliales and Arales) are susceptible to infection with *A. tumefaciens*. *A. rhizogenes* also has a wide host range, embracing most dicots and some gymnosperms, which includes members of the Leguminosae, Compositae, and Chenopodiaceae. Monocot plants can now be transformed with some success. European Patent Application Publication Number 604 662 A1 to Hiei et al. discloses a method for transforming monocots using Agrobacterium. Saito et al. discloses a method for transforming monocots with Agrobacterium using the scutellum of immature embryos (European Application 672 752 A1). Ishida el al. discusses a method for transforming maize by exposing immature embryos to *A. tumefaciens* (Ishida et al., *Nature Biotechnolog*, 1996, 14:745–750).

Once transformed, these cells can be used to regenerate transgenic plants, capable of degrading fumonisin. For example, whole plants can be infected with these vectors by wounding the plant and then introducing the vector into the wound site. Any part of the plant can be wounded, including leaves, stems and roots. Alternatively, plant tissue, in the form of an explant, such as cotyledonary tissue or leaf disks, can be inoculated with these vectors, and cultured under conditions, which promote plant regeneration. Roots or shoots transformed by inoculation of plant tissue with *A. rhizogenles* or *A. tumefaciens*, containing the gene coding for the fumonisin degradation enzyme, can be used as a source of plant tissue to regenerate fumonisin-resistant transgenic plants, either via somatic embryogenesis or organogenesis. Examples of such methods for regenerating plant tissue are disclosed in Shahin, E. A. (1985) *Theor. Appl. Genet*. 69:235–240; U.S. Pat. No. 4,658,082; Simpson, R. B., et al. (1986) *Plant Mol. Biol.* 6: 403–415; and U.S. patent applications Ser. Nos. 913,913 and 913,914, both filed Oct. 1, 1986, as referenced in U.S. Pat. No. 5,262,306, issued Nov. 16, 1993 to Robeson, et al.; the entire disclosures therein incorporated herein by reference.

Direct Gene Transfer

Despite the fact that the host range for Agrobacterium-mediated transformation is broad, some major cereal crop species and gymnosperms have generally been recalcitrant to this mode of gene transfer, even though some success has recently been achieved in rice (Hiei et al., (1994), *The Plant Journal* 6:271–282). Several methods of plant transformation, collectively referred to as direct gene transfer, have been developed as an alternative to Agrobacterium-mediated transformation.

A generally applicable method of plant transformation is microprojectile-mediated transformnation, where DNA is carried on the surface of microprojectiles measuring about 1 to 4 μm. The expression vector is introduced into plant tissues with a biolistic device that accelerates the microprojectiles to speeds of 300 to 600 m/s which is sufficient to penetrate the plant cell walls and membranes. (Sanford et al., (1987), *Part. Sci. Technol.* 5:27; Sanford, 1988, *Trends Biotech* 6:299; Sanford, (1990), *Physiol. Plant* 79:206: Klein et al., (1992), Biotechnology 10:268).

Another method for physical delivery of DNA to plants is sonication of target cells as described in Zang et al., (1991), *BioTechnology* 9:996. Alternatively, liposome or spheroplast fusions have been used to introduce expression vectors into plants. See, for example, Deshayes et al., (1985), *EMBO J.* 4:2731; and Christou et al., (1987), *PNAS USA* 84:3962. Direct uptake of DNA into protoplasts using $CaCl_2$ precipitation, polyvinyl alcohol, or poly-L-ornithine has also been reported. See, for example, Hain et al., (1985), *Mol. Gen. Genet.* 199:161; and Draper et al., (1982), *Plant Cell Physiol.* 23:451.

Electroporation of protoplasts and whole cells and tissues has also been described. See, for example, Donn et al., (1990), In: *Abstracts of the VIIth Int'l. Congress on Plant Cell and Tissue Culture IAPTC*, A2–38, page 53; D'Halluin et al., (1992), *Plant Cell* 4:1495–1505; and Spencer et al., (1994), *Plant Mol. Biol.* 24:51–61.

Thus, polynucleotide encoding a polypeptide able to degrade fumonisin or AP1 can be isolated and cloned in an appropriate vector and inserted into an organism normally sensitive to the Fusarium or its toxins. Furthermore, the polynucleotide imparting fumonisin or AP1 degradative activity can be transferred into a suitable plasmid, and transformed into a plant. Thus, a fumonisin or AP1 degrading transgenic plant can be produced. Organisms expressing the polynucleotide can be easily identified by their ability to degrade fumonisin or AP1. The protein capable of degrading fumonisin or AP1 can be isolated and characterized using techniques well known in the art.

APAO or trAPAO in a Transgenic Plant

Fumonisin esterase reduces but does not eliminate the toxicity of fumonisins. Therefore a second enzymatic modification to further reduce or abolish toxicity is desirable. The partially purified APAO enzyme from *Exophiala spinifera* has little or no activity on intact FB1, a form of fumonisin. However, recombinant APAO enzyme from *Exophiala spinifera*, expressed in *E. coli*, has significant but reduced activity on intact FB1 and other B-series fumonisins. APAO or trAPAO thus could potentially be used without fumonisin esterase since the amine group is the major target for detoxification. Alternatively, the two genes, fumoninsin esterase and APAO (or trAPAO) can be used together for degrading toxins.

APAO is predicted to be an enzyme that, when by itself or co-expressed in a heterologous expression system along with fumonisin esterase (either ESPI or BESTI), will result in the production of 2-oxo-FB1 and/or 2-ox6 pentol (2-OP) from fumonisin B1. The substrate range of recombinant, *E. coli*-expressed APAO is limited to fumonisins and their hydrolysis products and does not include amino acids, sphingolipid precursors such as phytosphingosine, or polyamines such as spermnidine. Thus, APAO is highly specific for fumonisin-like amines, and thus would have little deleterious effect on other cellular metabolites. In addition, if it is extracellularly localized, it will limit any contact with biologically important amines that might also be substrates. The end result will be a more effective detoxification of fumonisins than can be achieved with esterase alone. The oxidase activity of APAO is predicted to result in generation of hydrogen peroxide in stoichiometric amounts relative to AP1 or fumonisin oxidized. This may prove to be an additional benefit of this enzyme, since hydrogen peroxide is both antimicrobial and is thought to contribute to the onset of a defense response in plants (Przemylaw, *Biochem j.*, 322:681–692 (1997), Lamb, et al., *Ann Rev Plant Physiol Plant Mol Bio* 48:251–275 (1997), and Alverez, et al., *Oxidative Stress and the Molecular Biology of Antioxidant Defenses*, Cold Spring Harbor Press, 815–839 (1997)).

Because one of the embodiments of the present invention is to have both a fumonisin esterase polynucleotide and an APAO or trAPAO polynucleotide present in a plant, there are several ways to introduce more than one polynucleotide in a plant. One way is to transform plant tissue with polynucleotides to both fumonisin esterase and APAO or trAPAO at the same time. In some tissue culture systems it is possible to transform callus with one polynucleotide and then after establishing a stable culture line containing the first polynucleotide, transform the callus a second time with the second polynucleotide. One could also transform plant tissue with one polynucleotide, regenerate whole plants, then transform the second polynucleotide into plant tissue and regenerate whole plants. The final step would then be to cross a plant containing the first polynucleotide with a plant containing the second polynucleotide and select for progeny containing both polynucleotides.

Another method is to create a fusion protein between esterase and APAO or trAPAO, preferably with a spacer region between the two polypeptides. Both enzymes would be active although tethered to each other. In addition, an enzyme cleavage site engineered in the spacer region, would allow cleavage by an endogenous or introduced protease.

Transgenic plants containing both a fumonisin esterase enzyme and/or the APAO enzyme and thus able to degrade fumonisin or a structurally related mycotoxin would be able to reduce or eliminate the pathogenicity of any microorganism that uses fumonisin or a structurally related mycotoxin as a mode of entry to infect a plant. Fungal pathogens frequently use toxins to damage plants and weaken cell integrity in order to gain entry and expand infection in a plant. By preventing the damage induced by a toxin, a plant would be able to prevent the establishment of the pathogen and thereby become tolerant or resistant to the pathogen.

Another benefit of fumonisin degradation is the production of hydrogen peroxide. When fumonisin or AP1 is oxidatively deaminated at C-2, as occurs by exposure to APAO or trAPAO enzyme, hydrogen peroxide is produced as a by-product. Hydrogen peroxide production can trigger enhanced resistance responses in a number of ways. 1) Hydrogen peroxide has direct antimicrobial activity. 2) Hydrogen peroxide acts as a substrate for peroxidases associated with lignin polymerization and hence cell wall strengthening. 3) Via still to be determined mechanisms, hydrogen peroxide acts as a signal for activation of expression of defense related genes, including those that result in stimulation of salicylic acid accumulation. Salicylic acid is thought to act an endogenous signal molecule that triggers expression of genes coding for several classes of pathogenesis-related proteins. Moreover, salicylic acid may set up the oxidative burst and thus act in a feedback loop enhancing its own synthesis. Salicylic acid may also be involved in hypersensitive cell death by acting as an inhibitor of catalase, an enzyme that removes hydrogen peroxide. 4) Hydrogen peroxide may trigger production of additional defense compounds such as phytoalexins, antimicrobial low molecular weight compounds. For a review on the role of the oxidative burst and SA please see Lamb, C. and Dixon, R. A, *Ann. Rev. Plant Physiol. Plant Mol. Biol.*, 48: 251–275 (1997).

Detoxification of Harvested Grain, Silage, or Contaminated Food Crop

The present invention also relates to a method of detoxifying a fumonisin or a structurally related mycotoxin with an APAO enzyme during the processing of grain for animal or human food consumption, during the processing of plant material for silage, or food crops contaminated with a toxin producing microbe, such as but not limited to, tomato. Since the atmospheric ammoniation of corn has proven to be an ineffective method of detoxification (see B. Fitch Flaumann, *INFORM* 6:248–257 (1995)), such a methodology during processing is particularly critical where transgenic detoxification is not applicable.

In one embodiment of the present invention, fumonisin degradative enzymes are presented to grain, plant material for silage, or a contaminated food crop, or during the processing procedure, at the appropriate stages of the procedure and in amounts effective for detoxification of fumonisins and structurally related mycotoxins. Detoxification by the enzymes, microbial strains, or an engineered microorganism can occur not only during the processing, but also any time prior or during the feeding of the grain or plant material to an animal or incorporation of the grain or food crop into a human food product, or before or during ingestion of the food crop.

Another embodiment of the present invention is the engineering of a bacterium or fungus to express the detoxification enzymes and then using the bacterium or fungus rather than the enzyme itself. There are a number of microbes that could be engineered to express the polynucleotides of the present invention. One could also activate, either inducibly or constitutively, the endogenous genes for fumonisin esterase or APAO. By overexpressing the degradative enzymes and then treating plants, seed, or silage with the microorganism, it would be possible to degrade fumonisin in situ.

The polynucleotides of the invention can be introduced into microorganisms that multiply on plants (epiphytes) to deliver enzymes to potential target crops. Epiphytes can be gram-positive or gram-negative bacteria, for example.

The microorganisms that have been genetically altered to contain at least one degradative polynucleotide and resulting polypeptide may be used for protecting agricultural crops and products. In one aspect of the invention, whole, i.e. unlysed, cells of the transformed organism are treated with reagents that prolong the activity of the enzyme produced in the cell when the cell is applied to the environment of a target plant. A secretion leader may be used in combination with the gene of interest such that the resulting enzyme is secreted outside the host cell for presentation to the target plant.

The degradative enzymes can be fermented in a bacterial host and the resulting bacteria processed and used as a microbial spray. Any suitable microorganism can be used for this purpose. See, for example, Goertner, et al. (1993) in *Advanced Engineered Pesticides*, (ed. Kim, Marcel Dekker, Neew York).

The enzymes or microorganisms can be introduced during processing in appropriate manners, for example as a wash or spray, or in dried or lyophilized form or powered form, depending upon the nature of the milling process and/or the stage of processing at which the enzymatic treatment is carried out. See generally, Hoseney, R. C., *Principles of Cereal Science and Technology*, American Assn. of Cereal Chemists, Inc., 1990 (especially Chapters 5, 6 and 7); Jones, J. M., *Food Safety*, Eagan Press, St. Paul, Minn., 1992 (especially Chapters 7 and 9); and Jelen, P., *Introduction to Food Processing*, Restan Publ. Co., Reston, Va., 1985. Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase from *Exophiala spinifera*, ATCC 74269, showed a range of activity from about pH 3 to about pH 6, and the esterase from the bacterium of ATCC 55552 showed a range of activity from about pH 6 to about pH 9 (U.S. Pat. No. 5,716,820, supra). The APAO enzyme from *Exophiala spinifera* (ATCC 74269) has a pH range of activity from pH 6 to pH 9.

Genetic Engineering of Ruminant Microorganisms

Ruminant microorganisms can be genetically engineered to contain and express either the fumonisin esterase enzymes or APAO, or a combination of the enzymes. The genetic engineering of microorganisms is now an art recognized technique, and ruminant microorganisms so engineered can be added to feed in any art recognized manner, for example as a probiotic or inoculant. In addition, microorganisms capable of functioning as bioreactors can be engineered so as to be capable of mass producing either the fumonisin esterases or the APAO enzyme.

Use of the Fumonisin Esterase and APAO Enzymes for Detection of Reagents for Fumonisins and Related Compounds Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or othenvise detectable peroxidase product (e.g. Demmano, et al., *European Journal of Biochemistry* 238(3): 785–789 (1996)). Ammonia can be measured using ion-specific electrodes : Fritsche, er al., *Analytica Chimica Acia* 244(2): 179–182 (1991); West, et al., *Analytical Chemistry* 64(5): 533–540 (1992), and all herein incorporated by reference) or by GC or other chromatographic method.

For example, recombinant or non-recombinant, active fumonisin esterase (ESP1 or BEST) and APAO proteins are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1 or to 2-oxo-FB1, and correspondingly the AP1 to 2-OP, ammonia, and hydrogen peroxide. Alternatively, APAO or trAPAO is added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to 2-oxo FB1, ammonia, and hydrogen peroxide. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following non-limiting examples. It will be appreciated by those skilled in the art that other embodiments of the invention may be practiced without departing from the spirit and the scope of the invention as herein disclosed and claimed.

EXAMPLE 1

Fungal and bacterial isolates. Exophiala isolates from maize were isolated as described in U.S. Pat. No. 5,716,820, issued Feb. 10, 1998; U.S. Pat. No. 6,025,188, issued Feb. 15, 2000; and U.S. application Ser. No. 08/888,950, filed Jul. 7, 1997, and herein incorporated by reference.

Isolation methods. Direct isolation of black yeasts from seed was accomplished by plating 100 microliters of seed wash fluid onto YPD or Sabouraud agar augmented with cycloheximide (500 mg/liter) and chloramphenicol (50 mg/liter). Plates were incubated at room temperature for 7–14 days, and individual pigmented colonies that arose were counted and cultured for analysis of fumonisin-degrading ability as described in U.S. Pat. No. 5,716,820, issued Feb. 10, 1998; U.S. Pat. No. 6,025,188, issued Feb. 15, 2000; and U.S. application Ser. No. 08/888,950, filed Jul. 7, 1997.

Analysis of fumonisins and metabolism products. Analytical thin-layer chromatography was carried out on 100% silanized C18 silica plates (Sigma #T-7020; 10×10 cm; 0.1 mm thick) by a modification of the published method of Rottinghaus (Rottinghaus, et al., *J Vet Diagn Invest*, 4: 326 (1992), and herein incorporated by reference).

To analyze fumonisin esterase activity sample lanes were pre-wet with methanol to facilitate sample application. After application of from 0.1 to 2 µl of aqueous sample, the plates were air-dried and developed in MeOH:4% KCl (3:2) or MeOH:0.2 M KOH (3:2) and then sprayed successively with 0.1 M sodium borate (pH 9.5) and fluorescamine (0.4 mg/ml in acetonitrile). Plates were air-dried and viewed under long wave UV.

For analysis of APAO activity, an alternative method was used. Equal volumes of sample and $^{14}$C-AP1 (1 mg/ml, pH 8, 50 mM sodium phosphate) were incubated at room temperature for one to six days. Analytical thin-layer chromatography was then carried out on C60 HPK silica gel plates (Whatman #4807–700; 10×10 cm; 0.2 mm thick). After application of from 0.1 to 2 µl of aqueous sample, the plates were air-dried and developed in $CHCl_3$:MeOH:$CH_3COOH$:$H_2O$ (55:36:8:1). Plates were then air dried, and exposed to PhosphorImager screen (Molecular Dynamics) or autoradiographic film. A Storm™ PhosphorImager (Molecular Dynamics) was used to scan the image produced on the screen.

Alkaline hydrolysis of FB1 to AP1. FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to RT and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1") was analyzed by TLC.

Enzyme activity of culture filtrate and mycelium. *Exophiala spinifera* isolate 2141.10 was grown on YPD agar for 1 week, and conidia were harvested, suspended in sterile water, and used at $10^5$ conidia per ml to inoculate sterile Fries mineral salts medium containing 1 mg/ml purified FB1 (Sigma Chemical Co.). After 2 weeks incubation at 28° C in the dark, cultures were filtered through 0.45 micron cellulose acetate filters, and rinsed with Fries mineral salts. Fungal mycelium was suspended in 15 mL of 0.1% FB1, pH 5.2+1 mM EDTA+3 µg/mL Pepstatin A+1.5 µg/mL Leupeptin and disrupted in a Bead Beater™ using 0.1 mm beads and one minute pulses, with ice cooling. Hyphal pieces were collected by filtering through Spin X™ (0.22 µm), and both mycelial supernatant and original culture filtrates were assayed for fumonisin modification by methods outlined above.

Preparation of crude culture filtrate. Agar cultures grown as above were used to inoculate YPD broth cultures (500 ml) in conical flasks at a final concentration of $10^5$ conidia per ml culture. Cultures were incubated 5 days at 28° C. without agitation and mycelia harvested by filtration through 0.45 micron filters under vacuum. The filtrate was discarded and the mycelial mat was washed and resuspended in sterile carbon-free, low mineral salts medium (1 g/liter $NH_3NO_4$; 1 g/liter $NaH_2PO_4$; 0.5 g/liter $MgCl_2$; 0.1 g/liter NaCl; 0.13 g/liter $CaCl_2$; 0.02 g/liter $FeSO_4.7H_2O$, pH 4.5) containing 0.5 mg/ml alkaline hydrolyzed crude FB1. After 3–5 days at 28° C. in the dark with no agitation the cultures were filtered through low protein binding 0.45 micron filters to recover the culture filtrate. Phenylmethyl sulfonyl fluoride (PMSF) was added to a concentration of 2.5 mM and the culture filtrate was concentrated using an Amicon™ YM10 membrane in a stirred cell at room temperature, and resuspended in 50 mM sodium acetate, pH 5.2 containing 10 mM $CaCl_2$. The crude culture filtrate (approx. 200-fold concentrated) was stored at −20° C.

To obtain preparative amounts of enzyme-hydrolyzed fumonisin, 10 mg. of FB1 (Sigma) was dissolved in 20 mL of 50 mM sodium acetate at pH 5.2+10 mM $CaCl_2$, and 0.25 mL of 200×concentrated crude culture filtrate of 2141.10 was added. The solution was incubated at 37° C. for 14 hours, and then cooled to room temperature. The reaction mixture was brought to approx. pH 9.5 by addition of 0.4 mL of 4 N KOH, and the mixture was extracted twice with 10 mL ethyl acetate. The combined organic layers were dried under $N_2$ and resuspended in $dH_2O$. 2.5 milligrams of organic extracted material were analyzed by Fast Atom Bombardment (FAB) mass spectrometry. The resulting mass spectrum showed a major ion at M/z (+1)=406 mass units, indicating the major product of enzymatic hydrolysis was AP1 which has a calculated molecular weight of 405.

EXAMPLE 2

Preparation of AP1-induced and Non-induced Mycelium

Liquid cultures of *Exophiala spinifera* isolate 2141.10 were prepared from YPD agar plates (Yeast Extract 10 gm, Bacto-Peptone 20 gm, Dextrose 0.5 gm, and Bacto-Agar 15 gm per liter of water). Aliquots (400–500 uL) of a water suspension of *E. spinifera* cells from YPD agar were spread uniformly onto 150×15 mm YPD agar plates with 4 mm sterile glass beads. The plates were incubated at room temperature for 6–7 days. The mycelia/conidia were transferred from the agar plates into Mineral Salts Medium (MSM) ($Na_2HPO_4 \cdot 7H_2O$ 0.2 gm, $NH_4Cl$ 1.0 gm, $CaCl_2 \cdot 2H_2O$ 0.01 gm, $FeSO_4 \cdot 7H_2O$ 0.02 gm per liter of distilled water, pH 4.5) and centrifuged at 5000×g, 4° C., 20 minutes to pellet the cells. The cell pellet was rinsed once in 40 ml MSM and recentrifuged. The rinsed cell pellet was used to inoculate MSM at a 1:19 ratio of packed cells: MSM. The culture to be induced was supplemented with AP1 to a final concentration of 0.5–1.0 mg/ml and incubated at 28° C., 100 rpm, in the dark to induce catabolic enzymes. The non-induced cultures did not receive AP1 but were grown on media containing 4-ABA at the same concentration as AP1. The supernatants were removed by filtration through 0.45 cellulose acetate. The remaining mycelial mat was washed with sterile MSM and then frozen in liquid nitrogen for storage.

EXAMPLE 3

Effect of FB1 and AP1 on Maize Coleoptiles

Maize coleoptiles from 4 day dark-grown germinated maize seeds were excised above the growing point and placed in 96-well microtiter plates in the presence of 60 microliters of sterile distilled water containing FB1 or AP1 at approximately equimolar concentrations of 1.5, 0.5, 0.15, 0.05, 0.015, 0.005, 0.0015, or 0.0005 millimolar, along with water controls. After 2 days in the dark at 28° C. the coleoptiles were placed in the light and incubated another 3 days. Injury or lack thereof was evaluated as follows:

|     | 0 | .0005 | .0015 | .005 | .015 | .05 | .15 | .5 | 1.5 | mM |
|-----|---|-------|-------|------|------|-----|-----|----|-----|----|
| FB1 | – | –     | –     | –    | +/–  | +   | +   | +  | +   |    |
| AP1 | – | –     | –     | –    | –    | –   | –   | –  | +   |    |

+ = brown necrotic discoloration of coleoptile
– = no symptoms (same as water control)

The results (see table above) indicate there is at least a 30-fold difference in toxicity between FB1 and AP1 to maize coleoptiles of this genotype. This is in general agreement with other studies where the toxicity of the two compounds was compared for plant tissues: In Lemna tissues, AP1 was approx. 40-fold less toxic (Vcsonder et al.," *Arch Environ Contain Toxicol* 23: 464–467 (1992).). Studies with both AAL toxin and FB1 in tomato also indicate the hydrolyzed version of the molecule is much less toxic (Gilchrist et al., *Mycopathologia* 117: 57–64 (1992)). Larnprecht et al. also observed an approximate 100-fold reduction in toxicity to tomato by AP1 versus FB1 (Lamprecht et al., *Phytopathulugy* 84: 383391 (1994))

EXAMPLE 4

Effect of FB1 and AP1 on Maize Tissue Cultured Cells (Black Mexican Sweet, BMS)

FB1 or AP1 at various concentrations was added to suspensions of BMS cells growing in liquid culture medium in 96-well polystyrene plates. After 1 week the cell density in wells was observed under low power magnification and growth of toxin-treated wells was compared to control wells that received water. Growth of BMS cells was significantly inhibited at 0.4 micromolar FB1, but no inhibition was observed until 40 micromolar AP1. This represents an approximate 100-fold difference in toxicity to maize tissue cultured cells. Similarly Van Asch et al. (VanAsch et al., *Phytopathology* 82: 330–1332 (1992)) observed significant inhibition of maize callus grown on solid medium at 1.4 micromolar FB1. AP1 was not tested in that study, however.

EXMAPLE 5

APAO Activity

A cell-free extract that contains the deaminase activity was obtained by subjecting substrate-induced *Exophiala spinifera* cells to disruption using a Bead Beater™ in 50 mM Na-phosphate, pH 8.0, and recovering the cell-free supernatant by centrifugation and 0.45 micron filtration. Catabolic activity is assayed by incubating extracts with AP1 (hydrolyzed fumonisin BI backbone) or "$^4$C-labelled AP1 with the extract and evaluating by TLC on C18 or C60 silica. The product 2-OP has a lower Rf than AP1 and is detected either by radiolabel scan or by $H_2SO_4$ spray/charring of the TLC plate. 2-OP does not react with the amine reagent, fluorescamine, that is routinely used to detect AP1 on TLC plates, suggesting that the amine group is missing or chemically modified. Activity is greater at 37° C. than at room temperature, but following 30 min. at 65° C. or 100° C. (no AP1 catabolic activity remained). Activity is maximal at pH 9. At pH 9, complete conversion to 2-OP occurred in 30 minutes. Activity is retained by 30,000 dalton molecular weight cutoff membrane, but only partially retained by 100.000 dalton molecular weight cutoff membrane. Other amine-containing substrates were tested for modification by the crude extract. Fumonisin, with tricarballylic acids attached, is not modified by the extract, indicating that ester-hydrolysis must occur first for the APAO to be able to be effective in modifying FB1 (as noted below, the *E. coli*-expressed, recombinant APAO enzyme does in fact oxidize FB1 although at a lower rate than AP1). Other long-chain bases (sphingosine, sphinganine, and phytosphingosine) are apparently not modified by the crude APAO, suggesting the enzyme(s) is specific for the fumonisin backbone. Preparative amounts of the product, named 2-OP, have also been purified and analyzed by C13 nmr. The results indicate that 2-OP has a keto group at carbon 2 instead of an amine, consistent with an oxidative deamination by an amine oxidase. The C13 nmr data also indicate that 2-OP spontaneously forms an internal hemiketal between C-1 and C-5, resulting in a 5-membered ring with a new chiral center at C-2. All other carbon assignments are as in AP1, thus 2-OP is a compound of composition $C_{22}H_{44}O_6$, FW 404. The product of the enzyme acting on hydrolyzed fumonisin would not be expected to display any significant toxicity.

Other enzymes were tested for their ability to modify AP1. All enzymes were assayed by radiolabeled TLC, as described above, under optimal conditions at 37° Celsius, overnight or longer. The results are as follows:

| Deaminating | EC | Source | Result |
|---|---|---|---|
| Monoamine Oxidase | 1.4.3.4 | bovine plasma | negative |
| D-amino oxidase | 1.4.3.3 | porcine kidney: Type X | negative |
| L-amino oxidase | 1.4.3.2 | C. adamanteus venom: Type I | negative |
| Tyramine oxidase | 1.4.3.4 | Arthrobacter spp | negative |
| Methylamine dehydrogenase | 1.4.99.3 | Paracoccus denitrificans | negative |
| Aralkyl amine dehydrogenase | 1.4.99.4 | Alcaligenes faecalis | negative |
| Phenylalanine ammonia lyase | 4.3.1.5 | Rhodotorula glutinis: Type I | negative |
| Histidine ammonia lyase | 4.3.1.3 | Pseudomonas fluorescens | negative |
| L-aspartase | 4.3.1.1 | Hafnia alvei (Bacterium cadaveris) | negative |
| Tyrosine oxidase | 1.14.18.1 | mushroom | negative |
| Lysine oxidase | 1.4.3.14 | Trichoderma viride | negative |
| Diamine oxidase | 1.4.3.6 | porcine kidney | negative |

The results were negative for each enzyme tested. Therefore isolates from the American Type Culture Collection (ATCC) were collected. The ATCC isolates selected were listed as containing amine-modifying enzymes or were capable of growth/utilization on amine-containing substrates. The isolates were tested to determine if they could grow on or utilize AP1 as the sole carbon source and if any could modify AP1 to a new compound(s). The nitrogen sources that were used in liquid cultures were AP1 0.1% (w/v), s-butylamine 0.1% (v/v), n-butylamine 0.1% (v/v), and ammonium nitrate 0.2% (w/v). These were prepared in Vogel's Minimal Media (without $NH_4NO_3$) containing 2% sucrose. The isolates were inoculated into the various media and monitored for growth over 2–3 weeks. They were also assayed with the $^{14}C$-radiolabeled TLC assay for AP1 modification. In summary, none of the isolates tested exhibited modification of AP1 in vivo. Clearly the APAO enzyme is unique and unusual in its ability to modify the AP1 toxin.

EXAMPLE 6

Isolation of the trAPAO Polynucleotide

The trAPAO polynucleotide was identified using a proprietary transcript imaging method that compares transcript patterns in two samples and allows cloning of differentially expressed fragments. This technology was developed by CuraGen® (New Haven, Conn.). (see Published PCT patent application no. WO 97/15690, published May 1, 1997, and hereby incorporated by reference) Fluorescently-tagged, PCR amplified cDNA fragments representing expressed transcripts can be visualized as bands or peaks on a gel tracing, and the cDNA from differentially expressed (induced or suppressed) bands can be recovered from a duplicate gel, cloned and sequenced. Known cDNAs can be identified without the need for cloning, by matching the predicted size and partially known sequence of specific bands on the tracing.

In the present invention two RNA samples were obtained from cultures of E. spinifera grown for a specified period in a mineral salts medium containing either AP1 (induced condition), or gamma-aminobutyric acid (ABA; non-induced condition) as a sole carbon source. In the induced condition, fumonisin esterase and APAO enzyme activities are detected, whereas in the non-induced condition these activities are not detected. The methods used for induction of APAO and detection of activity are described earlier (see Example 2 and Example 5). RNA was extracted from induced mycelium by Tri-Reagent methods (Molecular Research Center Inc., Cincinnati, Ohio) only grinding a frozen slurry of tissue and Tri-Reagent with a mortar and pestle until almost melted and adding an additional extraction after the phase separation by extracting the aqueous phase one time with phenol, and two times with a phenol:chloroform:isoamyl alcohol mixture. The RNA's were submitted for CuraGen® transcript imaging to detect cDNA fragments that are induced specifically in-the presence AP1. In the resulting gel tracing several bands were found which showed induction of at least 2-fold and up to 79-fold or even 100-fold or more in AP1. In the resulting gel tracing several bands were found which showed induction of at least 10-fold in AP1-grown cells as compared to cells grown in ABA. The sequence of two highly induced bands can be found in Table 1.

TABLE 1

Nucleotide sequence of two CuraGen ® bands that were identified as strongly induced
by AP1 in cultures of Exophiala spinifera.

>k0n0-395.5_b (SEQ ID NO: 1)

GGGCCCCGGCGTTCTCGTAGGCTGCGCGGAGTTGGTCCCAGACAGACTTTTGTCGTACCTGCTTG
GACTGTTGGGACCACTTCCGTCCCGGGTCTCCGACCATGAAACAGGTAATGGACCATTGTCGAT
CGACGTCGATGCTGGTATCTCTGGCAAATGAGATGGGGTCACAGCTCGATTGGAGGACGCCCGA
GAAGCCTTGTTCGCGCCACCACGGCTTGTCCCATACGAAGACTATCTTGCTATAGTAGCCCAGG
ATAGAATTTTCCGCCAATGCTTGCTTCTCGGCGGGAAGAGGTGGTGAAAATGTCAAGGTGGGAT
ACAAGGTTGTCGGTAACGAAACCANCACCTTTTTGCTTCGGAACACGGCGC
>r0c0-182.3_6 (SEQ ID NO: 2)

GAATTTTCCGCCAATGCTTGCTTCTCGGCGGGAAGAGGTGGTGAAAATGTCAAGGTGGGATACA
AGGTTGTCGGTAACGAAACCACCACCTTTTTGCTTCGGAACACGGCGCCCGAGGCCGATCGTAC
TGTACAGCCGGATGCCGACTGCTCAATTTCAGCGACGGGGGTGTTGAGGTGCAC

Two of the highly induced bands, k0n0-395.5, and r0c0-182.3 showed significant sequence homology to a family of enzymes, flavin-containing amine oxidases (EC 1.4.3.4), that oxidize primary amines to an aldehyde or ketone, releasing ammonia and lo hydrogen peroxide (Table 2).

TABLE 2

Identification of a putative flavin amine oxidase from E. spinifera: AP1-induced transcript fragments with amine oxidase homology. BLAST 2.0 default parameters.

| Clone ID | Size | Best Hit | Best Hit Name, source | Prob | from | to | Likely function |
|---|---|---|---|---|---|---|---|
| k0n0-395.5 | 395 bp | P40974 | putrescine oxidase, Micrococcus rubens, EC 1.4.3.10 Length = 478 | 8.0 e−07 | 276 | 333 | oxidation of C-2 amine of AP1 |
| r0c0-182.3 (contigs with k0n0-395) | 182 bp | P12398 | monoamine oxidase type A (MAO-A) [Bos taurus] Length = 527 | 0.0039 | 238 | 296 | oxidation of C-2 amine of AP1 |

The chemical structure of the primary product of AP1 deamination is thought to be a 2-keto compound which cyclizes to a hemiketal at carbons 2 and 5. Therefore it is predicted that this induced enzyme is responsible for deamination of AP1.

Using sequence derived from k0n0-395.5, a partial cDNA was obtained by 3' and 5' RACE-PCR (Chenchik, et al, CLONTECHniques X 1:5–8 (1995); Chenchik, et al, A new method for full-length cDNA cloning by PCR. In A Laboratory Guide to RNA: Isolation, Analysis, and Synthesis. Ed. Krieg, P. A. (Wiley-Liss, Inc.), 273–321 (1996)). A RACE cloning kit from CLONTECH was used, to obtain the RACE amplicons. Briefly, poly A+RNA is transcribed to make first strand cDNA using a "lock-docking" poly T, cDNA synthesis primer, the second strand is synthesized and the Marathon cDNA adaptor is ligated to both ends of the ds cDNA. Diluted template is then used with the Marathon adapter primer and in separate reactions either a 5' Gene Specific Primer (GSP) or a 3'GSP is used to produce the 3' or 5' RACE amplicon. After characterization of the RACE product(s) and sequencing, full-length cDNAs may be generated by 1) end-to-end PCR using distal 5' and 3' GSPs with the adapter-ligated ds cDNA as template, or 2) the cloned 5' and 3'-RACE fragments may be digested with a restriction enzyme that cuts uniquely in the region of overlap, the fragments isolated and ligated. Subsequently, the RACE-generated full-length cDNAs from 1) and 2) may be cloned into a suitable vector.

In combination with the supplied adapter primer the following gene specific primers were used: for 3' RACE the oligonucleotide N21965: 5'-TGGTTTCGTTACCGACAACCTTGTATCCC-3' (SEQ ID NO: 3) and for 5' race; the oligonucleotide N21968: 5'-GAGTTGGTCCCAGACAGACTTTTGTCGI-3' (SEQ ID NO: 4. The polynucleotide sequence of the trAPAO polynucleotide, k0n0-395_6.5, from Exophiala spinifera is shown in SEQ ID NO: 5. The polypeptide sequence of trAPAO is shown in SEQ ID NO: 6.

A second clone of APAO containing an unspliced intron was also found. The polynucleotide sequence of trAPAO-I polynucleotide, k0n0-395_5.4, the intron containing clone, from Exophiala spinifera, can be found in SEQ ID NO: 7. The polypeptide sequence of trAPAO-I with the intron spliced out is shown in SEQ ID NO: 8. The polypeptide sequence of trAPAO-I without the intron spliced out is shown in SEQ ID NO: 9.

EXAMPLE 7

Heterologous Expression of trAPAO

Protein alignments generated with PileUp (GCG) indicate that k0n0-395_6.5 (trAPAO) is similar in size to other flavin amine oxidases and is close to being full length with respect to the amino terminus of their class of proteins. The k0n0-395_6.5 sequence contains a complete β-α-β fold that is required for dinucleotide (FAD) binding, close to the amino end. The k0n0-395 sequence appears to lack only a variable amino terminal segment that varies in length from 5 amino acids in rat monoamine oxidases A & B to 40 amino acids in length in Aspergillus MAO-N. The function of these amino terminal extensions is not known; they are not recognizable as secretion signals. Based on the likely localization of the Exophiala APAO outside the cell membrane, the prediction is that k0n0-395 would have a signal sequence similar to that of the fumonisin esterase cloned from the same organism (U.S. Pat. No. 5,716,820, supra). Using GenomeWalker™, it is possible to clone the 5' end of the transcript and upstream genomic regulatory elements. However, the signal sequence is not expected to be critical to the functionality of the enzyme; in fact, the preferred strategy for heterologous expression in maize and Pichia pasloris involves replacing the endogenous signal sequence (if present) with an optimized signal sequence for the organism, e.g. barley alpha amylase for maize and the yeast alpha factor secretion signal for Pichia. In maize transformed with fumonisin esterase, the barley alpha amylase signal sequence gave higher amounts of functional protein than the native fungal signal, therefore replacement of the native fungal signal sequence is a logical optimization step. Since many of the amine oxidases have a positively charged amino acid near the N-terminus and upstream of the dinucleotide binding site, an additional optimization step included adding a codon for the lysine (K) to the N-terminus of the trAPAO clone (k0n0-395_6.5, SEQ ID NO: 5). This clone is designated K:trAPAO and can be seen in SEQ ID NOS: 10 and 11. The extra lysine is at amino acid 1 and nuclcotides 1–3.

EXAMPLE 8

Pichia Expression of trAPAO

For optimum expression of trAPAO in Pichia pastoris the alpha mating factor signal peptide was operably linked in-frame with K:trAPAO coding sequence and can be seen in SEQ ID NOS: 16 and 17. The nucleotide sequence of clone pPicZalphaA:K:trAPAO contains a PCR-amplified insert comprising the k0n0-395 open reading frame with an additional lysine residue at the amino terminus, with a 5' EcoRI site and 3' NotI site for in-frame cloning into the alpha factor secretion vector pPicZalphaA. Nucleotides 1–267 contain the yeast α mating factor secretion signal. The amino acid sequence, shown in SEQ ID NO: 17, contains the trAPAO polypeptide produced from pPicZalphaA:K:trAPAO following transformation into *Pichia pastoris*.

For cloning into expression vectors, two cloning strategies were used. The cDNA k0n0-395_5.4 was generated by using end-to-end PCR using distal 5' and 3' GSPs with the adapter-ligated double stranded cDNA as a template. Each oligonucleotide primer was designed with 5' restriction enzyme sites that contain a 23–25 bp of anchored gene sequence. The 3' primer also included the stop codon. The primer sequences are N23256: 5'-ggggaattcAAAGACAACGTTGCGGACGTGGTAG-3' (SEQ ID NO: 12) and N23259: 5'-ggggcggccgcCTATGCTGCTGGCACCAGGCTAG-3' (SEQ ID NO: 13). A second method was used to generate k0n0-395_6.5. 5' RACE and 3' RACE products using a distal primer containing the necessary restriction enzyme sites, stop codon, etc as described above and paired with a "medial" GSP. The "medial primers" N21965: 5'-TGGTTTCGTTACCGACAACCTTGTATCCC-3' (SEQ ID NO: 14) for 3' RACE and for 5' race, the oligonucleotide N21968: 5'-GAGTTGGTCCCAGACAGACTTTTGTCGT-3' (SEQ ID NO: 15). Adapter-ligated double stranded cDNA was used as template. The isolated 5' and 3'-RACE fragments were digested with a restriction enzyme that cuts uniquely in the region of overlap, in this case Bgl I, isolated and ligated into the expression vector. The digestible restriction sites allow cloning of the inserts in-frame into EcoRI/NotI digested pPicZalphaA. pPicZalphaA is an *E. coli* compatible Pichia expression vector containing a functional yeast alpha factor secretion signal and peptide processing sites, allowing high efficiency, incurable secretion into the culture medium of Pichia. The resulting 1.4 kb bands were cloned into EcoRI/NotI digested pPicZalphaA plasmid.

SEQ ID NO: 16 contains the polynucleotide sequence of clone pPicZalphaA:K:trAPAO, a PCR-amplified insert that comprises the k0n0-395 open reading frame with an additional lysine residue at the amino terminus, and a 5' EcoRI site and 3' NotI site for in-frame cloning into the alpha factor secretion vector pPicZalphaA. SEQ ID NO: 17 contains the amino acid sequence of the trAPAO polypeptide produced from pPicZalphaA:K:trAPAO following transformation into *Pichia pasloris*. The alpha factor secretion signal and a lysine are added.

Pichia was transformed as described in Invitrogen Manual, Easy Select™ Pichia Expression Kit, Version B, #161219, with the trAPAO polynucleotide as described above with either an intron (trAPAO-I, negative control, no expression of active trAPAO since Pichia does not splice introns very efficiently) or without an intron (capable of making an active APAO protein). The Pichia culture fluids and pellets were assayed for APAO activity as described earlier.

The set of frozen six day Pichia culture cell pellets contained two samples with intron (SEQ ID NO: 7) in gene construct, #11, #14, and two samples without intron in gene construct (SEQ ID NO: 5), #6, #52. The six day culture fluids from the same cultures were used to spike with crude fungal enzyme for positive controls.

The 50 µl cell pellets were resuspended in 150 µl cold 50mM Na-phosphate, pH 8.0. and divided into two fresh 500 µl tubes. One tube was kept on ice with no treatment, the pellet suspension, and one tube was used for lysis. An equal volume of 0.1 mm zirconia-silica beads was added to each tube. The tubes were BeadBeatT™ for 15 seconds then cooled on ice 5 minutes. This was repeated three times. The crude lysate was then transferred to another tube for assay or lysate suspension.

The TLC assays were performed as follows, the samples are 1) pellet suspensions; 10 µl; 2) lysate suspensions; 10 µl; 3) media controls-mixed 5 µl media with 5 µl crude fungal enzyme; 10 µl; 4) positive control-used crude fungal enzyme undiluted; 10 µl; 5) substrate control-used 50 mM Na-phosphate, pH8.0; 10 µl. Ten microliters of each sample plus 10 µl of $^{14}$C-AP1 (1 mg/ml, 50 mM Na-phosphate, pH 8) was incubated at room temperature for 6 days. One microliter of the sample was spotted onto C18 and C60 TLC plates. The C18 plates were developed in MeOH:4% KCl (3:2). The C60 plates were developed in $CHCl_3$:MeOH:$CH_3COOH$:$H_2O$ (55:36:8:1). The plates were then air dried and then exposed to a PhosphorScreen™ for 2–3 days. A Storm™ PhosphorImager was used to develop the images.

A positive TLC result is obtained if an additional radioactive spot appears at a lower Rf of the produced AP1 modification earlier identified as 2-OP, a deaminated product of AP1. In samples #6 and #52 (without intron) the AP1-modifying enzyme activity (conversion of AP1 to 2-OP) was detected in pellet suspensions and pellet lysates, although the majority of activity was associated with the pellet suspensions. In samples #11 and #14 (with intron) a minimal amount of AP1-modifying enzyme activity was detectable in the pellet lysate of #14 only, which indicates Pichia cannot process the intron efficiently.

This experiment verified APAO activity can be detected in Pichia transformants, which verifies that trAPAO as described functions correctly in degrading AP1. The activity is associated with cell suspensions, which show higher activity than pellet lysates. Pellet lysates may show less activity due to release of endogenous proteases during lysis of the cells.

EXAMPLE 9

Expression of trAPAO or APAO in *E. coli*

The vector for expressing K:trAPAO in *E. coli* is pGEX-4T-1. This vector is a prokaryotic glutathione S-transferase (GST) fusion vector for incurable, high-level intracellular expression of genes or gene fragments as fusions with *Schislosoma japonicum* GST. GST gene fusion vectors include the following features, a lac promoter for incurable, high-level expression; an internal lac Iq gene for use in any *E. coli* host; and the thrombin factor Xa or PreScission Protease recognition sites for cleaving the desired protein from the fusion product. The insert of interest, k0n0-395_6.5 (K:trAPAO) or APAO, was subcloned into the 5' EcoRI site and a 3' NotI site allowing in-frame expression of the GST:K:trAPAO or GST:APAO fusion peptide.

The polynucleotide sequence of the GST:K:trAPAO fusion can be found in SEQ ID NO: 18. The GST fusion with polylinker can be found at nucleotides 1 to 687. The K:trAPAO can be found at nucleotides 688 to 2076. The resulting polypeptide for the GST:K:trAPAO fusion can be seen at SEQ ID NO: 19. Amino acids 1 to 229 represent the GST fusion plus polylinker and amino acids 230 to 692 represent the K:trAPAO portion of the fusion.

*E. coli* was transformed with the pGEX-4T-1 vector containing K:trAPAO or APAO as described in BRL catalogue, Life Technologies, Inc. catalogue; Hanahan, D., *J Mol. Biol.* 166:557 (1983) Jessee, J. *Focus* 6:4 (1984); King, P. V. and Blakesley, R., Focus 8:1, 1 (1986), and hereby incorporated by reference. The transformed *E. coli* was induced by addition of IPTG (isopropyl b-D-thiogalactopyranoside). Four samples of soluble extract and four samples of insoluble inclusion bodies were tested for trAPAO or APAO activity as described in Example 8. APAO activity was present in all soluble samples and two insoluble samples. Highest activity was found at 10 uM IPTG induction. Thus the pGEX-4T-1 vector containing K:trAPAO or APAO is capable of producing active APAO enzyme in *E. coli*.

EXAMPLE 10

The Complete Nucleotide Sequence of the Exophiala APAO Gene

Using Genome Walker, the complete nucleotide sequence of the Exophiala APAO gene was recovered. The nucleotide sequence described in SEQ ID NO: 5 is missing a portion of the 5' end of the native gene. The missing portion of the 5' end of the native gene is not necessary for expression of an active APAO enzyme, as can be seen in Examples 8 and 9. The complete nucleotide sequence of APAO can be seen in SEQ ID NO: 22. The translation of SEQ ID NO: 22 can be found in SEQ ID NO: 23.

EXAMPLE 11

Expression of APAO and ESP1 in Transgenic Maize Callus

One of the preferred constructs for expression in maize is the nucleotide sequence of the trAPAO operably linked to the barley alpha amylase signal sequence. The nucleotide sequence of K:trAPAO translational fusion with barley alpha amylase signal sequence, for expression and secretion of the mature trAPAO in maize can be seen in SEQ ID NO: 20. Nucleotides 1–72, represent the barley alpha amylase signal sequence; nucleotides 73–75, represent the added lysine residue; and nucleotides 76–1464, represent the trAPAO cDNA. The amino acid sequence translation of SEQ ID NO: 20 can be found in SEQ ID NO: 21. Amino acids 1 to 24 represent the barley alpha armylase signal sequence and amino acids 25 to 463 is the sequence of K:trAPAO.

Maize embryos were transformed with linear DNA (insert, lacking a bacterial antibiotic resistance marker), derived from constructs containing three transcription units: 1) a PAT selectable marker gene (Wohlleben et al., *Gene* 70, 25–37 (1988)), 2) fumonisin esterase ESP1 operably linked to a barley alpha amylase signal sequence, and 3) full length APAO without or with an amino-terminal barley alpha amylase signal sequence, (P13603, comprising a PAT selectable marker operably linked to a 35S promoter, fumonisin esterase ESPI operably linked to a barley alpha amylase signal sequence and the ubiquitin promoter, and APAO operably linked to the ubiquitin promoter and P13611, comprising a PAT selectable marker operably linked to the 35S promoter, fumonisin esterase ESP1 operably linked to a barley alpha amylase signal sequence and the ubiquitin promoter and APAO operably linked to a barley alpha amylase signal sequence and the ubiquitin promoter). In these constructs both ESP1 and APAO were linked to the maize ubiquitin promoter and first intron. In a third construct, the same three transcriptional units were cloned into an Agrobacterium T1 vector (P15258, the construct comprises a PAT selectable marker, fumonisin esterase ESP1 operably linked to a barley alpha amylase signal sequence and APAO). Stably transformed callus or T0 plants regenerated from callus were tested for ESP1 and APAO activity in buffer extracts of leaf tissue, using radiolabeled FB1 and/or AP1 and C18 thin-layer chromatography. Positive controls non-transformed tissue spiked with *E coli*-expressed recombinant ESP1 or APAO. The results indicate that both ESP1 and APAO activities can be detected in trasgenic maize callus and plants.

Expression of ESP1 and APAO in transgenic callus

| Construct | Sample ID Number | ESP1 activity (TLC) | APAO activity (TLC) |
|---|---|---|---|
| 13603 | 3065.031-2 | + | + |
| 13603 | 3065.034-3 | + | + |
| 13603 | 3065.1117-3 | + | + |
| 13603 | 3065.11s7-n13 | + | + |
| 13603 | 3065.117-2 | + | + |
| 13603 | 3065.1115-2 | + | + |
| 13603 | 3065.1115-6 | + | + |
| 13603 | 3065.1112-1 | + | + |
| 13603 | 3065.118-6 | + | + |
| 13603 | 3065.11s3-1 | + | + |
| 13603 | 3065.11s1-13 | + | + |
| 13603 | 2805.762-2 | + | + |
| 13603 | 3065.1110-2 | + | + |
| 13603 | 3065.039-2 | + | + |
| 13611 | 3065.293-3 | + | + |
| 13611 | 3065.263-1 | + | + |
| 13611 | 3070.24.2.3 | + | + |

Transgenic plants were regenerated from the transgenic callus positive for both ESP1 APAO activity by standard methods known in the art. Enzyme activity was tested described previously. As can be seen below transgenic maize plants can successfully express both ESP1 and APAO enzymes.

Expression of APAO and ESP1 in transgenic maize plants (T0)

| Construct | Sample ID Number | ESP1 activity (TLC) | APAO activity (TLC) |
|---|---|---|---|
| 13603 | 910080 | + | + |
| 13603 | 910081 | + | + |
| 13603 | 917065 | + | + |

Another preferred construct for expression of APAO in a plant is targeting the APAO to the peroxisome. Maize embryos were bombarded with insert containing APAO operably linked to ubiquitin promoter and a peroxisomal targeting sequence (Gould, et al., *J Cell Biol* 108:1657–1664 (1989)); ESP1 operably linked to ubiquitin promoter and the barley alpha amylase signal sequence; and a selectable marker of PAT operably linked to the 35S promoter (construct number 114952). Negative controls were unbombarded embryos/callus. Positive controls were unbombarded embryos/callus spiked with purified enzyme. Transformed callus was then tested for ESP1 or APAO activity as previously described. Out of 67 samples tested 18 samples contained both ESP1 activity and APAO activity. Peroxisomally targeted APAO and apoplast targeted fumonisin esterase can both be successfully expressed in a plant cell.

Another preferred construct for expression of APAO in a plant is targeting the APAO to the mitochondrial membrane. A C-terminal extension is required for targeting monoamine oxidases MAO-A and MAO-B to mammalian outer mitochondrial membranes. A MAO-A, MAO-B, or functionally similar C-terminal extension can be ligated in-frame to APAO or trAPAO to facilitate localization of this enzyme to the mitochondrial membrane of maize or other transformed species.

EXAMPLE 12

Comparison of APAO Sequence With Other Sequences

The Exophiala cDNA APAO (SEQ ID NO: 22) contains an 1800 bp open reading frame coding for a 600 amino acid polypeptide (SEQ ID NO: 23) with divergent homology to two classes of proteins. The carboxy three-fourths of APAO (amino acids 137 to 593) is strongly homologous to flavin amine oxidases, a group of enzymes catalyzing the oxidative deamination of primary amines at carbon 1. The amine oxidase function of the carboxy terminal domain was confirmed by expression of a truncated APAO polypeptide (from 137 to 600) in both *Pichia pastoris* and *E. coli*, using AP1 as a substrate (see Example 9). The amino terminal portion of APAO, in contrast, (from approx. 5 to 134) shows significant homology to a group of small deduced open reading frames (ORFs) reported in several bacteria and blue-green algae, as well as several higher organisms. These ORFs code for small proteins of unknown function, ranging in size from 14 to 17 kDA. The juxtaposition of these divergent homologies in a single polypeptide has not been reported previously.

Flavin amine oxidases (E.C. 4.1.4.3) are a group of flavoenzymes found in both higher and lower organisms, and serve a variety of functions in catabolism. They catalyze the oxidative deamination of primary amino groups located at the C-1 position of a variety of substrates, resulting in an aldehyde product plus ammonia and hydrogen peroxide. The APAO enzymes of the present invention are the first flavin amine oxidase known to attack a primary amine not located at C-1 (i.e. C-2 of AP1) and resulting in a keto rather than aldehydic product. However, amino acid oxidases, while not closely related to flavin amine oxidases, are flavoenzymes that oxidize a C-2 amine adjacent to a C-1 carboxyl group.

The monoamine oxidases MAO A & B, (from human, bovine, and trout), are localized in the mitochondrial outer membrane of higher organisms and regulate the level of neurotransmitters. Microbial examples include a fungal amine oxidase (*Aspergillus niger* (*niger*) MAO-N) involved in amine catabolism, and a bacterial putrescine oxidase from a gram (+) bacterium (*Micrococcus rubens*.). The primary polypeptides vary in length from 478 to 527 amino acids, and share regions of high amino acid sequence conservation at the 5' end as well as at various points through the coding region. Protein alignments generated with PileUp (GCG) indicate that trAPAO contains all conserved domains found in this class of proteins including those near the 5' end.

The amine oxidase domain of trAPAO contains several key features shared by this class of enzymes, including an amino-terminal dinucleotide (ADP) binding region characterized by a beta-alpha-beta stretch containing three invariant glycines (G-X-G-X-X-G) in the beta-alpha turn. In trAPAO, this sequence is (DVVVVGAGLSG) (SEQ ID NO: 55). This region is involved in FAD binding. Absent are several features unique to the mammalian amine oxidases, including several important cysteine residues (Wu et al., *Mol Pharm* 43:888 (1993)), one of which (Cys-406 of MAO-A) is involved in covalent binding of FAD, and a carboxy-terminal extension that has been demonstrated to be involved in transporting to and anchoring the MAO in the outer mitochondrial membrane. The Aspergillus enzyme MAO-N has been demonstrated to contain non-covalent FAD, and also lacks the conserved cysteine. Therefore it is possible that the APAO enzyme has a non-covalent FAD.

The Aspergillus MAO-N has a carboxy-terminal tripeptide Ala-Arg-Leu that is involved in peroxisomal targeting and localization; this sequence is absent from Exopniala MAO.

The amine oxidase domain of trAPAO contains a total of seven cysteines, compared to ten for the Aspergillus enzyme and only two for the Aficrococcus enzyme.

The mammalian MAO enzymes contain variable numbers of cysteines (at least ten), some of which are highly conserved (including the FAD binding residue mentioned above). The trAPAO sequence also has two putative glycosylation sites (NDS, NQS) towards the amino end.

The purpose of the amino-terminal extension of APAO and the basis for its homology to a group of 14–17 kDa proteins is not clear. In Synechocystis, a similar polypeptide ORF is located immediately upstream of the NADP-dependent glutamine dehydrogenase (gdhA) and has been shown to be required for functional expression of gdhA (Chavez et al, 1995). However, in trAPAO the domain is clearly not necessary for enzymatic activity, as shown by the results of the expression experiments using the truncated APAO. An interesting clue comes from the frequent association of this small ORF with gene clusters involved in oxidoreductase activity in bacteria, or induced by heat stress in mice, suggesting a possible role in redox protection. A byproduct of amine oxidase activity is hydrogen peroxide. Flavoenzymes and other redox enzymes are often susceptible to inactivation by hydrogen peroxide (Schrader et al., *App Microb Biotechnol* 45:458; Aguiree, et al., *J Bacteriol* 171:6243 (1989)), and it is possible that this protein has a protective role against oxidants such as hydrogen peroxide. Alternatively, this domain could be involved in enzyme function, localization or association of the enzyme with other structures. No signal peptide region can be detected in this amino terminal region.

In multiple sequence alignment using GCG PileUp, trA-PAO is most similar to putrescine oxidase of Micrococcus rubens, Swissprot accession number P40974, (30% identical amino acids, 40% similar). Homology with several mammalian monoamine oxidases A and B, Swissprot accession numbers P21397 (*Homo Sapiens* mao a), P19643 (*Ratus norvegicus* mao b), P21396 (*Rattus norvegicus* mao a), and P21398 (*Bos tautrus mao a*), is somewhat less, ranging from 25 to 28% identity and 36 to 40% similarity. Homology to the only other fungal flavin amine oxidase known, MAO-N from *Aspergillus niger* (Swissprot accession number P46882), is somewhat lower (24% identical, 34% similar). The microbial enzymes are considerably divergent from each other, while the mammalian monoamine oxidases share 65 to 87% identity.

The amino terminal domain (ATD) of APAO also shows homology to a 14.5 kD protein from human and rat phagocytes that shows translational inhibition activity in vitro (Swissprot accession #P52758, P52759) Schmiedeknecht, et al. *Eur J. Biochem* 242 (2), 339–351 (1996)), and includes a heat-responsive protein from mouse (Samuel, et al., *Hepatology* 25 (5), 1213–1222 (1997)). This suggests that this family of proteins is involved in regulating cellular metabolism. No example exists in which this domain is fused to a larger protein domain, however, making APAO unique. Without intending to be limited by theory, all of this suggests, that this domain plays a regulatory role in APAO gene expression, possibly to prevent translation of the message when it is not needed. This raises the question of how translation of the message is restored when active enzyme is required by the Exophiala cell. Possibly there are alternative start sites that begin downstream of the inhibitor domain; or proteolysis, complexing, degradation, or phosphorylation/dephosphorylation of the inhibitor domain when it is not needed. The first possibility is less likely because there are no other ATG codons prior to the ATG at 122–124 that constitutes the predicted start site of APAO. The second possibility cannot be easily tested, although there is a casein kinase site in the ATD. Alternative roles for the ATD include oligomerization of the APAO protein, or anchoring the protein to some intracellular site, such as the membrane.

A parallel example of regulatory control over another flavoenzyme, human flavin monooxygenase 4 (FMO-4), by a C-terminal extention has been reported (Itagaki, et al, *J of Biol Chem* 271(33): 20102–20107 (1996)). In this case the introduction of a stop codon prior to the 81 base C-terminal extension allowed expression of active enzyme in heterologous systems. The role of the C-terminal portion was not elucidated, however. In another example, alternative splicing led to a shorter gene product that complexed with and interfered with the function of the normally spliced version (Quinet, et al., *J of Biol Chem* 268(23): 16891–16894 (1993)). In another case, an alternative splicing-generated insert in another protein led to inhibition of cell growth (Bhat, et al., *Protein Engineering* 9(8): 713–718 (1996)). In yet another variation, fas/Apol splicing variants prevent apoptosis, apparently through a 49 amino acid domain shared by all variants ((Papoff, et al., *J of Immunology* 156(12): 46224630 (1996)).

EXAMPLE 13

Making a Chimera Protein Containing Fumonisin Esterase and APAO Activity in the Same Polypeptide The enzyme activities of fumonisin esterase and APAO can be combined in a single polypeptide by using the open reading frames together either with or without a spacer region between the two polypeptides. This creates a hybrid protein with dual enzyme activities that can be exported as a unit to the apoplast, and will allow both enzyme activities to be conveniently localized to the same area of the cell wall. The two cDNAs can be combined in either order, but the preferred method is to link them in the order $NH_3$-Esterase:APAO-COOH. The spacer, if present, may consist of a short stretch of amino acids such as GGGSGGGS (SEQ ID NO: 54), or a set of amino acids that comprises a protease cleavage site that can be acted on by an apoplastic protease. This would result in the production of stoichiometric amounts of both esterase and APAO enzymes in the apoplast. Alternatively, a polycystronic message could be engineered which is capable of direct translation of a downstream sequence, for example inclusion of an IRES sequence in the spacer region or a polynucleotide spacer region containing a polynucleotide cleavage site that can be recognized by RNAse or is a self-cleaving ribozyme. The length of the splice site could be of any length that ensures proper translation of the polynucleotide.

The esterase-APAO ligated protein can be made with any fumonisin esterase, including but not limited to, the fumonisin esterase from *E. spinifera* (ESP1) or fumonisin esterase from bacterium (BEST1). Since the pH range for maximum activity of BEST1 is similar to that of APAO (range 6.0 to 8.0), these may present the most effective combination in fusion form. In addition, any of the polynucleotides of the present invention, including APAO mutated to improve expression, may be used for an esterase-APAO ligation. As described in previous examples these fusion sequences can be placed in the appropriate expression vectors and used to express proteins in either bacteria or plants.

The nucleotide sequence of ESP1 contains three nucleotide differences and three corresponding amino acid differences for the ESP1 sequence disclosed in pending U.S. application Ser. No. 08/888,950, filed Jul. 7, 1997 and U.S. Pat. No. 6,025,188, issued Feb. 15, 2000. Both the sequences disclosed in the present application and the sequences disclosed in the pending US applications contain functional fumonisin esterase genes. For the purposes of the present invention, either the original ESP1 sequences or the ESP1 sequences may be used in combination with the APAO sequences or in fusion sequences. The nucleotide sequence of a BAA:ESP1:trAPAO construct for plant expression can be found in SEQ ID NO: 24 and the translation in SEQ ID NO: 25. The nucleotide sequence for a BAA:BEST1:K:trAPAO construct for plant expression can be found in SEQ ID NO: 26 and the translation in SEQ ID NO: 27. The nucleotide sequence of a GST:ESP1:K:trAPAO fusion for bacterial expression in a pGEX-4T-1 or similar vector can be found in SEQ ID NO: 28 and the translation in SEQ ID NO: 29. The nucleotide sequence for a GST:BEST1:K:trAPAO fusion for bacterial expression in a pGEX-4T-1 or similar vector can be seen in SEQ ID NO: 30 and the translation in SEQ ID NO: 31.

EXAMPLE 14

APAO Substrate Studies

The following assay was used to determine the substrate specificity of the APAO enzyme. Reaction mix: 436 μl of 200 mM Na-phosphate, pH8.0; 50 μl substrate (10 mM); 2 μl Amplex Red (1 mg in 200 μl DMSO); and 2 μof Peroxidase (5000 U/ml). The APAO enzyme was recombinant enzyme produced,as GST fusion in *E. coli*, purified over a glutathione affinity column and cleaved with thrombin to remove the GST. All components were mixed at room temperature. The initial rate was determined in a spectrophotometer at 572 nm over one minute by absorbance units/second (BLANK). Ten microliters of APAO at 70 ug/ml was added and mixed. The initial rate was again determined at 572 nm over one minute in absorbance units/second (SAMPLE). The rates were converted to absorbance units/minute. The BLANK value was subtracted from the SAMPLE value. The absorbance units were converted to μM $H_2O_2$ wherein 1 μM $H_2O_2$ equals 0.138 absorbance units at pH 8.0.

SUBSTRATES FOR APAO

| SUBSTRATE | RATE μM $H_2O_2$/min |
|---|---|
| 1 mM Fumonisin B1 | 0.1429 |
| 1 mM AP1 | 0.8876 |
| 0.5 mg/mL Fumonisin B2 | 0.3058 |
| 1 mM Fumonisin B3 | 0.1449 |
| 0.5 mg/mL Fumonisin B4 | 0.1728 |
| 1 mM norepinephrine | 0.0087 |
| 1 mM epinephrine | 0.0071 |
| 1 mM dopamine | 0.0040 |
| 1 mM spermine | 0.0002 |

NOT SUBSTRATES FOR APAO (defined as compounds resulting in less than 1% conversion to hydrogen peroxide by APAO relative to AP1 under similar conditions of time, pH, temperature, and substrate concentration): 2-phenylethylamine, spermidine. EDTA-$Na_2$, tryptamine, putrescine, benzamidine, serotonin, cadaverine, Pefabloc SC, tyramine, 1,3-diaminopropane, leupeptin, histamine, hydroxylamine, aprotinin, deprenyl, Fumonisin C4, isoniazid, sphingosine, phenelzine, sphinganine, phytosphingosine, D-alanine, DL-alanine, L-arginine, L-asparagine, L-aspartic acid, D-aspartic acid, L-cysteine, L-glutamine, L-glutamic acid, glycine, L-histidine, L-isoleucine, L-leucine, L-lysine, DL-lysine, L-methionine, DL-methionine, L-phenylalanine, L-proline, L-threonine, L-tryptophan, L-tyrosine, L-valine.

EXAMPLE 15

Sites on APAO for Possible Mutagenesis

Some cytosolic enzymes, when engineered for secretion by fusion with a heterologous signal peptide, lack function due to glycosylation at one or more potential glycosylation sites (amino acid consensus sequence N-X-S/T) that are not normally glycosylated in the native environment (Farrell et al., *Plant Mol Biol* 15(6):821–5 (1990)). Since APAO lacks a recognizable signal sequence, it may be cytoplasmically localized in *Exophiala spinifera*, although secretion by some other method not involving a signal peptide cannot be ruled out. APAO contains two potential glycosylation sites, which may be glycosylated when APAO is secreted in a plant or other eukaryotic cell. Other modifications to APAO can be made to improve its expression in a plant system, including site-directed mutagenesis to remove selected cysteine residues, which may be detrimental to proper folding when the protein is secreted into the endomembrane system for delivery to the apoplast.

Figures 2A, 2B:
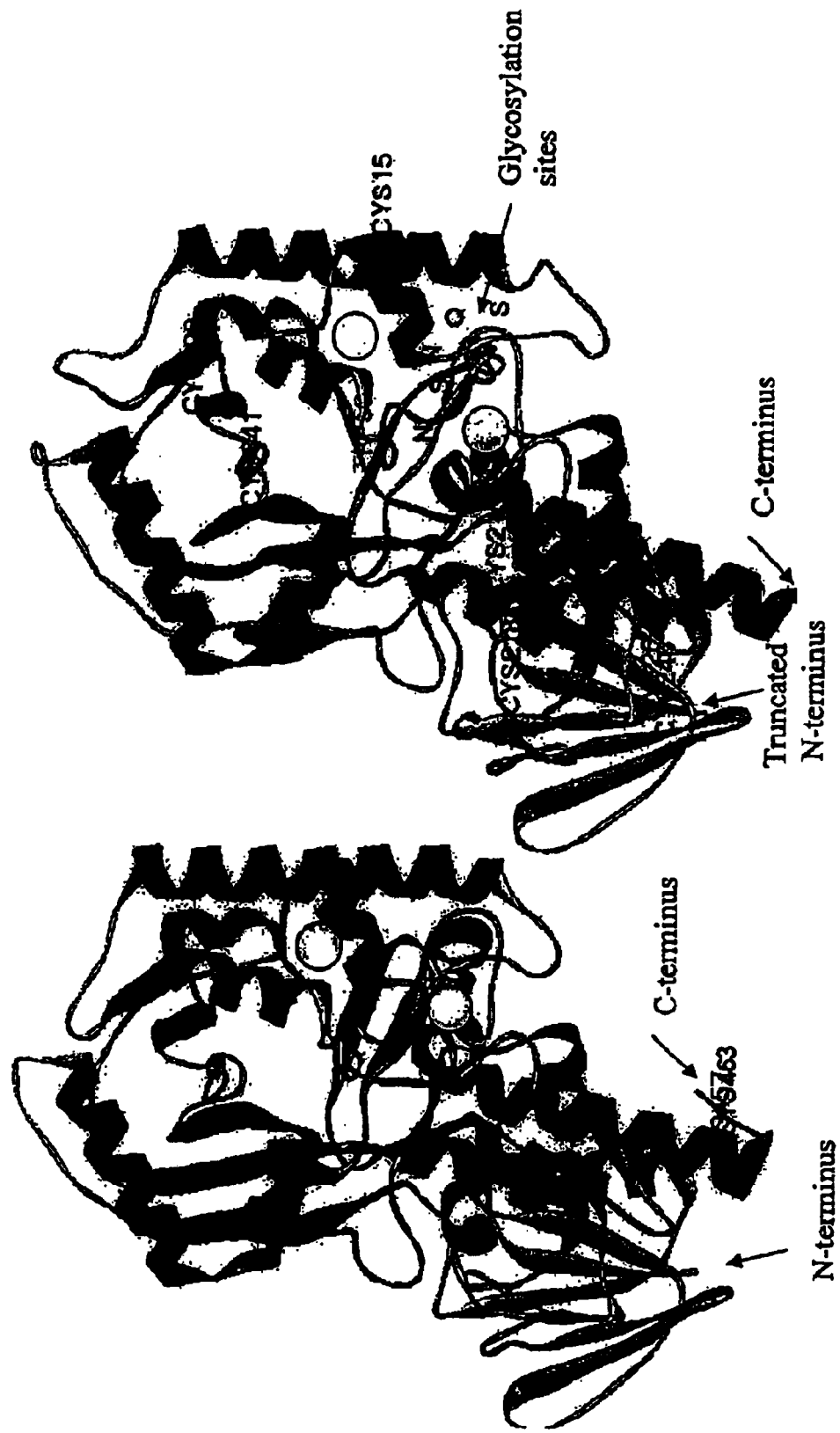

Knowledge of the 3-dimensional structure of APAO would help to evaluate the likelihood that particular amino acids could contribute to misfolding, and increase the odds of making rational changes in the APAO sequence for successful secretion. To this end a 3-dimensional model of APAO was developed based on the crystal structure of a related amine oxidase from maize, maize polyamine oxidase or MPAO (Binda el al., *Structure* 7:265–276 (1999)). The model was derived by automated modeling using the program Modeler (Molecular Simulations, Inc., San Diego, Calif. and the resulting 3-D structure showed excellent fit based on an RMS deviation of 0.68 Å for the backbone coordinates of the two structures. The 3-D model of APAO based on MPAO is shown in FIGS. 1 and 2. Some of the possible mutations of APAO, which would result in removal of glycosylation sites or removal of cysteine residues can be seen below and in FIG. 1.

Table of site-directed mutagenesis vectors and enzyme assay results.

| | | | | Residue number | | | | | | | | | | |
|---|---|---|---|---|---|---|---|---|---|---|---|---|---|---|
| 1 | 2 | 3 | 4 | 5 | 6 | 7 | 8 | 9 | Glyc Site 1a, b | | Glyc Site 2a, b | | *E. coli* expression vector, APAO or trAPAO activity | Maize expression vector, APAO or trAPAO Activity |
| | | | | Residue position in APAO or trAPAO | | | | | | | | | | |
| C64 | C109 | C167 | C292 | C351 | C359 | C387 | C461 | C482 | N201 | S203 | N204 | S206 | | |
| Construct | | | | Amino acid substitution | | | | | | | | | Plasmid  Act | Plasmid  Act |
| wild type APAO-1 | | | | | | | | | | | | | PHP13367 + | PHP – |
| Glyc(–)1a2a APAO | | | | | | | | | A | | A | | PHP16284 – | n/a |
| Glyc(–)1a2b APAO | | | | | | | | | A | | | A | PHP16285 – | n/a |
| Glyc(–)1b2a APAO | | | | | | | | | | A | A | | PHP16286 – | n/a |
| Glyc(–)1b2b APAO | | | | | | | | | | A | | A | PHP16287 – | n/a |
| Glyc(–)2a N204A APAO | | | | | | | | | | | A | | PHP16589 +/– | n/a |
| Glyc(–)2b S206A APAO | | | | | | | | | | | | A | PHP16590 + | PHP16711 – |
| Cys(–)#8 trAPAO | | | | | | | S | | | | | | PHP16737 + | n/a |
| Cys(–)#6,8 trAPAO | | | | | | S | S | | | | | | PHP16738 + | |
| Cys(–)#3,6,8 trAPAO | | | S | | | S | S | | | | | | PHP17089 +[1] | |
| Cys(–)#1,2,7 APAO | A | A | | | | | A | | | | | | | |

A = alanine
S = serine
[1] activity against FB1 equals wild type; activity against AP1 was reduced.

APAO and trAPAO polypeptide sequence, annotated. (SEQ ID NO: 47) The amino terminal domain is italicized. Cysteines and residues involved in putative glycosylation sites are underlined. Boxed residues represent amino acids that were successfully altered without complete loss of activity as *E. coli*-expressed protein.

M A L A P S Y I N P P N V A S P A G Y S H V G V G P D G - GRYVTIAGQIGQDASGVTDPAYEKQAQAFA NLRA CLAAVGATSNDVTKLNYYIVDYAPSKLTAIGDGLK- ATFALDRLPPCTLVPVSALSSP EYLFEVDATALVPG- HTTPDNVADVVVVGAGLSGLETARKVQAAG- LSCLVLEAMD RVGGKTLSVQSGPGRTTINDLGAA- WINDSNQSEVSRLFERFHLEGELQRTTGNSIH QAQ- DGTTTTFAPYGDSLLSEEVASALAELL- PVWSQLIEEHSLQDLKASPQAKRLDSV SFAHY CEKELNLPAVLGVANQITRALLGVEAHEISMLFLTDY- IKSATGLSNIFSDKK  DGGQYMRCKTGMQSCHAM- SKELVPGSVHLNTPVAEIEQSASGCTVRSASGAVF RSKKVVVSLPTTLYPTLTFSP- PLPAEKQALAENSILGYYSKIVFVWDKPWWREQGF

S G V L Q S S ⟦C⟧D P I S F A R D T S I D V D R Q W S I T
CFMVGDPGRKWSQQSKQVRQKSVWDQL RAAY-
ENAGAQVPEPANVLEIEWSKQQYFQGAP-
SAVYGLNDLITLGSALRTPFKSV
HFVGTETSLVWKGYMEGAIRSGQRGAAE-
VVASLVPAA

APAO enzyme activity is maintained when a serine residue at position 206 is mutated to alanine, eliminating a potential glycosylation site (N204-S206) close to the putative substrate binding site. Please see the tables entitled "Table of site-directed mutagenesis vectors and enzyme assay results" and "Glyc(–) APAO lysates from *E. coli*." The polynucleotide sequence of APAO mutated to alter the serine at position 206 to an alanine (S206A) can be seen in SEQ ID NO: 32. The resulting polypeptide is shown in SEQ ID NO: 33.

Solvent accessibility for cysteine residues of truncated APAO

| APAO Position[1] | Position[2] | Cys#[3] | aaMPAO | –1 | 0 | 1 | average | Conclusion |
|---|---|---|---|---|---|---|---|---|
| Cys | 26 | 167 | 3 | Leu | 32 | 0.675 | 0.253 | 0.24 | 0.389333 | maybe partially exposed |
| Cys | 151 | 292 | 4 | Asn | 147 | 0.069 | 0.122 | 0.147 | 0.112667 | buried |
| Cys | 210 | 351 | 5 | Tyr | 211 | 0.184 | 0.244 | 0.03 | 0.152667 | buried |
| Cys | 218 | 359 | 6 | Thr | 219 | 0.633 | 0.319 | 0.447 | 0.466333 | maybe partially exposed |
| Cys | 246 | 387 | 7 | Val | 247 | 0.145 | 0.046 | 0.366 | 0.185667 | buried |
| Cys | 320 | 461 | 8 | Ser | 324 | 0.199 | 0.789 | 0.643 | 0.543667 | exposed |
| Cys | 341 | 482 | 9 | Leu | 346 | 0.152 | 0.071 | 0.052 | 0.091667 | buried |

[1]Relative to amino acid 1 of truncated APAO
[2]Relative to amino acid 1 of full length APAO
[3]Cysteine number relative to full length APAO Glyc(–) APAO lysates from *E coli*

| Sample (lysate) | Substrate | M H$_2$O$_2$/min[1] | Conclusion |
|---|---|---|---|
| WT APAO | AP1 | 1.92 | Active (wild type) |
|  | FB1 | 0.12 | Slightly active (wt) |
| N204A | AP1 | 0.09 | Slightly active |
|  | FB1 | 0.04 | Slightly active |
| S206A | AP1 | 0.85 | Partially Active |
|  | FB1 | 0.07 | Slightly active |

However, in transient expression assays in maize, expression of S206A resulted in no detectable enzyme activity. Please see the table above entitled "Table of site-directed mutagenesis vectors and enzyme assay results." Thus, elimination of this glycosylation site is not in itself sufficient to have an active protein upon secretion. This could be due to glycosylation occurring at a second adjacent site (N201-S203). However, no active APAO was recovered when either N201 or S203 is mutated along with S206. Please see the table entitled "Table of site-directed mutagenesis vectors and enzyme assay results." While not to be limited by theory, the molecule may be inactive because both N201 and S203 are buried within the tertiary structure of APAO, and any modification of side chains disrupts proper folding or conformation, or FAD binding. This is backed up by predicted solvent accessibility numbers for these residues in the 3-D model based on the maize amine oxidase. Please see the table below entitled "Solvent accessibility for cysteine residues of truncated APAO." The elimination of APAO glycosylation site at amino acids 204 to 206 is not sufficient to allow APAO to be secreted from the ccil and retain full enzyme activity, but elimination of this site may improve chances for obtaining a fully active enzyme once the other roadblock(s) to secretability have been resolved. In other words, elimination of this site may be necessary but not sufficient to produce active secretable APAO.

APAO also contains nine cysteine residues, which are likely to be unpaired in the reducing environment of the cytosol but which may crosslink unfavorably upon secretion. Cysteines are present at residues 64, 109, 167, 292, 351, 359, 387, 461, and 482. The 3-D model helps predict the relative location of each amino acid in the structure, and whether it is solvent accessible or buried. Buried residues are more difficult to mutate without destroying structural integrity.

Proteins that are secreted to the apoplast are folded to their mature form in the highly oxidizing environment of the ER/Golgi. Among other things this promotes crosslinking of cysteine residues often found in secreted proteins. Unpaired cysteines that are solvent-accessible arc rare in secreted proteins, since they would rapidly be oxidized by other cysteine residues of the same protein or another protein. Although not to be limited by theory, it is possible that APAO is normally a cytosolic protein, and thus the presence of nine cysteine residues would not be unusual even though they may not be crosslinked in the mature protein. In fact, the 3-D model predicts that they would not be crosslinked because the intermolecular distances predicted would be too great. Therefore it is possible that secretion of APAO to the apoplast results in an improper folding and crosslinking of cysteines in the Golgi, and results in inactive enzyme. Using the solvent accessibility tables from APAO modeled against MPAO, the three most solvent-exposed cysteines were identified and then eliminated by site-directed mutagenesis of the APAO cDNA. The sequence of APAO mutated at cysteine 461 and used for expression in bacteria can be seen in SEQ ID NO: 48. The resulting protein is shown in SEQ ID NO: 49. The polynucleotide and resulting polypeptide sequence of APAO mutated at both cysteines 359 and 461 and used for in the bacterial expression system can be seen in SEQ ID NOS: 50 and 51. The polynucleotide and resulting polypeptide sequence of APAO mutated at cysteines 169, 359, and 461 can be seen in SEQ ID NOS: 52 and 53.

The APAO molecules mutated at specific cysteines were tested in a bacterial expression system using the previously described Amplex Red assay. The results can be seen in the table below entitled "Cys(–) APAO lysates from *E. coli*." The mutated APAO molecules can then be tested in maize, linked to a signal peptide, as previously described. Either one of the cysteines or two or three together could be mutated to serines without any measured loss in APAO enzyme activity of the *E coli*-expressed enzyme. In fact, one of the *E coli*-expressed clones (C359S+C461S; PHI16738) had more APAO activity in crude lysates than wild type enzyme and may represent a catalytic improvement. A triply Cys-mutated version of APAO does not show catalytic improvement but retains full activity of the wild type enzyme against FB1, although AP1 activity was somewhat reduced. The mutated versions of APAO operably linked to a signal sequence, which retain function when expressed as recombinant fusion proteins in *E. coli* may also provide additional stability or foldability when expressed in plants or other secretion expression systems.

| Sample (lysate) | Substrate | M $H_2O_2$/min[1] | Conclusion |
|---|---|---|---|
| Cys(−) APAO lysates from *E coli* | | | |
| WT APAO | AP1 | 2.14 | Active (wild type) |
| | FB1 | 0.11 | Slightly active (wt) |
| C461S | AP1 | 2.25 | Fully Active |
| | FB1 | 0.14 | Slightly active |
| C359S, C461S | AP1 | 3.90 | Fully/More Active |
| | FB1 | 0.16 | Slightly active |
| C167S, C359S, | AP1 | 0.27 | Slightly active |
| C461S | FB1 | 0.25 | Slightly active |
| Triple Cys(−) APAO lysates from *E coli* | | | |
| WT APAO | AP 1 | 1.16 | Active (wild type) |
| | FB1 | 0.27 | Slightly active (wt) |
| C167S, C359S, | AP1 | 0.27 | Slightly Active |
| C461S | FB1 | 0.26 | Slightly active |

It is expected that the S206A mutations will contribute to the functionality of secreted APAO by reducing the degree of glycosylation and the C167S, C359S, and C461S mutations (or combinations thereof) will improve the functionality of secreted APAO by reducing chances for spurious disulfide formation on folding.

To determine expression of a mutated APAO in maize, three APAO constructs were introduced into maize embryos by Agrobacterium-mediated transformation (Zhao et al, 1999, U.S. Pat. No. 5,981,840). The three constructs were PHP17105 (Ubi:BAA:Cys(−)K-trAPAO (C359S, C461S):PinII), PHP17108 (Ubi:Cys(−)K-trAPAO (C359S, C461S):PinII), and PHP17110 (Ubi:APAO:PinII). In addition, PHP16543 (NOS:CRC:PinII-Ubi:MO-PAT:T35) was introduced as a negative control and PHP15258 (Lfbi:APAO:PinII-Ubi:BAA:ESP1:PinII-P35S:PAT:T35S) was introduced as a non-targeted positive control. One experiment with two replications was performed. Samples were assayed for both APAO activity by TLC as described previously and by Enzyme Linked ImmunoSorbent Assay (ELISA). For a discussion of ELISA methods, please see, for example, *Current Protocols in Alolecular Biology*, 2:11.1.1–11.3.4, John Wiley & Sons, Inc. (Ausubel, et al., eds. 1994). The APAO ELISA is a capture format assay for the quantitative determination of APAO protein in the presence of extracted maize tissue protein. It was performed by co-incubation of biotinylated antibody with an extract prepared from leaf, seed, or callus in phosphate buffered saline with 0.5% Tween-20®. The detection of the antibody complex was accomplished through the added incubation of streptavidin-alkaline phosphatase (Bio-Rad Life Sciences Products #19542–018), followed by the addition of substrate (pNPP tablets, Sigma #104–105). The resultant color intensity was quantified by determining optical density and was directly proportional to the amount of APAO protein present in the sample extracts. The assay has no matrix effects at 1 $\mu$g/well or below for maize leaf, seed, or callus protein. The standard curve was spiked with wild type extract at levels above 1.0 $\mu$g/well. The transient testing results are summarized in the table below.

| | | Transient Testing of APAO Constructs (6-8-2000) | | |
|---|---|---|---|---|
| Experiment | Rep | Construct | APAO-TLC | APAO-ELISA (ppm) |
| negative control | none | none | 0 | −2 |
| 4350.08.01 | 1 | php16543, as a (−) control | 0 | −4 |
| 4350.08.02 | | php15258, non-targeted APAO as a (+) control | 3 | out high |
| 4350.08.03 | | php17105, UBI-BAA::CYS(−)K-TR-APAO (C359S, C461S) | 1 | 107 |
| 4350.08.04 | | php17108, UBI-CYS(−)K-TR-APAO (C359S, C461S) | 3 | 270 |
| 4350.08.05 | | php17110, UBI-APAO | 3 | out high |
| 4350.08.06 | 2 | php16543 | 0 | −5 |
| 4350.08.07 | | php15258 | 3 | 313 |
| 4350.08.08 | | php17105 | 0 | 52 |
| 4350.08.09 | | php17108 | 2 | 143 |
| 4350.08.10 | | php17110 | 2 | 123 |
| 3477.27.01 | transformed | php15258 as positive controls | 1 | 118 |
| 3477.27.02 | callus lines | | 2 | 141 |
| 3477.27.03 | | | 2 | 187 |
| 3477.27.04 | | | 2 | 184 |

As can be seen in the Table above, the BAA-targeted APAO (PHP17105) did not accumulate as much APAO as the non-BAA targeted counterpart (PHP 17108). Although not to be limited by theory, the lack of APAO protein accumulation rather than APAO function may play a role in the lack of detectable APAO activity with the BAA-targeted APAO construct. It appears that only when the APAO concentration exceeds 100 ppm can APAO activity be seen by TLC. Nevertheless, the double Cys(−) mutant is active in maize when expressed either cytosolically or extracellularly.

EXAMPLE 16

Other APAO Polynucleotides From *Exophiala spinifera* and *Rhinocladiella atrovirens*

Using primers designed from the APAO isolated from *Exophiala spinifera*, ATCC 74269(Table 15), three new APAO polynucleotides were isolated from *Exophiala spinifera* (isolates ESP002 and ESP003), designated ESP002_C2, ESP002_C3 and ESP003_C12 and three new APAO polynucleotides from *Rhinocladiella atrovirens* (isolate RAT011) designated RAT011_C1, RATOI 1_C2, RATO11_C4. The strains used to isolate the polynucleotides are described below.

| Isolate | Genus species | Source | FB1 degrader | APAO homologs isolated |
|---|---|---|---|---|
| ESP002 | *Exophiala spinifera* | Palm, ATCC 26089 | Yes | ESP002_c2 in pGEX4T1<br>ESP002_c3 in pGEX4T1 |
| ESP003 | *Exophiala spinifera* | Maize seed | Yes | ESP003_c12 in pGEX4T1 |
| RAT011 | *Rhinocladiella atrovirens* | Maize seed | Yes | RAT011_c1 in pGEM11Zf+<br>RAT011_c2 in pGEM4T1<br>RAT011_c4 in pGEM11Zf+ |

Growth Conditions and Production of Culture Material

1. Streak 150×15 mm YPD plates with a glycerol aliquot of the above fungal isolates.
2. Grow at 28° C. in the dark until there is sufficient growth for inoculating liquid medium usually at least two weeks.
3. Mycelia and spores were scraped from the plates or agar cubes used to inoculate 50 mls YPD broth in 250 ml baffled flasks.
4. Flasks of culture material were grown at 28° C in the dark at ~125 rpm.
5. After sufficient growth was obtained the cultures were harvested by pelleting the culture in 50 ml centrifuge tubes at 3400 rpm for 15 min.
6. The supernatant was discarded and the pellets were frozen at −20° C.

| YPD broth and agar medium | | |
|---|---|---|
| Amount per liter: | Yeast Extract | 10 g |
| | Bactopeptone | 20 g |
| | Dextrose | 0.5 g |
| | Bactoagar | 15 g (for agar media only) |

DNA Isolation,

The DNA was isolated according to a modified version of a plant CTAB DNA extraction protocol (Saghai-Maroof MA, et al., Proc Natl Acad Sci, LISA, 81:8014–8018 (1984)) as follows.

1. Place 0.2–0.5 g (dry weight) lyophilized fungal mycelium in a 50 ml disposable centrifuge tube, break up mat with a spatula or glass rod. Shake briefly.
2. Add 10 ml (per 0.5 g mat) of ClAB extraction buffer. Gently mix to wet all the powdered mat.
3. Place in 65° C water bath for 30 minutes.
4. Cool. Add an equal volume of phenol:chloroform. Shake briefly to mix.
5. Centrifuge 20 minutes at 3400 rpm.
6. To the aqueous phase add an equal volume of chloroform:isoamyl alcohol (24:1). Shake briefly to mix.
7. Centrifuge 15 minutes at 3400 rpm.
8. To aqueous phase add an equal volume of isopropanol.
9. Centrifuge for 30 minutes at 3400 rpm to pellet precipitated DNA.
10. Rinse DNA pellet with 70% ethanol.
11. Air dry pellet.
12. Resuspend pellet in 1–5 ml TE containing 20 ug/ml RNase A.

CTAB Extraction Buffer 0.1 M Tris, pH 7.5
1% CTAB (mixed hexadecyl trimethyl ammonium bromide)
0.7 M NaCl
10 mM EDTA
1% 2-mercaptoethanol
Add protcinase K to a final concentration of 0.3 mg/ml prior to use.

Primer Design

Primers used were gene specific primers based on APAO polynucleotide sequence (SEQ ID NO: 22) with restriction enzymes sites for cloning. The 5'-primer, 26194, contained the restriction enzyme recognition site, EcoRi. The complementary 3'-primer, 23259, contained the restriction enzyme recognition site, NotI.

26194
5' ggggaattcATGGCACTTGCACCGAGCTACATCAATC 3', 37-mer (SEQ ID NO: 34)
23259
5' gggGCGGCCGCCTATGCTGCTGGCACCAGGCTAG 3', 34-mer (SEQ ID NO: 13)

PCR conditions

| 1. The PCR cocktail: | 10 mM dNTPs | 1 ul |
|---|---|---|
| per 50 ul reaction | 10× Advantage polymerase buffer | 5 ul |
| per 0.2 ml tube | HPLC water | 38 ul |
| | 10 uM primer 26194 | 2 ul |
| | 10 uM primer 23259 | 2 ul |
| | 50× Advantage polymerase mix (Clontech) | 1 ul |
| | Template, genomic DNA, 50 ng/ul | 1 ul |

-continued

2. Thermocycling conditions:
   MJ PTC-100 AgV Thermocycler:

| Step | | | |
|---|---|---|---|
| 1 | 95° | 2 minutes | |
| 2 | 95° | 30 seconds | |
| 3 | 60° | 1 minute | |
| 4 | 72° | 1 minute 30 seconds | |
| 5 | Go to step 2, 34x more | | |
| 6 | 72° | 5 minutes | |
| 7 | 4° | Hold | |
| 8 | End | | |

3. PCR products were analyzed on a 1% LE-agarose, TAE plus ethidium bromide gel.
   Bands of about 1900 bp were seen on the gel. The band was not present in the no DNA control reaction.

Cloning Protocols

1. DNA was extracted from excised gel fragments using a QIAGEN Gel Extraction Kit (Catalog number 28704, QIAGEN, Santa Clara, Calif.).
2. PCR fragments were digested with EcoRI and Not I to free up the sites for cloning into EcoRI and Not I digested vector, either pGEX4T1 (Phamacia) or pGEM11 Zf+ (Promega).
3. Digests were cleaned up and desalted used a QIAquick PCR Purification Kit (Catalog number 28104).
4. Isolated fragment was quantified and checked for purity on a 1% LE-agarose, TAE+ethidium bromide gel.
5. Fragments were ligated into compatible sites in either pGEX4T1 (Phamacia) or pGEM11Zf+ (Promega).
6. After heat inactivation Library efficiency DH5 competent E. coli were transformed with a small amount of the ligation reaction.
7. LB+carbenicillin, 50 ug/ml, plates were spread with an aliquot of the transformation mix, grown overnight at 37° C.
8. Colonies were screened for full-length insert using a PCR miniprep method utilizing vector primers flanking the multiple cloning region.
9. Positive clones were identified and overnight cultures grown for pyramid isolation and verification by sequencing.
10. Positive clones are identified as follows:
    DH5: pGEX4T1:ESP002FL_c2 (from palm tree isolate)
    DH5: pGEX4T1:ESP002FL_c3 (from palm tree isolate)
    DH5: pGEX4T1:ESP003FL_c12 (from maize isolate)
    DH5: pGEM11Zf+:RAT011FL_c1 (from maize isolate)
    DH5: pGEM11Zf+:RAT011FL_c4 (from maize isolate)
    DH5: pGEX4T1:RAT011FL_c2 (from maize isolate)

**Important note: These Are Genomic Clones Containing Two Introns

Sequence Results

Three APAO pold-nucleotides and related polypeptides were isolated from *Ecphiala spinifera* (isolates ESP002 and ESP003), designated ESP002_C2, (SEQ ID NOS: 35 and 36) ESP002_C3 (SEQ ID NOS: 37 and 38) and ESP003_C 12 (SEQ ID NOS: 39 and 40). Three APAO polynucleotides were isolated from *Rhinocladiella atrouvirens* (isolate RAT11) designated RAT011_C1 (SEQ ID NOS: 41 and 42), RAT011_C2 (SEQ ID NOS: 43 and 44), and RAT011_C4 (SEQ ID NOS: 45 and 46). Introns were detected by comparison of the genomic sequence with the cDNA sequence of APAO from *E. spinifera* 2141.10 (SEQ ID NO: 22), and by identifying putative intron splice junctions in the gap domains (Shah, et al., *Journal of Molecular and Applied Genetics* 2:111–126 (1983)). Plasmids containing the polynucleotide sequences of the invention were deposited with American Type Culture Collection (ATCC), Manassas, Va., and assigned Accession No. 98812, 98813, 98814, 98815, 98816, (all deposited on July 15, 1998) and PTA-32 (deposited on May 7, 1999). The deposits will be maintained under the terms of the Budapest Treaty on the International Recognition of the Deposit of Microorganisms for the Purposes of Patent Procedure. The deposits were made merely as a convenience for those of skill in the art and are not an admission that a deposit is required under 35 U.S.C. §112.

Preliminary sequence results were entered into GCG, and nucleotide and protein alignments were done in a pileup using a software program called Genedoc for shading and homology comparisons (Nicholas, et al, *EMBNEW.NEWS* 4:14 (1997; or at the Internet site http://www.cris.com/Ketchup/genedoc.shtml). The first APAO (SEQ ID NO: 22) sequence was included for comparison. Comparing the reference sequence SEQ ID NO: 22 to the other homologs sequence identities range from 96 to 99% (identities are lower since APAO introns were not included). Homologies are slightly higher comparing Exophiala genes sequences. At the amino acid sequence level the comparison of the reference sequence (SEQ ID NO: 23) to the other homologs yielded sequence identities of approximately 97%.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. An isolated polynucleotide comprising an APAO encoding polynucleolide linked to a fumonisin esterase encoding polynucleotide, wherein the APAO encodin polynucleotide is selected from the group consisting of:

a) a polynucleotide encoding a polypeptide having deaminase enzyme activity as set forth in SEQ ID NO: 51; and b) a polynucleotide having at least 95% sequence identity to a polynucleotide set forth in SEQ ID NO: 50, and further wherein said fumonisin esterase is ESP1.

2. A recombinant expression cassette comprising a polynucleotide of claim 1 operably linked to a promoter.

3. The recombinant expression cassette of claim 2 wherein the polynucleotide is operably linked to a plant signal sequence.

4. A vector comprising the recombinant expression cassette of claim 2.

5. A host cell comprising the recombinant expression cassette of claim 2.

6. The host cell of claim 5 wherein the cell is a plapt cell.

7. The host cell of claim 6 wherein the plant ecll is selected from the group consisting of maize, sorghum, wheat, tomato, soybean, alfalfa, sunflower, canola, cotton, barley. millet, and rice.

8. A plant comprising the polynucleotide of claim 1.

9. A seed from the plant of claim 8, wherein the seed comprises the isolated polynucleotide.

10. The polynucleotide of claim 1 wherein the polynucleotide is set forth in SEQ ID NO:24.

11. A host cell of comprising an the APAO encoding polynucleotide linked to a fumonisin esterase encoding polynucleotide, wherein the APAO encoding polynueleotide is selected from the group consisting of:

a) a polynucleotide encoding a polypeptide having deaminase enzyme activity set forth in SEQ ID NO: 51; and b) a polynucleotide having at least 95% sequence identity to a polynucleotide set forth in SEQ ID NO: 50:

and further wherein the fumonisin esterase is ESP1.

12. The host cell of claim 1 wherein the cell is a plant cell.

13. The host cell of claim 12 wherein the cell is selected from maize, sorghum, wheat, tomato, soybean, alfalfa, sunflower, canola, cotton, and rice.

14. The host cell of claim 13 wherein the plant cell is regenerated into a plant.

* * * * *

UNITED STATES PATENT AND TRADEMARK OFFICE
CERTIFICATE OF CORRECTION

PATENT NO. : 6,943,279 B1
DATED : September 13, 2005
INVENTOR(S) : Duvick, Jonathan P. et al.

It is certified that error appears in the above-identified patent and that said Letters Patent is hereby corrected as shown below:

Title page,
Item [73], Assignee, should read:
-- Pioneer Hi-Bred International, Inc., Johnston, IA (US); and Curagen Corporation, New Haven, CT (US) --.
Item [57], ABSTRACT,
Line 3, should read:
-- *spinafera* and *Rhinocladiella atrovirens*. The polynucle- --.

Column 56,
Line 3, should read:
-- Three APAO polynucleotides and related polypeptides --.
Line 4, should read:
-- were isolated from *Exophiala spinifera* (isolated ESP002 and --.
Line 8, should read:
-- were isolated from *Rhinocladiella atrovirens* (isolate --.
Line 9, should read:
-- RAT011) designated RAT011_C1 (SEQ ID NOS: 41 and 42), --.

Column 223,
Line 33, should read:
-- encoding polynucleotide linked to a fumonisin esterase --.
Line 34, should read:
-- encoding polynucleotide, wherein the APAO encoding poly- --.
Line 41, should read:
-- and wherein said fumonisin esterase is ESP1. --.
Line 51, should read:
-- 6. The host cell of claim 5 wherein the cell is a plant cell. --.
Line 52, should read:
-- 7. The host cell of claim 6 wherein the plant cell is --.
Line 46, should read:
-- and wherein the fumonisin esterase is ESP1. --.

UNITED STATES PATENT AND TRADEMARK OFFICE
CERTIFICATE OF CORRECTION

PATENT NO. : 6,943,279 B1
DATED : September 13, 2005
INVENTOR(S) : Duvick, Jonathan P. et al.

It is certified that error appears in the above-identified patent and that said Letters Patent is hereby corrected as shown below:

Column 223 (cont'd),
Line 47, should read:
-- 12. The host cell of claim 11 wherein the cell is a plant cell. --.

Signed and Sealed this

Third Day of January, 2006

JON W. DUDAS
*Director of the United States Patent and Trademark Office*